US012480131B2

(12) United States Patent
Smolke et al.

(10) Patent No.: US 12,480,131 B2
(45) Date of Patent: Nov. 25, 2025

(54) TROPANE ALKALOID (TA) PRODUCING NON-PLANT HOST CELLS, AND METHODS OF MAKING AND USING THE SAME

(71) Applicant: The Board of Trustees of the Leland Stanford Junior University, Stanford, CA (US)

(72) Inventors: Christina D. Smolke, Menlo Park, CA (US); Prashanth Srinivasan, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1047 days.

(21) Appl. No.: 17/436,546

(22) PCT Filed: Mar. 6, 2020

(86) PCT No.: PCT/US2020/021577
§ 371 (c)(1),
(2) Date: Sep. 3, 2021

(87) PCT Pub. No.: WO2020/185626
PCT Pub. Date: Sep. 17, 2020

(65) Prior Publication Data

US 2022/0170026 A1 Jun. 2, 2022

Related U.S. Application Data

(60) Provisional application No. 62/891,771, filed on Aug. 26, 2019, provisional application No. 62/848,419,
(Continued)

(51) Int. Cl.
*C12N 15/52* (2006.01)
*C12N 9/02* (2006.01)
(Continued)

(52) U.S. Cl.
CPC .......... *C12N 15/52* (2013.01); *C12N 9/0006* (2013.01); *C12N 9/0022* (2013.01); *C12N 9/0032* (2013.01); *C12N 9/0071* (2013.01); *C12N 9/1007* (2013.01); *C12N 9/78* (2013.01); *C12N 9/88* (2013.01); *C12P 17/12* (2013.01); *C12P 17/188* (2013.01); *C12Y 101/01027* (2013.01); *C12Y 101/01206* (2013.01); *C12Y 101/01236* (2013.01); *C12Y 101/01237* (2013.01); *C12Y 102/01003* (2013.01); *C12Y 104/0301* (2013.01); *C12Y 104/03021* (2013.01); *C12Y 104/03022* (2013.01); *C12Y 105/03017* (2013.01); *C12Y 106/02004* (2013.01); *C12Y 114/11011* (2013.01); *C12Y 201/01053* (2013.01); *C12Y 203/01001* (2013.01); *C12Y 203/01035* (2013.01); *C12Y 204/02028* (2013.01); *C12Y 205/01022* (2013.01);
(Continued)

(58) Field of Classification Search
CPC .... C12N 15/52; C12N 9/0006; C12N 9/0022; C12N 9/0032; C12N 9/0071; C12N 9/1007; C12N 9/78; C12N 9/88; C12N 9/00; C12N 15/81; C12N 15/80; C12P 17/12; C12P 17/188; C12Y 101/01027; C12Y 101/01206; C12Y 101/01236; C12Y 101/01237; C12Y 102/01003; C12Y 104/0301; C12Y 104/03021; C12Y 104/03022; C12Y 105/03017; C12Y 106/02004; C12Y 114/11011; C12Y 201/01053; C12Y 203/01001; C12Y 203/01035; C12Y 204/02028; C12Y 205/01022; C12Y 206/01057; C12Y 207/07009; C12Y 207/11001; C12Y 305/01053; C12Y 305/03001; C12Y 305/03011; C12Y 305/03012; C12Y 401/01001; C12Y 401/01017; C12Y 401/01019; C12Y 402/01051; C12Y 403/01024; C12Y 403/01025; A61P 43/00
See application file for complete search history.

(56) References Cited

U.S. PATENT DOCUMENTS 2,778,832 A 1/1957 Gates, Jr. et al.
3,785,927 A 1/1974 Schoenewaldt et al.
(Continued)

FOREIGN PATENT DOCUMENTS

CA 2728766 A1 12/2009
CN 102657652 A 9/2012
(Continued)

OTHER PUBLICATIONS

Mugford et al. "A serine carboxypeptidase-like acyltransferase is required for synthesis of antimicrobial compounds and disease resistance in oats. Plant Cell. Aug. 2009;21" (Year: 2009).*
(Continued)

*Primary Examiner* — Nancy J Leith
*Assistant Examiner* — Morgan Taylor Lindgren Baltzel
(74) *Attorney, Agent, or Firm* — Bret E. Field; Bozicevic, Field & Francis LLP

(57) ABSTRACT

Provided herein, among other things, is an engineered non-plant cell that produces a tropane alkaloid product, a precursor of a tropane alkaloid product, or a derivative of a tropane alkaloid product. A method for producing a tropane alkaloid, a precursor of a tropane alkaloid product, or a derivative of a tropane alkaloid product that makes use of the cell is also described.

19 Claims, 65 Drawing Sheets

Specification includes a Sequence Listing.

Related U.S. Application Data filed on May 15, 2019, provisional application No. 62/815,709, filed on Mar. 8, 2019.

(51) Int. Cl.

| | |
|---|---|
| *C12N 9/04* | (2006.01) |
| *C12N 9/06* | (2006.01) |
| *C12N 9/10* | (2006.01) |
| *C12N 9/78* | (2006.01) |
| *C12N 9/88* | (2006.01) |
| *C12P 17/12* | (2006.01) |
| *C12P 17/18* | (2006.01) |

(52) U.S. Cl.

CPC ................ *C12Y 206/01057* (2013.01); *C12Y 207/07009* (2013.01); *C12Y 207/11001* (2013.01); *C12Y 305/01053* (2013.01); *C12Y 305/03001* (2013.01); *C12Y 305/03011* (2013.01); *C12Y 305/03012* (2013.01); *C12Y 401/01001* (2013.01); *C12Y 401/01017* (2013.01); *C12Y 401/01019* (2013.01); *C12Y 402/01051* (2013.01); *C12Y 403/01024* (2013.01); *C12Y 403/01025* (2013.01)

(56) References Cited

U.S. PATENT DOCUMENTS

| | | | |
|---|---|---|---|
| 4,764,615 | A | 8/1988 | Ayyangar et al. |
| 6,183,985 | B1 | 2/2001 | Shuster |
| 6,204,337 | B1 | 3/2001 | Corcoran et al. |
| 6,579,985 | B1 | 6/2003 | Hill |
| 6,949,645 | B1 | 9/2005 | Francis |
| 7,037,674 | B1 | 5/2006 | Kutchan et al. |
| 7,045,290 | B2 | 5/2006 | Lindquist et al. |
| 7,193,127 | B1 | 3/2007 | Kutchan et al. |
| 7,390,642 | B2 | 6/2008 | Kutchan et al. |
| 7,514,251 | B2 | 4/2009 | Kutchan et al. |
| 7,767,428 | B2 | 8/2010 | Kutchan et al. |
| 8,318,474 | B1 | 11/2012 | Smolke et al. |
| 8,710,226 | B2 | 4/2014 | Patel et al. |
| 8,735,111 | B2 | 5/2014 | Vanhercke et al. |
| 8,975,063 | B2 | 3/2015 | Smolke et al. |
| 8,993,280 | B2 | 3/2015 | Sato et al. |
| 9,200,261 | B2 | 12/2015 | Winzer et al. |
| 9,322,039 | B2 | 4/2016 | Smolke et al. |
| 9,376,696 | B1 | 6/2016 | Smolke et al. |
| 9,447,444 | B2 | 9/2016 | Winzer et al. |
| 9,458,481 | B2 | 10/2016 | Winzer et al. |
| 9,534,241 | B2 | 1/2017 | Smolke et al. |
| 9,725,732 | B2 | 8/2017 | Winzer et al. |
| 9,862,979 | B2 | 1/2018 | Winzer et al. |
| 9,926,329 | B2 | 3/2018 | Huntley et al. |
| 10,006,010 | B2 | 6/2018 | Winzer et al. |
| 10,017,799 | B2 | 7/2018 | Smolke et al. |
| 10,190,141 | B2 | 1/2019 | Facchini et al. |
| 10,240,175 | B2 | 3/2019 | Smolke et al. |
| 10,240,176 | B2 | 3/2019 | Smolke et al. |
| 10,519,453 | B2 | 12/2019 | Smolke et al. |
| 10,752,903 | B2 | 8/2020 | Smolke et al. |
| 10,858,681 | B2 | 12/2020 | Smolke et al. |
| 11,124,814 | B2 | 9/2021 | Siddiqui et al. |
| 11,859,225 | B2 | 1/2024 | Smolke et al. |
| 11,884,949 | B2 | 1/2024 | Smolke et al. |
| 12,018,304 | B2 | 6/2024 | Siddiqui et al. |
| 2004/0038352 | A1 | 2/2004 | Maier |
| 2005/0106588 | A1 | 5/2005 | Kutchan et al. |
| 2005/0139490 | A1 | 6/2005 | Chou et al. |
| 2005/0277179 | A1 | 12/2005 | Takai et al. |
| 2006/0185032 | A1 | 8/2006 | Kutchan et al. |
| 2007/0065910 | A1 | 3/2007 | Stephanopoulos et al. |
| 2007/0199090 | A1 | 8/2007 | Apuya et al. |
| 2007/0298481 | A1 | 12/2007 | Sato |
| 2008/0102499 | A1 | 5/2008 | Templeton et al. |
| 2008/0176754 | A1 | 7/2008 | Smolke et al. |
| 2008/0196123 | A1 | 8/2008 | Kutchan et al. |
| 2010/0075385 | A1 | 3/2010 | Kutchan et al. |
| 2010/0184166 | A1 | 7/2010 | Sato et al. |
| 2013/0130340 | A1 | 5/2013 | Yan et al. |
| 2013/0340119 | A1 | 12/2013 | Plesch et al. |
| 2014/0013465 | A1 | 1/2014 | Coombs et al. |
| 2014/0273109 | A1 | 9/2014 | Smolke et al. |
| 2015/0267233 | A1 | 9/2015 | Smolke et al. |
| 2016/0201101 | A1 | 7/2016 | Facchini et al. |
| 2016/0251688 | A1* | 9/2016 | Siddiqui ............... C12P 13/001 435/108 |
| 2016/0304923 | A1 | 10/2016 | Smolke et al. |
| 2016/0312256 | A1 | 10/2016 | Facchini et al. |
| 2016/0319314 | A1 | 11/2016 | Smolke et al. |
| 2016/0340704 | A1 | 11/2016 | Martin et al. |
| 2017/0058267 | A1 | 3/2017 | Winzer et al. |
| 2017/0058305 | A1 | 3/2017 | Facchini |
| 2017/0130250 | A1 | 5/2017 | Facchini |
| 2017/0198299 | A1 | 7/2017 | Winzer et al. |
| 2017/0253898 | A1 | 9/2017 | Smolke et al. |
| 2017/0267686 | A1 | 9/2017 | Facchini |
| 2017/0280647 | A1 | 10/2017 | Fist et al. |
| 2017/0306301 | A1 | 10/2017 | Martin et al. |
| 2017/0362617 | A1 | 12/2017 | Peralta-Yahya et al. |
| 2018/0085355 | A1* | 3/2018 | Abramovitch .......... A61P 31/06 |
| 2018/0163212 | A1 | 6/2018 | Smolke et al. |
| 2018/0163241 | A1 | 6/2018 | Smolke et al. |
| 2018/0251801 | A1 | 9/2018 | Aharoni et al. |
| 2018/0273967 | A1* | 9/2018 | Hashimoto ........ C12N 15/8286 |
| 2019/0055567 | A1 | 2/2019 | Smolke et al. |
| 2019/0100781 | A1 | 4/2019 | Smolke et al. |
| 2019/0127770 | A1 | 5/2019 | Siddiqui et al. |

FOREIGN PATENT DOCUMENTS

| | | | |
|---|---|---|---|
| CS | 277517 | B6 | 2/1993 |
| EP | 1512748 | A1 | 3/2005 |
| EP | 1837396 | A1 | 9/2007 |
| JP | H05504252 | A | 7/1993 |
| JP | 2000-300277 | A | 10/2000 |
| JP | 2009225669 | A | 10/2009 |
| JP | 2014525255 | A | 9/2014 |
| WO | WO2000058333 | A1 | 10/2000 |
| WO | WO2002101052 | A2 | 12/2002 |
| WO | WO2005021763 | A2 | 3/2005 |
| WO | WO2006015887 | A2 | 2/2006 |
| WO | WO2008067070 | A2 | 6/2008 |
| WO | WO2008067070 | A3 | 10/2008 |
| WO | WO2008153094 | A1 | 12/2008 |
| WO | WO2009122436 | A2 | 10/2009 |
| WO | WO2011058446 | A2 | 5/2011 |
| WO | WO2011161431 | A2 | 12/2011 |
| WO | WO2012039438 | A1 | 3/2012 |
| WO | WO2012135389 | A2 | 10/2012 |
| WO | WO2013136057 | A2 | 9/2013 |
| WO | WO2014143744 | A2 | 9/2014 |
| WO | WO2015021561 | A1 | 2/2015 |
| WO | WO2015066642 | A1 | 5/2015 |
| WO | WO2015081437 | A1 | 6/2015 |
| WO | WO2015103711 | A1 | 7/2015 |
| WO | WO2014143744 | A3 | 11/2015 |
| WO | WO2015164960 | A1 | 11/2015 |
| WO | WO2015173590 | A1 | 11/2015 |
| WO | WO2016049364 | A2 | 3/2016 |
| WO | WO2016081371 | A1 | 5/2016 |
| WO | WO2016149821 | A1 | 9/2016 |
| WO | WO2016179296 | A1 | 11/2016 |
| WO | WO2016207643 | A1 | 12/2016 |
| WO | WO2017083632 | A1 | 5/2017 |
| WO | WO2017122011 | A1 | 7/2017 |
| WO | WO2018000089 | A1 | 1/2018 |
| WO | WO2018005553 | A1 | 1/2018 |
| WO | WO2018027324 | A1 | 2/2018 |
| WO | WO2018029282 | A1 | 2/2018 |
| WO | WO2018039749 | A1 | 3/2018 |
| WO | WO2018136654 | A1 | 7/2018 |

(56) References Cited

FOREIGN PATENT DOCUMENTS

WO WO2018203947 A9 11/2018
WO WO2019013696 A1 1/2019

OTHER PUBLICATIONS

Methods of Analysis: Tropane Alkaloids from Plant Origin Profile image of Philippe ChristenPhilippe Christen 2013, Natural Products pdf (Year: 2013).*
Robins, R.J., Parr, A.J., Bent, E.G et al. Studies on the biosynthesis of tropane alkaloids in *Datura stramonium* L. transformed root cultures. Planta 183, 185-195 (1991). https://doi.org/10.1007/BF00197787 (Year: 1991).*
Nguyen ("Unravelling the architecture and dynamics of tropane alkaloid biosynthesis pathways using metabolite correlation networks" Phytochemistry, vol. 116, 2015). (Year: 2015).*
Junker ("Evolution of the key alkaloid enzyme putrescine N-methyltransferase from spermidine synthase" Front. Plant Sci., Jul. 28, 2013) (Year: 2013).*
Viladomat ((2015) "General Overview of Plant Secondary Metabolism." Plant Biology and Biotechnology. Springer, New Delhi.) (Year: 2015).*
Muthana et al. ("Modifications of glycans: biological significance and therapeutic opportunities." ACS Chem Biol. Jan. 20, 2012;7(1): 31-43. doi: 10.1021/cb2004466. Epub Jan. 11, 2012. PMID: 22195988; PMCID: PMC3262866. (Year: 2012).*
Cardillo et al., Expression of Brugmansia candida Hyoscyamine 6beta-Hydroxylase gene in *Saccharomyces cerevisiae* and its potential use as biocatalyst, Microb Cell Fact 7, 17 (May 27, 2008).
Kohnen-Johannsen et al., Tropane Alkaloids: Chemistry, Pharmacology, Biosynthesis and Production, Molecules, 24(4), 796 (Feb. 22, 2019).
Ping et al., Building Microbial Hosts for Heterologous Production of N-Methylpyrrolinium, ACS Synth. Biol., 8, 2, 257-263 (Jan. 29, 2019).
Srinivasan et al., Engineering a microbial biosynthesis platform for de novo production of tropane alkaloids, Nat Commun 10, 3634 (Aug. 12, 2019 ).
Srinivasan et al., Biosynthesis of medicinal tropane alkaloids in yeast, Nature 585, 614-619 (Sep. 2, 2020).
Srinivasan et al., Engineering cellular metabolite transport for biosynthesis of computationally predicted tropane alkaloid derivatives in yeast, PNAS, vol. 118, No. 25 (Jun. 17, 2021).
Pasternak et al., Preclinical Pharmacology and Opioid Combinations, Pain Med. Mar. 1, 2012; 13(s1): S4-S11.
Facchini et al., Synthetic biosystems for the production of high-value plant metabolites, Trends in Biotechnology, 30 (3):127-31, Dec. 29, 2011.
Singh et al., Protein Engineering Approaches in the Post-Genomic Era, Curr Protein Pept Sci, 18:1-11, 2017.
Zhang et al., Propagated Perturbations from a Peripheral Mutation Show Interactions Supporting WW Domain Thermostability, Structure, 26(11):1474-85, Nov. 6, 2018.
Sadowski et al., The sequence-structure relationship and protein function prediction, Curr Opin Struct Biol, Jun. 2009;19(3):357-62.
Tang et al., Identification of Dehalobacter reductive dehalogenases that catalyse dechlorination of chloroform, 1,1,1-trichloroethane and 1,1-dichloroethane, Phil Trans R Soc B 368: Mar. 18, 2012.
Alcantara et al., Sanguinarine Biosynthesis Is Associated with the Endoplasmic Reticulum in Cultured Opium Poppy Cells after Elicitor Treatment, Plant Physiology, Apr. 22, 2005, 138:173-183.
Allen et al., RNAi-Mediated Replacement of Morphine with the Nonnarcotic Alkaloid Reticuline in Opium Poppy, Nat. Biotechnol. (Nov. 2004), 22:1559-1566.
Altschul et al., Basic Local Alignment Search Tool, J. Molec. Biol. 215:403-410 (May 1990).
Avalos et al., Compartmentalization of Metabolic Pathways in Yeast Mitochondria Improves the Production of Branched-Chain Alcohols, Nat. Biotechnol. (Apr. 2013), 31:335-341.
Axelsson et al., Cell separation, centrifugation. Enc. Indust. Biotechnol: Bioprocess, Bioseparation and Cell Technol., 2010, pp. 1-20; Ed., Flickinger M.C., John Wiley & Sons, Inc.
Ba et al., Semi-Rational Engineering of Cytochrome P450sca-2 in a Hybrid System for Enhanced Catalytic Activity: Insights Into the Important Role of Electron Transfer, Biotechnology and Bioengineering, Nov. 2013, 110(11):2815-2825.
Babiskin et al., A synthetic library of RNA control modules for predictable tuning of gene expression in yeast, Mol. Syst Biol., Jan. 2011;7:471.
Backes et al., Organization of Multiple Cytochrome P450s with NADPH-Cytochrome P450 Reductase in Membranes, Pharmacol. Ther. (May 2003), 98:221-233.
Bairoch, The ENZYME database in 2000, Nucleic Acids Research, Jan. 2000, 28(1):304-305.
Banerjee et al., Improving Enzymes for Biomass Conversion: A Basic Research Perspective, Bioenerg. Res., Jan. 2010, 3:82-92.
Bayer et al., Synthesis of Methyl Halides from Biomass Using Engineered Microbes, J. Am. Chem. Soc. (Apr. 2009), 131:6508-6515.
Beaudoin, Characterization of Oxidative Enzymes Involved in the Biosynthesis of Benzylisoquinoline Alkaloids in Opium Poppy, Mar. 2015, University of Calgary, 409 pages.
Beaudoin et al., Isolation and Characterization of a cDNA Encoding (S)-cis-N-Methylstylopine 14-Hydroxylase from Opium Poppy, a Key Enzyme in Sanguinarine Biosynthesis, Biochem. Biophys. Res. Commun. (Jan. 2013), 431:597-603.
Bitter, Heterologous Gene Expression in Yeast, Methods in Enzymology, 152:673-684 (1987).
Branden et al., Introduction to Protein Structure, Garland Publishing Inc., New York, p. 247 (1991).
Braus, Aromatic amino acid biosynthesis in the yeast *Saccharomyces cerevisiae*: a model system for the regulation of a eukaryotic biosynthetic pathway, Microbiol Rev., Sep. 1991;55(3):349-70.
Broun et al., Catalytic plasticity of fatty acid modification enzymes underlying chemical diversity of plant lipids, Science. Nov. 13, 1998, 282(5392):1315-7.
Bruce et al., Microbial Degradation of the Morphine Alkaloids. Purification and Characterization of Morphine Dehydrogenase from Pseudomonas putida M10, Biochem. J. (Mar. 1991), 274(3):875-880.
Carillo et. al., The Multiple Sequence Alignment Problem in Biology, SIAM J. Applied Math., 48(5)1078-1083 (Oct. 1988).
CAS Registry No. 466-99-9 (Hydromorphone) Nov. 16, 1984, (Modify Date: Jun. 10, 2019), 3 pages.
CAS Registry No. 57-27-2 (Morphine) Nov. 16, 1984, (Modify Date: Jun. 10, 2019), 19 pages.
CAS Registry No. 86709-01-5 (Neomorphine) Nov. 16, 1984, (Modify Date: Apr. 9, 2021), 3 pages.
Cautha, Model based design of a *Saccharomyces cerevisiae* platform strainwitt1 improved tyrosine production capabilities, Masters Thesis, Toronto, Canada, 72 pages (2012). Retrieved from the internet on Jan. 28, 2015 at: http://hdl. tland le. net/"1 807 /33358.
Chavez-Bejar et al., Metabolic Engineering of *Escherichia coii* for L-Tyrosine Production by Expression of Genes Coding for the Chorismate Mutase Domain of the Native Chorismate Mutase-Preptlenate Detlydratase and a Cyclohexadienyl Dehydro~lenase from Zymomonas mobi!is, Applied and Environmental Microbiology, American Society for Microbiology, US, 74(10):3284-3290 (May 2008).
Chica et al., Semi-rational approaches to engineering enzyme activity: combining the benefits of directed evolution and rational design, Current Opinion in Biotechnology, Jul. 2005, 16:378-384.
Choi et al., Molecular Cloning and Characterization of Coclaurine N-Methyltransferase from Cultured Cells of Coptis japonica, J. Biol. Chem. (Jan. 2002), 277:830-835.
Clark, Plant Molecular Biology: A Laboratory Manual, Chapter 7, Clark, Ed., Springer, Published in 1997.
clinical trials.gov, Fasting Study of Hydromorphone Hydrochloride 8 mg Tablets and Dilaudid 8 mg Tablets, ClinicalTrials.gov, https://web.archive.org/web/20121216193456/https://clinicaltrails.gov/ct2/show/NCT00853554, Dec. 16, 2012.

(56) References Cited

OTHER PUBLICATIONS clinical trials.gov, Morphine vs. Oxycodone for Postoperative Pain Management, ClinicalTrials.gov, https://clinicaltrials.gov/ct2/show/NCT00528177, 2011, 4 pages.
Cooper et al., On the amine oxidases of Klebsiella aerogenes strain W70, FEMS Microbiol. Lett., 146(1):85-89 (Jan. 1997).
Cravens et al., Synthetic biology strategies for microbial biosynthesis of plant natural products, Nature Communications vol. 10, Article No. 2142 (May 2019).
Curran et al., Metabolic engineering of muconic acid production in *Saccharomyces cerevisiae*, Metabolic Engineering, Academic Press, US, Nov. 17, 2012, 15:55-66.
Dang et al., CYP82Y1 Is N-Methylcanadine 1-Hydroxylase, a Key Noscapine Biosynthetic Enzyme in Opium Poppy, The Journal of Biological Chemistry, 289(4):2013-2026, Jan. 2014.
Dang et al., Cloning and characterization of canadine synthase involved in noscapine biosynthesis in opium poppy, FEBS Lett. Jan. 3, 2014;588(1):198-204.
Dang et al., Elucidation of the noscapine biosynthetic pathway in opium poppy, Doctoral Thesis, University of Calgary, 2014, 207 pages.
Dastmalchi et al., Neopinone isomerase is involved in codeine and morphine biosynthesis in opium poppy, Nat Chem Biol. Apr. 2019;15(4):384-390.
Daubner et al., Tyrosine Hydroxylase and Regulation of Dopamine Synthesis, Arch Biochem Biophys, Apr. 1, 2011, 508(1):1-12.
De-Eknamkul et al., Purification and properties of 1,2-dehydroreticuline reductase from Papaver somniferum seedlings, Mar. 1992, 31(3):813-821.
De-Eknannkul et al., Enzymic Formation of ( R)-Reticuline from 1,2-Dehydroreticuline in the Opium Poppy Plant, Tetrahedron Letters, 31(34):4855-4858, 1990.
Desgagne-Penix et al., Integration of deep transcriptome and proteome analyses reveals the components of alkaloid metabolism in opium poppy cell cultures, BMC Plant Biology, 10(1):1-17 (2010).
Devereaux et al., A comprehensive set of sequence analysis programs for the VAX, Nucleic Acids Res., 12(1):387-395 (1984).
Devos et al., Practical limits of function prediction, Proteins. Oct. 1, 2000;41(1):98-107.
Diaz Chavez et al., Characterization of two Methylenedioxy Bridge-Forming Cytochrome P450-Dependent Enzymes of Alkaloid Formation in the Mexican Prickly Poppy Argemone mexicana, Arch. Biochem. Biophys. (Mar. 2011), 507:186-193.
Dumas et al., 11 Beta-Hydroxylase Activity in Recombinant Yeast Mitochondria. In vivo Conversion of 11-Deoxycortisol to Hydrocortisone, Eur. J. Biochem. (Mar. 1996), 238:495-504.
Englaender et al., Effect of Genomic Integration Location on Heterologous Protein Expression and Metabolic Engineering in *E. coli*, ACS Synth Biol. Apr. 21, 2017, 6(4):710-720.
Enzyme, https://www.enzyme.expasy.org/cgi-bin/enzyme/enzyme-search-de, Nov. 1, 2021, 1 page.
Facchini et al., Differential and Tissue-Specific Expression of a Gene Family for Tyrosine/Dopa Decarboxylase in Opium Poppy, J. Biol. Chem., 269(43):26684-26690 (Oct. 1994).
Farhi et al., Harnessing Yeast Subcellular Compartments for the Production of Plant Terpenoids, Metab. Eng. (May 2011), 13:474-481.
Farrow et al., Dioxygenases Catalyze O-Demethylation and O,Odemethylenation with Widespread Roles in Benzylisoquinoline Alkaloid Metabolism in Opium Poppy, J. Biol. Chem. (Aug. 2013), 288:28997-29012.
Farrow et al., Stereochemical inversion of (S)-reticuline by a cytochrome P450 fusion in opium poppy, Nat Chem Biol. Sep. 2015;11(9):728-32.
Fisinger et al., Thebaine Synthase: a New Enzyme in the Morphine Pathway in Papaver somniferum, Natural Product Communications (2007), 2(3):249-253.
Fossati et al., Reconstitution of a 10-gene pathway for synthesis of the plant alkaloid dihydrosanguinarine in *Saccharomyces cerevisiae*, Nature Communications., Feb. 2014, 5(1):1-11.
French et al., Biological Production of Semisynthetic Opiates Using Genetically Engineered Bacteria, Biotechnology (N Y) (1995), 13:674-676.
French et al., Purification and Characterization of Morphinone Reductase from Pseudomonas putida M10, Biochem. J. (1994), 301(1):97-103.
French et al., Bacterial morphinone reductase is related to Old Yellow Enzyme, Biochem J. Dec. 15, 1995;312 ( Pt 3):671-8.
Fukuda et al., Breeding of Brewing Yeast Producing a Large Amount of Beta-Phenylethyl Alcohol and Beta-Phenylethyl Acetate, Agricultural and Biological Chemistry, Tokyo, Japan, 54(1):269-271 (1990).
Fukuda et al., Feedback-Insensitive Mutation of 3-Deoxy-D-Arabino-Hepturosonate-7-Phosphate Synthase Caused by a Single Nucleotide Substitution of AR04 Structural Gene in *Saccharomyces cerevisiae*, Journal of Fermentation and Bioengineering, 74(2):117-119 (1992).
Fukuda et al., Molecular Breeding of a Sake Yeast with a Mutated AR04 Gene VWhich Causes Both Resistance to o-Fluoro-DL-Phenylalanine and Increased Production of Beta-Phenethyl Alcohol, Journal of Fermentation and Bioengineering, 73(5):366-369 (1992).
Fukuda et al., A mutated ARO4 gene for feedback-resistant DAHP synthase which causes both o-fluoro-DL-phenylalanine resistance and beta-phenethyl-alcohol overproduction in *Saccharomyces cerevisiae*, Curr Genet., Dec. 1991;20(6):453-6.
Galanie et al., Complete biosynthesis of opioids in yeast, Science, Sep. 2015, 349(6252):1095-1100.
Geissler et al., Molecular Modeling and Site-Directed Mutagenesis Reveal the Benzylisoquinoline Binding Site of the Short-Chain Dehydrogenase/Reductase Salutaridine Reductase, Plant Physiol. (2007), 143(4):1493-503.
Gesell et al., CVP719B1 Is Salutaridine Synthase. the C-C Phenol-coupling Enzyme of Morphine Biosynthesis in Opium Poppy, Journal of Biological Chemistry, Sep. 4, 2009, 284(36):24432-24442.
Gesell et al., Heterologous Expression of Two FAD-Dependent Oxidases with (S) Tetrahydroprotoberberine Oxidase Activity from Argemone mexicana and Berberis wilsoniae in Insect Cells, Planta. (2011), 233:1185-1197.
Gold et al., Metabolic engineering of a tyrosine-overproducing yeast platform using targeted metabolomics, Microbial Cell Factories, vol. 14, Article No. 73 (2015).
Grothe et al., Molecular Characterization of the Salutaridinol 7-O-Acetyltransferase Involved in Morphine Biosynthesis in Opium Poppy Papaver somniferum, J. Biol. Chem. (2001), 276:30717-30723.
Guo et al., Mini-review: In vitro Metabolic Engineering for Biomanufacturing of High-value Products, Comput Struct Biotechnol J. Jan. 19, 2017;15:161-167.
Guo et al., Protein tolerance to random amino acid change, PNAS, Jun. 2004, 101(25):9205-9210.
Gustafsson et al., Codon bias and heterologous protein expression, Trends in Biotechnology, 22(7):346-353 (Jul. 2004).
Hagel et al., Benzylisoquinoline Alkaloid Metabolism: a Century of Discovery and a Brave New World, Plant Cell Physiol. (2013), 54:647-672.
Hagel et al., Characterization of a Flavoprotein Oxidase from Opium Poppy Catalyzing the Final Steps in Sanguinarine and Papaverine Biosynthesis, J. Biol. Chem. (2012), 287:42972-42983.
Hagel et al., Dioxygenases Catalyze the O-Demethylation Steps of Morphine Biosynthesis in Opium Poppy, Nat. Chem. Biol. (2010), 6:273-275.
Hartmann et al., Evolution of feedback-inhibited beta/alpha barrel isoenzymes by gene duplication and a single mutation, PNAS, 100(3):862-867 (Feb. 4, 2003).
Hawkins et al., Production of benzylisoquinoline alkaloids in *Saccharomyces cerevisiae*, Nat Chem Biol. Sep. 2008; 4(9): 564-573.
Hawkins et al., Supplementary Text and Figures. Production of benzylisoquinoline alkaloids in *Saccharomyces cerevisiae*, Nature Chemical Biology, Aug. 10, 2008, 15 pages.
Hawkins, Metabolic Engineering of *Saccharomyces cerevisiae* for the Production Of Benzylisoquinoline Alkaloids, Ph.D. Thesis, California Institute of Technology, Pasadena, California, 2009, pp. 1-154.

(56) References Cited

OTHER PUBLICATIONS

Henikoff et al., Amino acid substitution matrices from protein blocks, Proc. Natl. Acad. Sci. USA, 89:10915-10919 (1992).
Higashi et al., Atomic Structure of Salutaridine Reductase from the Opium Poppy (*Papaver somniferum*), J. Biol. Chem. (2011), 286:6532-6541.
Hinnen et al., Chapter 10: Heterologous Gene Expression in Yeast, Yeast Genetic Engineering, Barr et al. eds., Buttervvorths, pp. 193-213 (1989).
Hirata et al., 1,2-Dehydroreticuline synthase, the branch point enzyme opening the morphinan biosynthetic pathway, Phytochemistry, 2004, 65:1039-1046.
Hiroi et al., Dopamine Formation from Tyramine by CYP2D6, Biochemical & Biophysical Research Communications, 249:838-843 (1998).
Ikezawa et al., Molecular Cloning and Characterization of CYP719, a Methylenedioxy Bridge-Forming Enzyme that Belongs to a Novel P450 Family, from Cultured Coptis japonica Cells, J. Biol. Chem. (2003), 278:38557-38565.
Ikezawa et al., Molecular Cloning and Characterization of Methylenedioxy Bridge-Forming Enzymes Involved in Stylopine Biosynthesis in Eschscholzia californica, FEBS J. (2007), 274:1019-1035.
Imai, Substrate recognition: diversity Structural Basis of Chemistry: An Organism, 36(8): 530-533 (1998).
Iraqui et al., Characterisation of *Saccharomyces cerevisiae* AR08 and AR09 genes encoding aromatic aminotransferases I and II reveals a new aminotransferase subfamily, Mol. Gen. Genet., 257(2):238-248 (1998).
Jensen et al., Plant NADPH-Cytochrome P450 Oxidoreductases, Phytochemistry (2010). 71:132-141.
Jez et al., A new nomenclature for the aldo-keto reductase superfamily, Biochem. Pharmacol., 54:639-647 (1997).
Julien et al., Isolation and Characterization of the epothilone biosynthetic gene cluster from Sorangium cellulosm, Gene, 2000, 249:153-160.
KEGG Compound C06172, Neopinone, https://web.archive.org/web/20130117233034/https://www.genome.jp/dbget-bin/www_bget?C06172, Downloaded on Jul. 8, 2021, 1 page.
Kim et al., Improvement of Reticuline Productivity from Dopamine by Using Engineered *Escherichia coli*, Biosci. Biotechnol. Biochem. (2013), 77(10):2166-2168.
Kimchi-Sarfaty et al., A "Silent" Polymorphism in the MDR1 Gene Changes Substrate Specificity, Science, Jan. 2007, 315(5811):525-528.
Kisselev, Polypeptide Release Factors in Prokaryotes and Eukaryotes-:Same Function, Different Structure, Structure, vol. 10, Jan. 2002, 2 pages.
Kocharin, Metabolic Engineering of *Saccharomyces cerevisiae* for Polyhydroxybutyrate Production, PhD Thesis, Apr. 2013, 168 pages.
Koopman et al., De novo production of the flavonoid naringenin in engineered *Saccharomyces cerevisiae*, Microbial Cell Factories, Biomed Central, GB, Dec. 8, 2012, 11(1):155 (15 pages).
Kushnirov, Rapid and Reliable Protein Extraction from Yeast, Yeast (2000), 16:857-860.
Kutchan et al., Molecular Genetics of Plant Alkaloid Biosynthesis, Alkaloids, 50:257-316 (1998).
Kutchan, Heterologous expression of alkaloid biosynthetic genes—a review, Gene, Nov. 7, 1996, 179(1):73-81.
Larkin et al., Increasing Morphinan Alkaloid Production by Over-Expressing Codeinone Reductase in Transgenic Papaver somniferum, Plant Biotechnol. J. (2007), 5:26-37.
Lechner et al., Library of Norcoclaurine Synthases and Their Immobilization for Biocatalytic Transformations, Biotechnol J., Mar. 2018;13(3).
Lee et al., Bacillus licheniformis APase I gene promoter: a strong well-regulated promoter in B. Subtilis, Journal of General Microbiology, 137:1127-1133 (1991).
Lee et al., Metabolic engineering of microorganisms: general strategies and drug production, Drug Discovery Today, 14( 1/2): 78-88 (Jan. 2009).
Lee et al., Norcoclaurine Synthase Is a Member of the Pathogenesis-Related 10/Bet v1 Protein Family[W], Plant Cell. Oct. 2010; 22(10): 3489-3503.
Lenz et al., Acetyl Coenzyme A:Salutaridinol-7-O Acetyltransferase from Papaver somniferum Plant Cell Cultures, J. Biol. Chem. (1995), 270:31091-31096.
Lenz et al., Purification and Properties of Codeinone Reductase (NADPH) from Papaver somniferum Cell Cultures and Differentiated Plants, Eur. J. Biochem. (1995), 233:132-139.
Li et al., Engineering biosynthesis of the anticancer alkaloid noscapine in yeast, Nature Communications, vol. 7, Article No. 12137 (2016).
Li et al., Strategies for microbial synthesis of high-value phytochemicals, Nat Chem, Apr. 2018;10(4):395-404.
Liscombe et al., Molecular cloning and characterization of tetrahydroprotoberberine cis-N-methyltransferase, an enzyme involved in alkaloid biosynthesis in opium poppy, J Biol Chem. May 18, 2007;282(20).
Liscombe et al., Targeted Metabolite and Transcript Profiling for Elucidating Enzyme Function: Isolation of Novel N Methyltransferases from Three Benzylisoquinoline Alkaloid-Producing Species, Plant J. (2009), 60:729-743.
Lister et al., Transformations of codeine to important semisynthetic opiate derivatives by Pseudomonas putida m10,FEMS Microbiol Lett. Dec. 1, 1999;181(1):137-44.
Lütke-Eversloh et al., L-Tyrosine production by deregulated strains of *Escherichia coli*, Applied Microbiology and Biotechnology, Springer, Berlin, DE, Jan. 13, 2007, 75(1):103-110.
Lütke-Eversloh et al., Perspectives of biotechnological production of L-tyrosine and its applications, Appl Microbiol Biotechnol. Dec. 2007;77(4):751-62.
Luttik et al., Alleviation of feedback inhibition in *Saccharomyces cerevisiae* aromatic amino acid biosynthesis: Quantification of metabolic impact, Metabolic Engineering, vol. 10, pp. 141-153 (2008).
Lv et al., LC-MS-MS Simultaneous Determination of L-Dopa and Its Prod rug L-Dopa n-Pentyl Hydrochloride in Rat Plasma, Chromatographia, 72(3/4):239-243, (2010).
Millgate et al., Morphine-pathway block in top1 poppies, Nature; Sep. 2004, 431:413-414.
Minami et al., Microbial Production of Plant Benzylisoquinoline Alkaloids, Proc. Natl. Acad. Sci. U S A (2008), 105:7393-7398.
Minami, Fermentative Production of Plant Benzylisoquinoline Alkaloids in Microbes, Bioscience, Biotechnology, and Biochemistry, 77(8):1617-1622 (Aug. 7, 2013).
Mishra et al., Wound Induced Tanscriptional Regulation of Benzylisoquinoline Pathway and Characterization of Wound Inducible PsWRKY Transcription Factor from Papaver somniferum, PLoS One, Jan. 30, 2013, 8(1):1-15.
Mitchell et al., Circular permutation of a synthetic eukaryotic chromosome with the telomerator, PNAS, 2014,111,17003-17010.
Mizutani et al., Diversification of P450 Genes During Land Plant Evolution, Annu. Rev. Plant Biol. (2010), 61:291-315.
Moerner et al., Illuminating single molecules in condensed matter, Science, 283(5408):1670-1676 (1999).
Morishige et al., Molecular Characterization of the Sadenosyl-L-Methionine:3'-Hydroxy-N-Methylcoclaurine 4'-O-Methyltransferase Involved in Isoquinoline Alkaloid Biosynthesis in Coptis japonica, J. Biol. Chem. (2000), 275:23398-23405.
Morris et al., Plug-and-Play Benzylisoquinoline Alkaloid Biosynthetic Gene Discovery in Engineered Yeast, in Methods in Enzymology, 144-178 (Elsevier 2016).
Munoz et al., Metabolic engineering of *Escherichia coli* for improving L-3,4-dihydroxyphenylalanine (L-DOPA) synthesis from glucose, Journal of Industrial Microbiology and Biotechnology; 38(11):845-1852 (Apr. 22, 2011).
Nackley et al., Human Catechol-O-Methyltransferase Haplotypes Modulate Protein Expression by Altering mRNA Secondary Structure, Science, Dec. 2006, 314(5807):1930-1933.
Nakagawa et al., A bacterial platform for fermentative production of plant alkaloids, Nature Communications, vol. 2, Article No. 326, 8 pages (May 24, 2011).

(56) References Cited

OTHER PUBLICATIONS

Nakagawa et al., Bench-Top Fermentative Production of Plant Benzylisoquinoline Alkaloids Using a Bacterial Platform, Bioeng. Bugs (2012), 3:49-53.
Nakagawa et al., (R,S)-Tetrahydropapaveroline production by stepwise fermentation using engineered *Escherichia coli*, Scientific Reports vol. 4, Article No. 6695 (2014).
Nakagawa et al., Bioengineering of Isoquinoline Alkaloid Production in Microbial Systems, Advances in Botanical Research 68:183-203, 2013.
Needleman et al., A General Method Applicable to the Search for Similarities in the Amino Acid Sequence of Two Proteins, J. Mol. Biol., 48:443-453 (1970).
Neviogt et al., Engineering promoter regulation, Biotechnol Bioeng, . Feb. 15, 2007;96(3):550-8.
Ng et al., Production of 2,3-butanediol in *Saccharomyces cerevisiae* by in silica aided metabolic engineering, Microbial Cell Factories, Biomed Central, GB, May 28, 2012, 11(1):68 (14 pages).
Niedz et al., Green fluorescent protein: an in vivo reporter of plant gene expression, Plant Cell Rep., 14:403-406 (1995).
Olson et al., Production of tyrosine from sucrose or glucose achieved by rapid genetic changes to ptlenylalanine-producing *Escherichia coli* strains, Applied Microbiology and Biotechnology, 74(5):1031-1040 (Jan. 11, 2007).
Onoyovwe et al., Morphine Biosynthesis in Opium Poppy Involves Two Cell Types: Sieve Elements and Laticifers, Plant Cell (2013), 25(10): 4110-4122.
Ounaroon et al., (R,S)-Reticuline 7-O-Methyltransferase and (R,S)-Norcoclaurine 6-O-Methyltransferase of Papaver somniferum-cDNA Cloning and Characterization of Methyl Transfer Enzymes of Alkaloid Biosynthesis in Opium Poppy, Plant J. (2003), 36:808-819.
Paterson, The DNA Revolution, Chapter 2 in: Genome Mapping in Plants; Academic Press/R.G. Landis Company, Austin, TX (1996).
Pauli et al., Molecular cloning and functional heterologous expression of two alleles encoding (S)-N-methylcoclaurine 39-hydroxylase (CYP80B1), a new methyl jasmonateinducible cytochrome P-450-dependent mono-oxygenase of benzylisoquinoline alkaloid biosynthesisT.M., The Plant Journal; 1998, 13(6):793-801.
Rodrigue, et al., Establishment of a yeast platform strain for production of p-coumaric acid through metabolic engineering of aromatic amino acid biosynthesi, Metab Eng., Sep. 2015;31:181-8.
Rueffer et al., (S)-Norlaudanosoline Synthase—The 181 Enzyme the Benzylisoquinoline Biosynthetic-Pathway, FEBS Letters, 129(1):5-9 (Jun. 1981 ).
Runguphan et al., Redesign of a dioxygenase in morphine biosynthesis, Chem Biol. Jun. 22, 2012;19(6):674-8.
Ruohonen et al., Modifications to the ADHI promoter of *Saccharomyces cerevisiae* for efficient production of heterologous proteins, Journal of Biotechnology, 39:193-203 (1995).
Saez-Vasquez et al., Genome Organization and Function: A View from Yeast and *Arabidopsis*, Molecular Plant, 3(4):678-690, Jul. 2010.
Salis et al., Automated Design of Synthetic Ribosome Binding Sites to Precisely Control Protein Expression, Nat Biotechnol. Oct. 2009; 27(10):946-950.
Samanani et al., Molecular cloning and characterization of norcoclaurine synthase, an enzyme catalyzing the first committed step in benzylisoquinoline alkaloid biosynthesis, Plant J., 40(2):302-313 (2004).
Sandig et al., Regulation of Endoplasmic Reticulum Biogenesis in Response to Cytochrome P450 Overproduction, Drug Metab. Rev. (1999), 31:393-410.
Sariyar et al., Six Alkaloids from Papaver Species, Phytochemistry, 1986, 25(10):2403-2406.
Sato et al., Purification and Characterization of S-adenosyl-L-methionine: norcoclaurine 6-O-methyltransferase from Cultured Coptis japonica Cells, Eur. J. Biochem. (1994), 225:125-131.
Sato et al., Microbial production of isoquinoline alkaloids as plant secondary metabolites based on metabolic engineering research, Proc Jpn Acad Ser B Phys Biol Sci. May 10, 2013; 89(5): 165-182.
Sauna et al., Silent Polymorphisms Speak: How They Affect Pharmacogenomics and the Treatment of Cancer, Cancer Res., Oct. 2007, 67(20):9609-9612.
Schmidheini et al., A Single Point Mutation Results in a Constitutively Activated and Feedback-Resistant Chorismate Mutase of *Saccharomyces cerevisiae*, Journal of Bacteriology, 171(3):1245-1253 (Mar. 1989).
Schmidt et al., Poppy alkaloid profiling by electrospray tandem mass spectrometry and electrospray FT-ICR mass spectrometry after [ring-13 C6}-tyramine feeding, Phytochemistry, vol. 68, No. 2, pp. 189-202 (2007).
Seffernick et al., Melamine Deaminase and Atrazine Chlorohydrolase: 98 Percent Identical but Functionally Different, J. Bacteriol. Apr. 2001, 183(8):2405-2410.
Sen et al., Developments in Directed Evolution for Improving Enzyme Functions, Appl Biochem Biotechnol, Aug. 2007, 143:212-223.
Sharafi et al., Metabolic engineering of morphinan alkaloids by over-expression of codeinone reductase in transgenic hairy roots of Papaver bracteatum, the Iranian poppy, Biotechnol Lett. Mar. 2013;35(3):445-53.
Shi et al., Regulation of Tetrahydrobiopterin Synthesis and Bioavailability in Endothelial Cells, Cell Biochemistry and Biophysics, 41, 415-433 (2004).
Siddiqui et al., Advancing Secondary Metabolite Biosynthesis in Yeast with Synthetic Biology Tools, FEMS Yeast Res. (2012), 12:144-170.
Siddiqui et al., A system for multilocus chromosomal integration and transformation-free selection marker rescue, FEMS Yeast Res. Dec. 2014, 14(8):1171-85.
Single Molecule Detection and Manipulation Workshop, Apr. 17-18, 2000, 28 pages. Retrieved from http://www.nigms.nih.gov/news/reports/single_molecules.html.
Smirnova et al., Optical isomerism and biological activity of pharmaceutical preparations. Moscow Univ. Chem. Bull., 2012, 67(3): 95-102.
Smith et al., Comparison of Biosequences, Adv. Appl. Math., 2:482-489 (1981).
Soares, Flocculation in *Saccharomyces cerevisiae*: a review. J. Appl. Microbial., 2010, 110: 1-18.
Stewart et al., A Chemist's Perspective on the Use of Genetically Engineered Microbes as Reagents for Organic Synthesis, Biotechnology and Genetic Engineering Reviews, 14:67-143 (1997).
Takemura et al., Molecular Cloning and Characterization of a Cytochrome P450 in Sanguinarine Biosynthesis from Eschscholzia californica Cells, Phytochemistry (2013), 91:100-108.
Teitel et al., An Improved Synthesis of Various Racemic Polyphenolic Tetrahydroisoquinoline alkaloids, Journal of Heterocyclic Chemistry 5:825-829 (1968).
Thompson et al., Clustal W: Improving the Sensitivity of Progressive Multiple Sequence Alignment through sequence weighting, position-specific gap penalties and weight matrix choice, Nucleic Acid Res., 22(22):4673-4680 (1994).
Trenchard et al., De novo production of the key branch point benzylisoquinoline alkaloid reticuline in yeast, Metab. Eng., Jul. 10, 2015, 31:74-83.
Uniprotkb Database, ARO1, ARO1, ARO7, TYR1, https://www.uniprot.org/prg/uniprot/, 2019.
Unterlinner et al., Molecular Cloning and Functional Expression of Codeinone Reductase: the Penultimate Enzyme in Morphine Biosynthesis in the Opium Poppy Papaver somniferum, Plant J. (1999), 18:465-475.
Vuralhan et al., Identification and characterization of phenylpyruvate decarboxylase genes in *Saccharomyces cerevisiae*, Appl. Environ. Microbial., 69(8):4534-4541 (2003).
Vuralhan, Engineering of aromatic amino acid metabolism in *Saccharomyces cerevisiae*, Ph. D. Thesis. Apr. 11, 2006, pp. 1-110.
Walker et al., Mechanistic studies of morphine dehydrogenase and stabilization against covalent inactivation, Biochem J. Feb. 1, 2000;345 Pt 3:687-92.
Whisstock et al., Prediction of protein function from protein sequence and structure, Q Rev Biophys. Aug. 2003, 36(3):307-40.

(56) References Cited

OTHER PUBLICATIONS

Wijekoon et al., Systematic Knockdown of Morphine Pathway Enzymes in Opium Poppy Using Virus-Induced Gene Silencing, Plant J. (2012), 69:1052-1063.
Willey et al., Nucleotide sequence and over-expression of morphine dehydrogenase, a plasmid-encoded gene from Pseudomonas putida M10, Biochem J. Mar. 1, 1993; 290(Pt 2): 539-544.
Winzer et al., A Papaver somniferum 10-gene cluster for synthesis of the anticancer alkaloid noscapine, Science. Jun. 29, 2012;336(6089):1704-8.
Witkowski et al., Conversion of a beta-ketoacyl synthase to a malonyl decarboxylase by replacement of the active-site cysteine with glutamine, Biochemistry. Sep. 7, 1999;38(36):11643-50.
Yoshida et al., 2. Diversozyme P450's Evolution and diversity, Chemistry: An Organism, 36(6): 392-398 (1998).
Zeng et al., Integration of Transcriptome, Proteome and Metabolism Data Reveals the Alkaloids Biosynthesis in Macleaya cordata and Macleaya microcarpa, PLOS ONE, 8(1):1-18, 2013.
Zenk et al., Benzylisoquinoline Biosynthesis by Cultivated Plant Cells and Isolated Enzymes, Journal of Natural Products, 48(5):725-738 (1985).
Zhang et al., 14-Hydroxylation of Opiates: Catalytic Direct Autoxidation of Codeinone to 14-Hydroxycodeinone, J. Am. Chem. Soc. (2005), 127:7286-7287.
Ziegler et al., Removal of Substrate Inhibition and Increase in Maximal Velocity in the Short Chain Dehydrogenase/Reductase Salutaridine Reductase Involved in Morphine Biosynthesis, J. Biol. Chem. (2009), 284:26758-26767.
Zimmer et al., Protein Quality—a Determinant of the Intracellular Fate of Membrane-Bound Cytochromes P450 in Yeast, DNA Cell Biol. (1997), 16:501-514.
Zulak et al., GenBank Accession No. FE967184, Mar. 31, 2008 (Mar. 31, 2008), [online] [retrieved on Sep. 19, 2017].
Chattopadhyay et al., Studies on the regulation of ornithine decarboxylase in yeast: Effect of deletion in the MEU1 gene, PNAS, Nov. 8, 2005, 102(45):16158-16163.
Morita et al., Vacuolar transport of nicotine is mediated bya multidrug and toxic compound extrusion(MATE) transporter inNicotiana tabacum, PNAS, Feb. 17, 2009, 106(7):2447-2452.
Beaudoin et al., Benzylisoquinoline alkaloid biosynthesis in opium poppy, Planta (2014) 240:19-32.
Kurtzman et al., Yeast Systematics and Phylogeny—Implications of Molecular Identification Methods for Studies in Ecology, In: Peter, G., Rosa, C. (eds) Biodiversity and Ecophysiology of Yeasts, The Yeast Handbook. Springer, Berlin, Heidelberg, pp. 11-30, Mar. 2006.
Winzer et al., Morphinan biosynthesis in opium poppy requires a P450-oxidoreductase fusion protein, Science, Jun. 25, 2015, vol. 349, Issue 6245, pp. 309-312.
Dang et al., Characterization of Three O-Methyltransferases Involved in Noscapine Biosynthesis in Opium Poppy, Plant Physiology, 159:618-631 (Jun. 2012).
Annett et al., Proceedings of the Society of Public Analysts and other Analytical Chemists, The Analyst, XLV(534): 321-328 (Sep. 1920).
Bhandari et al., Recent updates on codeine, Pharm Methods, 2(1):3-8 (Jan.-Mar. 2011).
Certificate of Analysis, Codeine, Sigma-Aldrich (Jun. 5, 2012).
Dastmalchi et al., Purine Permease-Type Benzylisoquinoline Alkaloid Transporters in Opium Poppy, Plant Physiol, 181(3):916-933 (Nov. 2019).
Larsen et al., Advances in methods for identification and characterization of plant transporter function, J Exp Bot, 68 (15):4045-4056 (Jul. 10, 2017).
Shitan et al., Alkaloid transporters in plants, Plant Biotechnology 31(5):453-463 (Dec. 2014).

* cited by examiner

Arginine
Agmatine
Ornithine
Spermine
Putrescine
Spermidine
N-Methylputrescine
4-Methylaminobutanal
4-(1-Methyl-2-pyrrodinyl)-3-oxobutanoic acid
N-Methylpyrrolinium
Tropinone
Pseudotropine

| | CEN.PK2 | CSY1225 | CSY1226 | CSY1227 | CSY1235 |
|---|---|---|---|---|---|
| Endogenous pathway (*ARG2, CAR1, FMS1, SPE1*) | — | + | — | + | + |
| Heterologous pathway (*AsADC, speB*) | — | — | + | + | + |
| Regulatory knockouts (*meu1, oaz1*) | — | — | — | — | + |

| | Plant cell | | | | | | Yeast (fungal) cell | | | | |
|---|---|---|---|---|---|---|---|---|---|---|---|
| | CYT | NUC | VAC | CHL | MIT | POX | CYT | NUC | VAC | MIT | POX |
| *SPE1* | 0.59 | 0.00 | 0.00 | 0.00 | 0.00 | 0.40 | 0.61 | 0.01 | 0.01 | 0.02 | 0.35 |
| *AbPMT1* | 0.41 | 0.02 | 0.00 | 0.00 | 0.00 | 0.55 | 0.46 | 0.02 | 0.08 | 0.02 | 0.39 |
| *NtMPO1* | 0.06 | 0.01 | 0.01 | 0.34 | 0.04 | 0.53 | 0.00 | 0.00 | 0.00 | 0.00 | 1.00 |

FIG. 14

| | A | | | B | | |
|---|---|---|---|---|---|---|
| CSY# | 1235 | 1240 | 1241 | 1235 | 1240 | 1241 |
| *HFD1* | + | — | — | + | — | — |
| *ALD2* | + | + | — | + | + | — |
| *ALD3* | + | + | — | + | + | — |
| *ALD4* | + | — | — | + | — | — |
| *ALD5* | + | — | — | + | — | — |
| *ALD6* | + | — | — | + | — | — |

| | PLA | CA | FA |
|---|---|---|---|
| BFP | 0.0 ± 0.0 | 0.0 ± 0.0 | 0.0 ± 0.0 |
| $AbUGT^{WT}$ | 1.2 ± 3.6 | 64.6 ± 2.3 | 89.8 ± 1.2 |
| $AbUGT^{F130Y}$ | 2.5 ± 1.5 | 14.6 ± 3.7 | 88.6 ± 0.7 |
| $AbUGT^{L200F}$ | 0.3 ± 0.7 | 70.0 ± 2.2 | 89.7 ± 1.3 |
| $AbUGT^{I203Q}$ | 0.3 ± 2.5 | 19.7 ± 3.7 | 76.2 ± 0.9 |

FIG. 36

| Signal sequence | Terminus | Residues |
|---|---|---|
| Dap2p | N | 1-46 |
| Pep4p | N | 1-23 |
| Mns1p | N | 1-25 |
| Cit1p | N | 1-52 |
| Prc1p | N | 1-19 |
| Och1p | N | 1-35 |
| PTS1 | C | SKL |

FIG. 56
AtSCT
AtSMT
AbLS
AsSCPL1
TaCBP2
yPRC1

SEQUENCE LISTING

```
<160> NUMBER OF SEQ ID NOS: 35

<210> SEQ ID NO 1
<211> LENGTH: 328
<212> TYPE: PRT
<213> ORGANISM: Atropa belladonna

<400> SEQUENCE: 1

Met Leu Glu Thr Val Lys Tyr Leu Leu Gly Ser Ala Gly Pro Ser Gly
1               5                   10                  15

Tyr Gly Ser Lys Ser Thr Ala Glu Lys Val Thr Glu Gln Ser Ile His
            20                  25                  30

Leu Arg Ser Ile Thr Ala Ile Ile Thr Gly Ala Thr Ser Gly Ile Gly
        35                  40                  45

Ala Glu Thr Ala Arg Val Leu Ala Lys Arg Gly Ala Lys Leu Ile Leu
    50                  55                  60

Pro Ala Arg Ser Leu Lys Ala Ala Glu Glu Thr Lys Ser Arg Ile Leu
65                  70                  75                  80

Ser Glu Ser Pro Asp Ala Asp Ile Ile Val Met Ser Leu Asp Leu Ser
                85                  90                  95

Ser Leu Ser Ser Val Arg Lys Phe Val Ala Gln Phe Glu Tyr Leu Asn
            100                 105                 110

Phe Arg Leu Asn Ile Leu Ile Asn Asn Ala Gly Lys Phe Ala His Gln
        115                 120                 125

His Ala Ile Ser Glu Asp Gly Ile Glu Met Thr Phe Ala Thr Asn His
    130                 135                 140

Leu Gly His Phe Leu Leu Thr Lys Leu Leu Leu Lys Asn Met Ile Glu
145                 150                 155                 160

Thr Ala Asn Lys Thr Gly Val Gln Gly Arg Ile Val Asn Val Ser Ser
                165                 170                 175

Ser Ile His Gly Trp Phe Ser Gly Asp Ala Ile Gln Tyr Leu Arg Leu
            180                 185                 190

Ile Thr Lys Asp Lys Ser Gln Tyr Asp Ala Thr Arg Ala Tyr Ala Leu
        195                 200                 205

Ser Lys Leu Ala Asn Val Leu His Thr Lys Glu Leu Ala Gln Ile Leu
    210                 215                 220

Lys Lys Met Val Ala Asn Val Thr Val Asn Cys Val His Pro Gly Ile
225                 230                 235                 240

Val Arg Thr Arg Leu Thr Arg Glu Arg Glu Gly Leu Val Thr Asp Leu
                245                 250                 255

Val Phe Phe Leu Thr Ser Lys Leu Leu Lys Thr Ile Pro Gln Ala Ala
            260                 265                 270

Ala Thr Thr Cys Tyr Val Ala Thr His Pro Arg Leu Ala Asp Val Ser
        275                 280                 285

Gly Lys Tyr Phe Ala Asp Cys Asn Glu Ile Ser Ser Ser Lys Leu Gly
    290                 295                 300
```

```
Ser Asn Leu Thr Glu Ala Ala Arg Ile Trp Ser Ala Ser Glu Ile Met
305                 310                 315                 320

Val Ala Lys Asn Ser Asn Ala Asn
                325


<210> SEQ ID NO 2
<211> LENGTH: 360
<212> TYPE: PRT
<213> ORGANISM: Atropa belladonna

<400> SEQUENCE: 2

Met Ser Lys Thr Thr Pro Asn His Thr Gln Ala Val Ser Gly Trp Ala
1               5                   10                  15

Ala Leu Asp Ser Ser Gly Lys Ile Thr Pro Tyr Ile Phe Asn Arg Arg
            20                  25                  30

Glu Asn Gly Val Asn Asp Val Thr Ile Lys Ile Leu Tyr Cys Gly Ile
        35                  40                  45

Cys His Thr Asp Leu His Tyr Ala Lys Asn Asp Trp Gly Val Thr Ile
    50                  55                  60

Tyr Pro Val Val Pro Gly His Glu Ile Thr Gly Ile Val Val Glu Val
65                  70                  75                  80

Gly Ser Asn Val Thr Asn Phe Lys Thr Gly Asp Lys Val Gly Val Gly
                85                  90                  95

Cys Met Ser Ala Ser Cys Leu Gln Cys Glu Ser Cys Lys Asn Ser Glu
            100                 105                 110

Glu Asn Tyr Cys Asp Lys Val Gln Phe Thr Tyr Asn Gly Val Phe Trp
        115                 120                 125

Asp Gly Ser Ile Thr Tyr Gly Gly Tyr Ser Lys Met Leu Val Ala Asp
    130                 135                 140

Tyr Arg Phe Val Val Ala Val Pro Glu Asn Leu Pro Met Asp Arg Ala
145                 150                 155                 160

Ala Pro Leu Leu Cys Ala Gly Val Thr Val Phe Val Pro Met Lys Asp
                165                 170                 175

Asn Asn Leu Ile Gly Ser Pro Arg Lys Asn Ile Gly Val Ile Gly Leu
            180                 185                 190

Gly Gly Leu Gly His Leu Ala Ile Lys Phe Ala Lys Ala Phe Gly His
        195                 200                 205

Arg Val Thr Val Ile Ser Thr Ser Leu Ser Lys Glu Lys Asp Ala Lys
    210                 215                 220

Thr Lys Leu Gly Ala Asp Asp Phe Ile Val Ser Ser Asn Ala Gln Gln
225                 230                 235                 240

Met Gln Ser Arg Gln Lys Thr Leu Asp Phe Ile Leu Asp Thr Val Ser
                245                 250                 255

Ala Asp His Ser Leu Gly Pro Tyr Leu Glu Leu Leu Lys Ile Lys Gly
            260                 265                 270

Thr Phe Val Ile Val Gly Ala Pro Asp Lys Pro Met Gly Leu Pro Ala
        275                 280                 285

Phe Pro Leu Ile Phe Gly Lys Arg Thr Val Lys Gly Ser Met Ile Gly
    290                 295                 300

Ser Ile Lys Glu Thr Gln Glu Met Leu Asp Ile Cys Gly Lys Tyr Asn
305                 310                 315                 320

Ile Met Cys Asp Ile Glu Ile Val Thr Pro Asp Arg Ile Asn Glu Ala
                325                 330                 335

Tyr Glu Arg Ile Glu Lys Asn Asp Ile Lys Tyr Arg Phe Val Ile Asp
```

340 345 350

Ile Asp Gly Gln Ser Ser Lys Leu
355 360

<210> SEQ ID NO 3
<211> LENGTH: 346
<212> TYPE: PRT
<213> ORGANISM: Atropa belladonna

<400> SEQUENCE: 3

Met Ala Met Glu Gly Thr Lys Val Ala Arg Ile Lys Leu Gly Ser Asp
1 5 10 15

Gly Leu Glu Val Ser Ala Gln Gly Leu Gly Cys Met Gly Met Ser Ala
20 25 30

Phe Tyr Gly Pro Pro Lys Pro Glu Pro Asp Met Ile Gln Leu Ile His
35 40 45

His Ala Ile Asn Ser Gly Val Thr Phe Leu Asp Thr Ser Asp Ile Tyr
50 55 60

Gly Pro His Thr Asn Glu Ile Leu Leu Gly Lys Ala Leu Lys Gly Gly
65 70 75 80

Ile Arg Glu Arg Val Glu Leu Ala Thr Lys Phe Gly Ile Ser Phe Ala
85 90 95

Asp Gly Lys Arg Glu Val Arg Gly Asp Pro Ala Tyr Val Arg Ala Thr
100 105 110

Cys Val Ala Ser Leu Lys Arg Leu Asp Val Asp Cys Ile Asp Leu Tyr
115 120 125

Tyr Gln His Arg Ile Asp Thr Arg Val Pro Ile Glu Val Thr Val Gly
130 135 140

Glu Leu Lys Lys Leu Val Glu Glu Gly Lys Val Lys Tyr Ile Gly Leu
145 150 155 160

Ser Glu Ala Ser Ala Ser Thr Ile Arg Arg Ala His Ala Val His Pro
165 170 175

Ile Thr Ala Val Glu Leu Glu Trp Ser Leu Trp Ser Arg Asp Val Glu
180 185 190

Glu Glu Leu Val Pro Thr Cys Arg Glu Leu Gly Ile Gly Ile Val Ala
195 200 205

Tyr Ser Pro Leu Gly Arg Gly Phe Leu Ser Ser Gly Ser Lys Leu Leu
210 215 220

Glu Asp Met Ser Asn Glu Asp Tyr Arg Lys His Leu Pro Arg Phe Gln
225 230 235 240

Ser Glu Asn Leu Glu His Asn Lys Lys Leu Tyr Glu Arg Ile Cys Gln
245 250 255

Thr Ala Ala Arg Met Gly Cys Thr Pro Ser Gln Leu Ala Leu Ala Trp
260 265 270

Val His His Gln Gly Asn Asp Val Cys Pro Ile Pro Gly Thr Thr Lys
275 280 285

Ile Glu Asn Leu Asn Gln Asn Ile Glu Ala Leu Ser Ile Lys Leu Thr
290 295 300

Ser Glu Asp Met Thr Glu Leu Glu Ser Ile Ala Ser Ala Asn Ala Val
305 310 315 320

Gln Gly Asp Arg Tyr Gly Ser Gly Ala Ser Thr Tyr Lys Asp Ser Glu
325 330 335

Thr Pro Pro Leu Ser Ala Trp Lys Val Thr
340 345

<210> SEQ ID NO 4
<211> LENGTH: 346
<212> TYPE: PRT
<213> ORGANISM: Atropa belladonna

<400> SEQUENCE: 4

```
Met Glu Val Lys Asn Lys Tyr Val Ala Ile Lys Ser Asn Ile Asn Gly
1               5                   10                  15

Ala Pro Gln Glu Ser His Phe Glu Ile Lys Val Glu Asn Leu Ser Leu
            20                  25                  30

Ile Val Glu Pro Asp Ser Lys Glu Val Ile Ile Lys Asn Leu Phe Val
        35                  40                  45

Ser Ile Asp Pro Tyr Gln Leu Asn Arg Met Lys Ser Glu Ser Ser Ser
    50                  55                  60

Gln Ala Ala Ile Ser Tyr Ala Ser Ala Ile Thr Pro Gly Lys Ala Ile
65                  70                  75                  80

Asp Thr Tyr Gly Val Gly Arg Val Leu Val Ser Asp Arg Pro Glu Phe
                85                  90                  95

Lys Lys Asp Asp Leu Val Ala Gly Leu Leu Thr Trp Gly Glu Tyr Thr
            100                 105                 110

Val Val Lys Glu Gly Ser Leu Leu Asn Lys Leu Asp Pro Leu Gly Phe
        115                 120                 125

Pro Leu Ser Asn His Val Gly Val Leu Gly Phe Ser Gly Leu Ala Ala
    130                 135                 140

Tyr Gly Gly Phe Phe Glu Val Cys Lys Pro Lys Pro Gly Glu Lys Val
145                 150                 155                 160

Phe Val Ser Ala Ala Ser Gly Ser Val Gly Asn Leu Val Gly Gln Tyr
                165                 170                 175

Ala Lys Leu Leu Gly Cys His Val Val Gly Ser Ala Gly Ser Gln Glu
            180                 185                 190

Lys Val Lys Leu Leu Lys Glu Thr Leu Gly Phe Asp Asp Ala Phe Asn
        195                 200                 205

Tyr Lys Glu Glu Thr Asp Leu Lys Ser Ala Leu Lys Arg Cys Phe Pro
    210                 215                 220

Gln Gly Ile Asp Val Cys Phe Asp Asn Val Gly Gly Lys Met Leu Glu
225                 230                 235                 240

Ala Ala Val Ala Asn Met Asn Leu Phe Gly Arg Val Ala Ile Cys Gly
                245                 250                 255

Val Ile Ser Glu Tyr Thr Asn Ala Ser Thr Arg Ala Ala Pro Glu Met
            260                 265                 270

Leu Asp Ile Val Tyr Lys Arg Ile Thr Ile Gln Gly Phe Leu Ala Ala
        275                 280                 285

Asp Phe Met Lys Val Tyr Ala Asp Phe Leu Ser Glu Thr Val Glu Tyr
    290                 295                 300

Leu Gln Asp Gly Lys Leu Lys Ala Val Glu Asp Val Ser Glu Gly Val
305                 310                 315                 320

Glu Ser Ile Pro Ser Ala Phe Ile Gly Leu Phe Asn Gly Asp Asn Ile
                325                 330                 335

Gly Lys Lys Ile Val Lys Val Ala Asp Glu
            340                 345
```

<210> SEQ ID NO 5
<211> LENGTH: 296
<212> TYPE: PRT
<213> ORGANISM: Atropa belladonna

<400> SEQUENCE: 5

Met Leu Arg Ile Arg Ser Arg Ile Ile Ser Ile Ser Arg Ser Leu Ile
1               5                   10                  15

Leu Arg Gln Thr Ser Ser Asn Lys Phe Ser Thr His Ser Glu Arg Lys
            20                  25                  30

Leu Glu Gly Lys Val Ala Val Ile Thr Gly Ala Ala Ser Gly Ile Gly
        35                  40                  45

Lys Glu Thr Ala Ala Lys Phe Ile Ser His Gly Ala Lys Val Ile Ile
    50                  55                  60

Ala Asp Ile Gln Lys Gln Leu Gly Gln Glu Thr Ala Ser Glu Leu Gly
65                  70                  75                  80

Pro Asn Ala Thr Phe Val Ser Cys Asp Val Thr Lys Glu Ser Asp Ile
                85                  90                  95

Ser Asp Val Val Asp Phe Ala Val Ser Lys His Gly Gln Leu Asp Ile
            100                 105                 110

Met Tyr Asn Asn Ala Gly Ile Ala Cys Arg Thr Thr Phe Ser Ile Val
        115                 120                 125

Asp Leu Asp Leu Ala Gln Phe Asp Arg Ile Met Ala Ile Asn Val Arg
    130                 135                 140

Gly Val Val Ala Gly Ile Lys His Ala Ala Arg Val Met Ile Pro Gln
145                 150                 155                 160

Gly Ser Gly Cys Ile Leu Cys Thr Gly Ser Ile Thr Gly Val Met Gly
                165                 170                 175

Gly Leu Ala Gln Pro Thr Tyr Ser Thr Thr Lys Ser Cys Val Ile Gly
            180                 185                 190

Ile Val Lys Ser Thr Thr Gly Glu Leu Cys Lys His Gly Ile Arg Ile
        195                 200                 205

Asn Cys Ile Ser Pro Phe Ala Ile Pro Thr Ala Phe Ser Leu Asp Glu
    210                 215                 220

Met Lys Glu Tyr Phe Pro Gly Val Glu Pro Glu Gly Leu Val Lys Ile
225                 230                 235                 240

Leu Gln Asn Ala Ser Glu Leu Lys Gly Ala Tyr Cys Glu Pro Ile Asp
                245                 250                 255

Val Ala Asn Ala Ala Ile Phe Leu Ala Ser Glu Asp Ala Lys Phe Ile
            260                 265                 270

Ser Gly Glu Asn Leu Met Val Asp Gly Gly Phe Thr Ser Phe Lys Lys
        275                 280                 285

Leu Asn Leu Ser His Leu Val Gln
    290                 295

<210> SEQ ID NO 6
<211> LENGTH: 389
<212> TYPE: PRT
<213> ORGANISM: Atropa belladonna

<400> SEQUENCE: 6

Met Ala Ser Asn Gly Ile Ser His Val Asn Gly Thr Leu Ala Lys Val
1               5                   10                  15

Ile Thr Cys Arg Ala Ala Val Ala Tyr Gly Pro Gly Gln Pro Leu Val
            20                  25                  30

Val Glu Gln Val Gln Val Asp Pro Pro Gln Lys Met Glu Val Arg Ile
        35                  40                  45

Lys Ile Leu Phe Thr Ser Ile Cys His Thr Asp Leu Ser Ala Trp Lys
    50                  55                  60

```
Gly Glu Asn Glu Ala Gln Arg Val Tyr Pro Arg Ile Leu Gly His Glu
65                  70                  75                  80

Ala Ser Gly Val Val Glu Ser Val Gly Glu Gly Val Thr Asp Met Lys
                85                  90                  95

Thr Gly Asp His Val Val Pro Ile Phe Asn Gly Glu Cys Gly Glu Cys
            100                 105                 110

Val Tyr Cys Asn Ser Ser Lys Lys Thr Asn Leu Cys Gly Lys Phe Arg
        115                 120                 125

Val Asn Pro Phe Lys Ser Val Met Ala Asn Asp Gly Lys Cys Arg Phe
    130                 135                 140

Arg Asn Lys Asp Gly Asn Pro Ile Tyr His Phe Leu Asn Thr Ser Thr
145                 150                 155                 160

Phe Ser Glu Tyr Thr Val Val Asp Ser Ala Cys Leu Val Asn Ile Asp
                165                 170                 175

Pro His Ala Pro Leu Asp Lys Met Thr Leu Leu Ser Cys Gly Val Ser
            180                 185                 190

Thr Gly Leu Gly Ala Ala Trp Asn Thr Ala Asp Val Gln Thr Gly Glu
        195                 200                 205

Thr Val Ala Val Phe Gly Leu Gly Ala Val Gly Leu Ala Val Val Glu
    210                 215                 220

Gly Ala Arg Thr Arg Gly Ala Ser Arg Ile Ile Gly Val Asp Ile Asn
225                 230                 235                 240

Ser Glu Lys Arg Ile Lys Gly Gln Ala Ile Gly Ile Thr Asp Phe Ile
                245                 250                 255

Asn Pro Lys Glu Ile Asp Val Pro Val His Glu Lys Ile Arg Glu Met
            260                 265                 270

Thr Gly Gly Gly Val His Tyr Ser Phe Glu Cys Ala Gly Asn Leu Glu
        275                 280                 285

Val Leu Arg Glu Ala Phe Ser Ser Thr His Asp Gly Trp Gly Met Thr
    290                 295                 300

Ile Val Leu Gly Ile His Pro Thr Pro Arg Leu Leu Pro Leu His Pro
305                 310                 315                 320

Met Glu Leu Phe Asp Gly Arg Arg Ile Val Ala Ser Val Phe Gly Asp
                325                 330                 335

Phe Lys Gly Lys Ser Gln Leu Pro Phe Phe Ala Lys Gln Cys Met Ala
            340                 345                 350

Gly Val Val Lys Leu Asp Glu Phe Ile Thr His Glu Leu Pro Phe Glu
        355                 360                 365

Lys Ile Asn Glu Gly Phe Gln Leu Leu Val Asp Gly Lys Ser Leu Arg
    370                 375                 380

Cys Leu Leu His Leu
385
```

<210> SEQ ID NO 7
<211> LENGTH: 315
<212> TYPE: PRT
<213> ORGANISM: Atropa belladonna

<400> SEQUENCE: 7

```
Met Ala Glu Lys Ile Thr Ser Leu Glu Ser Thr Arg Tyr Ala Val Val
1               5                   10                  15

Thr Gly Gly Asn Lys Gly Ile Gly Tyr Glu Thr Cys Arg Gln Leu Val
            20                  25                  30

Ser Lys Gly Val Val Val Val Leu Thr Ala Arg Asp Glu Lys Arg Gly
```

```
        35                  40                  45

Ile Glu Ala Thr Glu Arg Leu Lys Glu Glu Ser Ser Phe Thr Asp Asp
    50                  55                  60

Gln Ile Met Phe His Gln Leu Asp Val Val Asp Pro Asp Ser Ile Ser
65                  70                  75                  80

Ser Leu Val Asp Phe Ile Asn Thr Lys Phe Gly Arg Leu Asp Ile Leu
                85                  90                  95

Val Asn Asn Ala Gly Val Gly Gly Leu Met Val Glu Gly Asp Val Val
            100                 105                 110

Ile Leu Lys Asp Leu Ile Glu Gly Asp Phe Val Ser Val Ser Thr Glu
        115                 120                 125

Asn Glu Glu Glu Gly Asp Thr Glu Lys Ser Ile Glu Gly Ile Val Thr
    130                 135                 140

Asn Tyr Glu Leu Thr Lys Gln Cys Val Glu Thr Asn Phe Tyr Gly Ala
145                 150                 155                 160

Lys Arg Met Ser Glu Ala Phe Ile Pro Leu Leu Gln Leu Ser Asn Ser
                165                 170                 175

Pro Thr Ile Val Asn Val Ala Ser Phe Leu Gly Lys Leu Lys Leu Leu
            180                 185                 190

Cys Asn Glu Trp Ala Ile Lys Val Leu Ser Asn Ala Asn Asn Leu Thr
        195                 200                 205

Glu Asp Arg Val Asp Glu Val Val Asn Glu Phe Leu Lys Asp Phe Thr
    210                 215                 220

Glu Lys Ser Ile Glu Ala Lys Gly Trp Pro Thr Tyr Phe Ala Ala Tyr
225                 230                 235                 240

Lys Val Ser Lys Ala Ala Met Ile Ala Tyr Thr Arg Val Leu Ala Thr
                245                 250                 255

Lys Tyr Pro Asn Phe Arg Ile Asn Ser Val Cys Pro Gly Tyr Cys Lys
            260                 265                 270

Thr Asp Leu Thr Ala Asn Thr Gly Ser Leu Thr Ala Glu Glu Gly Ala
        275                 280                 285

Glu Ser Leu Val Lys Leu Ala Leu Leu Pro Asn Asp Gly Pro Ser Gly
    290                 295                 300

Leu Phe Phe Tyr Arg Lys Asp Val Ala Ala Leu
305                 310                 315


<210> SEQ ID NO 8
<211> LENGTH: 276
<212> TYPE: PRT
<213> ORGANISM: Atropa belladonna

<400> SEQUENCE: 8

Met Ala Ser Val Ser Phe Leu Ser Thr Ile Gly Lys Arg Leu Glu Gly
1               5                   10                  15

Lys Val Ala Met Val Thr Gly Gly Ala Ser Gly Ile Gly Glu Ala Ile
            20                  25                  30

Ala Lys Leu Phe Tyr Glu His Gly Ala Lys Val Ala Ile Ala Asp Val
        35                  40                  45

Gln Asp Glu Leu Gly Asn Ser Val Ser Asn Ala Leu Gly Gly Ser Ser
    50                  55                  60

Asn Ser Ile Tyr Ile His Cys Asp Val Thr Asn Glu Asp Asp Val Gln
65                  70                  75                  80

Glu Ala Val Asp Lys Thr Ile Ser Thr Phe Gly Lys Leu Asp Ile Met
                85                  90                  95
```

-continued

```
Ile Cys Asn Ala Gly Ile Ser Asp Glu Thr Lys Pro Arg Ile Ile Asp
            100                 105                 110

Asn Thr Lys Ala Asp Phe Glu Arg Val Leu Ser Ile Asn Val Thr Gly
        115                 120                 125

Val Phe Leu Thr Met Lys His Ala Ala Arg Val Met Val Pro Ala Arg
    130                 135                 140

Ile Gly Cys Ile Ile Ser Thr Ser Ser Val Ser Ser Arg Val Gly Ala
145                 150                 155                 160

Ala Ala Ser His Ala Tyr Cys Ser Ser Lys His Ala Val Leu Gly Leu
                165                 170                 175

Thr Lys Asn Leu Ala Val Glu Leu Gly Gln Phe Gly Ile Arg Val Asn
            180                 185                 190

Cys Leu Ser Pro Tyr Ala Met Val Thr Pro Leu Ala Glu Lys Val Ile
        195                 200                 205

Gly Leu Glu Asn Glu Glu Leu Glu Lys Ala Leu Asp Met Val Gly Asn
    210                 215                 220

Leu Lys Gly Val Thr Leu Arg Val Asp Asp Val Ala Lys Ala Ala Leu
225                 230                 235                 240

Phe Leu Ala Ser Asp Asp Ser Lys Tyr Ile Ser Gly His Asn Leu Phe
                245                 250                 255

Ile Asp Gly Gly Phe Thr Val Tyr Asn Pro Gly Leu Gly Met Phe Lys
            260                 265                 270

Tyr Pro Glu Ser
        275


<210> SEQ ID NO 9
<211> LENGTH: 297
<212> TYPE: PRT
<213> ORGANISM: Atropa belladonna

<400> SEQUENCE: 9

Met Leu Arg Ile Ala Ser Arg Gly Gly Ile Thr Ser Arg Ser Leu Gln
1               5                   10                  15

Leu Leu Gln Thr Phe Asn Lys Glu Phe Ser Thr His Ile Glu Arg Lys
            20                  25                  30

Leu Glu Gly Lys Val Ala Leu Ile Thr Gly Ala Ala Ser Gly Ile Gly
        35                  40                  45

Lys Glu Thr Ala Ala Lys Phe Ile Asn Asn Gly Ala Lys Val Ile Ile
    50                  55                  60

Ala Asp Val Gln Lys Gln Leu Gly Gln Glu Thr Ala Ser Gln Leu Gly
65                  70                  75                  80

Pro Asn Ala Thr Phe Val Leu Cys Asp Val Thr Lys Glu Ser Asp Val
                85                  90                  95

Ser Asn Ala Val Asp Phe Ala Val Ser Asn His Gly Gln Leu Asp Ile
            100                 105                 110

Met Tyr Asn Asn Ala Gly Ile Ile Cys Arg Thr Pro Arg Asn Ile Ala
        115                 120                 125

Asp Leu Asp Leu Asp Ala Phe Asp Arg Val Met Ala Ile Asn Val Arg
    130                 135                 140

Gly Met Met Ala Gly Ile Lys His Ala Ala Arg Val Met Ile Pro Arg
145                 150                 155                 160

Lys Ala Gly Ser Ile Leu Cys Thr Ala Ser Ile Thr Gly Thr Met Gly
                165                 170                 175

Gly Leu Ala Gln Pro Thr Tyr Ser Thr Thr Lys Ser Cys Val Ile Gly
            180                 185                 190
```

-continued

```
Met Met Arg Ser Val Thr Ala Glu Leu Cys Gln Asn Gly Ile Arg Ile
        195                 200                 205

Asn Cys Ile Ser Pro Phe Ala Ile Pro Thr Pro Phe Tyr Ile Asp Glu
    210                 215                 220

Met Lys Ser Tyr Tyr Pro Gly Val Glu Pro Glu Val Leu Val Lys Met
225                 230                 235                 240

Leu Tyr Arg Ala Ser Glu Leu Asn Gly Ala Tyr Cys Glu Pro Val Asp
                245                 250                 255

Val Ala Asn Ala Ala Val Phe Leu Ala Ser Asp Asp Ala Lys Tyr Val
            260                 265                 270

Ser Gly Gln Asn Leu Val Ile Asp Gly Gly Phe Thr Ser Tyr Lys Ser
        275                 280                 285

Leu Asn Phe Pro Met Ser Asp Gln Glu
    290                 295
```

<210> SEQ ID NO 10
<211> LENGTH: 279
<212> TYPE: PRT
<213> ORGANISM: Atropa belladonna

<400> SEQUENCE: 10

```
Met Gly Ile Pro Ser Ser Val Thr Pro Ile Val Arg Arg Leu Glu Gly
1               5                   10                  15

Lys Val Ala Val Ile Thr Gly Gly Ala Ser Gly Ile Gly Glu Ala Ala
            20                  25                  30

Thr Arg Leu Phe Val Lys His Gly Ala Lys Val Val Val Ala Asp Val
        35                  40                  45

Arg Asp Asp Leu Gly Arg Ala Leu Cys Lys Glu Leu Gly Ser Asn Asp
    50                  55                  60

Thr Ile Ser Phe Ala His Cys Ser Val Thr Asp Glu Asn Asp Val Gln
65                  70                  75                  80

Asn Ala Ile Asp Gly Ala Val Ser Arg Tyr Gly Met Leu Asp Ile Met
                85                  90                  95

Phe Asn Asn Ala Gly Ile Thr Gly Asn Met Lys Asp Pro Ser Ile Leu
            100                 105                 110

Ala Thr Asp Tyr Lys Asn Phe Lys Asn Val Phe Asp Val Asn Val Tyr
        115                 120                 125

Gly Ala Phe Leu Gly Ala Arg Ile Ala Ala Lys Ala Met Ile Pro Thr
    130                 135                 140

Lys Gln Gly Ser Ile Leu Phe Thr Ala Ser Ile Ala Ser Val Ile Gly
145                 150                 155                 160

Gly Ile Ala Ser Pro Ile Thr Tyr Ala Ser Ser Lys His Ala Val Val
                165                 170                 175

Gly Leu Thr Asn His Leu Ala Val Glu Leu Gly Gln Tyr Gly Ile Arg
            180                 185                 190

Val Asn Cys Ile Ser Pro Tyr Thr Val Ala Thr Pro Leu Val Arg Glu
        195                 200                 205

Ile Leu Gly Lys Met Asp Lys Glu Lys Ala Glu Glu Val Ile Met Glu
    210                 215                 220

Thr Ala Asn Leu Lys Gly Lys Ile Leu Glu Pro Glu Asp Ile Ala Glu
225                 230                 235                 240

Ala Ala Val Tyr Leu Gly Ser Asp Glu Ser Lys Tyr Val Ser Gly Ile
                245                 250                 255

Asn Leu Val Ile Asp Gly Gly Tyr Ser Lys Thr Asn Pro Leu Ala Ser
```

```
            260                 265                 270

Met Val Met Gln Asn Tyr Ile
        275


<210> SEQ ID NO 11
<211> LENGTH: 327
<212> TYPE: PRT
<213> ORGANISM: Atropa belladonna

<400> SEQUENCE: 11

Met Glu Ser Lys Ser Gly Glu Gly Lys Ile Val Cys Val Thr Gly Ala
1               5                   10                  15

Ser Gly Phe Ile Ala Ser Trp Leu Val Lys Leu Leu Leu His Arg Gly
            20                  25                  30

Tyr Thr Val Asn Ala Thr Val Arg Asn Leu Lys Asp Thr Ser Lys Val
        35                  40                  45

Ala His Leu Leu Gly Leu Asp Gly Ala Asn Glu Arg Leu His Leu Phe
    50                  55                  60

Lys Ala Glu Leu Leu Glu Glu Gln Ser Phe Asp Ala Ala Val Asp Gly
65                  70                  75                  80

Cys Glu Gly Val Phe His Thr Ala Ser Pro Val Ser Leu Thr Ala Lys
                85                  90                  95

Ser Lys Glu Glu Leu Val Asp Pro Ala Val Lys Gly Thr Leu Asn Val
            100                 105                 110

Leu Arg Ser Cys Ala Lys Ser Pro Ser Val Leu Arg Val Val Ile Thr
        115                 120                 125

Ser Ser Thr Ala Ser Val Ile Cys Asn Lys Asn Met Ser Thr Pro Gly
    130                 135                 140

Ala Val Ala Asp Glu Thr Trp Tyr Ser Asp Pro Glu Phe Cys Glu Glu
145                 150                 155                 160

Arg Glu Glu Trp Tyr Gln Leu Ser Lys Thr Leu Ala Glu Gln Ala Ala
                165                 170                 175

Trp Lys Phe Ala Lys Glu Asn Glu Met Asp Leu Val Thr Leu His Pro
            180                 185                 190

Gly Leu Val Ile Gly Pro Leu Leu Gln Pro Thr Leu Asn Phe Ser Cys
        195                 200                 205

Glu Ala Ile Val Asn Phe Ile Lys Glu Gly Lys Glu Ala Trp Ser Gly
    210                 215                 220

Gly Val Tyr Arg Phe Val Asp Val Arg Asp Val Ala Asn Ala His Ile
225                 230                 235                 240

Leu Ala Phe Glu Val Pro Ser Ala Asn Gly Arg Tyr Cys Leu Val Gly
                245                 250                 255

Val Asn Gly Tyr Ser Ser Leu Val Leu Lys Ile Val Gln Lys Leu Tyr
            260                 265                 270

Pro Ser Ile Thr Leu Pro Glu Asn Phe Glu Asp Gly Leu Pro Leu Thr
        275                 280                 285

Pro His Phe Gln Val Ser Ser Glu Arg Ala Lys Gly Leu Gly Val Lys
    290                 295                 300

Phe Thr Pro Leu Glu Leu Ser Val Lys Asp Thr Val Glu Ser Leu Met
305                 310                 315                 320

Glu Lys Asn Phe Leu His Ile
                325


<210> SEQ ID NO 12
<211> LENGTH: 327
```

<212> TYPE: PRT
<213> ORGANISM: Atropa belladonna

<400> SEQUENCE: 12

```
Met Glu Ser Lys Ser Gly Glu Gly Lys Ile Val Cys Val Thr Gly Ala
1               5                   10                  15

Ser Gly Phe Ile Ala Ser Trp Leu Val Lys Leu Leu Leu His Arg Gly
            20                  25                  30

Tyr Thr Val Asn Ala Thr Val Arg Asn Leu Lys Asp Thr Ser Lys Val
        35                  40                  45

Ala His Leu Leu Gly Leu Asp Gly Ala Asn Glu Arg Leu His Leu Phe
    50                  55                  60

Lys Ala Glu Leu Leu Glu Glu Gln Ser Phe Asp Ala Ala Val Asp Gly
65                  70                  75                  80

Cys Glu Gly Val Phe His Thr Ala Ser Pro Val Ser Leu Thr Ala Lys
                85                  90                  95

Ser Lys Glu Glu Leu Val Asp Pro Ala Val Lys Gly Thr Leu Asn Val
            100                 105                 110

Leu Arg Ser Cys Ala Lys Ser Pro Ser Val Leu Arg Val Val Ile Thr
        115                 120                 125

Ser Ser Thr Ala Ser Val Ile Cys Asn Lys Asn Met Ser Thr Pro Gly
    130                 135                 140

Ala Val Ala Asp Glu Thr Trp Tyr Ser Asp Pro Glu Phe Cys Glu Glu
145                 150                 155                 160

Arg Lys Glu Trp Tyr Gln Leu Ser Lys Thr Leu Ala Glu Lys Ala Ala
                165                 170                 175

Arg Arg Phe Ala Lys Glu Asn Gly Ile Asp Leu Val Thr Leu His Pro
            180                 185                 190

Gly Leu Val Ile Gly Pro Leu Leu Gln Pro Thr Leu Asn Phe Ser Cys
        195                 200                 205

Glu Ala Ile Val Asn Phe Ile Lys Glu Gly Lys Glu Ala Trp Ser Gly
    210                 215                 220

Gly Val Tyr Arg Phe Val Asp Val Arg Asp Val Ala Asn Ala His Ile
225                 230                 235                 240

Leu Ala Phe Glu Val Pro Ser Ala Asn Gly Arg Tyr Cys Leu Val Gly
                245                 250                 255

Val Asn Gly Tyr Ser Ser Leu Val Leu Lys Ile Val Gln Lys Leu Tyr
            260                 265                 270

Pro Ser Ile Thr Leu Pro Glu Asn Phe Glu Asp Gly Leu Pro Leu Thr
        275                 280                 285

Pro His Phe Gln Val Ser Ser Glu Arg Ala Lys Gly Leu Gly Val Lys
    290                 295                 300

Phe Thr Pro Leu Glu Leu Ser Val Lys Asp Thr Val Glu Ser Leu Met
305                 310                 315                 320

Glu Lys Asn Phe Leu His Ile
                325
```

<210> SEQ ID NO 13
<211> LENGTH: 365
<212> TYPE: PRT
<213> ORGANISM: Atropa belladonna

<400> SEQUENCE: 13

```
Met Ala Ser Glu Lys Ser Leu Glu Glu Lys Gln Ala Glu Asn Thr Phe
1               5                   10                  15
```

-continued

```
Gly Trp Ala Ala Met Asp Ser Ser Gly Val Leu Ser Pro Phe Thr Phe
            20                  25                  30

Ser Arg Arg Ala Thr Gly Glu Glu Asp Val Arg Leu Lys Val Leu Tyr
        35                  40                  45

Cys Gly Ile Cys His Ser Asp Leu Gly Cys Ile Lys Asn Glu Trp Gly
    50                  55                  60

Trp Cys Ser Tyr Pro Leu Val Pro Gly His Glu Ile Val Gly Ile Ala
65                  70                  75                  80

Thr Glu Val Gly Ser Lys Val Thr Lys Phe Lys Val Gly Asp Arg Val
                85                  90                  95

Gly Val Gly Cys Met Val Gly Ser Cys Gly Thr Cys Gln Asn Cys Thr
            100                 105                 110

Gln Asn Gln Glu Ser Tyr Cys Pro Glu Val Ile Met Thr Cys Ala Ser
        115                 120                 125

Ala Tyr Pro Asp Gly Thr Pro Thr Tyr Gly Gly Phe Ser Asn Gln Met
    130                 135                 140

Val Ala Asn Glu Lys Phe Val Ile Arg Ile Pro Asn Ser Leu Pro Leu
145                 150                 155                 160

Asp Ala Ala Ala Pro Leu Leu Cys Ala Gly Ser Thr Val Tyr Ser Ala
                165                 170                 175

Met Lys Phe Tyr Gly Leu Cys Ser Gln Gly Leu His Leu Gly Val Val
            180                 185                 190

Gly Leu Gly Gly Leu Gly His Val Ala Val Lys Phe Ala Lys Ala Phe
        195                 200                 205

Gly Met Lys Val Thr Val Ile Ser Thr Ser Leu Gly Lys Lys Glu Glu
    210                 215                 220

Ala Ile Asn Gln Leu Gly Ala Asp Ser Phe Leu Ile Asn Thr Asp Thr
225                 230                 235                 240

Glu Gln Met Gln Gly Ala Met Glu Val Met Asp Gly Ile Ile Asp Thr
                245                 250                 255

Val Ser Ala Leu His Pro Ile Glu Pro Leu Leu Gly Leu Leu Lys Ser
            260                 265                 270

His Gln Gly Lys Leu Ile Ile Val Gly Leu Pro Asn Lys Gln Pro Glu
        275                 280                 285

Leu Pro Val Phe Ser Leu Ile Asn Gly Arg Lys Met Ile Gly Gly Ser
    290                 295                 300

Ala Val Gly Gly Val Lys Glu Thr Gln Glu Met Ile Asp Phe Ala Ala
305                 310                 315                 320

Glu His Asn Ile Thr Ala Asp Ile Glu Ile Val Pro Met Asp Tyr Val
                325                 330                 335

Asn Thr Ala Met Glu Arg Leu Glu Lys Gly Asp Val Lys Phe Arg Phe
            340                 345                 350

Val Ile Asp Val Glu Asn Thr Leu Val Ala Ala Gln Thr
        355                 360                 365
```

<210> SEQ ID NO 14
<211> LENGTH: 364
<212> TYPE: PRT
<213> ORGANISM: Datura innoxia

<400> SEQUENCE: 14

```
Met Ala Ala Glu Lys Leu Ser Glu Glu Glu Ala Val Lys Thr Phe Gly
1               5                   10                  15

Trp Ala Ala Met Asp Ser Ser Gly Val Leu Ser Pro Phe Glu Phe Ser
            20                  25                  30
```

```
Arg Arg Ala Thr Gly Ala Glu Asp Val Arg Leu Lys Val Leu Tyr Cys
        35                  40                  45

Gly Ile Cys His Ser Asp Leu Gly Cys Val Lys Asn Glu Trp Gly Trp
    50                  55                  60

Cys Ser Tyr Pro Leu Val Pro Gly His Glu Ile Val Gly Ile Ala Thr
65                  70                  75                  80

Glu Val Gly Ser Arg Val Thr Lys Phe Lys Val Gly Asp Arg Val Gly
                85                  90                  95

Val Gly Cys Met Val Gly Ser Cys Gly Ser Cys Gln Asn Cys Ser Gln
            100                 105                 110

Asn Leu Glu Ser Tyr Cys Pro Glu Val Ile Met Thr Cys Ala Ser Ala
        115                 120                 125

Tyr Pro Asp Gly Thr Pro Thr Tyr Gly Gly Phe Ser Asn Gln Met Val
    130                 135                 140

Ala Asn Glu Lys Phe Val Ile Gln Ile Pro Glu Lys Leu Pro Leu Asp
145                 150                 155                 160

Ala Ala Ala Pro Leu Leu Cys Ala Gly Ser Thr Val Tyr Ser Pro Met
                165                 170                 175

Lys Phe Tyr Gly Leu Cys Ser Pro Gly Leu His Leu Gly Val Val Gly
            180                 185                 190

Leu Gly Gly Leu Gly His Val Ala Val Lys Phe Ala Lys Ala Phe Gly
        195                 200                 205

Met Lys Val Thr Val Ile Ser Thr Ser Ile Gly Lys Lys Glu Glu Ala
    210                 215                 220

Ile Asn Gln Leu Gly Ala Asp Ser Phe Leu Thr Ser Thr Asp Thr Glu
225                 230                 235                 240

Gln Met Gln Gly Ala Met Glu Thr Met Asp Gly Ile Ile Asp Thr Val
                245                 250                 255

Ser Ala Leu His Pro Ile Glu Pro Leu Val Gly Leu Leu Lys Ser His
            260                 265                 270

Gln Gly Lys Leu Ile Ile Val Gly Leu Pro Asn Lys Gln Pro Glu Leu
        275                 280                 285

Pro Val Phe Ser Leu Ile Asn Gly Arg Lys Met Ile Gly Gly Ser Ala
    290                 295                 300

Val Gly Gly Val Lys Glu Thr Gln Glu Met Ile Asp Phe Ala Ala Lys
305                 310                 315                 320

His Asn Ile Thr Ala Asp Ile Glu Ile Val Arg Met Asp Tyr Val Asn
                325                 330                 335

Thr Ala Met Glu Arg Leu Glu Lys Gly Asp Val Lys Phe Arg Phe Val
            340                 345                 350

Ile Asp Val Glu Asn Thr Leu Val Pro Ala Gln Thr
        355                 360


<210> SEQ ID NO 15
<211> LENGTH: 364
<212> TYPE: PRT
<213> ORGANISM: Datura stramonium

<400> SEQUENCE: 15

Met Ala Ala Glu Lys Leu Glu Glu Arg Lys Arg Trp Glu Thr Phe Gly
1               5                   10                  15

Trp Ala Ala Met Asp Ser Ser Gly Val Leu Ser Pro Phe Glu Phe Ser
            20                  25                  30

Arg Arg Ala Thr Gly Glu Glu Asp Val Arg Leu Lys Val Leu Tyr Cys
```

```
        35                  40                  45

Gly Ile Cys His Ser Asp Leu Gly Cys Ile Lys Asn Glu Trp Gly Trp
    50                  55                  60

Cys Ser Tyr Pro Leu Val Pro Gly His Glu Ile Val Gly Ile Ala Thr
65                  70                  75                  80

Glu Val Gly Ser Arg Val Thr Lys Phe Lys Val Gly Asp Arg Val Gly
                85                  90                  95

Val Gly Cys Met Val Gly Ser Cys Gly Ser Cys Gln Asn Cys Ser Gln
            100                 105                 110

Asn Leu Glu Ser Tyr Cys Pro Glu Val Ile Met Thr Cys Ala Ser Ala
        115                 120                 125

Tyr Pro Asp Gly Thr Pro Thr Tyr Gly Gly Phe Ser Asn Gln Met Val
    130                 135                 140

Ala Asn Glu Lys Phe Val Ile Gln Ile Pro Glu Lys Leu Pro Leu Asp
145                 150                 155                 160

Ala Ala Ala Pro Leu Leu Cys Ala Gly Ser Thr Val Tyr Ser Pro Met
                165                 170                 175

Lys Phe Tyr Gly Leu Cys Ser Pro Gly Leu His Leu Gly Val Val Gly
            180                 185                 190

Leu Gly Gly Leu Gly His Val Ala Val Lys Phe Ala Lys Ala Phe Gly
        195                 200                 205

Met Lys Val Thr Val Ile Ser Thr Ser Ile Gly Lys Lys Glu Glu Ala
    210                 215                 220

Ile Asn Gln Leu Gly Ala Asp Ser Phe Leu Ile Ser Thr Asp Thr Glu
225                 230                 235                 240

Gln Met Gln Gly Ala Met Glu Thr Met Asp Gly Ile Ile Asp Thr Val
                245                 250                 255

Ser Ala Leu His Pro Ile Glu Pro Leu Val Gly Leu Leu Lys Ser His
            260                 265                 270

Arg Gly Lys Leu Ile Ile Val Gly Leu Pro Asn Lys Gln Pro Glu Leu
        275                 280                 285

Pro Val Phe Ser Leu Ile Asn Gly Arg Lys Met Ile Gly Gly Ser Ala
    290                 295                 300

Val Gly Gly Val Lys Glu Thr Gln Glu Met Ile Asp Phe Ala Ala Lys
305                 310                 315                 320

His Asn Ile Thr Ala Asp Ile Glu Ile Val Gly Met Asp Tyr Val Asn
                325                 330                 335

Thr Ala Met Glu Arg Leu Glu Lys Gly Asp Val Lys Phe Arg Phe Val
            340                 345                 350

Ile Asp Val Glu Asn Thr Leu Val Pro Ala Gln Thr
        355                 360


<210> SEQ ID NO 16
<211> LENGTH: 238
<212> TYPE: PRT
<213> ORGANISM: Aequorea Victoria

<400> SEQUENCE: 16

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

-continued

```
Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Ile His Gly Met Asp Glu Leu Tyr Lys
225                 230                 235


<210> SEQ ID NO 17
<211> LENGTH: 233
<212> TYPE: PRT
<213> ORGANISM: artificial sequence
<220> FEATURE:
<223> OTHER INFORMATION: Synthetic sequence

<400> SEQUENCE: 17

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175
```

```
Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230


<210> SEQ ID NO 18
<211> LENGTH: 238
<212> TYPE: PRT
<213> ORGANISM: artificial sequence
<220> FEATURE:
<223> OTHER INFORMATION: Synthetic sequence

<400> SEQUENCE: 18

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 19
<211> LENGTH: 98
<212> TYPE: PRT
<213> ORGANISM: artificial sequence
<220> FEATURE:
<223> OTHER INFORMATION: Synthetic sequence

<400> SEQUENCE: 19

Met Ser Asp Ser Glu Val Asn Gln Glu Ala Lys Pro Glu Val Lys Pro
1               5                   10                  15
```

Glu Val Lys Pro Glu Thr His Ile Asn Leu Lys Val Ser Asp Gly Ser
20 25 30

Ser Glu Ile Phe Phe Lys Ile Lys Lys Thr Thr Pro Leu Arg Arg Leu
35 40 45

Met Glu Ala Phe Ala Lys Arg Gln Gly Lys Glu Met Asp Ser Leu Thr
50 55 60

Phe Leu Tyr Asp Gly Ile Glu Ile Gln Ala Asp Gln Thr Pro Glu Asp
65 70 75 80

Leu Asp Met Glu Asp Asn Asp Ile Ile Glu Ala His Arg Glu Gln Ile
85 90 95

Gly Gly

<210> SEQ ID NO 20
<211> LENGTH: 236
<212> TYPE: PRT
<213> ORGANISM: artificial sequence
<220> FEATURE:
<223> OTHER INFORMATION: Synthetic sequence

<400> SEQUENCE: 20

Met Val Ser Lys Gly Glu Glu Asp Asn Met Ala Ile Ile Lys Glu Phe
1 5 10 15

Met Arg Phe Lys Val His Met Glu Gly Ser Val Asn Gly His Glu Phe
20 25 30

Glu Ile Glu Gly Glu Gly Glu Gly Arg Pro Tyr Glu Gly Thr Gln Thr
35 40 45

Ala Lys Leu Lys Val Thr Lys Gly Gly Pro Leu Pro Phe Ala Trp Asp
50 55 60

Ile Leu Ser Pro Gln Phe Met Tyr Gly Ser Lys Ala Tyr Val Lys His
65 70 75 80

Pro Ala Asp Ile Pro Asp Tyr Leu Lys Leu Ser Phe Pro Glu Gly Phe
85 90 95

Lys Trp Glu Arg Val Met Asn Phe Glu Asp Gly Gly Val Val Thr Val
100 105 110

Thr Gln Asp Ser Ser Leu Gln Asp Gly Glu Phe Ile Tyr Lys Val Lys
115 120 125

Leu Arg Gly Thr Asn Phe Pro Ser Asp Gly Pro Val Met Gln Lys Lys
130 135 140

Thr Met Gly Trp Glu Ala Ser Ser Glu Arg Met Tyr Pro Glu Asp Gly
145 150 155 160

Ala Leu Lys Gly Glu Ile Lys Gln Arg Leu Lys Leu Lys Asp Gly Gly
165 170 175

His Tyr Asp Ala Glu Val Lys Thr Thr Tyr Lys Ala Lys Lys Pro Val
180 185 190

Gln Leu Pro Gly Ala Tyr Asn Val Asn Ile Lys Leu Asp Ile Thr Ser
195 200 205

His Asn Glu Asp Tyr Thr Ile Val Glu Gln Tyr Glu Arg Ala Glu Gly
210 215 220

Arg His Ser Thr Gly Gly Met Asp Glu Leu Tyr Lys
225 230 235

<210> SEQ ID NO 21
<211> LENGTH: 490
<212> TYPE: PRT
<213> ORGANISM: Atropa belladonna -continued

<400> SEQUENCE: 21

```
Met Gly Ser Gln Gly Thr Asn Ile Asp Ser Ile Ile His Val Phe Leu
1               5                   10                  15

Ile Ser Phe Pro Gly Gln Gly His Val Asn Pro Leu Leu Arg Leu Gly
            20                  25                  30

Lys Arg Leu Ala Ser Lys Gly Val Leu Val Ser Phe Cys Ala Pro Glu
        35                  40                  45

Cys Val Gly Lys Asp Met Arg Ala Ala Asn Asn Asn Ile Ile Ser Asp
    50                  55                  60

Glu Pro Thr Pro Tyr Gly Asp Gly Phe Ile Arg Phe Glu Phe Phe Asp
65                  70                  75                  80

Gly Trp Glu Tyr Thr Gln Pro Lys Glu Asn Arg Gln Leu Glu Ile Glu
                85                  90                  95

Leu Ala Asn Leu Glu Val Val Gly Arg Ala Val Leu Pro Ala Met Leu
            100                 105                 110

Lys Glu Asn Glu Ala Lys Gly Arg Pro Val Ser Cys Leu Ile Asn Asn
        115                 120                 125

Pro Phe Ile Pro Trp Val Cys Asp Val Ala Asp Ser Leu Gly Ile Pro
    130                 135                 140

Cys Ala Val Leu Trp Val Gln Ser Cys Ala Ser Phe Ser Ala Tyr Tyr
145                 150                 155                 160

His Tyr His Phe Asn Leu Ala Pro Phe Pro Asn Glu Ser Asn Pro Asn
                165                 170                 175

Ile Asp Val His Leu Pro Asn Met Pro Ile Leu Lys Trp Asp Glu Leu
            180                 185                 190

Pro Ser Phe Leu Leu Pro Ser Asn Pro Tyr Pro Ala Leu Ala Asn Ala
        195                 200                 205

Ile Leu Arg Gln Phe Asn Tyr Leu Ser Lys Pro Ile Arg Ile Phe Ile
    210                 215                 220

Glu Ser Phe Asp Glu Leu Glu Lys Asp Ile Val Asp Tyr Met Ser Asp
225                 230                 235                 240

Phe Leu Pro Ile Lys Thr Val Gly Pro Leu Leu Val Glu Asp Pro Lys
                245                 250                 255

Ile Glu Gln Val Val Arg Ala Asp Leu Val Lys Ala Asp Ser Ser Ile
            260                 265                 270

Thr Gln Trp Leu Asn Ser Lys Pro Pro Ser Ser Val Val Tyr Ile Ser
        275                 280                 285

Phe Gly Ser Ile Val Val Pro Ser Gln Glu Gln Val Asp Glu Ile Ala
    290                 295                 300

Tyr Gly Ile Leu Asn Ser Gly Leu Asn Phe Leu Trp Ile Met Lys Pro
305                 310                 315                 320

Pro Arg Lys Asn Ser Ser Phe Pro Thr Val Val Leu Pro Gln Gly Tyr
                325                 330                 335

Leu Asp Lys Ile Gly Asp Lys Gly Lys Val Val Glu Trp Cys Leu Gln
            340                 345                 350

Glu Gln Val Leu Ala His Pro Ser Leu Ala Cys Phe Val Thr His Cys
        355                 360                 365

Gly Trp Asn Ser Ser Met Glu Val Ile Ala Asn Gly Val Pro Ile Val
    370                 375                 380

Ala Phe Pro Gln Trp Gly Asp Gln Val Thr Asp Ala Lys Tyr Leu Val
385                 390                 395                 400

Asp Glu Phe Lys Ile Gly Val Arg Leu Ser Arg Gly Val Thr Glu Asn
                405                 410                 415
```

```
Arg Val Ile Pro Arg Asp Glu Val Glu Arg Ser Leu His Asp Val Thr
            420                 425                 430

Ser Gly Pro Lys Val Ala Glu Met Lys Glu Asn Ala Leu Lys Trp Lys
        435                 440                 445

Met Lys Ala Thr Glu Ala Val Ala Glu Gly Gly Ser Ser Asp Leu Asn
    450                 455                 460

Leu Lys Ser Phe Val Asp Glu Leu Arg Thr Leu Gln Asn Ser Asn Lys
465                 470                 475                 480

Asn Leu Ala Lys Leu Ala Pro Leu Ser Asn
                485                 490


<210> SEQ ID NO 22
<211> LENGTH: 225
<212> TYPE: PRT
<213> ORGANISM: artificial sequence
<220> FEATURE:
<223> OTHER INFORMATION: Synthetic sequence

<400> SEQUENCE: 22

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Arg Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225


<210> SEQ ID NO 23
<211> LENGTH: 470
<212> TYPE: PRT
<213> ORGANISM: Nicotiana tabacum

<400> SEQUENCE: 23
```

-continued

```
Met Val Glu Glu Leu Pro Gln Ser Leu Lys Glu Lys Lys Trp Gln Ile
1               5                   10                  15

Asn Trp Asp Ala Val Ser Gln Glu Leu Lys Lys Thr Ser Arg Phe Met
            20                  25                  30

Ala Pro Met Val Ala Val Thr Val Phe Gln Tyr Leu Leu Gln Val Val
        35                  40                  45

Ser Val Met Met Val Gly His Leu Gly Glu Leu Ala Leu Ser Ser Val
    50                  55                  60

Ala Ile Ala Thr Ser Leu Thr Asn Val Thr Gly Phe Ser Leu Leu Thr
65                  70                  75                  80

Gly Leu Val Gly Gly Met Glu Thr Leu Cys Gly Gln Ala Tyr Gly Ala
                85                  90                  95

Gln Gln Tyr His Lys Leu Ser Thr Tyr Thr Tyr Thr Ala Ile Ile Ser
            100                 105                 110

Leu Phe Leu Val Cys Ile Pro Ile Cys Val Leu Trp Cys Phe Met Asp
        115                 120                 125

Lys Leu Leu Ile Leu Thr Gly Gln Asp His Ser Ile Ser Val Glu Ala
    130                 135                 140

Arg Lys Tyr Ser Leu Trp Val Ile Pro Ala Ile Phe Gly Gly Ala Ile
145                 150                 155                 160

Ser Lys Pro Leu Ser Arg Tyr Ser Gln Ala Gln Ser Leu Ile Leu Pro
                165                 170                 175

Met Leu Leu Ser Ser Phe Ala Val Leu Cys Phe His Leu Pro Ile Ser
            180                 185                 190

Trp Ala Leu Ile Phe Lys Leu Glu Leu Gly Asn Ile Gly Ala Ala Ile
        195                 200                 205

Ala Phe Ser Ile Ser Ser Trp Leu Tyr Val Leu Phe Leu Ala Ser Tyr
    210                 215                 220

Val Lys Leu Ser Ser Ser Cys Glu Lys Thr Arg Ala Pro Phe Ser Met
225                 230                 235                 240

Glu Ala Phe Leu Cys Ile Arg Gln Phe Phe Arg Leu Ala Val Pro Ser
                245                 250                 255

Ala Val Met Val Cys Leu Lys Trp Trp Ser Phe Glu Val Leu Ala Leu
            260                 265                 270

Val Ser Gly Leu Leu Pro Asn Pro Lys Leu Glu Thr Ser Val Met Ser
        275                 280                 285

Ile Cys Ile Thr Ile Ser Gln Leu His Phe Ser Ile Pro Tyr Gly Phe
    290                 295                 300

Gly Ala Ala Ala Ser Thr Arg Val Ser Asn Glu Leu Gly Ala Gly Asn
305                 310                 315                 320

Pro Gln Lys Ala Arg Met Ala Val Gln Val Val Met Phe Leu Thr Val
                325                 330                 335

Val Glu Thr Leu Val Phe Asn Thr Ser Leu Phe Gly Ser Arg His Val
            340                 345                 350

Leu Gly Lys Ala Phe Ser Asn Glu Lys Gln Val Val Asp Tyr Ile Ala
        355                 360                 365

Ala Met Thr Pro Phe Leu Cys Leu Ser Ile Val Thr Asp Ser Leu Gln
    370                 375                 380

Ile Val Ile Thr Gly Ile Ala Arg Gly Ser Gly Trp Gln His Ile Gly
385                 390                 395                 400

Ala Tyr Ile Asn Leu Val Val Phe Tyr Val Ile Ala Ile Pro Leu Ala
                405                 410                 415

Val Val Leu Gly Phe Val Leu His Leu Lys Ala Lys Gly Leu Trp Ile
```

```
            420                 425                 430

Gly Ile Val Val Gly Cys Ala Ile Gln Ser Ile Val Leu Ser Ile Val
        435                 440                 445

Thr Gly Phe Thr Asp Trp Glu Lys Gln Ala Lys Lys Ala Arg Glu Arg
    450                 455                 460

Val His Glu Gly Arg Ser
465                 470


<210> SEQ ID NO 24
<211> LENGTH: 500
<212> TYPE: PRT
<213> ORGANISM: Nicotiana tabacum

<400> SEQUENCE: 24

Met Gly Lys Ser Met Lys Ser Glu Val Glu Gln Pro Leu Leu Ile Ala
1               5                   10                  15

Ala His Gly Gly Ser Ser Glu Leu Glu Glu Val Leu Ser Asp Thr Gln
            20                  25                  30

Leu Pro Tyr Phe Arg Arg Leu Arg Tyr Ala Ser Trp Ile Glu Phe Gln
        35                  40                  45

Leu Leu Tyr Arg Leu Ala Ala Pro Ser Val Ala Val Tyr Met Ile Asn
    50                  55                  60

Asn Ala Met Ser Met Ser Thr Arg Ile Phe Ser Gly Gln Leu Gly Asn
65                  70                  75                  80

Leu Gln Leu Ala Ala Ala Ser Leu Gly Asn Gln Gly Ile Gln Leu Phe
                85                  90                  95

Ala Tyr Gly Leu Met Leu Gly Met Gly Ser Ala Val Glu Thr Leu Cys
            100                 105                 110

Gly Gln Ala Tyr Gly Ala His Arg Tyr Glu Met Leu Gly Val Tyr Leu
        115                 120                 125

Gln Arg Ala Thr Val Val Leu Ser Val Thr Gly Ile Pro Leu Thr Val
    130                 135                 140

Val Tyr Leu Phe Ser Lys Asn Ile Leu Leu Ala Leu Gly Glu Ser Lys
145                 150                 155                 160

Leu Val Ala Ser Ala Ala Ala Val Phe Val Tyr Gly Leu Ile Pro Gln
                165                 170                 175

Ile Phe Ala Tyr Ala Val Asn Phe Pro Ile Gln Lys Phe Leu Gln Ala
            180                 185                 190

Gln Ser Ile Val Ala Pro Ser Ala Phe Ile Ser Leu Gly Thr Leu Phe
        195                 200                 205

Val His Ile Leu Leu Ser Trp Val Val Val Tyr Lys Ile Gly Leu Gly
    210                 215                 220

Leu Leu Gly Ala Ser Leu Val Leu Ser Phe Ser Trp Trp Ile Ile Val
225                 230                 235                 240

Val Ala Gln Phe Ile Tyr Ile Ile Lys Ser Glu Arg Cys Lys Ala Thr
                245                 250                 255

Trp Ala Gly Phe Arg Trp Glu Ala Phe Ser Gly Leu Cys Gln Phe Val
            260                 265                 270

Lys Leu Ser Ala Gly Ser Ala Val Met Leu Cys Leu Glu Thr Trp Tyr
        275                 280                 285

Met Gln Ile Leu Val Leu Leu Ser Gly Leu Leu Lys Asn Pro Glu Ile
    290                 295                 300

Ala Leu Ala Ser Ile Ser Val Cys Leu Ala Val Asn Gly Leu Met Phe
305                 310                 315                 320
```

-continued

Met Val Ala Val Gly Phe Asn Ala Ala Ala Ser Val Arg Val Ser Asn
325 330 335

Glu Leu Gly Ala Ala His Ser Lys Ser Ala Ala Phe Ser Val Phe Met
340 345 350

Val Thr Phe Ile Ser Phe Leu Ile Ala Val Val Glu Ala Ile Ile Val
355 360 365

Leu Ser Leu Arg Asn Val Ile Ser Tyr Ala Phe Thr Glu Gly Glu Ile
370 375 380

Val Ala Lys Glu Val Ser Glu Leu Cys Pro Phe Leu Ala Val Thr Leu
385 390 395 400

Ile Leu Asn Gly Ile Gln Pro Val Leu Ser Gly Val Ala Val Gly Cys
405 410 415

Gly Trp Gln Ala Phe Val Ala Tyr Val Asn Val Gly Cys Tyr Tyr Gly
420 425 430

Val Gly Ile Pro Leu Gly Cys Leu Leu Gly Phe Lys Phe Asp Leu Gly
435 440 445

Ala Lys Gly Ile Trp Thr Gly Met Ile Gly Gly Thr Val Met Gln Thr
450 455 460

Val Ile Leu Leu Trp Val Thr Phe Arg Thr Asp Trp Asn Lys Lys Val
465 470 475 480

Glu Cys Ala Lys Lys Arg Leu Asp Lys Trp Glu Asn Leu Lys Gly Pro
485 490 495

Leu Asn Lys Glu
500

<210> SEQ ID NO 25
<211> LENGTH: 500
<212> TYPE: PRT
<213> ORGANISM: Nicotiana tabacum

<400> SEQUENCE: 25

Met Gly Lys Ser Met Lys Ser Glu Val Glu Gln Pro Leu Leu Ala Ala
1 5 10 15

Ala His Gly Gly Ser Ser Glu Leu Glu Glu Val Leu Ser Asp Ser Gln
20 25 30

Leu Pro Tyr Phe Arg Arg Leu Arg Tyr Ala Ser Trp Ile Glu Phe Gln
35 40 45

Leu Leu Tyr Arg Leu Ala Ala Pro Ser Val Ala Val Tyr Met Ile Asn
50 55 60

Asn Ala Met Ser Met Ser Thr Arg Ile Phe Ser Gly Gln Leu Gly Asn
65 70 75 80

Leu Gln Leu Ala Ala Ala Ser Leu Gly Asn Gln Gly Ile Gln Leu Phe
85 90 95

Ala Tyr Gly Leu Met Leu Gly Met Gly Ser Ala Val Glu Thr Leu Cys
100 105 110

Gly Gln Ala Tyr Gly Ala His Arg Tyr Glu Met Leu Gly Val Tyr Leu
115 120 125

Gln Arg Ala Thr Val Val Leu Ser Leu Thr Gly Ile Pro Leu Ala Val
130 135 140

Val Tyr Leu Phe Ser Lys Asn Ile Leu Leu Ala Leu Gly Glu Ser Lys
145 150 155 160

Leu Val Ala Ser Ala Ala Ala Val Phe Val Tyr Gly Leu Ile Pro Gln
165 170 175

Ile Phe Ala Tyr Ala Val Asn Phe Pro Ile Gln Lys Phe Leu Gln Ser
180 185 190

```
Gln Ser Ile Val Ala Pro Ser Ala Phe Ile Ser Leu Gly Thr Leu Phe
        195                 200                 205

Val His Ile Leu Leu Ser Trp Val Val Val Tyr Lys Ile Gly Leu Gly
    210                 215                 220

Leu Leu Gly Ala Ser Leu Val Leu Ser Phe Ser Trp Trp Ile Ile Val
225                 230                 235                 240

Val Ala Gln Phe Ile Tyr Ile Leu Lys Ser Glu Arg Cys Lys Ala Thr
                245                 250                 255

Trp Ala Gly Phe Arg Trp Glu Ala Phe Ser Gly Leu Trp Gln Phe Val
            260                 265                 270

Lys Leu Ser Ala Gly Ser Ala Val Met Leu Cys Leu Glu Thr Trp Tyr
        275                 280                 285

Phe Gln Ile Leu Val Leu Leu Ser Gly Leu Leu Lys Asn Pro Glu Ile
    290                 295                 300

Ala Leu Ala Ser Ile Ser Val Cys Leu Ala Val Asn Gly Leu Met Phe
305                 310                 315                 320

Met Val Ala Val Gly Phe Asn Ala Ala Ala Ser Val Arg Val Ser Asn
                325                 330                 335

Glu Leu Gly Ala Ala His Pro Lys Ser Ala Ala Phe Ser Val Phe Met
            340                 345                 350

Val Thr Phe Ile Ser Phe Leu Ile Ala Val Val Glu Ala Ile Ile Val
        355                 360                 365

Leu Ser Leu Arg Asn Val Ile Ser Tyr Ala Phe Thr Glu Gly Glu Val
    370                 375                 380

Val Ala Lys Glu Val Ser Ser Leu Cys Pro Tyr Leu Ala Val Thr Leu
385                 390                 395                 400

Ile Leu Asn Gly Ile Gln Pro Val Leu Ser Gly Val Ala Val Gly Cys
                405                 410                 415

Gly Trp Gln Ala Phe Val Ala Tyr Val Asn Val Gly Cys Tyr Tyr Gly
            420                 425                 430

Val Gly Ile Pro Leu Gly Cys Leu Leu Gly Phe Lys Phe Asp Phe Gly
        435                 440                 445

Ala Lys Gly Ile Trp Thr Gly Met Ile Gly Gly Thr Val Met Gln Thr
    450                 455                 460

Ile Ile Leu Leu Trp Val Thr Phe Ser Thr Asp Trp Asn Lys Glu Val
465                 470                 475                 480

Glu Ser Ala Arg Lys Arg Leu Asp Lys Trp Glu Asn Leu Lys Gly Pro
                485                 490                 495

Leu Asn Lys Glu
            500
```

<210> SEQ ID NO 26
<211> LENGTH: 5
<212> TYPE: PRT
<213> ORGANISM: artificial sequence
<220> FEATURE:
<223> OTHER INFORMATION: Synthetic sequence

<400> SEQUENCE: 26

```
Gly Gly Gly Gly Ser
1               5
```

<210> SEQ ID NO 27
<211> LENGTH: 790
<212> TYPE: PRT
<213> ORGANISM: Nicotiana tabacum

<400> SEQUENCE: 27

Met Ala Thr Thr Lys Gln Lys Val Thr Ala Pro Ser Pro Ser Pro Ser
1               5                   10                  15

Ser Ser Thr Ala Ser Cys Cys Pro Ser Thr Ser Ile Leu Arg Arg Glu
            20                  25                  30

Ala Thr Ala Ala Ile Ala Val Val Gly Asp Gly Leu Gln Asn Trp Thr
        35                  40                  45

Asn Ile Pro Ser Val Asp Glu Lys Gln Lys Lys Thr Ala Ser Ser Ala
    50                  55                  60

Leu Ala Ser Leu Pro Thr Thr Glu Pro Leu Ser Thr Asn Thr Ser Thr
65                  70                  75                  80

Lys Gly Ile Gln Ile Met Thr Arg Ala Gln Thr Cys His Pro Leu Asp
                85                  90                  95

Pro Leu Ser Ala Ala Glu Ile Ser Val Ala Val Ala Thr Val Arg Ala
            100                 105                 110

Ala Gly Glu Thr Pro Glu Val Arg Asp Gly Met Arg Phe Ile Glu Val
        115                 120                 125

Val Leu Val Glu Pro Asp Lys Ser Val Val Ala Leu Ala Asp Ala Tyr
    130                 135                 140

Phe Phe Pro Pro Phe Gln Ser Ser Leu Met Pro Arg Thr Lys Gly Gly
145                 150                 155                 160

Ser Gln Ile Pro Thr Lys Leu Pro Pro Arg Arg Ala Arg Leu Ile Val
                165                 170                 175

Tyr Asn Lys Lys Thr Asn Glu Thr Ser Ile Trp Ile Val Glu Leu Asn
            180                 185                 190

Glu Val His Ala Ala Ala Arg Gly Gly His His Arg Gly Lys Val Ile
        195                 200                 205

Ala Ser Asn Val Val Pro Asp Val Gln Pro Pro Ile Asp Ala Gln Glu
    210                 215                 220

Tyr Ala Glu Cys Glu Ala Val Val Lys Ser Tyr Pro Pro Phe Arg Asp
225                 230                 235                 240

Ala Met Arg Arg Arg Gly Ile Asp Asp Leu Asp Leu Val Met Val Asp
                245                 250                 255

Pro Trp Cys Val Gly Tyr His Ser Glu Ala Asp Ala Pro Ser Arg Arg
            260                 265                 270

Leu Ala Lys Pro Leu Val Phe Cys Arg Thr Glu Ser Asp Cys Pro Met
        275                 280                 285

Glu Asn Gly Tyr Ala Arg Pro Val Glu Gly Ile Tyr Val Leu Val Asp
    290                 295                 300

Val Gln Asn Met Lys Ile Ile Glu Phe Glu Asp Arg Lys Leu Val Pro
305                 310                 315                 320

Leu Pro Pro Val Asp Pro Leu Arg Asn Tyr Thr Ala Gly Glu Thr Arg
                325                 330                 335

Gly Gly Val Asp Arg Ser Asp Val Lys Pro Leu His Ile Ile Gln Pro
            340                 345                 350

Glu Gly Pro Ser Phe Arg Ile Ser Gly Asn Tyr Val Glu Trp Gln Lys
        355                 360                 365

Trp Asn Phe Arg Ile Gly Phe Thr Pro Arg Glu Gly Leu Val Ile His
    370                 375                 380

Ser Val Ala Tyr Leu Asp Gly Ser Arg Gly Arg Arg Pro Ile Ala His
385                 390                 395                 400

Arg Leu Ser Phe Val Glu Met Val Val Pro Tyr Gly Asp Pro Asn Asp 405 410 415

Pro His Tyr Arg Lys Asn Ala Phe Asp Ala Gly Glu Asp Gly Leu Gly
420 425 430

Lys Asn Ala His Ser Leu Lys Arg Gly Cys Asp Cys Leu Gly Tyr Ile
435 440 445

Lys Tyr Phe Asp Ala His Phe Thr Asn Phe Thr Gly Gly Val Glu Thr
450 455 460

Thr Glu Asn Cys Val Cys Leu His Glu Glu Asp His Gly Met Leu Trp
465 470 475 480

Lys His Gln Asp Trp Arg Thr Gly Leu Ala Glu Val Arg Arg Ser Arg
485 490 495

Arg Leu Thr Val Ser Phe Val Cys Thr Val Ala Asn Tyr Glu Tyr Ala
500 505 510

Phe Tyr Trp His Phe Tyr Gln Asp Gly Lys Ile Glu Ala Glu Val Lys
515 520 525

Leu Thr Gly Ile Leu Ser Leu Gly Ala Leu Gln Pro Gly Glu Tyr Arg
530 535 540

Lys Tyr Gly Thr Thr Ile Leu Pro Gly Leu Tyr Ala Pro Val His Gln
545 550 555 560

His Phe Phe Val Ala Arg Met Asn Met Ala Val Asp Cys Lys Pro Gly
565 570 575

Glu Ala His Asn Gln Val Val Glu Val Asn Val Lys Val Glu Glu Pro
580 585 590

Gly Lys Glu Asn Val His Asn Asn Ala Phe Tyr Ala Glu Glu Thr Leu
595 600 605

Leu Arg Ser Glu Leu Gln Ala Met Arg Asp Cys Asp Pro Phe Ser Ala
610 615 620

Arg His Trp Ile Val Arg Asn Thr Arg Thr Val Asn Arg Thr Gly Gln
625 630 635 640

Leu Thr Gly Tyr Lys Leu Val Pro Gly Pro Asn Cys Leu Pro Leu Ala
645 650 655

Gly Pro Glu Ala Lys Phe Leu Arg Arg Ala Ala Phe Leu Lys His Asn
660 665 670

Leu Trp Val Thr Gln Tyr Ala Pro Gly Glu Asp Phe Pro Gly Gly Glu
675 680 685

Phe Pro Asn Gln Asn Pro Arg Val Gly Glu Gly Leu Ala Ser Trp Val
690 695 700

Lys Gln Asp Arg Pro Leu Glu Glu Ser Asp Ile Val Leu Trp Tyr Ile
705 710 715 720

Phe Gly Ile Thr His Val Pro Arg Leu Glu Asp Trp Pro Val Met Pro
725 730 735

Val Glu His Ile Gly Phe Val Leu Gln Pro His Gly Tyr Phe Asn Cys
740 745 750

Ser Pro Ala Val Asp Val Pro Pro Pro Phe Ala Cys Asp Ser Glu Ser
755 760 765

Arg Asp Ser Asp Val Thr Glu Thr Ser Val Ala Lys Ser Thr Ala Thr
770 775 780

Ser Leu Leu Ala Lys Leu
785 790

<210> SEQ ID NO 28
<211> LENGTH: 646
<212> TYPE: PRT
<213> ORGANISM: Atropa belladonna

<400> SEQUENCE: 28

```
Met Phe Pro Pro Phe Gln Ser Ser Leu Met Pro Arg Thr Lys Gly Gly
1               5                   10                  15

Leu Leu Val Pro Ser Arg Leu Pro Pro Arg Arg Ala Arg Leu Ile Val
            20                  25                  30

Tyr Asn Lys Lys Thr Asn Glu Thr Ser Val Trp Ile Val Gln Leu Thr
        35                  40                  45

Glu Val His Ala Ile Ala Arg Gly Gly Gln His Arg Gly Lys Val Ile
    50                  55                  60

Ser Ser Lys Val Val Pro Asp Val Gln Pro Pro Ile Asp Ala Gln Glu
65                  70                  75                  80

Tyr Ala Asp Cys Glu Ser Val Val Lys Asn Tyr Pro Ser Phe Ile Glu
                85                  90                  95

Ala Met Lys Arg Arg Gly Ile Asp Asp Met Asp Leu Val Met Val Asp
            100                 105                 110

Pro Trp Cys Val Gly Tyr His Ser Glu Ala Asp Ala Pro Ser Arg Arg
        115                 120                 125

Leu Ala Lys Pro Leu Val Phe Cys Arg Thr Glu Ser Asp Cys Pro Met
    130                 135                 140

Glu Asn Gly Tyr Ala Arg Pro Val Glu Gly Ile His Val Leu Val Asp
145                 150                 155                 160

Val Gln Asn Met Gln Val Ile Glu Phe Glu Asp Arg Lys Val Val Pro
                165                 170                 175

Leu Pro Pro Ala Asp Pro Leu Arg Asn Tyr Thr Ala Gly Glu Thr Arg
            180                 185                 190

Gly Gly Val Asp Arg Ser Asp Val Lys Pro Leu Gln Ile Ile Gln Pro
        195                 200                 205

Asp Gly Pro Ser Phe Arg Val Asp Gly Asn Tyr Val Gln Trp Gln Lys
    210                 215                 220

Trp Asn Phe Arg Val Gly Phe Thr Pro Arg Glu Gly Leu Val Ile His
225                 230                 235                 240

Ser Val Ala Tyr Leu Asp Gly Ser Arg Gly Arg Arg Ser Ile Ala His
                245                 250                 255

Arg Leu Ser Phe Val Glu Met Val Val Pro Tyr Gly Asp Pro Asn Asp
            260                 265                 270

Pro His Tyr Arg Lys Asn Ala Phe Asp Ala Gly Glu Asp Gly Leu Gly
        275                 280                 285

Lys Asn Ala His Ser Leu Lys Arg Gly Cys Asp Cys Leu Gly Tyr Ile
    290                 295                 300

Lys Tyr Phe Asp Ala Asn Phe Thr Asn Phe Thr Gly Gly Val Glu Thr
305                 310                 315                 320

Ile Glu Asn Cys Val Cys Leu His Glu Glu Asp His Gly Met Leu Trp
                325                 330                 335

Lys His Gln Asp Trp Arg Thr Gly Leu Ala Glu Val Arg Arg Ser Arg
            340                 345                 350

Arg Leu Thr Val Ser Phe Ile Cys Thr Val Ala Asn Tyr Glu Tyr Gly
        355                 360                 365

Phe Tyr Trp His Phe Tyr Gln Asp Gly Lys Ile Glu Ala Glu Val Lys
    370                 375                 380

Leu Thr Gly Ile Leu Ser Leu Gly Ala Leu Gln Pro Gly Glu Ser Arg
385                 390                 395                 400

Lys Tyr Gly Thr Thr Ile Thr Pro Gly Leu Tyr Ala Pro Val His Gln
```

-continued

```
                405                 410                 415

His Phe Phe Val Ala Arg Met Asn Met Ala Val Asp Cys Lys Pro Gly
            420                 425                 430

Glu Ala His Asn Gln Ile Val Glu Val Asn Val Arg Val Glu Glu Pro
        435                 440                 445

Gly Lys Glu Asn Val His Asn Asn Ala Phe Tyr Ala Glu Glu Thr Leu
    450                 455                 460

Leu Arg Ser Glu Leu Gln Ala Met Arg Asp Cys Asp Pro Leu Ser Ala
465                 470                 475                 480

Arg His Trp Ile Val Arg Asn Thr Arg Thr Ala Asn Arg Thr Gly Lys
                485                 490                 495

Leu Thr Gly Tyr Lys Leu Val Pro Gly Pro Asn Cys Leu Pro Leu Ala
            500                 505                 510

Gly Pro Glu Ala Lys Phe Leu Arg Arg Ala Ala Phe Leu Lys His Asn
        515                 520                 525

Leu Trp Val Thr Gln Tyr Ala Pro Gly Glu Asp Phe Pro Gly Gly Glu
    530                 535                 540

Phe Pro Asn Gln Asn Pro Arg Val Gly Glu Gly Leu Ala Ser Trp Val
545                 550                 555                 560

Lys Gln Asp Arg Ser Leu Glu Glu Ser Asp Ile Val Leu Trp Tyr Val
                565                 570                 575

Phe Gly Ile Thr His Val Pro Arg Leu Glu Asp Trp Pro Val Met Pro
            580                 585                 590

Val Glu His Ile Gly Phe Met Leu Gln Pro His Gly Phe Phe Asn Cys
        595                 600                 605

Ser Pro Ala Val Asp Val Pro Pro Pro Arg Gly Cys Asp Leu Glu Ser
    610                 615                 620

Lys Asp Ser Asp Val Ser Glu Asn Gly Val Gly Lys His Thr Ala Thr
625                 630                 635                 640

Gly Leu Met Ala Lys Leu
                645


<210> SEQ ID NO 29
<211> LENGTH: 786
<212> TYPE: PRT
<213> ORGANISM: Datura metel

<400> SEQUENCE: 29

Met Ser Gln Lys Val Thr Lys Pro Ser Ala Ala Ala Ala Val Cys Cys
1               5                   10                  15

Pro Ser Thr Pro Val Leu Arg Arg Glu Ala Thr Ala Ala Ala Ala Ala
            20                  25                  30

Ile Met Ser Asp Gly Gly Leu Gln Asn Trp Thr Val Arg Pro Ser Val
        35                  40                  45

Asp His Asn Lys Gln Lys Lys Thr Ser Ser Ala Ile Ala Ser Leu Glu
    50                  55                  60

Ser Asn Thr Glu Thr Arg Ser Ser Asn Thr Ser Thr Lys Gly Ile Gln
65                  70                  75                  80

Ile Met Pro Arg Ala Gln Thr Cys His Pro Leu Asp Pro Leu Cys Ala
                85                  90                  95

Ala Glu Ile Ser Val Ala Val Ala Thr Val Arg Ala Ala Gly Glu Thr
            100                 105                 110

Pro Glu Val Arg Asp Gly Met Arg Phe Ile Glu Val Val Leu Leu Glu
        115                 120                 125
```

-continued

```
Pro Asp Lys Asn Val Val Ala Leu Ala Asp Ala Tyr Phe Phe Pro Pro
    130                 135                 140

Phe Gln Ser Ser Leu Ile Arg Arg Thr Lys Gly Gly Ser Leu Ile Pro
145                 150                 155                 160

Thr Lys Leu Pro Pro Arg Arg Ala Arg Leu Ile Val Tyr Asn Lys Lys
                165                 170                 175

Thr Asn Glu Thr Ser Ile Trp Ile Val Glu Leu Thr Glu Val His Ala
            180                 185                 190

Ala Ala Arg Gly Gly His His Arg Gly Lys Val Ile Ser Ser Asn Gly
        195                 200                 205

Val Pro Asp Val Gln Pro Pro Ile Asp Ala Gln Glu Tyr Ala Glu Cys
    210                 215                 220

Glu Ala Val Val Lys Asn Tyr Pro Pro Phe Arg Glu Ala Met Lys Arg
225                 230                 235                 240

Arg Gly Ile Asp Asp Met Asp Leu Val Met Val Asp Pro Trp Cys Val
                245                 250                 255

Gly Tyr His Ser Glu Ala Asp Ala Pro Ser His Arg Leu Ala Lys Pro
            260                 265                 270

Leu Val Phe Cys Arg Thr Glu Ser Glu Cys Pro Met Glu Asn Gly Tyr
        275                 280                 285

Ala Arg Pro Val Glu Gly Ile Tyr Val Leu Val Asp Val Gln Asn Met
    290                 295                 300

Gln Ile Ile Glu Phe Glu Asp Arg Lys Leu Val Pro Leu Pro Pro Ile
305                 310                 315                 320

Asp Pro Leu Arg Asn Tyr Thr Ala Gly Glu Thr Arg Gly Gly Val Asp
                325                 330                 335

Arg Ser Asp Val Lys Pro Leu His Ile Ile Gln Pro Glu Gly Pro Ser
            340                 345                 350

Phe Arg Ile Ser Gly Asn Tyr Val Glu Trp Gln Lys Trp Asn Phe Arg
        355                 360                 365

Ile Gly Phe Thr Pro Arg Glu Gly Leu Val Ile His Ser Val Ala Tyr
    370                 375                 380

Leu Asp Gly Ser Arg Gly Arg Arg Pro Ile Ala His Arg Leu Ser Phe
385                 390                 395                 400

Val Glu Met Val Val Pro Tyr Gly Asp Pro Asn Asp Pro His Tyr Arg
                405                 410                 415

Lys Asn Ala Phe Asp Ala Gly Glu Asp Gly Leu Gly Lys Asn Ala His
            420                 425                 430

Ser Leu Lys Arg Gly Cys Asp Cys Leu Gly Tyr Ile Lys Tyr Phe Asp
        435                 440                 445

Ala His Phe Thr Asn Phe Thr Gly Gly Val Glu Thr Thr Glu Asn Cys
    450                 455                 460

Val Cys Leu His Glu Glu Asp His Gly Met Leu Trp Lys His Gln Asp
465                 470                 475                 480

Trp Arg Thr Gly Leu Ala Glu Val Arg Arg Ser Arg Arg Leu Thr Val
                485                 490                 495

Ser Phe Val Cys Thr Val Ala Asn Tyr Glu Tyr Ala Phe Tyr Trp His
            500                 505                 510

Phe Tyr Gln Asp Gly Lys Ile Glu Ala Glu Val Lys Leu Thr Gly Ile
        515                 520                 525

Leu Ser Leu Gly Ala Leu Gln Pro Gly Glu Ser Arg Lys Tyr Gly Thr
    530                 535                 540

Thr Ile Ala Pro Gly Leu Tyr Ala Pro Val His Gln His Phe Phe Val
```

-continued

```
545                 550                 555                 560

Ala Arg Met Asn Met Ala Val Asp Cys Lys Pro Gly Glu Ala His Asn
                565                 570                 575

Gln Val Val Glu Val Asn Val Lys Val Glu Glu Pro Gly Lys Glu Asn
            580                 585                 590

Val His Asn Asn Ala Phe Tyr Ala Glu Glu Thr Leu Leu Arg Ser Glu
        595                 600                 605

Ser Glu Ala Met Arg Asp Cys Asp Pro Phe Ser Ala Arg His Trp Ile
    610                 615                 620

Val Arg Asn Thr Arg Thr Val Asn Arg Thr Gly Gln Leu Thr Gly Tyr
625                 630                 635                 640

Lys Leu Val Pro Gly Pro Asn Cys Leu Pro Leu Ala Gly His Glu Ala
                645                 650                 655

Lys Phe Leu Arg Arg Ala Ala Phe Leu Lys His Asn Leu Trp Val Thr
            660                 665                 670

Gln Tyr Ala Pro Gly Glu Asp Phe Pro Gly Gly Glu Phe Pro Asn Gln
        675                 680                 685

Asn Pro Arg Ala Gly Glu Gly Leu Ala Ser Trp Val Lys Gln Asp Arg
    690                 695                 700

Pro Leu Glu Glu Ser Asp Ile Val Leu Trp Tyr Ile Phe Gly Ile Thr
705                 710                 715                 720

His Val Pro Arg Leu Glu Asp Trp Pro Val Met Pro Val Glu His Ile
                725                 730                 735

Gly Phe Met Leu Gln Pro His Gly Phe Phe Asn Cys Ser Pro Ala Val
            740                 745                 750

Asp Val Pro Pro Pro Ser Gly Cys Asp Ser Glu Ser Arg Asp Ser Asp
        755                 760                 765

Val Thr Glu Asn Ser Val Ala Lys His Thr Pro Thr Gly Leu Met Ala
    770                 775                 780

Lys Leu
785


<210> SEQ ID NO 30
<211> LENGTH: 465
<212> TYPE: PRT
<213> ORGANISM: Arabidopsis thaliana

<400> SEQUENCE: 30

Met Arg Asn Leu Ser Phe Ile Val Leu Phe Leu Leu Thr Leu Phe Phe
1               5                   10                  15

Ile His His Leu Val Asp Ala Ser Leu Leu Val Lys Ser Leu Pro Gly
            20                  25                  30

Phe Glu Gly Pro Leu Pro Phe Glu Leu Glu Thr Gly Tyr Val Ser Ile
        35                  40                  45

Gly Glu Ser Gly Asp Val Glu Leu Phe Tyr Tyr Phe Val Lys Ser Glu
    50                  55                  60

Arg Asn Pro Glu Asn Asp Pro Leu Met Ile Trp Leu Thr Gly Gly Pro
65                  70                  75                  80

Gly Cys Ser Ser Ile Cys Gly Leu Leu Phe Ala Asn Gly Pro Leu Ala
                85                  90                  95

Phe Lys Gly Asp Glu Tyr Asn Gly Thr Val Pro Pro Leu Glu Leu Thr
            100                 105                 110

Ser Phe Ser Trp Thr Lys Val Ala Asn Ile Leu Tyr Leu Glu Ala Pro
        115                 120                 125
```

-continued

Ala Gly Ser Gly Tyr Ser Tyr Ala Lys Thr Arg Arg Ala Phe Glu Ser
    130                 135                 140

Ser Asp Thr Lys Gln Met His Gln Ile Asp Gln Phe Leu Arg Ser Trp
145                 150                 155                 160

Phe Val Lys His Pro Glu Phe Ile Ser Asn Pro Phe Tyr Val Gly Gly
                165                 170                 175

Asp Ser Tyr Ser Gly Lys Ile Val Pro Gly Ala Val Gln Gln Ile Ser
            180                 185                 190

Leu Gly Asn Glu Lys Gly Leu Thr Pro Leu Ile Asn Ile Gln Gly Tyr
        195                 200                 205

Val Leu Gly Asn Pro Val Thr Asp Lys Asn Ile Glu Thr Asn Tyr Arg
    210                 215                 220

Val Pro Phe Ala His Gly Met Gly Leu Ile Ser Asp Glu Leu Phe Glu
225                 230                 235                 240

Ser Leu Glu Arg Ser Cys Gly Gly Lys Phe Phe Asn Val Asp Pro Ser
                245                 250                 255

Asn Ala Arg Cys Ser Asn Asn Leu Gln Ala Tyr Asp His Cys Met Ser
            260                 265                 270

Glu Ile Tyr Ser Glu His Ile Leu Leu Arg Asn Cys Lys Val Asp Tyr
        275                 280                 285

Val Leu Ala Asp Thr Pro Asn Ile Arg Thr Asp Arg Arg Arg Val Met
    290                 295                 300

Lys Glu Phe Ser Val Asn Asp Ser Ser Ser Leu Pro Pro Pro Ser Cys
305                 310                 315                 320

Phe Thr Tyr Arg Tyr Phe Leu Ser Ala Phe Trp Ala Asn Asp Glu Asn
                325                 330                 335

Val Arg Arg Ala Leu Gly Val Lys Lys Glu Val Gly Lys Trp Asn Arg
            340                 345                 350

Cys Asn Ser Gln Asn Ile Pro Tyr Thr Phe Glu Ile Phe Asn Ala Val
        355                 360                 365

Pro Tyr His Val Asn Asn Ser Leu Lys Gly Phe Arg Ser Leu Ile Tyr
    370                 375                 380

Ser Gly Asp His Asp Ser Met Val Pro Phe Ser Ser Thr Gln Ala Trp
385                 390                 395                 400

Ile Arg Ala Leu Asn Tyr Ser Ile Val Asp Asp Trp Arg Pro Trp Met
                405                 410                 415

Met Ser Ser Asn Gln Val Ala Gly Tyr Thr Arg Thr Tyr Ala Asn Lys
            420                 425                 430

Met Thr Phe Ala Thr Ile Lys Gly Gly Gly His Thr Ala Glu Tyr Thr
        435                 440                 445

Pro Asp Gln Cys Ser Leu Met Phe Arg Arg Trp Ile Asp Gly Glu Pro
    450                 455                 460

Leu
465

<210> SEQ ID NO 31
<211> LENGTH: 433
<212> TYPE: PRT
<213> ORGANISM: Arabidopsis thaliana

<400> SEQUENCE: 31

Met Ser Leu Lys Ile Lys Phe Leu Leu Leu Leu Val Leu Tyr His His
1               5                   10                  15

Val Asp Ser Ala Ser Ile Val Lys Phe Leu Pro Gly Phe Glu Gly Pro
            20                  25                  30

```
Leu Pro Phe Glu Leu Glu Thr Gly Tyr Ile Gly Ile Gly Glu Asp Glu
        35                  40                  45

Asn Val Gln Phe Phe Tyr Tyr Phe Ile Lys Ser Glu Asn Asn Pro Lys
    50                  55                  60

Glu Asp Pro Leu Leu Ile Trp Leu Asn Gly Gly Pro Gly Cys Ser Cys
65                  70                  75                  80

Leu Gly Gly Ile Ile Phe Glu Asn Gly Pro Val Gly Leu Lys Phe Glu
                85                  90                  95

Val Phe Asn Gly Ser Ala Pro Ser Leu Phe Ser Thr Thr Tyr Ser Trp
            100                 105                 110

Thr Lys Met Ala Asn Ile Ile Phe Leu Asp Gln Pro Val Gly Ser Gly
        115                 120                 125

Phe Ser Tyr Ser Lys Thr Pro Ile Asp Lys Thr Gly Asp Ile Ser Glu
    130                 135                 140

Val Lys Arg Thr His Glu Phe Leu Gln Lys Trp Leu Ser Arg His Pro
145                 150                 155                 160

Gln Tyr Phe Ser Asn Pro Leu Tyr Val Val Gly Asp Ser Tyr Ser Gly
                165                 170                 175

Met Ile Val Pro Ala Leu Val Gln Glu Ile Ser Gln Gly Asn Tyr Ile
            180                 185                 190

Cys Cys Glu Pro Pro Ile Asn Leu Gln Gly Tyr Met Leu Gly Asn Pro
        195                 200                 205

Val Thr Tyr Met Asp Phe Glu Gln Asn Phe Arg Ile Pro Tyr Ala Tyr
    210                 215                 220

Gly Met Gly Leu Ile Ser Asp Glu Ile Tyr Glu Pro Met Lys Arg Ile
225                 230                 235                 240

Cys Asn Gly Asn Tyr Tyr Asn Val Asp Pro Ser Asn Thr Gln Cys Leu
                245                 250                 255

Lys Leu Thr Glu Glu Tyr His Lys Cys Thr Ala Lys Ile Asn Ile His
            260                 265                 270

His Ile Leu Thr Pro Asp Cys Asp Val Thr Asn Val Thr Ser Pro Asp
        275                 280                 285

Cys Tyr Tyr Tyr Pro Tyr His Leu Ile Glu Cys Trp Ala Asn Asp Glu
    290                 295                 300

Ser Val Arg Glu Ala Leu His Ile Glu Lys Gly Ser Lys Gly Lys Trp
305                 310                 315                 320

Ala Arg Cys Asn Arg Thr Ile Pro Tyr Asn His Asp Ile Val Ser Ser
                325                 330                 335

Ile Pro Tyr His Met Asn Asn Ser Ile Ser Gly Tyr Arg Ser Leu Ile
            340                 345                 350

Tyr Ser Gly Asp His Asp Ile Ala Val Pro Phe Leu Ala Thr Gln Ala
        355                 360                 365

Trp Ile Arg Ser Leu Asn Tyr Ser Pro Ile His Asn Trp Arg Pro Trp
    370                 375                 380

Met Ile Asn Asn Gln Ile Ala Gly Tyr Thr Arg Ala Tyr Ser Asn Lys
385                 390                 395                 400

Met Thr Phe Ala Thr Ile Lys Gly Gly Gly His Thr Ala Glu Tyr Arg
                405                 410                 415

Pro Asn Glu Thr Phe Ile Met Phe Gln Arg Trp Ile Ser Gly Gln Pro
            420                 425                 430

Leu
```

```
<210> SEQ ID NO 32
<211> LENGTH: 493
<212> TYPE: PRT
<213> ORGANISM: Atropa belladonna

<400> SEQUENCE: 32

Met Glu Lys Leu Leu Val Val Val Leu Leu Leu Val Thr Ile Leu Ala
1               5                   10                  15

Leu Gly Ala Ala Ala Glu Arg Thr Arg Val Thr His Leu Lys Gly Phe
            20                  25                  30

Asp Gly Pro Leu Pro Phe Ser Leu Glu Thr Gly Tyr Val Glu Val Asp
        35                  40                  45

Glu Thr His Gly Val Glu Leu Phe Tyr Tyr Phe Ile Glu Ser Glu Arg
    50                  55                  60

Lys Pro Ala Glu Asp Pro Val Ile Leu Trp Val Ser Gly Gly Pro Gly
65                  70                  75                  80

Cys Ser Gly Leu Asn Ala Leu Phe Phe Glu Ile Gly Pro Leu Lys Leu
                85                  90                  95

Asp Met Ala Ser Tyr Ala Ala Thr Gly Gly Lys Gly Phe Pro Gly Leu
            100                 105                 110

Leu Tyr Phe Glu Asp Ala Trp Thr Lys Ala Ser Asn Met Ile Phe Leu
        115                 120                 125

Asp Ala Pro Val Gly Ala Gly Phe Ser Tyr Ala Arg Gln Thr Glu Gly
    130                 135                 140

Leu Asn Ser Thr Val Thr Gly Leu Gly Arg His Val Arg Val Phe Leu
145                 150                 155                 160

Gln Lys Trp Met Ala Gln His Pro Glu Leu Ala Ser Asn Pro Leu Tyr
                165                 170                 175

Ile Gly Gly Asp Ser Phe Ser Gly Tyr Thr Val Thr Val Ser Ala Leu
            180                 185                 190

Glu Val Ala Asn His Pro Ala Ala Ser Ser Glu Leu Asn Leu Lys Gly
        195                 200                 205

Tyr Met Val Gly Asn Ala Arg Gly Glu Val Asn Asn Asp Asn Ala Cys
    210                 215                 220

Arg Ile Pro Tyr Leu His Gly Met Gly Leu Ile Ser Asp Glu Leu Tyr
225                 230                 235                 240

Glu Ala Ala Leu Ser Ser Cys Val Val Gly Thr Asp Ser Lys Asn Lys
                245                 250                 255

Gln Gln Gln Ser Ala Ala Arg Cys Ser Glu Ala Gln Gln Ala Ile Ser
            260                 265                 270

Glu Ala Thr Thr Asp Leu Asn Pro Ala His Ile Leu Glu Pro Ala Cys
        275                 280                 285

Gly Ala Asp Phe Ser Pro Arg Ala Pro Tyr Leu Ser Leu Thr Thr Pro
    290                 295                 300

Ser Ser Ser Ser Ser Ser Ser Ser Ser Ser Ser Ser Ser Ser Ser Ser
305                 310                 315                 320

Ser Tyr Tyr Tyr Leu Ser Leu Ser Ser Val Arg Ser Arg Thr Pro Thr
                325                 330                 335

Lys Glu Met Leu Leu Glu Cys Arg Val Tyr Gly Tyr Glu Leu Ser Tyr
            340                 345                 350

Met Trp Ala Asn Asp Ala Glu Val Arg Glu Asn Leu Gly Val Arg Glu
        355                 360                 365

Gly Thr Ile Gly Asp Gly Asn Trp Ala Leu Cys Pro Glu Val Pro Lys
    370                 375                 380
```

-continued

```
Leu His Leu Thr Asn Asp Val Pro Thr Thr Val Pro Tyr His Arg Arg
385                 390                 395                 400

Leu Thr Gln Arg Gly Tyr Arg Ala Leu Val Tyr Asn Gly Asp His Asp
                405                 410                 415

Leu Leu Met Thr His Ile Gly Thr His Ala Trp Ile Arg Ser Leu Gly
            420                 425                 430

Tyr Pro Val Val Ala Pro Trp Arg Ala Trp Tyr Ser Asn Asn Glu Val
        435                 440                 445

Ala Gly Phe Thr Val Glu Tyr Ser Asn Asn Leu Thr Phe Ala Thr Val
    450                 455                 460

Lys Gly Ala Gly His Met Ala Pro Glu Ser Arg Pro Lys Gln Cys Leu
465                 470                 475                 480

Asp Met Val Arg Arg Trp Ile Ser Pro Ala Gly Lys Leu
                485                 490


<210> SEQ ID NO 33
<211> LENGTH: 532
<212> TYPE: PRT
<213> ORGANISM: Avena strigosa

<400> SEQUENCE: 33

Met Lys Ala Phe Thr Ser Leu Leu Cys Gly Leu Gly Leu Ser Thr Thr
1               5                   10                  15

Leu Ala Lys Ala Ile Ser Leu Gln Arg Pro Leu Gly Leu Asp Lys Asp
            20                  25                  30

Val Leu Leu Gln Ala Ala Glu Lys Phe Gly Leu Asp Leu Asp Leu Asp
        35                  40                  45

His Leu Leu Lys Glu Leu Asp Ser Asn Val Leu Asp Ala Trp Ala Gln
    50                  55                  60

Ile Glu His Leu Tyr Pro Asn Gln Val Met Ser Leu Glu Thr Ser Thr
65                  70                  75                  80

Lys Pro Lys Phe Pro Glu Ala Ile Lys Thr Lys Lys Asp Trp Asp Phe
                85                  90                  95

Val Val Lys Asn Asp Ala Ile Glu Asn Tyr Gln Leu Arg Val Asn Lys
            100                 105                 110

Ile Lys Asp Pro Lys Ile Leu Gly Ile Asp Pro Asn Val Thr Gln Tyr
        115                 120                 125

Thr Gly Tyr Leu Asp Val Glu Asp Glu Asp Lys His Phe Phe Phe Trp
    130                 135                 140

Thr Phe Glu Ser Arg Asn Asp Pro Ala Lys Asp Pro Val Ile Leu Trp
145                 150                 155                 160

Leu Asn Gly Gly Pro Gly Cys Ser Ser Leu Thr Gly Leu Phe Phe Glu
                165                 170                 175

Leu Gly Pro Ser Ser Ile Gly Pro Asp Leu Lys Pro Ile Gly Asn Pro
            180                 185                 190

Tyr Ser Trp Asn Ser Asn Ala Thr Val Ile Phe Leu Asp Gln Pro Val
        195                 200                 205

Asn Val Gly Phe Ser Tyr Ser Gly Ser Ser Gly Val Ser Asn Thr Val
    210                 215                 220

Ala Ala Gly Lys Asp Val Tyr Asn Phe Leu Glu Leu Phe Phe Asp Gln
225                 230                 235                 240

Phe Pro Glu Tyr Val Asn Lys Gly Gln Asp Phe His Ile Ala Gly Glu
                245                 250                 255

Ser Tyr Ala Gly His Tyr Ile Pro Val Phe Ala Ser Glu Ile Leu Ser
            260                 265                 270
```

His Lys Asp Arg Asn Phe Asn Leu Thr Ser Val Leu Ile Gly Asn Gly
275 280 285

Leu Thr Asp Pro Leu Thr Gln Tyr Asn Tyr Tyr Glu Pro Met Ala Cys
290 295 300

Gly Glu Gly Gly Glu Pro Ser Val Leu Pro Ser Glu Glu Cys Ser Ala
305 310 315 320

Met Glu Asp Ser Leu Glu Arg Cys Leu Gly Leu Ile Glu Ser Cys Tyr
325 330 335

Asp Ser Gln Ser Val Trp Ser Cys Val Pro Ala Thr Ile Tyr Cys Asn
340 345 350

Asn Ala Gln Leu Ala Pro Tyr Gln Arg Thr Gly Arg Asn Val Tyr Asp
355 360 365

Ile Arg Lys Asp Cys Glu Gly Gly Asn Leu Cys Tyr Pro Thr Leu Gln
370 375 380

Asp Ile Asp Asp Tyr Leu Asn Gln Asp Tyr Val Lys Glu Ala Val Gly
385 390 395 400

Ala Glu Val Asp His Tyr Glu Ser Cys Asn Phe Asp Ile Asn Arg Asn
405 410 415

Phe Leu Phe Ala Gly Asp Trp Met Lys Pro Tyr His Thr Ala Val Thr
420 425 430

Asp Leu Leu Asn Gln Asp Leu Pro Ile Leu Val Tyr Ala Gly Asp Lys
435 440 445

Asp Phe Ile Cys Asn Trp Leu Gly Asn Lys Ala Trp Thr Asp Val Leu
450 455 460

Pro Trp Lys Tyr Asp Glu Glu Phe Ala Ser Gln Lys Val Arg Asn Trp
465 470 475 480

Thr Ala Ser Ile Thr Asp Glu Val Ala Gly Glu Val Lys Ser Tyr Lys
485 490 495

His Phe Thr Tyr Leu Arg Val Phe Asn Gly Gly His Met Val Pro Phe
500 505 510

Asp Val Pro Glu Asn Ala Leu Ser Met Val Asn Glu Trp Ile His Gly
515 520 525

Gly Phe Ser Leu
530

<210> SEQ ID NO 34
<211> LENGTH: 444
<212> TYPE: PRT
<213> ORGANISM: Triticum aestivum

<400> SEQUENCE: 34

Val Glu Pro Ser Gly His Ala Ala Asp Arg Ile Ala Arg Leu Pro Gly
1 5 10 15

Gln Pro Ala Val Asp Phe Asp Met Tyr Ser Gly Tyr Ile Thr Val Asp
20 25 30

Glu Gly Ala Gly Arg Ser Leu Phe Tyr Leu Leu Gln Glu Ala Pro Glu
35 40 45

Asp Ala Gln Pro Ala Pro Leu Val Leu Trp Leu Asn Gly Gly Pro Gly
50 55 60

Cys Ser Ser Val Ala Tyr Gly Ala Ser Glu Glu Leu Gly Ala Phe Arg
65 70 75 80

Val Lys Pro Arg Gly Ala Gly Leu Val Leu Asn Glu Tyr Arg Trp Asn
85 90 95

Lys Val Ala Asn Val Leu Phe Leu Asp Ser Pro Ala Gly Val Gly Phe

-continued

```
            100                 105                 110

Ser Tyr Thr Asn Thr Ser Ser Asp Ile Tyr Thr Ser Gly Asp Asn Arg
        115                 120                 125

Thr Ala His Asp Ser Tyr Ala Phe Leu Ala Lys Trp Phe Glu Arg Phe
    130                 135                 140

Pro His Tyr Lys Tyr Arg Asp Phe Tyr Ile Ala Gly Glu Ser Tyr Ala
145                 150                 155                 160

Gly His Tyr Val Pro Glu Leu Ser Gln Leu Val His Arg Ser Lys Asn
                165                 170                 175

Pro Val Ile Asn Leu Lys Gly Phe Met Val Gly Asn Gly Leu Ile Asp
            180                 185                 190

Asp Tyr His Asp Tyr Val Gly Thr Phe Glu Phe Trp Trp Asn His Gly
        195                 200                 205

Ile Val Ser Asp Asp Thr Tyr Arg Arg Leu Lys Glu Ala Cys Leu His
    210                 215                 220

Asp Ser Phe Ile His Pro Ser Pro Ala Cys Asp Ala Ala Thr Asp Val
225                 230                 235                 240

Ala Thr Ala Glu Gln Gly Asn Ile Asp Met Tyr Ser Leu Tyr Thr Pro
                245                 250                 255

Val Cys Asn Ile Thr Ser Ser Ser Ser Ser Ser Ser Ser Ser Leu Ser
            260                 265                 270

Gln Gln Arg Arg Ser Arg Gly Arg Tyr Pro Trp Leu Thr Gly Ser Tyr
        275                 280                 285

Asp Pro Cys Thr Glu Arg Tyr Ser Thr Ala Tyr Tyr Asn Arg Arg Asp
    290                 295                 300

Val Gln Met Ala Leu His Ala Asn Val Thr Gly Ala Met Asn Tyr Thr
305                 310                 315                 320

Trp Ala Thr Cys Ser Asp Thr Ile Asn Thr His Trp His Asp Ala Pro
                325                 330                 335

Arg Ser Met Leu Pro Ile Tyr Arg Glu Leu Ile Ala Ala Gly Leu Arg
            340                 345                 350

Ile Trp Val Phe Ser Gly Asp Thr Asp Ala Val Val Pro Leu Thr Ala
        355                 360                 365

Thr Arg Tyr Ser Ile Gly Ala Leu Gly Leu Pro Thr Thr Thr Ser Trp
    370                 375                 380

Tyr Pro Trp Tyr Asp Asp Gln Glu Val Gly Gly Trp Ser Gln Val Tyr
385                 390                 395                 400

Lys Gly Leu Thr Leu Val Ser Val Arg Gly Ala Gly His Glu Val Pro
                405                 410                 415

Leu His Arg Pro Arg Gln Ala Leu Val Leu Phe Gln Tyr Phe Leu Gln
            420                 425                 430

Gly Lys Pro Met Pro Gly Gln Thr Lys Asn Ala Thr
        435                 440


<210> SEQ ID NO 35
<211> LENGTH: 476
<212> TYPE: PRT
<213> ORGANISM: Saccharomycescerevisiae

<400> SEQUENCE: 35

Met Lys Lys Thr Ile Val Val Pro Ile Leu Lys Tyr His Lys Ile Leu
1               5                   10                  15

Leu Leu Phe Val Leu Ile Leu Val Leu Leu Leu Cys Pro Leu Ile Glu
            20                  25                  30
```

-continued

```
Ala Ala Gly Thr Pro Val Lys Tyr Leu Pro Gly Phe Gly Pro Leu Pro
        35                  40                  45

Phe Glu Phe Glu Thr Gly Tyr Val Gly Leu Gly Glu Ser Glu Glu Val
    50                  55                  60

Gln Leu Phe Tyr Tyr Phe Phe Lys Ser Glu Ser Asn Pro Glu Val Asp
65                  70                  75                  80

Pro Leu Ile Leu Trp Ile Thr Gly Gly Pro Gly Cys Gly Ala Leu Asn
                85                  90                  95

Ala Ile Thr Thr Glu Leu Gly Pro Val Leu Leu Asp Ala Lys Glu Tyr
            100                 105                 110

Asp Gly Ser Leu Pro Thr Leu Ser Leu Asn Pro Tyr Ser Tyr Thr Lys
        115                 120                 125

Val Ala Asn Ile Ile Phe Leu Asp Ser Pro Val Thr Gly Gly Phe Ser
    130                 135                 140

Tyr Ala Thr Thr Lys Glu Ala Asn His Ser Asp Asn Val Gln Met Ala
145                 150                 155                 160

Leu His Thr His Gln Phe Val Gln Lys Trp Leu Val Asp His Ser Glu
                165                 170                 175

Tyr Leu Ser Asn Asp Phe Tyr Val Ala Gly Asp Ser Tyr Ser Gly Ile
            180                 185                 190

Ser Val Pro Ile Ile Thr Gln Val Ile Ser Asp Gly Asn Glu Ala Gly
        195                 200                 205

Asn Lys Pro Trp Ile Asn Leu Lys Gly Tyr Ile Leu Gly Asn Ala Val
    210                 215                 220

Thr Phe Arg Pro Asp Glu Gln Asn Tyr Arg Ile Pro His Ala His Gly
225                 230                 235                 240

Leu Ala Leu Ile Ser Asp Glu Leu Tyr Lys Ser Leu Glu Ser Ser Cys
                245                 250                 255

Gly Gly Glu Tyr Gln Tyr Ile Asp Gln Thr Asn Thr His Cys Leu Gln
            260                 265                 270

His Val Gln Thr Phe Asn Arg Leu Val Ser Gly Ile Tyr Phe Glu His
        275                 280                 285

Ile Leu Glu Pro Ile Cys Asn Pro Val Ser Thr Lys Ala Arg His Leu
    290                 295                 300

Ser Pro Gln Arg Arg Tyr Leu Asn Gln Lys Leu Gly Gln Leu Lys Asn
305                 310                 315                 320

Pro Thr Met Leu Pro Gly Val Lys Cys Arg Asp Glu Trp His Leu Leu
                325                 330                 335

Ser Glu Ile Trp Val Asn Asp Glu Thr Val Gln Glu Ala Leu His Val
            340                 345                 350

Arg Lys Gly Thr His Gly Ile Trp Lys Gln Cys Pro Asn Tyr Glu Lys
        355                 360                 365

Met Pro Phe Thr Arg Thr Ile Asn Asn Thr Ile Pro Phe His Ala Ser
    370                 375                 380

Leu Ser Lys Lys Gly Tyr Arg Ser Leu Ile Tyr Ser Gly Asp Tyr Asp
385                 390                 395                 400

Leu Tyr Val Pro Phe Leu Ser Thr Gln Ala Trp Ile Arg Ser Leu Asn
                405                 410                 415

Tyr Ser Ile Asp Thr Glu Trp Arg Arg Trp Phe Val Asp Gly Gln Val
            420                 425                 430

Ala Gly Tyr Val Thr Thr Tyr Ser Asn Gln Met Thr Phe Thr Thr Ile
        435                 440                 445
```

-continued

```
Lys Gly Ala Gly His Thr Ala Pro Glu Tyr Lys Pro Ala Glu Cys Leu
    450                 455                 460

Ala Met Leu Lys Arg Trp Ile Tyr Tyr Gln Pro Leu
465                 470                 475
```

TROPANE ALKALOID (TA) PRODUCING NON-PLANT HOST CELLS, AND METHODS OF MAKING AND USING THE SAME

CROSS-REFERENCING

This application is a § 371 national phase of International Application No. PCT/US2020/021577, filed on Mar. 6, 2020, which claims the benefit of U.S. provisional application Ser. No. 62/815,709, filed on Mar. 8, 2019, 62/848,419, filed on May 15, 2019 and 62/891,771, filed on Aug. 26, 2019, which applications are incorporated by reference herein.

GOVERNMENT RIGHTS

This invention was made with Government support under contracts GM110699 and AT007886 awarded by the National Institutes of Health. The Government has certain rights in the invention.

INTRODUCTION

Tropane alkaloids (TAs) are a class of anticholinergic secondary metabolites produced by plants of the nightshade family (Solanaceae). Several TAs, including atropine, hyoscyamine, and scopolamine, are classified as essential medicines by the World Health Organization for the treatment of diverse neurological disorders such as organophosphate and nerve agent poisoning, gastrointestinal spasms, and cardiac arrhythmia, as well as to control symptoms of Parkinson's disease. As such, an adequate and consistent supply of these TA molecules so that they are available to researchers and physicians is of interest. Current supply chains for medicinal TAs rely on extraction from unsustainable and geographically restricted plant monocultures, in which TAs accumulate to only 0.2-4% dry weight, and which are susceptible to pests, changes in land use, and climate. No total chemical syntheses for TAs from simple feedstocks have yet proven sufficiently economical for industrial use due to difficulties arising from TA stereochemistry. Moreover, poor economies of scale and long generation times have thus far rendered the engineering of transgenic plants or plant cultures with improved TA production an unviable strategy for sourcing these compounds. As such, methods for preparing TAs are of interest.

SUMMARY

This invention includes non-plant organisms engineered for the production of diverse tropane alkaloids (TAs) from precursors and sugar. For example, included in this invention are engineered microbial strains for the production of medicinal TAs, which are hereby defined as naturally occurring TAs with established uses in current medical practice, including hyoscyamine, atropine, anisodamine, and scopolamine, and precursors and derivatives thereof. Also included in this invention are engineered microbial strains for the production of non-medicinal TAs, which are hereby defined as naturally occurring TAs without established uses in current medical practice but which may possess bioactivities of medicinal interest, including calystegines, cocaine, and precursors and derivatives thereof. This invention further includes engineered microbial strains for the production of non-natural TAs, which are hereby defined as TAs not produced by unmodified organisms, such as TAs produced via esterification of acyl donor and acyl acceptor compounds which are not esterified in naturally-occurring organisms, including derivatives of medicinal TAs and derivatives of non-medicinal TAs. An example of the schemes included in this invention are detailed in FIGS. 1-3.

The invention encompasses methods of producing pseudotropine and alkaloids derived from pseudotropine, for example calystegines, using microorganisms engineered to express at least one heterologous enzyme as microbial catalysts. This invention further includes methods of producing diverse compounds which can be used as acyl donors for the biosynthesis of TA scaffolds using microorganisms engineered to express at least one heterologous enzyme as microbial catalysts. This invention also includes methods of esterifying acyl donors and acceptors for the production of TA scaffolds using microorganisms engineered to express at least one heterologous enzyme as microbial catalysts. The invention further includes methods of modifying and culturing engineered microbial strains for the production of medicinal TAs such as hyoscyamine and scopolamine, non-medicinal TAs such as calystegines, and non-natural TAs such as those derived from esterification of tropine with acyl donor compounds other than 3-phenyllactic acid (PLA).

Host cells that are engineered to produce tropane alkaloids (TAs) that are of interest, such as hyoscyamine and scopolamine, are provided. TAs of interest may include TA precursors, TAs, and modifications of TAs, including derivatives of TAs. The host cells may have one or more modifications selected from: a feedback inhibition alleviating mutation in an enzyme gene; a transcriptional modulation modification of a biosynthetic enzyme gene; an inactivating mutation in an enzyme; and a heterologous coding sequence. Also provided are methods of producing a TA of interest using the host cells and compositions, e.g., kits, systems etc., that find use in methods of the invention.

An aspect of the invention provides a method for forming a product stream having a tropane alkaloid (TA) product. The method comprises providing engineered non-plant cells and a feedstock including nutrients and water to a batch reactor, which engineered non-plant cells have at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. Additionally, the method comprises, in the batch reactor, subjecting the engineered non-plant cells to fermentation by incubating the engineered non-plant cells for a time period of at least about 5 minutes to produce a solution comprising the TA product and cellular material. The method also comprises using at least one separation unit to separate the TA product from the cellular material to provide said product stream comprising the TA product.

In another aspect, the invention provides a method for forming a product stream having a TA product. The method comprises providing engineered non-plant cells and a feedstock including nutrients and water to a reactor. The method also comprises, in the reactor, subjecting the engineered non-plant cells to fermentation by incubating the engineered yeast cells for a time period of at least about 5 minutes (e.g., 5 minutes or longer) to produce a solution comprising cellular material and the TA product. Additionally, the method comprises using at least one separation unit to separate the TA product from the cellular material to provide the product stream comprising the TA product.

Another aspect of the invention provides an engineered non-plant cell that produces a tropane alkaloid (TA) product, the engineered non-plant cell having at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. The engineered non-plant cell comprises at least one heterologous coding sequence encoding at least one enzyme that is selected from the group of arginine decarboxylase, agmatine ureohydrolase, agmatinase, putrescine N-methyltransferase, N-methylputrescine oxidase, pyrrolidine ketide synthase, tropinone synthase, cytochrome P450 reductase, tropinone reductase, phenylpyruvate reductase, 3-phenyllactic acid UDP-glucosyltransferase 84A27, littorine synthase, littorine mutase, hyoscyamine dehydrogenase, hyoscyamine 6β-hydroxylase/dioxygenase, and cocaine synthase. In some examples, the engineered non-plant cell comprises a plurality of heterologous coding sequences encoding an enzyme that is selected from the group of arginine decarboxylase, agmatine ureohydrolase, agmatinase, putrescine N-methyltransferase, N-methylputrescine oxidase, pyrrolidine ketide synthase, tropinone synthase, cytochrome P450 reductase, tropinone reductase, phenylpyruvate reductase, 3-phenyllactic acid UDP-glucosyltransferase 84A27, littorine synthase, littorine mutase, hyoscyamine dehydrogenase, hyoscyamine 6β-hydroxylase/dioxygenase, and cocaine synthase. In some examples, the heterologous coding sequences may be operably connected. Heterologous coding sequences that are operably connected may be within the same pathway of producing a particular tropane alkaloid product. In some examples, the engineered non-plant cell comprises one or more modifications to intracellular compartmentalization that is selected from the group including, but not limited to, modified intracellular trafficking of enzymes, modified intracellular localization of enzymes, and modified intracellular transport of metabolites.

In another aspect of the invention, a therapeutic agent is provided. The therapeutic agent comprises a tropane alkaloid product.

BRIEF DESCRIPTION OF THE FIGURES

The invention is best understood from the following detailed description when read in conjunction with the accompanying drawings. It is emphasized that, according to common practice, the various features of the drawings are not-to-scale. On the contrary, the dimensions of the various features are arbitrarily expanded or reduced for clarity. Included in the drawings are the following figures.

FIG. 14 shows an in silico prediction of subcellular localization for NMPy biosynthetic genes in plant and yeast/fungal cells using the SherLoc2 web server. Values and coloring indicate probability scores (0 to 1) for localization to each compartment: CYT, cytosol; NUC, nucleus; VAC, vacuole; CHL, chloroplast; MIT, mitochondria; POX, peroxisome.

Figure 33:
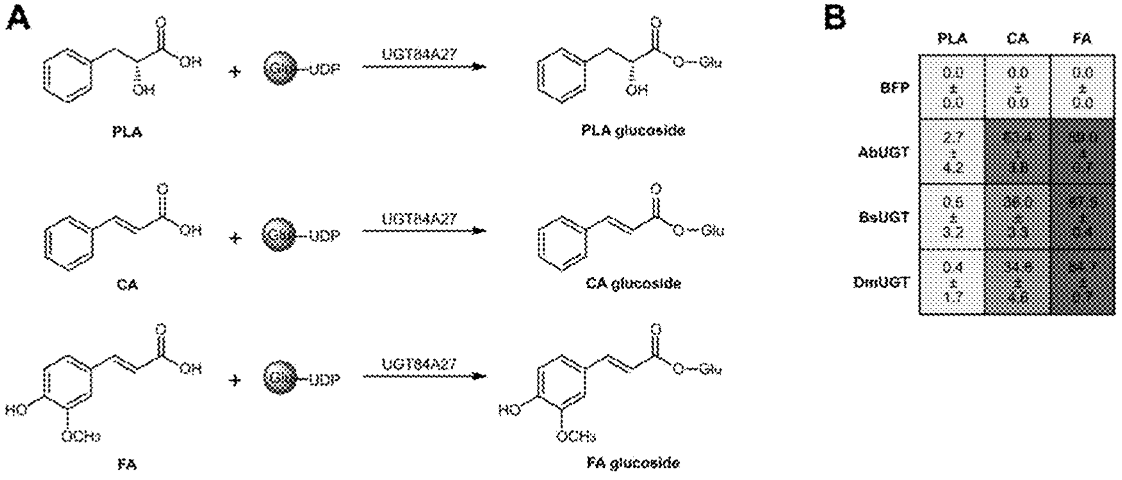
FIG. 33 illustrates the substrate specificity of UDP-glucosyltransferase 84A27 (UGT84A27) orthologs from TA-producing Solanaceae expressed in engineered yeast. This figure shows a comparison of the activity of UGT84A27 orthologs on three different phenylpropanoid compounds expressed in engineered yeast. (A) Phenylpropanoids tested as glucose (Glu) acceptors for UGT84A27 in engineered yeast. Top, (D)-3-phenyllactic acid (PLA); middle, trans-cinnamic acid (CA); bottom, trans-ferulic acid (FA). (B) Heatmap of percent conversion of fed phenylpropanoids to glucosides by yeast engineered for UGT84A27 expression. UGT84A27 orthologs or a BFP negative control were expressed from low-copy plasmids in CSY1251. Transformed cells were cultured in selective media supplemented with 500 μM PLA, CA, or FA for 72 h prior to LC-MS/MS analysis. Data represent the mean of n=3 biologically independent samples ±standard deviation.
Figure 34:
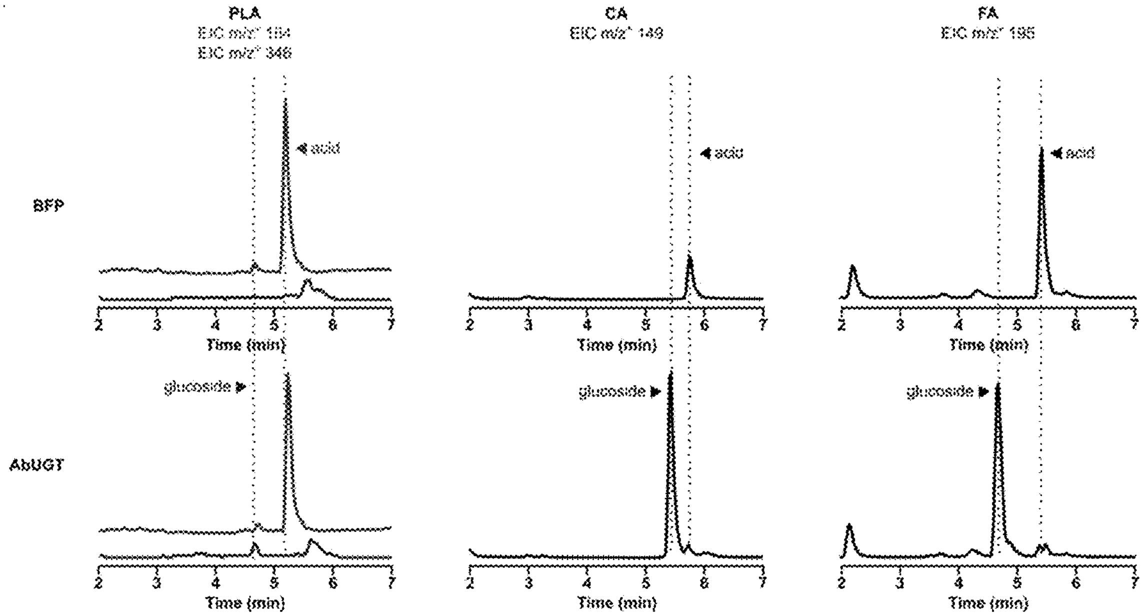

FIG. 34 illustrates an example of chromatographic and mass spectrometric analysis of UGT84A27 activity. This figure depicts representative LC-MS/MS traces showing conversion of PLA, CA, and FA to cognate glucosides by AbUGT in CSY1251 cultured as in FIG. 33B for 120 h to enable more complete glucosylation. For PLA, acid (top trace in each panel) and glucoside (bottom trace in each panel) were distinguished by different $NH_4^+$ adduct parent masses as well as different retention times. For CA and FA, rapid fragmentation necessitated detection of the glucosides based on the lower-retention peaks produced by their phenylpropanoid fragments.

Figure 35:
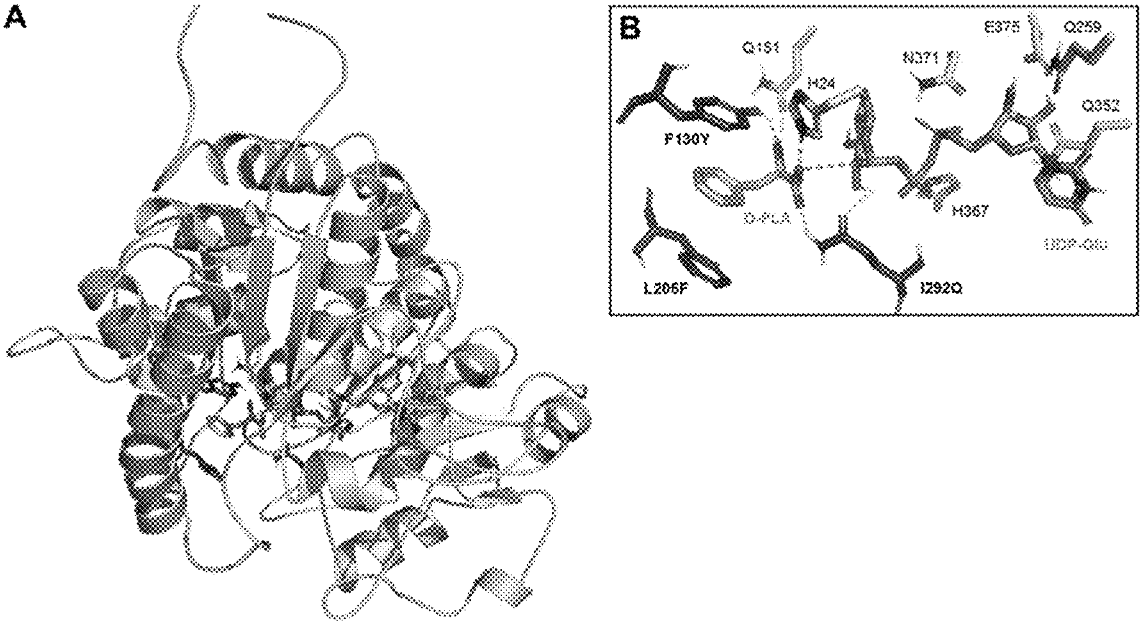

FIG. 35 illustrates structure-guided active site engineering of AbUGT to alter substrate specificity. This figure shows structural analysis of the AbUGT 3D structure to identify potential mutations which increase activity on PLA. (A) Homology model of AbUGT84A27 constructed based on the crystal structure of *Arabidopsis thaliana* salicylate UDP-glucosyltransferase UGT74F2 with bound UDP (PDB: 5V2K). PLA (orange) is shown in the preferred binding pose with UDP-glucose (pink) based on docking simulations. (B) Zoomed view of AbUGT active site with docked D-PLA and UDP-glucose. Potential mutations identified to improve PLA selectivity (F130Y, L205F, 12920) are shown; dashed lines indicate putative polar/hydrogen bond interactions.

FIG. 36 illustrates the substrate specificity of AbUGT84A27 active site mutants. This figure shows a heatmap of percent conversion of fed phenylpropanoids to glucosides by yeast engineered for expression of AbUGT mutants. AbUGT wild-type, active site mutants, or a BFP negative control were expressed from low-copy plasmids in CSY1251. Transformed cells were cultured in selective media supplemented with 500 μM PLA, CA, or FA for 72 h prior to LC-MS/MS analysis. Data represent the mean of n=3 biologically independent samples ±standard deviation.

Figure 37:
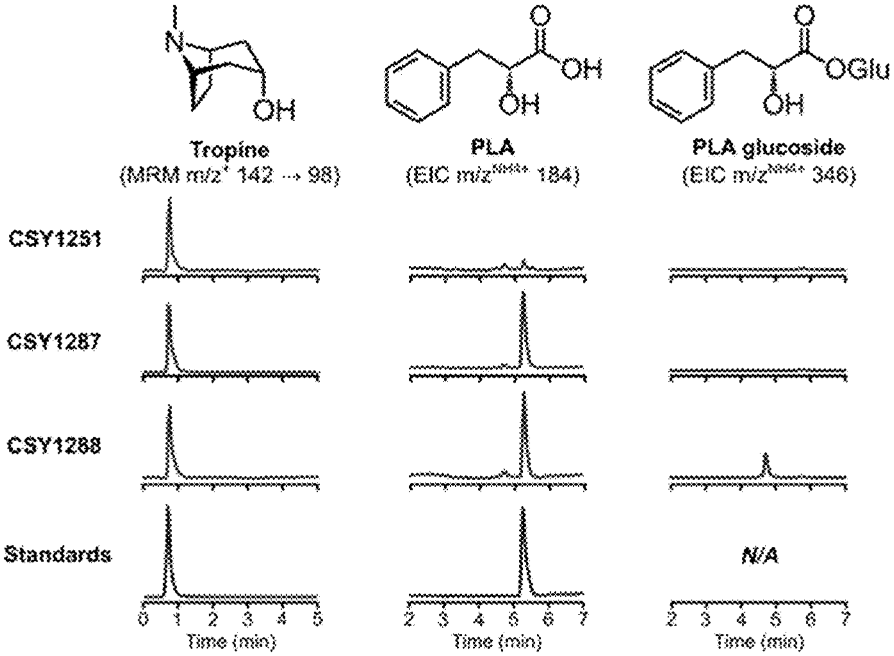

FIG. 37 shows LC-MS/MS chromatograms validating the step-wise biosynthesis of PLA glucoside in yeast engineered for tropine production. This figure shows multiple reaction monitoring (MRM) and extracted ion chromatogram (EIC) traces from culture media of yeast strains engineered for step-wise reconstitution of PLA glucoside. Strains were grown in non-selective media for 72 h prior to LC-MS/MS analysis of culture supernatant. Chromatogram traces are representative of three biological replicates.

Figure 38:
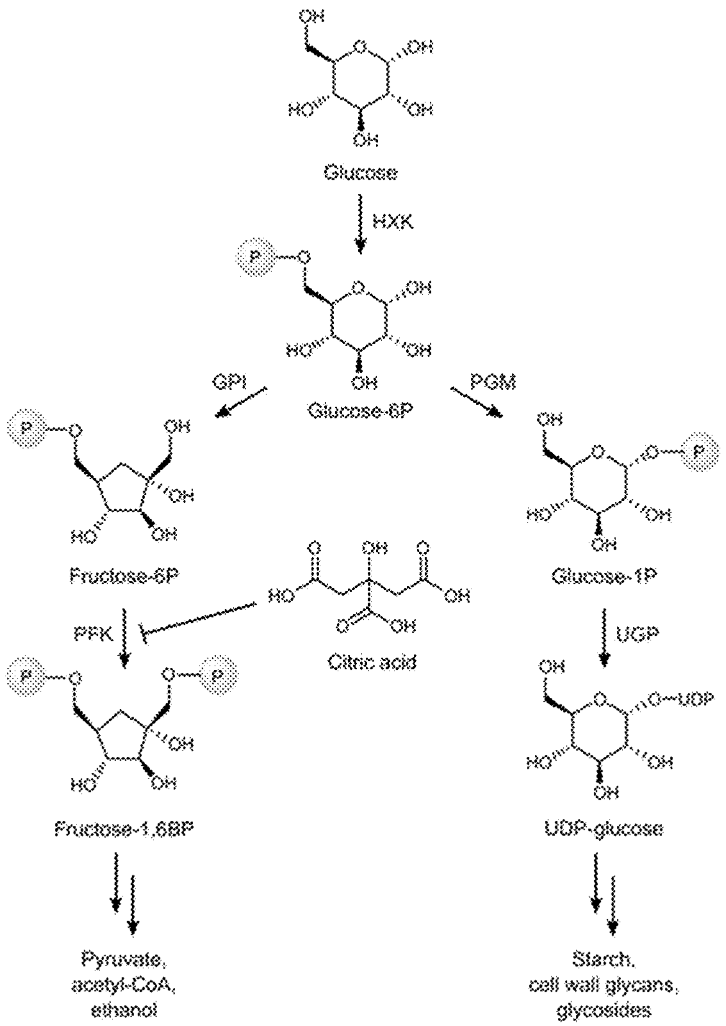

FIG. 38 shows a biosynthetic pathway schematic of the dual metabolic fates of glucose in yeast. This figure illustrates the effect of citrate on glucoside production via inhibition of glycolysis. Abbreviations: HXK, hexokinase; GPI, glucose-6-phosphate isomerase; PFK, phosphofructokinase; PGM, phosphoglucomutase; UGP, UDP-glucose pyrophosphorylase.

Figure 39:
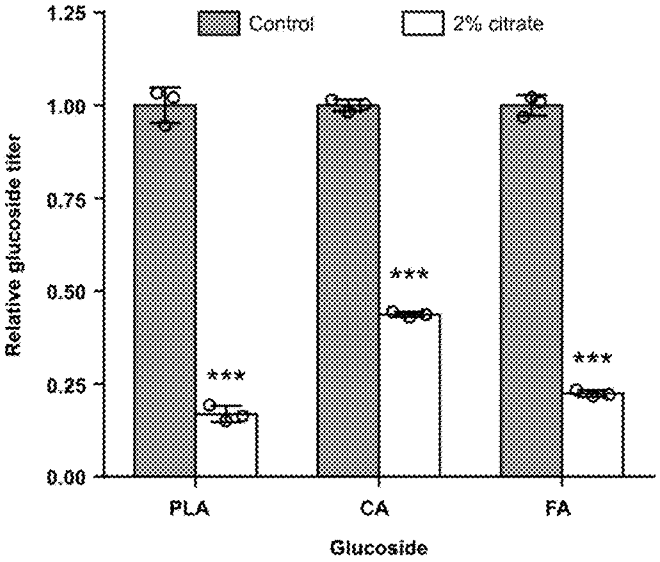

FIG. 39 illustrates the effect of citrate supplementation on heterologous glucoside production in engineered yeast. This figure shows the effect of 2% citrate supplementation on conversion of phenylpropanoid acids to glucosides by yeast engineered for AbUGT expression. Strain CSY1288 was cultured in non-selective media with or without 2% citrate and no additional supplementation to evaluate glucosylation of endogenously produced PLA, or with supplementation of 500 μM trans-cinnamic acid (CA) or trans-ferulic acid (FA). Cultures were grown for 72 h prior to LC-MS/MS analysis. Data represent the mean of n=3 biologically independent samples (open circles) and error bars show standard deviation. Student's two-tailed t-test: $^*P<0.05$, $^{}P<0.01$, $^{*}P<0.001$.

Figure 40:
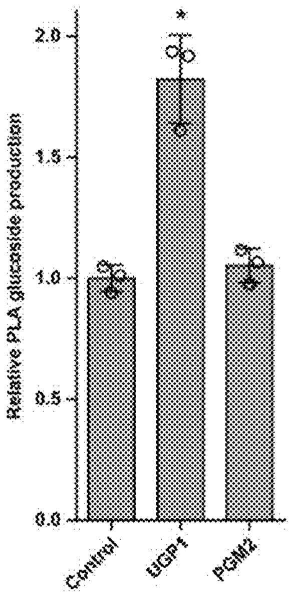

FIG. 40 shows relative PLA glucoside production in yeast strains engineered for overexpression of UDP-glucose biosynthetic enzymes. This figure illustrates the effect of overexpressing native enzymes involved in biosynthesis of the glucoside precursor UDP-glucose on production of PLA glucoside in engineered yeast. Enzymes or negative control (BFP) were expressed from low-copy plasmids in strain CSY1288. Strains were cultured for 72 h in selective media prior to LC-MS/MS analysis of metabolites in culture supernatant. Data represent the mean of n=3 biologically independent samples (open circles) and error bars show standard deviation. Student's two-tailed t-test: $^*P<0.05$, $^{}P<0.01$, $^{*}P<0.001$. Statistical significance is shown relative to the corresponding control.

Figure 41:
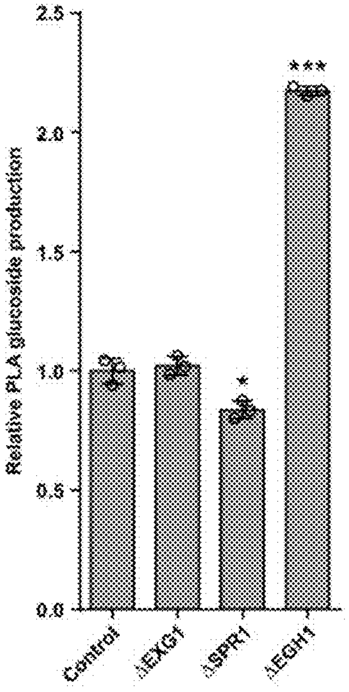

FIG. 41 shows relative PLA glucoside production in CSY1288 with disruptions to endogenous glucosidases. This figure illustrates the effect of disrupting each of three native glycosidase genes on accumulation of PLA glucoside in engineered yeast. Strains were cultured in non-selective media for 72 h prior to LC-MS/MS analysis of culture supernatant. Data represent the mean of n=3 biologically independent samples (open circles) and error bars show standard deviation. Student's two-tailed t-test: $^*P<0.05$, $^{}P<0.01$, $^{*}P<0.001$. Statistical significance is shown relative to the corresponding control.

Figure 42:
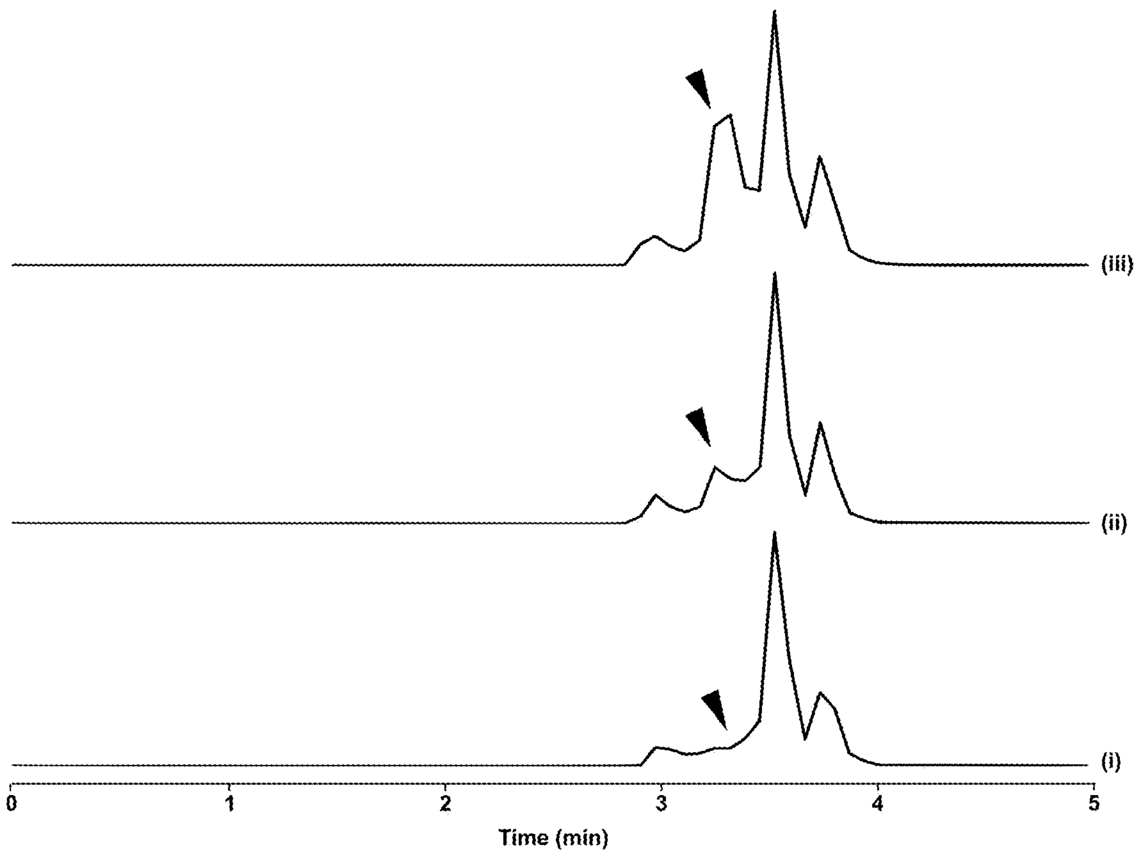

FIG. 42 shows LC-MS/MS chromatograms illustrating the production of the medicinal TA precursor hyoscyamine aldehyde from littorine in liquid culture for engineered yeast cells expressing AbCYP80F1. This figure shows LC-MS/MS analysis of yeast strains engineered to convert (R)-littorine to hyoscyamine aldehyde. Yeast strains are engineered to have a low-copy CEN/ARS plasmid harboring a LEU2 selection marker, a TDH3 promoter, and a coding sequence for littorine mutase CYP80F1 from *A. belladonna* (AbCYP80F1). Strains additionally have a second low-copy plasmid harboring a TRP1 selection marker, a TDH3 promoter, and a coding sequence for (i) BFP as a negative control, (ii) *S. cerevisiae* CPR (NCP1), or (iii) *A. thaliana* CPR (AtATR1). Yeast were grown from freshly transformed colonies in 300 μL selective media (-Leu--Trp) supplemented with 1 mM littorine in 96-well deep-well microtiter plates. After 48 hours of growth in a shaking incubator at 30° C. and 460 rpm, the yeast were pelleted and the media supernatant was analyzed by LC-MS/MS. Chromatogram traces show hyoscyamine aldehyde produced by these strains based on the most abundant MRM transition (m/z+× 288→124). Arrowheads indicate putative hyoscyamine aldehyde peak. Each trace is representative of three samples.

Figure 43:
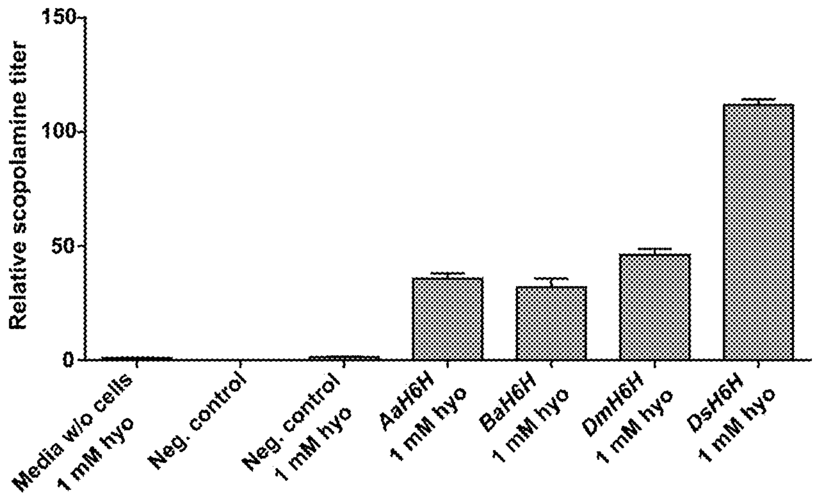

FIG. 43 illustrates the production of the medicinal TA scopolamine from the medicinal TA hyoscyamine in liquid cultures for engineered yeast cells expressing orthologs of hyoscyamine 6β-hydroxylase/dioxygenase (H6H). This figure shows the conversion of (5)-hyoscyamine to (S)-scopolamine by engineered yeast strains expressing H6H orthologs. Yeast strains are engineered to have a low-copy CEN/ARS plasmid harboring a LEU2 selection marker, a TDH3 promoter, and a coding sequence for BFP as a negative control or an H6H variant from *D. stramonium* (DsH6H), *A. acutangulus* (AaH6H), *B. arborea* (BaH6H), or *D. metel* (DmH6H). Yeast were grown from freshly transformed colonies in 300 μL selective media (-Leu) supplemented with 1 mM hyoscyamine in 96-well deep-well microtiter plates. After 48 hours of growth in a shaking incubator at 30° C. and 460 rpm, the yeast were pelleted and the media supernatant was analyzed by LC-MS/MS. Data represent the mean of three biological replicates and are normalized to the quantity of scopolamine contaminant in the fed hyoscyamine. Error bars represent standard deviation. Relative scopolamine titer was quantified based on the peak area of the m/z+ 304→138 MRM transition.

Figure 44:
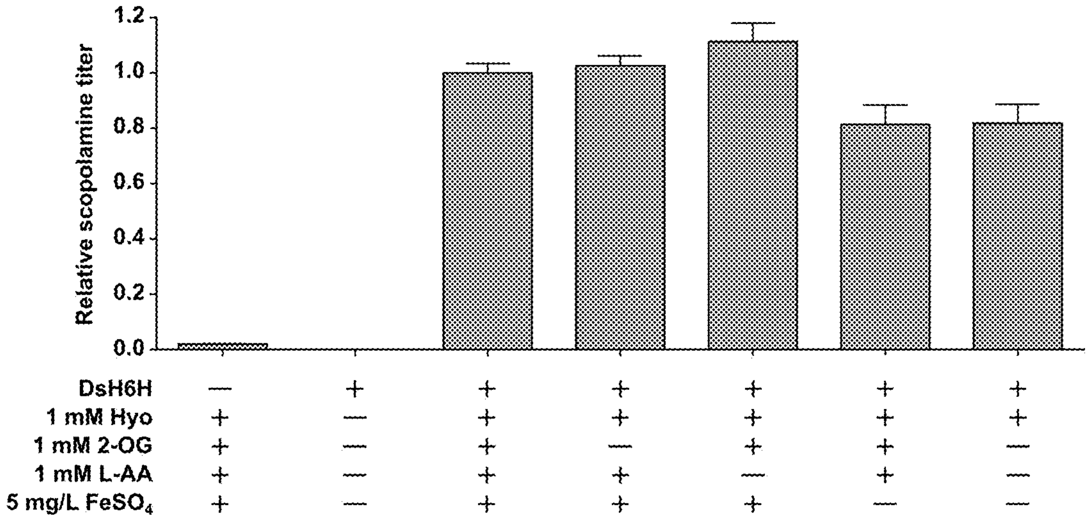

FIG. 44 illustrates the effect of cofactor availability and supplementation in media on the conversion of hyoscyamine to scopolamine in liquid cultures of engineered yeast cells expressing DsH6H. This figure shows the effect of cofactor supplementation on conversion of (S)-hyoscyamine to (S)-scopolamine in engineered yeast. Yeast strains are engineered to have a low-copy CEN/ARS plasmid harboring a LEU2 selection marker, a TDH3 promoter, and a coding sequence for (i) BFP as a negative control or (iii) hyoscyamine 6β-hydroxylase/dioxygenase from *D. stramonium* (DsH6H). Yeast were grown from freshly transformed colonies in 300 μL selective media (-Leu) supplemented with the indicated substrates and/or cofactors in 96-well deep-well microtiter plates. After 48 hours of growth in a shaking incubator at 30° C. and 460 rpm, the yeast were pelleted and the media supernatant was analyzed by LC-MS/MS. Relative (S)-scopolamine titers were quantified based on integrated peak area of the m/z+ 304→138 MRM transition and normalized to the strain expressing DsH6H and with all supplemented cofactors and substrates. Data represent mean of three biological replicates and error bars indicate standard deviation. Hyo, (S)-hyoscyamine; 2-OG, 2-oxoglutarate; L-AA, L-ascorbic acid.

Figure 45:
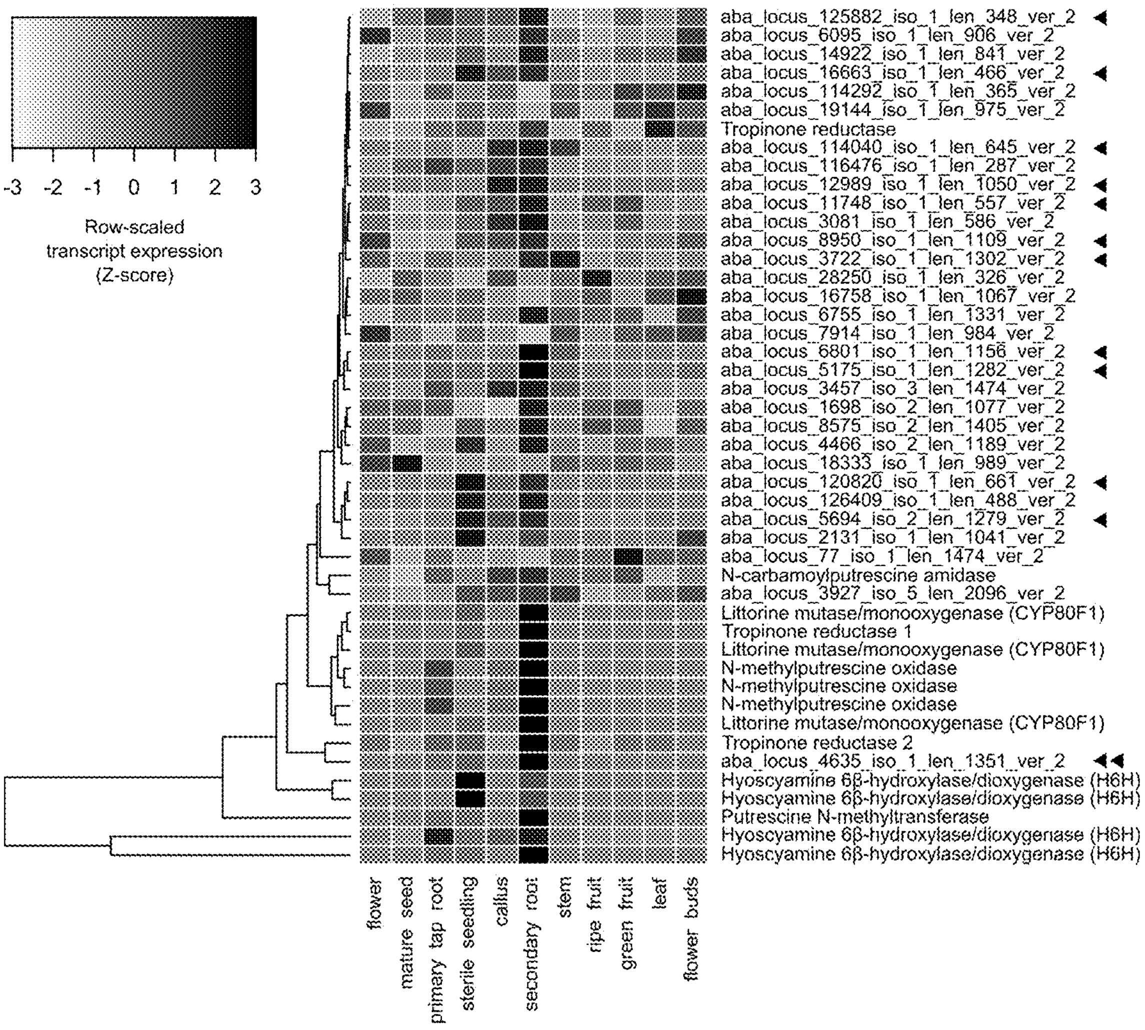

FIG. 45 shows a hierarchical clustering heatmap of hyoscyamine dehydrogenase gene candidates identified from the *A. belladonna* transcriptome via analysis of tissue coexpression data. This figure shows clustering of tissue-specific expression profiles of transcripts in the *A. belladonna* transcriptome which potentially encode enzymes with hyoscyamine dehydrogenase activity. Transcript expression for each candidate is scaled by row using a normal distribution. Dendrogram indicates hierarchical clustering of candidates by tissue-specific expression profile. Known TA pathway genes are identified by name; putative HDH candidates are indicated with locus ID. Black triangles indicate candidates screened for activity; double black triangle indicates candidate with experimentally verified HDH activity.

Figure 46:
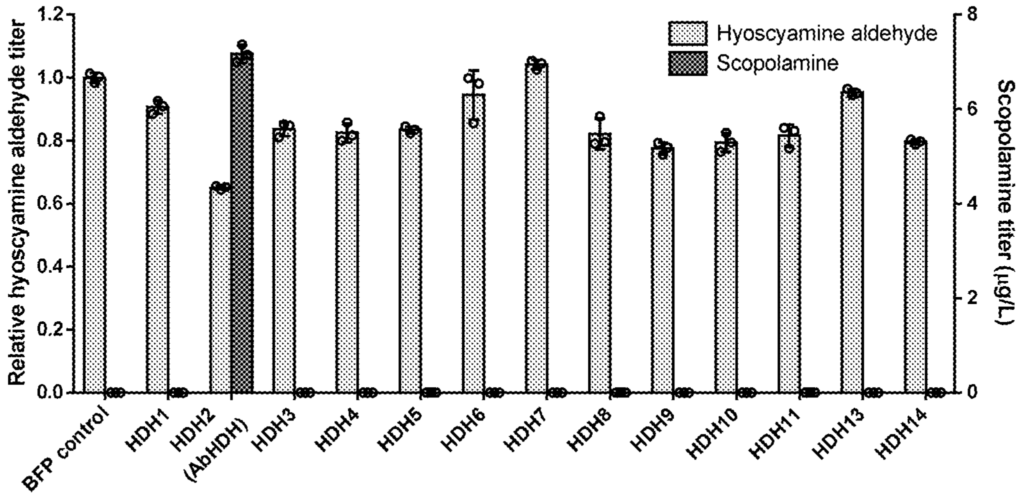

FIG. 46 illustrates the production of the medicinal TA scopolamine from littorine in liquid cultures of engineered yeast cells expressing hyoscyamine dehydrogenase (HDH) candidates. This figure illustrates the experimental screening for activity of HDH candidates identified from the transcriptome of *A. belladonna* in engineered yeast. Yeast strains are engineered to express *A. belladonna* littorine mutase (AbCYP80F1) and *D. stramonium* hyoscyamine 6β-hydroxylase/dioxygenase (DsH6H) from constitutive promoters within expression cassettes integrated into the genome, as well as one of each of the 13 HDH candidates from a low-copy CEN/ARS plasmid harboring a TRP1 selection marker and a TDH3 promoter. Yeast were grown from freshly transformed colonies in 300 μL selective media (-Trp) supplemented with 1 mM littorine in 96-well deep-well microtiter plates. After 72 hours of growth in a shaking incubator at 30° C. and 460 rpm, the yeast were pelleted and the media supernatant was analyzed by LC-MS/MS. Relative hyoscyamine aldehyde titers were quantified based on integrated peak area of the m/z⁺ 288→124 MRM transition and normalized to that of the engineered strain expressing BFP instead of an HDH candidate. (S)-scopolamine titers were quantified based on integrated peak area of the m/z⁺ 304→138 MRM transition and a standard curve of a genuine scopolamine standard. Data represent mean of three biological replicates and error bars indicate standard deviation.

Figure 47:
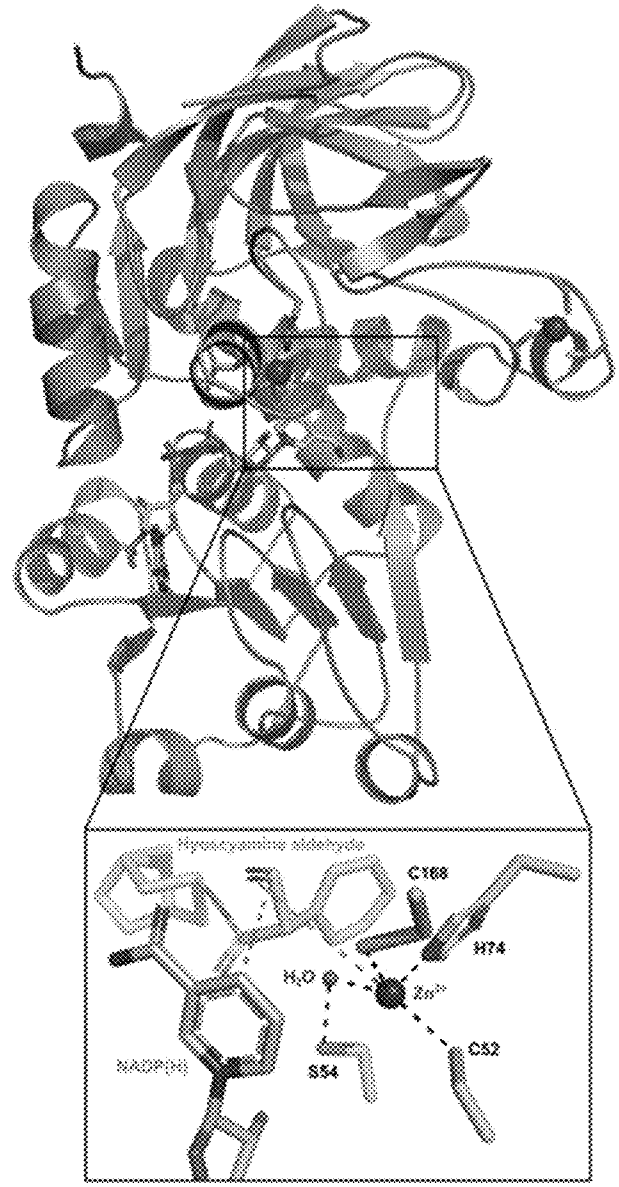

FIG. 47 illustrates the three-dimensional structure of hyoscyamine dehydrogenase from *A. belladonna*. This figure shows a cartoon representation of the structure of AbHDH as a homology model constructed based on the crystal structure of *Populus tremuloides* sinapyl alcohol dehydrogenase (PtSAD; PDB: 1YQD) as a template. NADPH and $Zn^{2+}$ are shown in the active site. The inset box shows a zoomed view of the AbHDH active site with NADPH and docked hyoscyamine aldehyde. Dashed lines indicate interactions important for catalysis.

Figure 48:
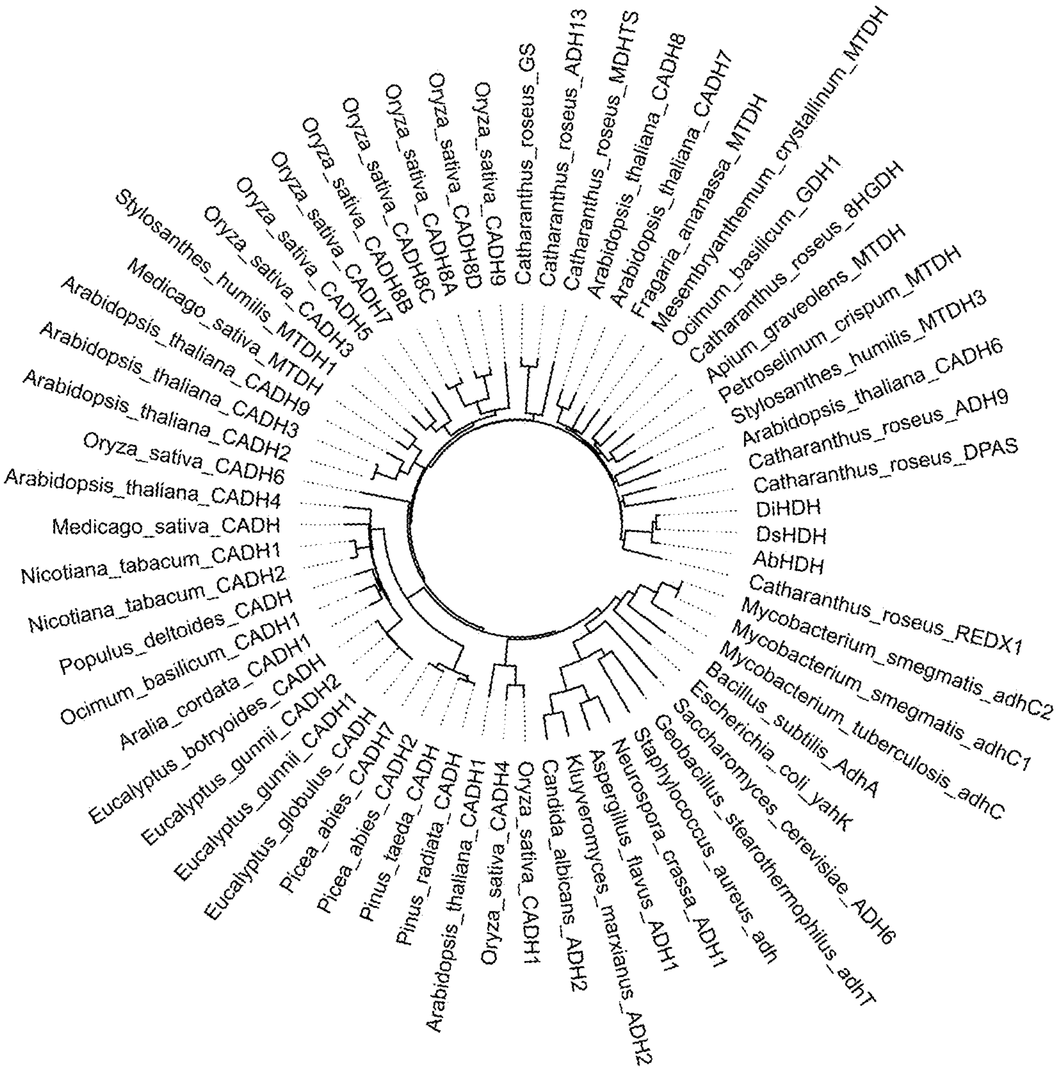

FIG. 48 shows a phylogenetic tree of the three identified HDH orthologs (AbHDH, DiHDH, DsHDH) together with closest protein hits in the UniProt/SwissProt database. This figure shows clustering of the three identified HDH enzyme orthologs with closely related protein sequences based on a BLAST search of the UniProt/SwissProt database. Sequences shown include top 50 BLASTp hits based on E-value, as well as 10 additional hits selected from among the next 100 ranks. Phylogenetic relationships were derived via bootstrap neighbor-joining with n=1000 trials in ClustalX2 and the resulting tree was visualized with FigTree software. Abbreviations: ADH, alcohol dehydrogenase; CADH, cinnamyl alcohol dehydrogenase; MTDH, mannitol dehydrogenase; DPAS, dehydroprecondylocarpine acetate synthase; 8HGDH, 8-hydroxygeraniol dehydrogenase; GDH, geraniol dehydrogenase; GS, geissoschizine synthase; REDX, unspecified redox protein.

Figure 49:
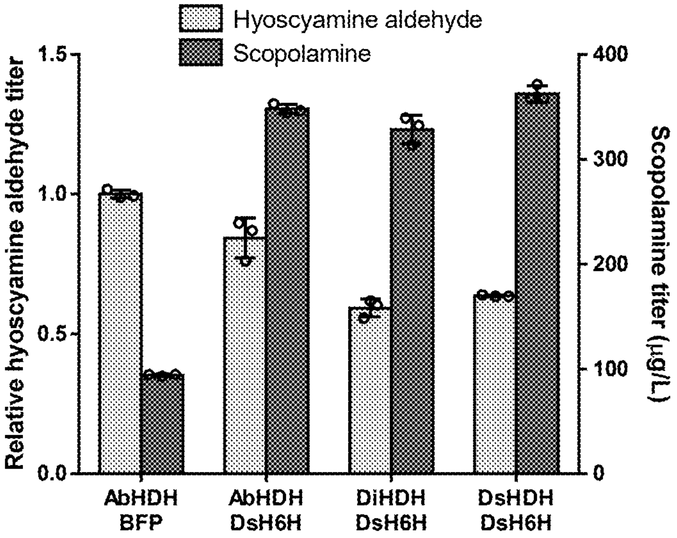

FIG. 49 illustrates the production of the medicinal TA scopolamine from littorine in liquid cultures of engineered yeast cells expressing hyoscyamine dehydrogenase orthologs. This figure illustrates a comparison of activities between identified HDH enzyme orthologs expressed in engineered yeast. Yeast strains are engineered to express *A. belladonna* littorine mutase (AbCYP80F1) and *D. stramonium* hyoscyamine 6β-hydroxylase/dioxygenase (DsH6H) from constitutive promoters within expression cassettes integrated into the genome, one of each of the three HDH orthologs (AbHDH, DiHDH, DsHDH) from a low-copy CEN/ARS plasmid harboring a TRP1 selection marker and a TDH3 promoter, and an additional copy of DsH6H from a low-copy CEN/ARS plasmid harboring a LEU2 selection marker and a TDH3 promoter. Yeast were grown from freshly transformed colonies in 300 μL selective media (-Leu-Trp) supplemented with 1 mM littorine in 96-well deep-well microtiter plates. After 72 hours of growth in a shaking incubator at 30° C. and 460 rpm, the yeast were pelleted and the media supernatant was analyzed by LC-MS/MS. Relative hyoscyamine aldehyde titers were quantified based on integrated peak area of the m/z⁺ 288→124 MRM transition and normalized to that of the engineered strain expressing AbHDH and BFP instead of DsH6H. (S)-scopolamine titers were quantified based on integrated peak area of the m/z⁺ 304→138 MRM transition and a standard curve of a genuine scopolamine standard. Data represent mean of three biological replicates and error bars indicate standard deviation.

Figure 50:
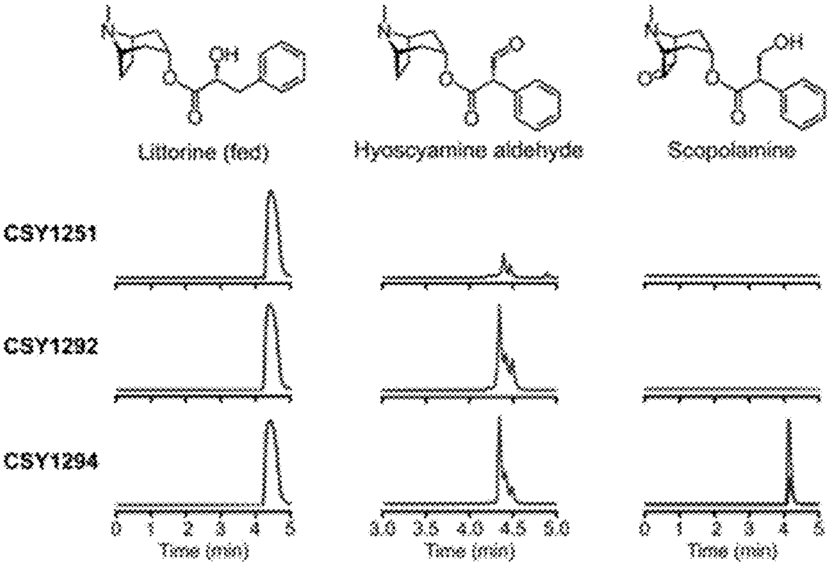
Figure 51:
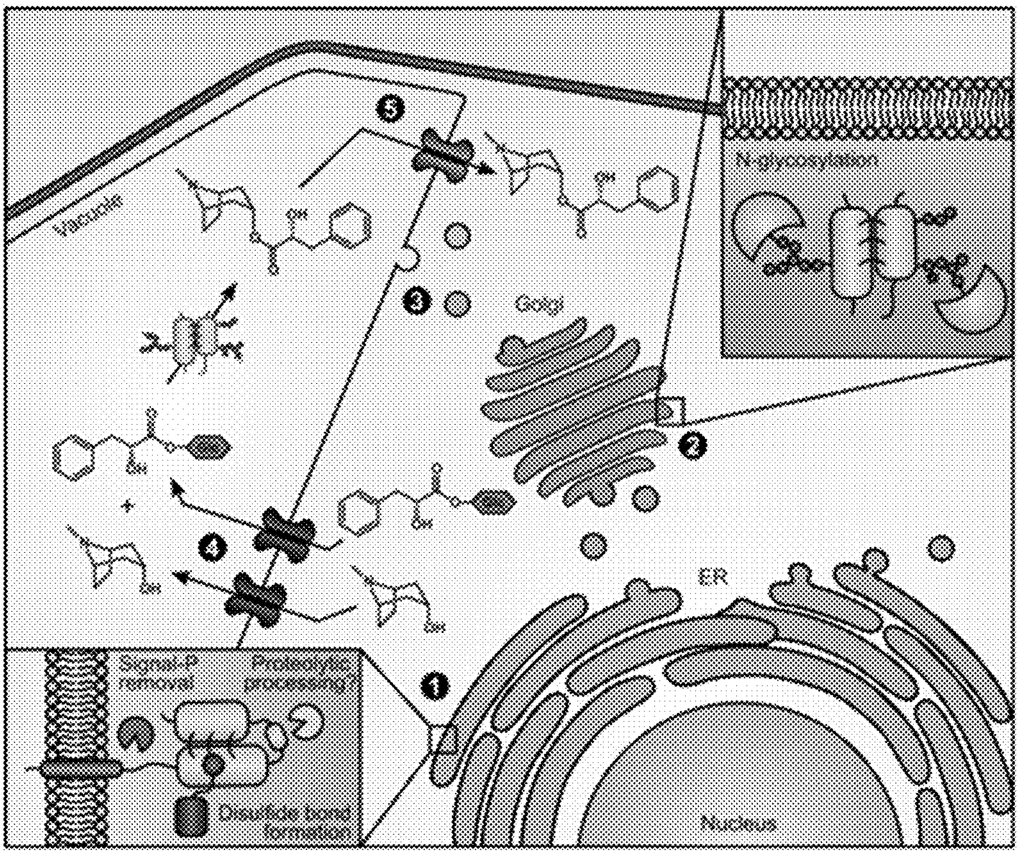

FIG. 50 illustrates experimental validation of conversion of fed littorine to scopolamine by yeast engineered for expression of CYP80F1, HDH, and H6H. This figure shows multiple reaction monitoring (MRM) LC-MS/MS traces from culture media of yeast strains engineered for conversion of littorine to scopolamine. Strains were cultured for 72 h in non-selective media supplemented with 1 mM littorine prior to LC-MS/MS analysis of metabolites in culture supernatant. Dark trace in bottom-right panel (CSY1294, scopolamine) represents 125 nM (38 μg/L) scopolamine standard. Chromatogram traces are representative of three biological replicates FIG. 51 illustrates the canonical plant ER-to-vacuole trafficking and maturation pathway for SCPL acyltransferases (SCPL-ATs). This figure shows a schematic representation of a typical ER-to-vacuole protein trafficking pathway followed by SCPL-ATs in plants, with *A. belladonna* littorine synthase (AbLS) shown as an example. Circled numbers indicate major steps in SCPL-AT expression and activity, including maturation in the (1) ER lumen and (2) Golgi, (3) trafficking to the vacuole, and vacuolar (4) substrate import and (5) product export.

Figure 52:
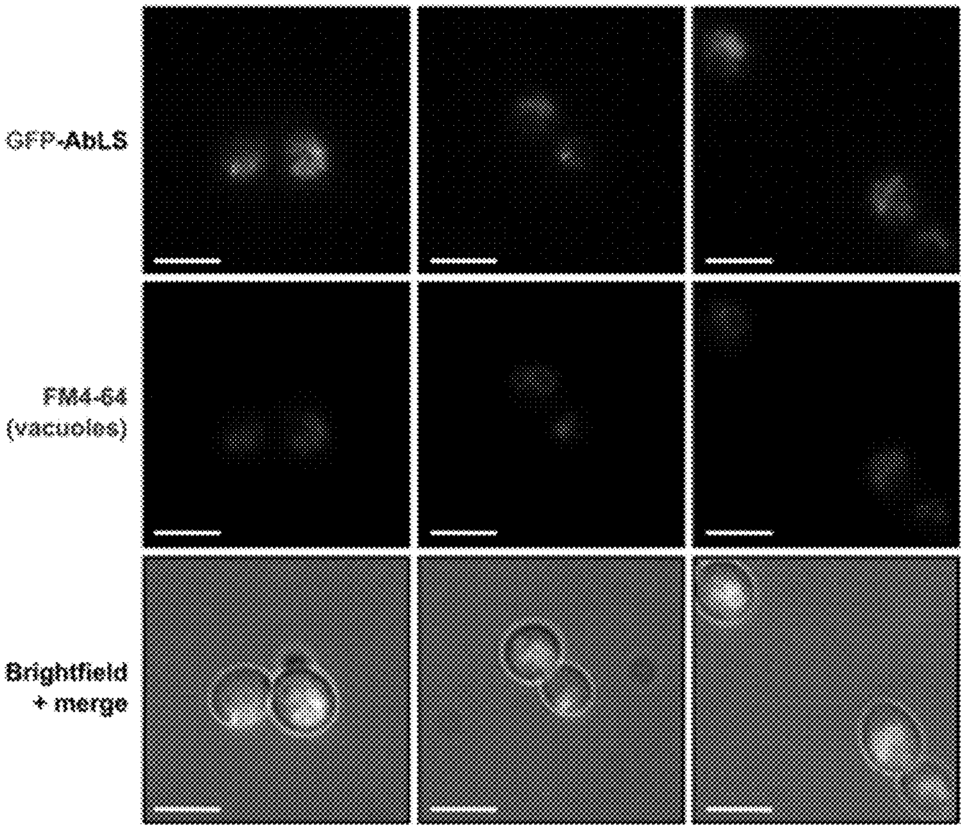

FIG. 52 shows co-localization of wild-type littorine synthase from *A. belladonna* expressed in engineered yeast. This figure shows epifluorescence microscopy of yeast engineered for expression of N-terminal GFP-tagged AbLS (GFP-AbLS) and stained with the vacuolar membrane stain FM4-64. Microscopy was performed on CSY1294 expressing GFP-AbLS from a low-copy plasmid. Scale bar, 5 μm.

Figure 53:
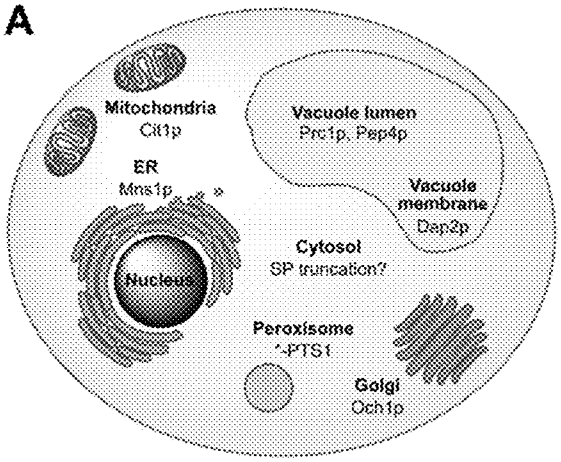

FIG. 53 illustrates a strategy for forced localization of littorine synthase to different yeast sub-cellular compartments via signal sequence replacement. This figure illustrates a protein engineering approach to modifying the sub-cellular localization of AbLS to address potential restrictions on substrate availability in different compartments. (A) Schematic of yeast sub-cellular compartments targeted for localization of AbLS via signal sequence swapping. Signal sequence source proteins are indicated for each compartment. (B) Termini and residues selected for AbLS signal sequence replacement. Residues comprising each signal sequence domain were selected based on structural annotations in the UniProt/SwissProt database.

Figure 54:
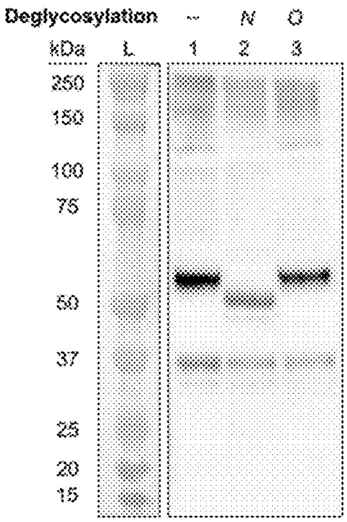

FIG. 54 shows a Western blot of wild-type AbLS expressed in tobacco and treated with deglycosylases. This figure illustrates the identification of glycosylation modification types for AbLS expressed in plants. C-terminal HA-tagged AbLS was transiently expressed in *N. benthamiana* leaves via agroinfiltration. Crude leaf extracts were either untreated (lane 1: '--'), or treated with peptide N-glycosidase F (PNGase F; lane 2: 'N') or O-glycosidase (lane 3: 'O') to remove N- or O-linked glycosylation, respectively. Crude extracts were separated by electrophoresis on a NuPAGE 4-12% Bis-Tris gel and then transferred to a nitrocellulose membrane for immunodetection using a chimeric rabbit IgGK anti-HA HRP-conjugated antibody. All electrophoresis and blotting steps were performed under disulfide reducing conditions (see Online Methods). Lane 'L', Bio-Rad Precision Plus Dual Color protein ladder.

Figure 55:
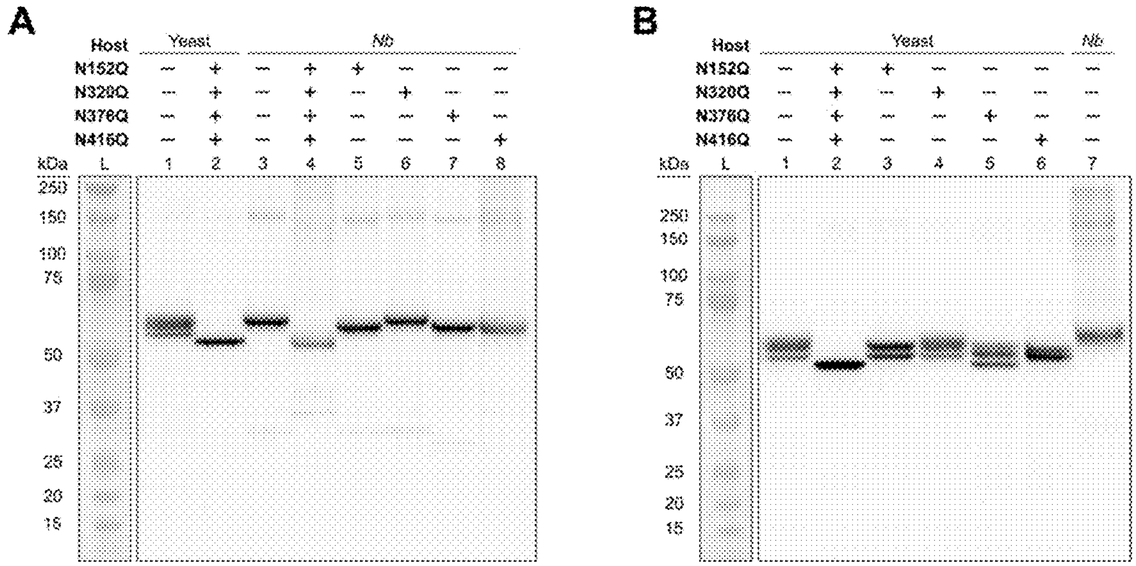

FIG. 55 shows Western blots of AbLS glycosylation site mutants expressed in yeast and tobacco. This figure shows a comparison of the N-glycosylation patterns present for AbLS expressed in yeast and in tobacco. C-terminal HA-tagged wild-type AbLS, single glycosylation site point mutants (N→Q), or a quadruple mutant were expressed transiently via agroinfiltration in *N. benthamiana* ('Nb') (A) or from low-copy plasmids in CSY1294 ('Yeast') (B). Preparation of tobacco and yeast crude extracts was performed under denaturing, disulfide-reducing conditions (see Online Methods). Crude extracts were separated by electrophoresis on a NuPAGE 4-12% Bis-Tris gel and then transferred to a nitrocellulose membrane for immunodetection using a chimeric rabbit IgGK anti-HA HRP-conjugated antibody. All electrophoresis and blotting steps were performed under disulfide reducing conditions (see Online Methods). For (A) and (B), corresponding yeast- and tobacco-expressed controls are included for comparison. Lane 'L', Bio-Rad Precision Plus Dual Color protein ladder.

Figure 56:

FIG. 56 shows phylogenetic identification of putative endoproteolytic propeptide removal in littorine synthase. This figure shows a sequence alignment of AbLS with characterized serine carboxypeptidases and SCPL acyltransferases known to possess (AtSCT, AsSCPL1, TaCBP2) or lack (AtSMT, yPRC1) proteolytically-removed internal propeptide linkers (bold, grey). Putative N-terminal signal peptides are indicated in bold (black); disulfide bonds are indicated as connecting lines. AtSCT, *Arabidopsis thaliana* sinapoylglucose:choline sinapoyltransferase; AtSMT, *A. thaliana* sinapoylglucose:malate sinapoyltransferase; AbLS, *Atropa belladonna* littorine synthase; AsSCPL1, *Avena strigosa* avenacin synthase; TaCBP2, *Triticum aestivum* carboxypeptidase 2; yPRC1, yeast carboxypeptidase Y. From top to bottom: SEQ ID NO: 30-35.

Figure 57:
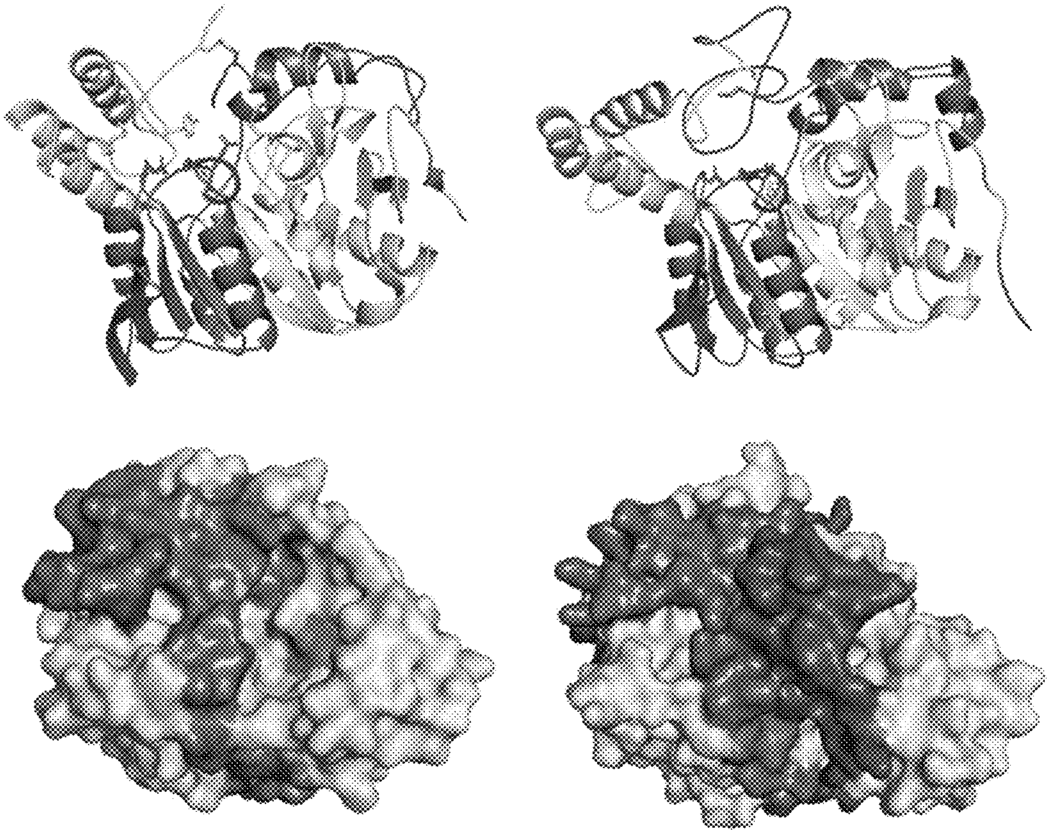

FIG. 57 shows structural identification of putative endoproteolytic propeptide removal in littorine synthase. This figure shows a comparison of the three-dimensional structures of two SCPL-ATs, one of which is known to contain a proteolytically removed internal propeptide sequence. Left: Crystal structure of TaCBP2 (PDB: 1WHT) in (top) cartoon and (bottom) surface representation showing disulfide bonds and internal propeptide removal sites. Right: Homology model of AbLS based on the crystal structure of TaCBP2 in (top) cartoon and (bottom) surface representation showing N-terminal signal peptide, disulfide bonds, and putative internal propeptide which appears to block active site access.

Figure 58:
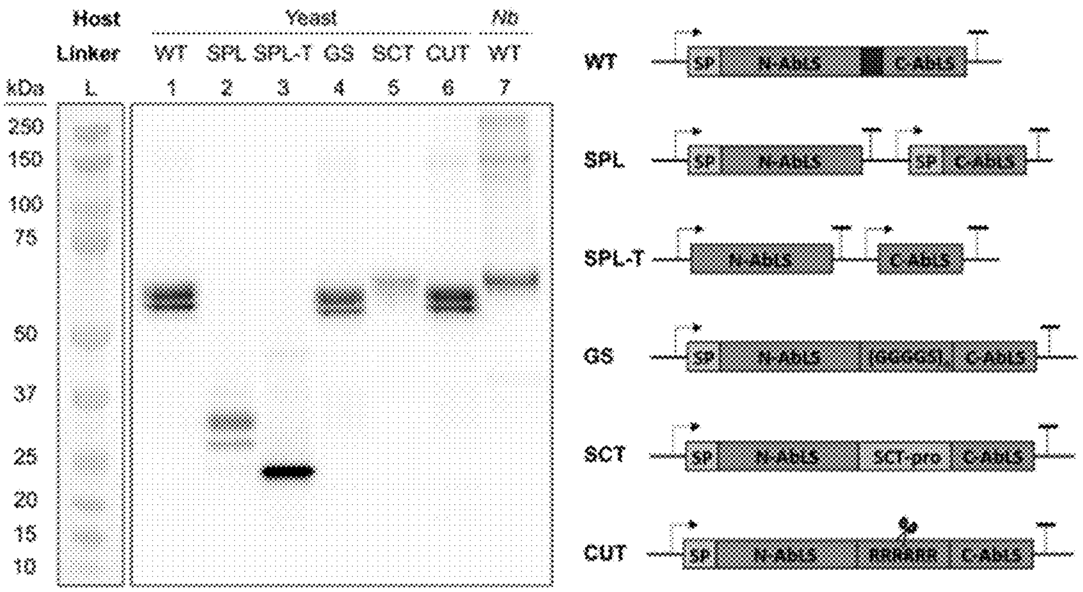

FIG. 58 shows analysis of proteolytic cleavage patterns for AbLS split controls and putative propeptide-swapped variants in yeast. This figure shows Western blot analysis of protein fragment sizes produced by AbLS split controls and propeptide variants expressed in engineered yeast. C-terminal HA-tagged AbLS variants were expressed from low-copy plasmids in CSY1294 (lanes 1-6); HA-tagged wild-type AbLS expressed in *Nicotiana benthamiana* (Nb) is shown as an additional control (lane 7). Gel electrophoresis and blotting were performed under disulfide-reducing conditions and detection was performed using an anti-HA antibody (see Online Methods). Lane symbols: L, protein molecular weight ladder; WT, wild-type AbLS; SPL, AbLS split at putative propeptide with signal peptides on both fragments; SPL-T, AbLS split at putative propeptide without signal peptides on either fragment; GS, AbLS variant with wild-type propeptide swapped for flexible Gly-Ser linker; SCT, AbLS variant with wild-type propeptide swapped for AtSCT propeptide sequence; CUT, AbLS variant with wild-type propeptide swapped for synthetic poly-arginine site recognized and cleaved by Kex2p protease.

Figure 59:
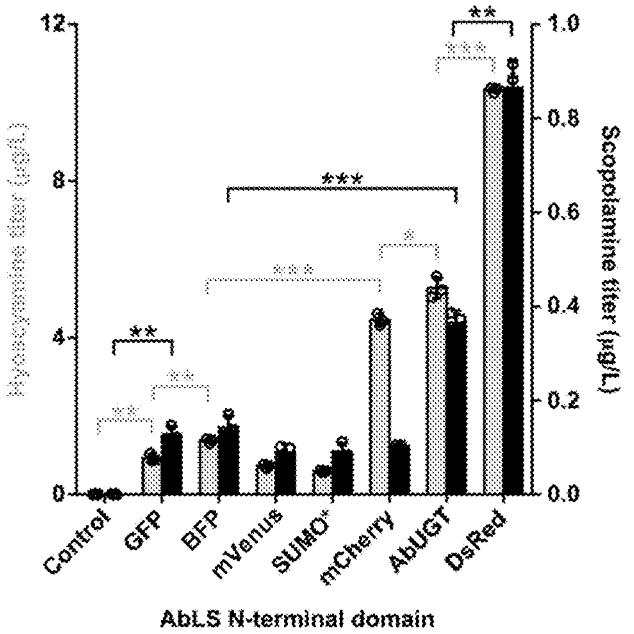

FIG. 59 illustrates de novo hyoscyamine and scopolamine production in yeast strains engineered for expression of AbLS N-terminal fusions. This figure shows a comparison of de novo hyoscyamine and scopolamine production in yeast strains expressing AbLS with different soluble protein domains fused to the N-terminus. Wild-type (control) or AbLS fusions were expressed from low-copy plasmids in CSY1294. Transformed strains were cultured for 96 h in selective media prior to LC-MS/MS analysis of metabolites in culture supernatant. Data represent the mean of n=3 biologically independent samples (open circles) and error bars show standard deviation. Student's two-tailed t-test: *$P<0.05$, $P<0.01$, *$P<0.001$.

Figure 60:
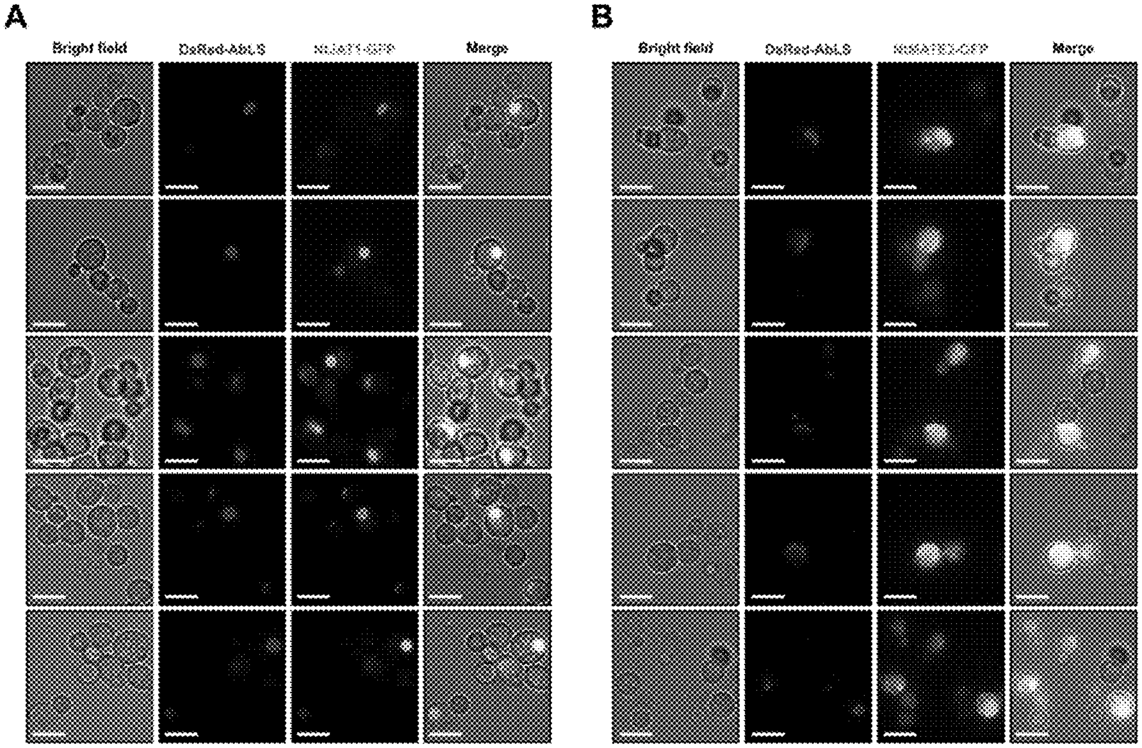

FIG. 60 shows fluorescence microscopy of tobacco alkaloid transporters expressed in CSY1296 for alleviation of vacuolar TA transport limitations. This figure shows fluorescence microscopy images of engineered yeast expressing tobacco alkaloid transporters fused at their C-termini to GFP, to enable identification of their sub-cellular localization. C-terminal GFP fusions of (A) NtJAT1 and (B) NtMATE2 were expressed from low-copy plasmids in CSY1296. Scale bar, 5 μm.

Figure 61:
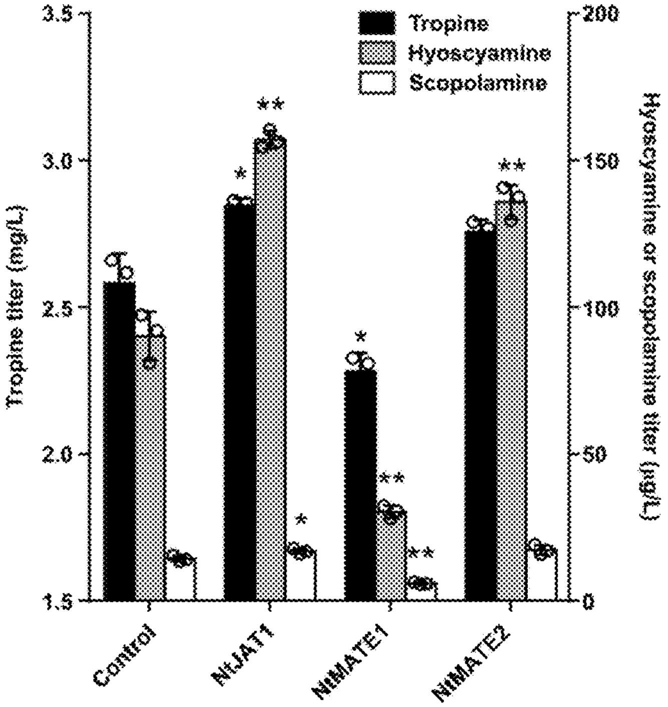

FIG. 61 shows production of tropine, hyoscyamine, and scopolamine in CSY1296 engineered for expression of heterologous alkaloid transporters. This figure illustrates the utility of different plant alkaloid transporters in alleviating intracellular substrate transport limitations in yeast engineered for TA production. *Nicotiana tabacum* jasmonate-inducible alkaloid transporter 1 (NtJAT1), multidrug and toxin extrusion (MATE) transporters 1 or 2, or a negative control (BFP) were expressed from low-copy plasmids in CSY1296. Transformed strains were cultured for 96 h in selective media prior to LC-MS/MS analysis of metabolites in culture supernatant. Data represent the mean of n=3 biologically independent samples (open circles) and error bars show standard deviation. Student's two-tailed t-test: *$P<0.05$, $P<0.01$, *$P<0.001$.

Figure 62:
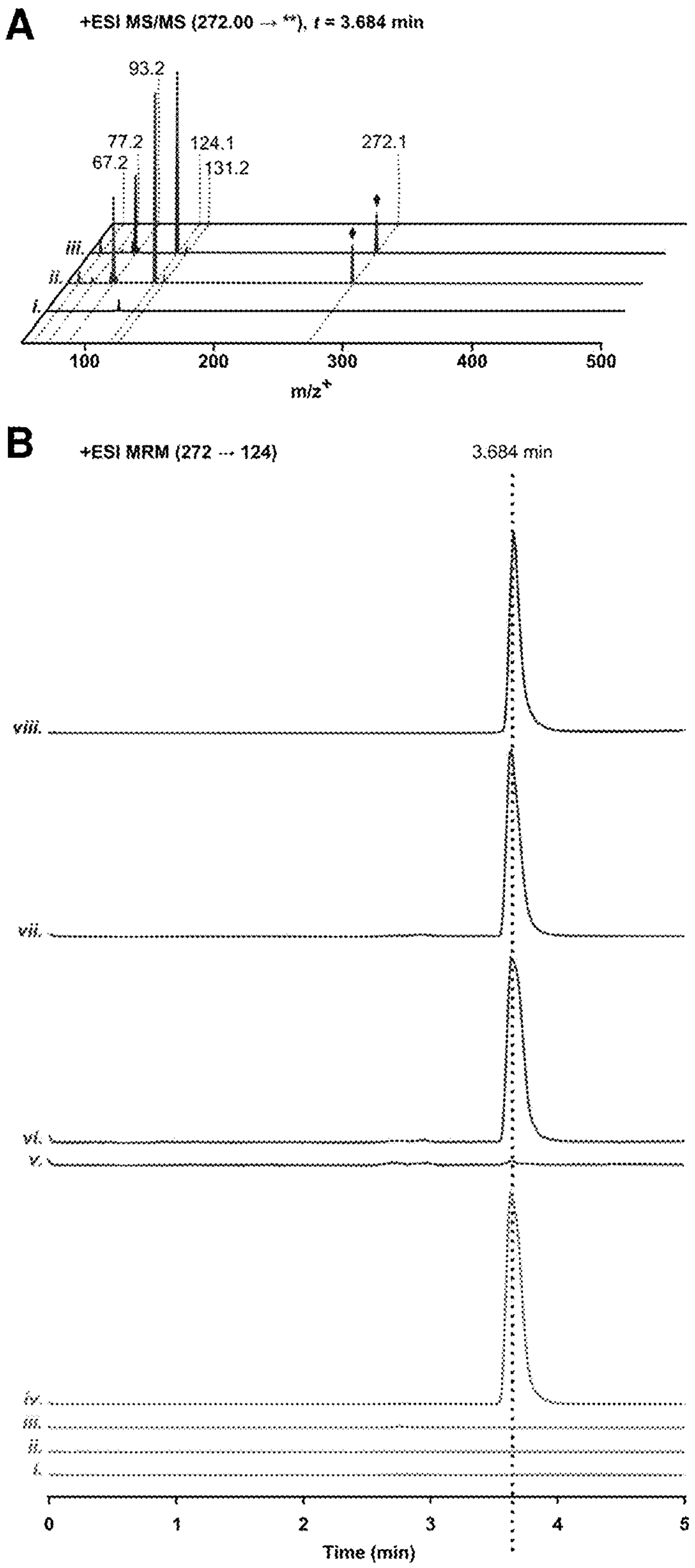

FIG. 62 shows LC-MS/MS chromatograms in (A) product ion mode and (B) multiple reaction monitoring mode illustrating the de novo production of the non-natural TA cinnamoyltropine in engineered yeast. This figure shows LC-MS/MS analysis of engineered yeast strains producing the non-natural TA cinnamoyltropine. (A) Tandem MS/MS spectra of extracellular medium of (i) tropine-producing strain CSY1251; (ii) CSY1251 expressing phenylalanine ammonia-lyase (AtPAL1), 4-coumarate-CoA ligase 5 (At4CL5), and cocaine synthase (EcCS), denoted CSY1282; or (iii) a genuine cinnamoyltropine standard for a parent mass of m/z+=272. Blue diamond indicates parent compound peak. (B) Validation of EcCS acyltransferase activity on cinnamic acid and α-tropine via substrate feeding. Strains were transformed with combinations of plasmids expressing AtPAL1 (low-copy plasmid pCS4252) and/or At4CL5 and EcCS (high-copy plasmid pCS4207), and then cultured in media with different supplemented substrates, as follows: (i) CEN.PK2+At4CL5+EcCS+0.1 mM trans-cinnamic acid; (ii) CEN.PK2+At4CL5+EcCS+0.5 mM α-tropine; (iii) CEN.PK2+AtPAL1+At4CL5+EcCS; (iv) CEN.PK2+AtPAL1+At4CL5+EcCS+0.5 mM α-tropine; (v) CSY1251+At4CL5+EcCS; (vi) CSY1251+At4CL5+EcCS+0.2 mM trans-cinnamic acid; (vii) CSY1251+AtPAL1+At4CL5+EcCS; (viii) 25 nM cinnamoyltropine standard. For (A) and (B), yeast strains were cultured in selective media (YNB-DO+2% dextrose+5% glycerol) at 25° C. for 72 h prior to LC-MS/MS analysis.

Figure 63:
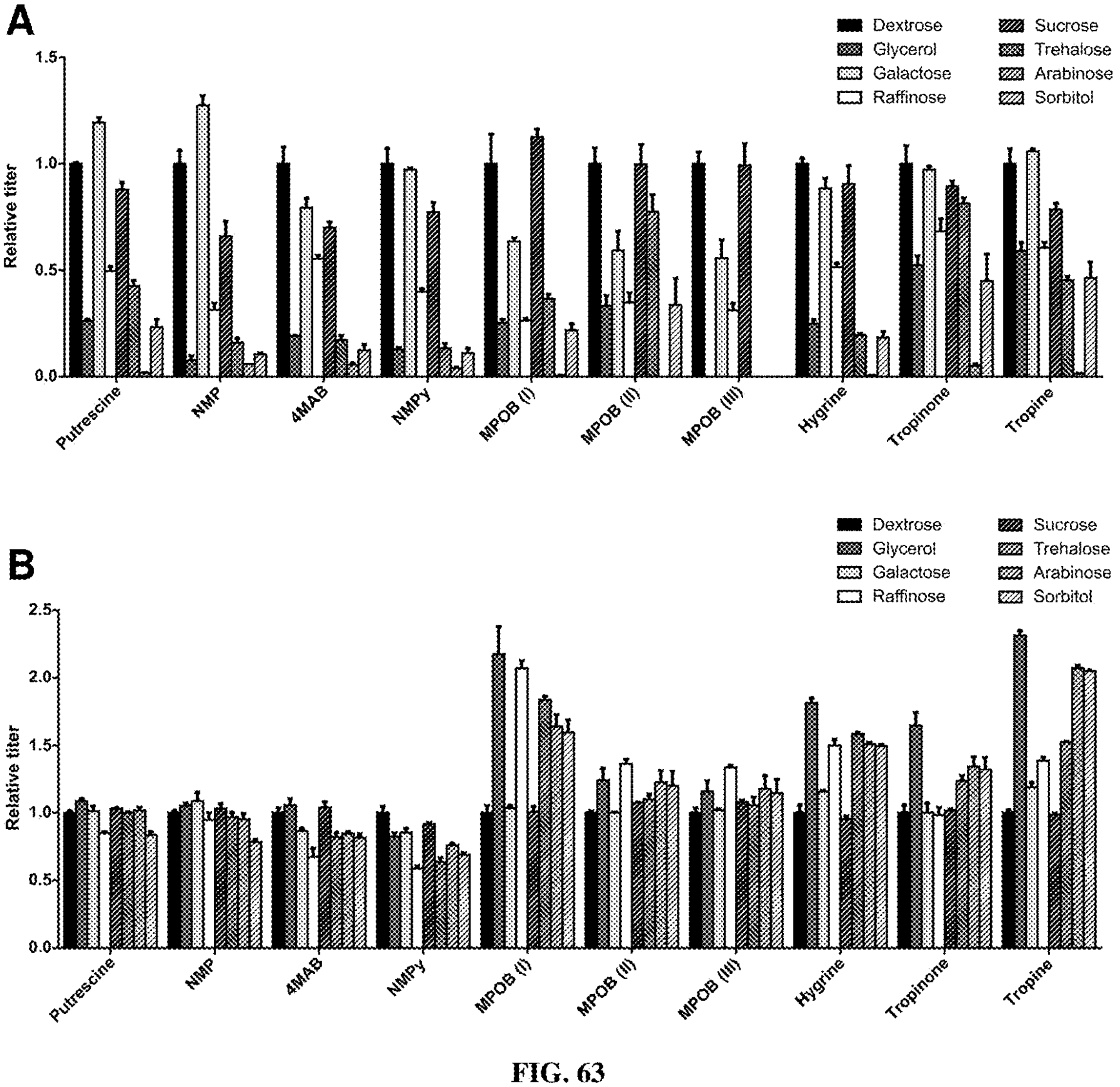

FIG. 63 illustrates the impact of varied carbon sources fed (A) alone or (B) together with dextrose on the production of tropine and related TA precursors in liquid cultures of engineered yeast. This figure shows the optimization of carbon source to improve tropine production in engineered yeast. Overnight cultures of tropine-producing strain CSY1249 (see Example 3.3.4) were grown in non-selective rich media (YPD). Overnight cultures were pelleted and resuspended in non-selective defined medium (YNB-SC) with all amino acids and (A) 2% of each carbon source or (B) 2% dextrose and 2% of each additional carbon source, including dextrose. Cultures were grown at 25° C. for 48 h prior to analysis of growth medium by LC-MS/MS. Data show relative titer of each metabolite normalized to (A) 2% dextrose or (B) 2%+2% dextrose. Data represent the mean of three biological replicates and error bars indicate standard deviation.

Figure 64:
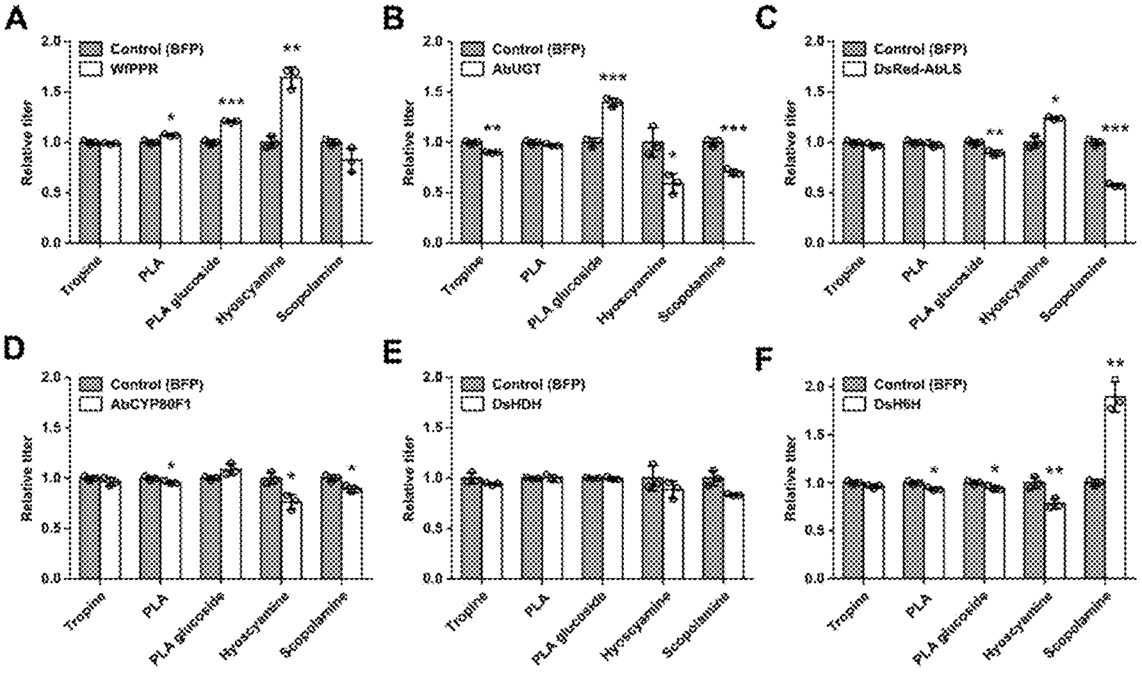

FIG. 64 illustrates metabolic bottleneck analysis of scopolamine-producing strain CSY1296. This figure shows the effect of expressing additional copies of flux-limiting enzymes on production of TAs and TA precursors in engineered yeast. An additional copy of each biosynthetic enzyme between tropine and scopolamine was expressed from the following low-copy plasmids in strain CSY1296: (A) WfPPR, pCS4436; (B) AbUGT, pCS4440; (C) DsRed-AbLS, pCS4526; (D) AbCYP80F1, pCS4438; (E) DsHDH, pCS4478; (F) DsH6H, pCS4439; or a BFP control (pCS4208, pCS4212, or pCS4213) corresponding to the same auxotrophic marker as each biosynthetic gene plasmid. Transformed strains were cultured in appropriate selective media at 25° C. for 96 hours prior to quantification of metabolites in the growth medium by LC-MS/MS. Data indicate the mean of n=3 biologically independent samples (open circles) and error bars show standard deviation. Student's two-tailed t-test: *$P<0.05$, $P<0.01$, *$P<0.001$.

Figure 65:
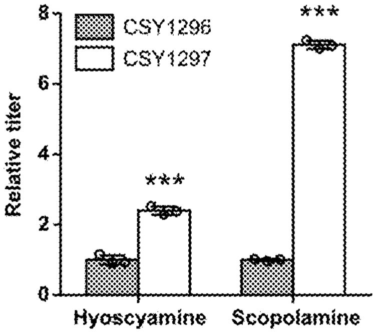

FIG. 65 shows the effect of alleviating flux and transport limitations on hyoscyamine and scopolamine production in engineered yeast. This figure shows a comparison of de novo hyoscyamine and scopolamine production in yeast strain CSY1296 and CSY1297, where the latter possesses additional genomic copies of flux-limiting enzymes (WfPPR and DsH6H) as well as a tobacco vacuolar alkaloid importer (NtJAT1). Strains were cultured in non-selective media for 96 h prior to LC-MS/MS analysis of metabolites in culture supernatant. Data represent the mean of n=3 biologically independent samples (open circles) and error bars show standard deviation. Student's two-tailed t-test: *$P<0.05$, $P<0.01$, *$P<0.001$.

DEFINITIONS

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims are drafted to exclude any optional element. As such, this statement is intended to serve as antecedent basis for use of such exclusive terminology as "solely," "only" and the like in connection with the recitation of claim elements, or use of a "negative" limitation.

As used herein, the terms "determining," "measuring," "assessing," and "assaying" are used interchangeably and include both quantitative and qualitative determinations.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

As used herein, the term "encoded by" refers to a nucleic acid sequence which codes for a polypeptide sequence, wherein the polypeptide sequence or a portion thereof contains an amino acid sequence of 3 or more amino acids, such as 5 or more, 8 or more, 10 or more, 15 or more, or 20 or more amino acids from a polypeptide encoded by the nucleic acid sequence. Also encompassed by the term are polypeptide sequences that are immunologically identifiable with a polypeptide encoded by the sequence.

A "vector" is capable of transferring gene sequences to target cells. As used herein, the terms, "vector construct," "expression vector," and "gene transfer vector," are used interchangeably to mean any nucleic acid construct capable of directing the expression of a gene of interest and which may transfer gene sequences to target cells, which is accomplished by genomic integration of all or a portion of the vector, or transient or inheritable maintenance of the vector as an extrachromosomal element. Thus, the term includes cloning, and expression vehicles, as well as integrating vectors.

An "expression cassette" includes any nucleic acid construct capable of directing the expression of a gene/coding sequence of interest, which is operably linked to a promoter of the expression cassette. Such cassette is constructed into a "vector," "vector construct," "expression vector," or "gene transfer vector," in order to transfer the expression cassette into target cells. Thus, the term includes cloning and expression vehicles, as well as viral vectors.

A "plurality" contains at least 2 members. In certain cases, a plurality may have 10 or more, such as 100 or more, 1000 or more, 10,000 or more, 100,000 or more, 106 or more, 107 or more, 108 or more, or 109 or more members. In any embodiments, a plurality can have 2-20 members.

The term "tropane alkaloid product" is intended to refer to any molecule whose skeleton contains an 8-azabicyclo [3.2.1]octane core group comprising a cycloheptane ring and a nitrogen bridge connecting carbon atoms 1 and 5, wherein the 8-azabicyclo[3.2.1]octanyl group is covalently bonded to an acyl group by means of an ester linkage at the 3 position, and/or wherein the 8-azabicyclo[3.2.1]octanyl group is functionalized with a hydroxyl group at the 3 position and one or more hydroxyl groups at the 2, 4, 5, 6, and/or 7 positions. Tropane alkaloid products include, but are not limited to, littorine, hyoscyamine, atropine, anisodamine, scopolamine, cocaine, and any other similar tropine/pseudotropine+acyl group natural or non-natural tropane alkaloids (e.g., calystegines).

The term "precursor of a tropane alkaloid product" is intended to refer to any molecule that can be biosynthesized by an organism from a carbon source and a nitrogen source and which can be converted to a tropane alkaloid product in one or more (e.g., one or two) biosynthetic steps; wherein the carbon source is a carbohydrate, a non-carbohydrate sugar, a sugar alcohol, a lipid, a fatty acid, or a substrate which is converted to one or more of the above carbon sources through a metabolic pathway; and wherein the nitrogen source is ammonia, urea, nitrate, nitrite, any amino acid excluding glutamic acid, arginine, ornithine, and citrulline, a peptide, a protein, or any substrate which is converted to one or more of the above nitrogen sources through a metabolic pathway.

The term "derivative of a tropane alkaloid product" is intended to refer to any molecule not naturally produced by an unmodified organism, wherein the skeleton of the molecule comprises a tropane alkaloid product and which differs from said tropane alkaloid product by the attachment of functional groups without modification of the skeleton itself. As used herein, attachment of functional groups includes, but is not limited to, hydroxylation, alkylation and N-alkylation, acetylation and N-acetylation, acylation and N-acylation, and halogenation.

Numeric ranges are inclusive of the numbers defining the range.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more, and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Other definitions of terms may appear throughout the specification.

DETAILED DESCRIPTION

Host cells that are engineered to produce tropane alkaloids (TAs) that are of interest, such as hyoscyamine and scopolamine, are provided. The host cells may have one or more engineered modifications selected from: a feedback inhibition alleviating mutation in an enzyme gene; a transcriptional modulation modification of a biosynthetic enzyme gene; an inactivating mutation in an enzyme; and a heterologous coding sequence. Also provided are methods of producing a TA of interest using the host cells and compositions, e.g., kits, systems etc., that find use in methods of the invention.

Before the present invention is described in greater detail, it is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein may also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method is carried out in the order of events recited or in any other order which is logically possible.

In further describing the subject invention, TA precursors of interest, TAs, and modifications of TAs, including derivatives of TAs, are described first in greater detail, followed by host cells for producing the same. Next, methods of interest in which the host cells find use are reviewed. Kits that may be used in practicing methods of the invention are also described.

Tropane Alkaloid (TA) Precursors

As summarized above, host cells which produce tropane alkaloid precursors (TA precursors) are provided. The TA precursor may be any intermediate or precursor compound in a synthetic pathway (e.g., as described herein) that leads to the production of a TA of interest (e.g., as described herein). In some cases, the TA precursor has a structure that may be characterized as a TA or a derivative thereof. In certain cases, the TA precursor has a structure that may be characterized as a fragment of a TA. In some cases, the TA precursor is an early TA. As used herein, by "early TA" is meant an early intermediate in the synthesis of a TA of interest in a cell, where the early TA is produced by a host cell from a host cell feedstock or simple starting compound. In some cases, the early TA is a TA intermediate that is produced by the subject host cell solely from a host cell feedstock (e.g., a carbon and nutrient source) without the need for addition of a starting compound to the cells. The term early TA may refer to a precursor of a TA end product of interest whether or not the early TA may itself be characterized as a tropane alkaloid.

Figure 2:
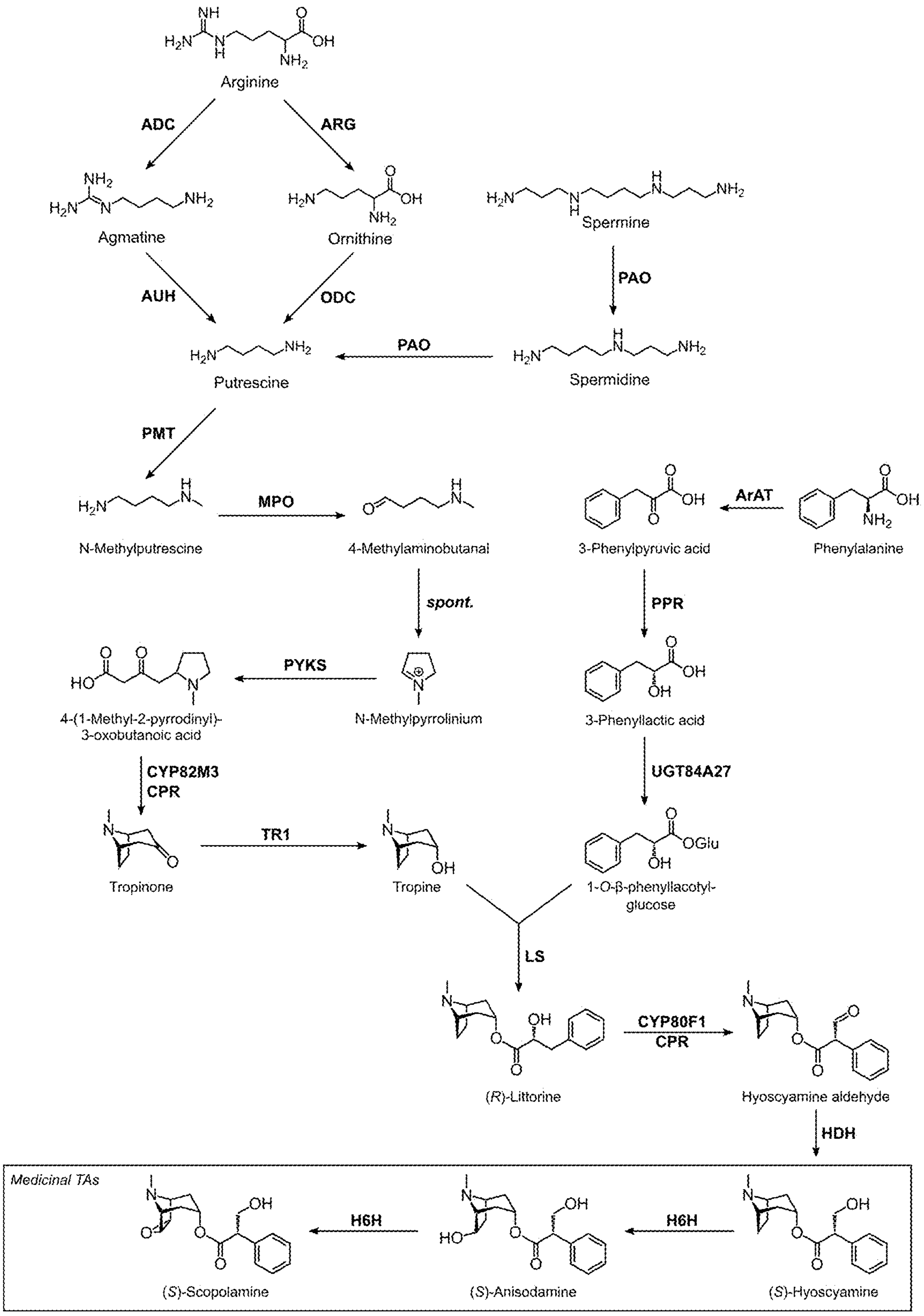
FIG. 2 illustrates an exemplary biosynthetic pathway by which amino acids can be converted to medicinal TA molecules of interest and precursor molecules thereof. This example shows the conversion of L-arginine and L-phenylalanine to medicinal TAs. ADC, arginine decarboxylase; ARG, arginase; AUH, agmatine ureohydrolase; ODC, ornithine decarboxylase; PAO, polyamine oxidase; PMT, putrescine N-methyltransferase; MPO, N-methylputrescine oxidase; spont., spontaneous (non-enzymatic) step; PYKS, pyrrolidine ketide synthase; CYP82M3, tropinone synthase; CPR, cytochrome P450-NADP+ reductase; TR1, tropinone reductase 1; ArAT, aromatic aminotransferase; PPR, phenylpyruvate reductase; UGT84A27, 3-phenyllactate UDP-glucosyltransferase; LS, littorine synthase; CYP80F1, littorine mutase; HDH, (S)-hyoscyamine dehydrogenase; H6H, (S)-hyoscyamine 6β-hydroxylase/dioxygenase. Arginine, ornithine, spermine, spermidine, putrescine, phenylalanine, 3-phenylpyruvic acid, and trace amounts of 3-phenyllactic acid are naturally synthesized in yeast. All other metabolites shown are not naturally produced in yeast. The final products, indicated inside the box, are examples of medicinal TAs.

In some cases, the TA precursor is an early TA, such as a pre-tropine tropane alkaloid or a pre-littorine tropane alkaloid. As such, host cells which produce pre-tropine tropane alkaloids (pre-tropine TAs) and pre-littorine tropane alkaloids (pre-littorine TAs) are provided. Tropine is a major branch point intermediate of interest in the synthesis of downstream TAs via cell engineering efforts to produce end products such as medicinal TA products derived from littorine (FIG. 2). The subject host cells may produce TA precursors from simple and inexpensive starting materials that may find use in the production of tropine, littorine, and downstream TA end products.

As used herein, the terms "pre-esterification tropane alkaloid", "pre-esterification TA", and "pre-esterification TA precursor" are used interchangeably and refer to a biosynthetic precursor of littorine, cinnamoyltropine, or other product of acyl donor and acyl acceptor esterification, whether or not the structure of the esterification precursor itself is characterized as a tropane alkaloid. The term pre-esterification TA is meant to include biosynthetic precursors, intermediates and metabolites thereof, of any convenient member of a host cell biosynthetic pathway that may lead to esterification products such as littorine. In some cases, the pre-esterification TA includes a tropane alkaloid fragment, such as a tropine fragment, a phenylpropanoid fragment or a precursor or derivative thereof. In certain instances, the pre-esterification TA has a structure that may be characterized as a tropane alkaloid or a derivative thereof.

Figure 1:
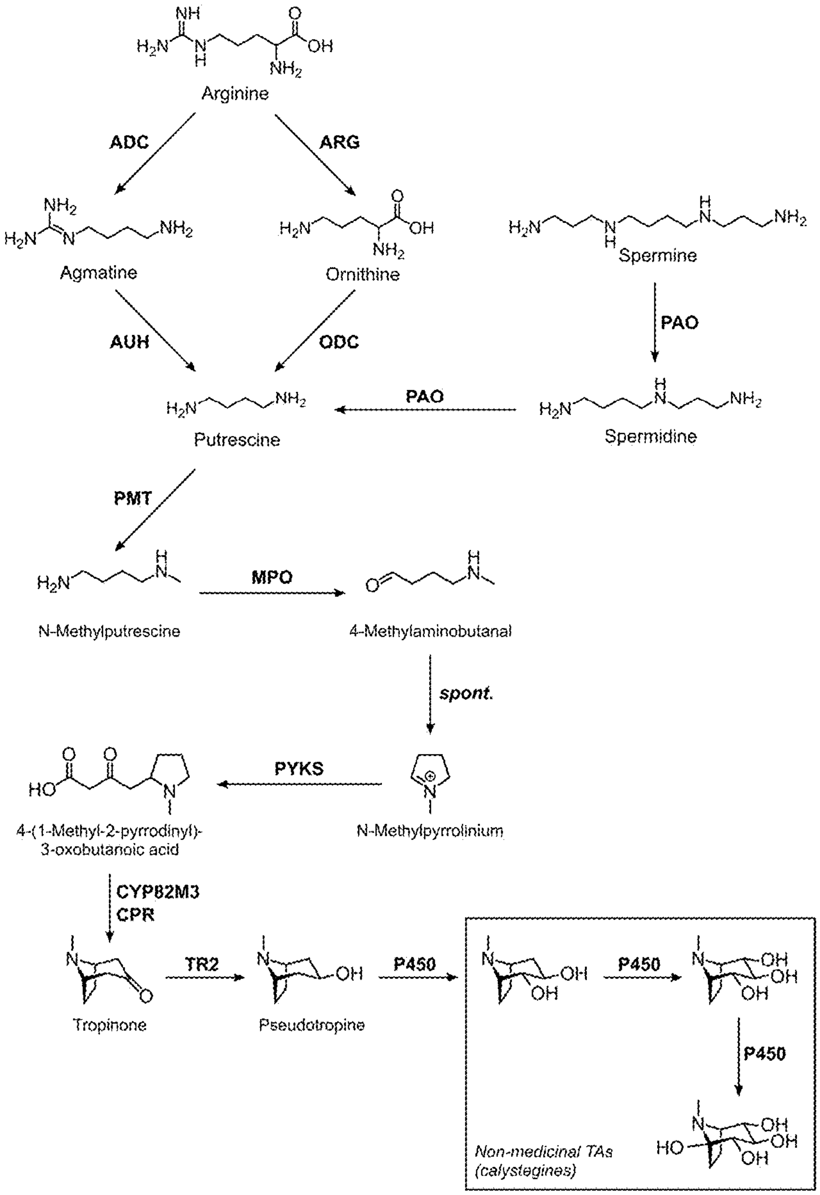
FIG. 1 illustrates an exemplary biosynthetic scheme for converting L-arginine to non-medicinal TAs. ADC, arginine decarboxylase; ARG, arginase; AUH, agmatine ureohydrolase; ODC, ornithine decarboxylase; PAO, polyamine oxidase; PMT, putrescine N-methyltransferase; MPO, N-methylputrescine oxidase; spont., spontaneous (non-enzymatic) step; PYKS, pyrrolidine ketide synthase; CYP82M3, tropinone synthase; CPR, cytochrome P450-$NADP^+$ reductase; TR2, tropinone reductase 2; P450, cytochrome P450. Arginine, ornithine, spermine, spermidine, and putrescine are naturally synthesized in yeast. All other metabolites shown are not naturally produced in yeast. The final products, indicated inside the box, are examples of non-medicinal TAs.
Figure 3:
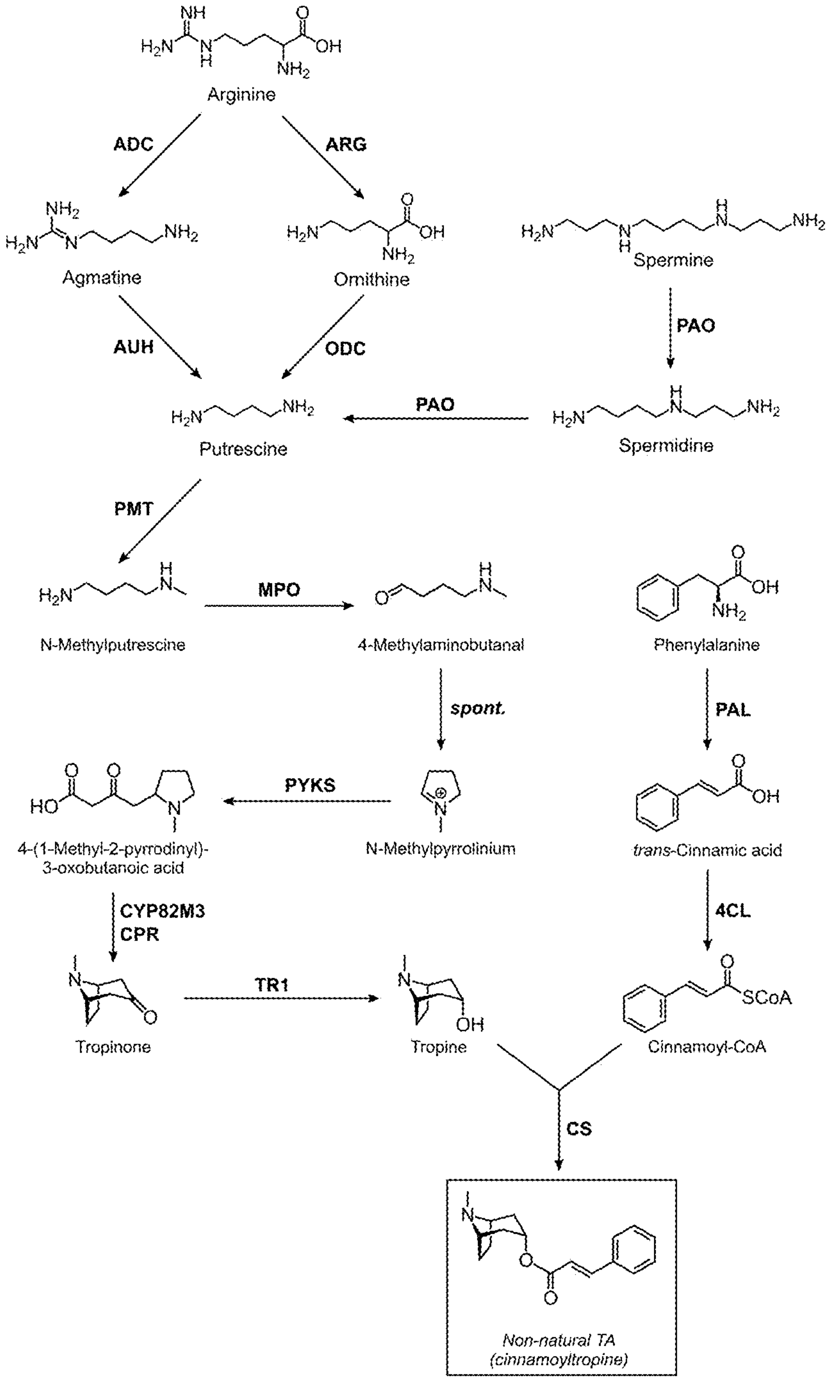
FIG. 3 illustrates an exemplary biosynthetic pathway by which amino acids can be converted to a non-natural TA and precursor molecules thereof. In this example, L-arginine and L-phenylalanine are converted to non-natural TAs. ADC, arginine decarboxylase; ARG, arginase; AUH, agmatine ureohydrolase; ODC, ornithine decarboxylase; PAO, polyamine oxidase; PMT, putrescine N-methyltransferase; MPO, N-methylputrescine oxidase; spont., spontaneous (non-enzymatic) step; PYKS, pyrrolidine ketide synthase; CYP82M3, tropinone synthase; CPR, cytochrome P450-$NADP^+$ reductase; TR1, tropinone reductase 1; PAL, phenylalanine ammonia-lyase; 4CL, 4-coumarate-CoA ligase; CS, cocaine synthase. Arginine, ornithine, spermine, spermidine, putrescine, and phenylalanine are naturally synthesized in yeast. All other metabolites shown are not naturally produced in yeast. The final product, indicated inside the box, is an example of a non-natural TAs.

TA precursors of interest include, but are not limited to, tropine and phenyllactic acid (PLA), as well as tropine and PLA precursors, such as arginine, ornithine, agmatine, N-carbamoylputrescine (NCP), putrescine, N-methylputrescine (NMP), 4-methylaminobutanal, N-methylpyrrolinium (NMPy), 4-(1-methyl-2-pyrrodinyl)-3-oxobutanoic acid (MPOB), tropinone, phenylalanine, prephenic acid, and phenylpyruvic acid (PPA). In some embodiments, the one or more TA precursors are tropine and PLA. In certain instances, the one or more TA precursors are tropine and a phenylpropanoid carboxylic acid other than PLA, such as cinnamic acid. FIGS. 1, 2, and 3 illustrate the biosynthesis of non-medicinal, medicinal, and non-natural TAs respectively from various TA and non-TA precursor molecules.

Synthetic pathways to a TA precursor may be generated in the host cells, and may start with any convenient starting compound(s) or materials. FIGS. 1-4 illustrate a synthetic pathway of interest to TA precursors starting from amino acids. The starting material may be non-naturally occurring or the starting material may be naturally occurring in the host cell. Any convenient compounds and materials may be used as the starting material, based upon the synthetic pathway present in the host cell. The source of the starting material may be from the host cell itself, e.g., arginine or phenylalanine, or the starting material may be added or supplemented to the host cell from an outside source. As such, in some cases, the starting compound refers to a compound in a synthetic pathway of the cell that is added to the host cell from an outside source that is not part of a growth feedstock or cell growth media. Starting compounds of interest include, but are not limited to, N-methylputrescine, 4-methylaminobutanal, tropinone, tropine, PLA, cinnamic acid, as well as any of the compounds shown in FIGS. 1-4. For example, if the host cells are growing in liquid culture, the cell media may be supplemented with the starting material, which is transported into the cells and converted into the desired products by the cell. Starting materials of interest include, but are not limited to, inexpensive feedstocks and simple precursor molecules. In some cases, the host cell utilizes a feedstock including a simple carbon source as the starting material, which the host cell utilizes to produce compounds of the synthetic pathway of the cell. The host cell growth feedstock may include one or more components, such as a carbon source such as cellulose, starch, free sugars and a nitrogen source, such as ammonium salts or inexpensive amino acids. In some cases, a growth feedstock that finds use as a starting material may be derived from a sustainable source, such as biomass grown on marginal land, including switchgrass and algae, or biomass waste products from other industrial or farming activities.

Tropane Alkaloids (TAs)

As summarized above, host cells which produce tropane alkaloids (TAs) of interest are provided. In some embodiments, the engineered strains of the invention will provide a platform for producing tropane alkaloids of interest and modifications thereof across several classes including, but not limited to, medicinal TAs such as those derived from tropine and PLA; non-medicinal TAs such as those derived from tropinone, pseudotropine, or norpseudotropine; and non-natural TAs such as those derived from the esterification of TA precursors (e.g., acyl donor and acyl acceptor compounds) other than tropine and PLA. Each of these classes is meant to include biosynthetic precursors, intermediates, and metabolites thereof, of any convenient member of a host cell biosynthetic pathway that may lead to a member of the class. Non-limiting examples of compounds are given below for each of these classes. In some embodiments, the structure of a given example may or may not be characterized itself as a tropane alkaloid. The present chemical entities are meant to include all possible isomers, including single enantiomers, racemic mixtures, optically pure forms, mixtures of diastereomers and intermediate mixtures.

Medicinal TAs may include, but are not limited to, littorine, hyoscyamine, atropine, anisodamine, scopolamine, and derivatives thereof that are naturally produced by plants.

Non-medicinal TAs may include, but are not limited to, calystegines, cocaine, and derivatives thereof that are naturally produced by plants.

Non-natural TAs may include, but are not limited to, cinnamoyltropine, cinnamoyl-3β-tropine, coumaroyltropine, coumaroyl-3β-tropine, benzoyltropine, benzoyl-3β-tropine, caffeoyltropine, caffeoyl-3β-tropine, feruloyltropine, and feruloyl-3β-tropine.

Modifications of TAs Including Derivatives

As summarized above, host cells which produce modified derivatives of tropane alkaloids (TAs) of interest are provided. In some embodiments, the engineered strains of the invention will provide a platform for derivatizing TAs of interest, including derivatizing TA precursors, medicinal TAs, non-medicinal TAs, and non-natural TAs which are produced by engineered host cells or which are fed to engineered host cells in the growth media.

As used herein, the terms "derivatization", "functionalization", "modification by derivatization", and "modification by functionalization" refer to the modification of TAs or of TA precursors via the attachment of functional groups without modification of the TA skeleton itself. As used herein, attachment of functional groups includes, but is not limited to, hydroxylation, alkylation and N-alkylation, acetylation and N-acetylation, acylation and N-acylation, and halogenation.

In some embodiments of the invention, derivatization of TAs of interest may be achieved enzymatically by feeding pre-functionalized TA precursors, for example halogenated or alkylated amino acids, to host cells engineered to uptake and then convert fed TA precursors into TAs of interest. In other embodiments of the invention, derivatization of TAs of interest may be achieved enzymatically by engineering host cells to express enzymes which possess the desired activity in attaching a functional group to a target TA, in addition to the enzymes and cellular modifications required to produce the unmodified TA. In other embodiments of the invention, derivatization of TAs of interest may be achieved enzymatically by treating unmodified TAs produced by engineered host cells with purified enzymes capable of attaching desired functional groups, or with crude lysate of host cells engineered to express enzymes that have the desired derivatizing activity. In other embodiments of the invention, derivatization of TAs of interest may be achieved non-enzymatically by treating unmodified TAs produced by engineered host cells with chemical agents with attach desired functional groups.

Modified derivatives of TAs include, but are not limited to, p-hydroxyatropine, p-hydroxyhyoscyamine, p-fluorohyoscyamine, p-chlorohyoscyamine, p-bromohyoscyamine, p-fluoroscopolamine, p-chloropscopolamine, p-bromoscopolamine, N-methylhyoscyamine, N-butylhyoscyamine, N-methylscopolamine, N-butylscopolamine, N-acetylhyoscyamine, and N-acetylscopolamine.

Host Cells

As summarized above, one aspect of the invention is a host cell that produces one or more TAs of interest. Any convenient cells may be utilized in the subject host cells and methods. In some cases, the host cells are non-plant cells. In some instances, the host cells may be characterized as microbial cells. In certain cases, the host cells are insect cells, mammalian cells, bacterial cells, or fungal cells. Any convenient type of host cell may be utilized in producing the subject TA-producing cells, see, e.g., US2008/0176754 now published as U.S. Pat. No. 8,975,063, US2014/0273109 and WO2014/143744); the disclosures of which are incorporated by reference in their entirety. Host cells of interest include, but are not limited to, bacterial cells, such as *Bacillus subtilis, Escherichia coli, Streptomyces, Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella, Zymomonas*, and *Salmonella typhimuium* cells, insect cells such as *Drosophila melanogaster* S2 and *Spodoptera frugiperda* Sf9 cells, and yeast cells such as *Saccharomyces cerevisiae, Schizosaccharomyces pombe, Pichia pastoris, Yarrowia lipolytica, Candida albicans, Aspergillus* spp., *Rhizopus* spp., *Penicillium* spp., and *Trichoderma reesei* cells. In some embodiments, the host cells are yeast cells or *E. coli* cells. In some cases, the host cell is a yeast cell. In some instances the host cell is from a strain of yeast engineered to produce a TA of interest. Any of the host cells described in US2008/0176754 now published as U.S. Pat. No. 8,975,063, US2014/0273109 and WO2014/143744, may be adapted for use in the subject cells and methods. In certain embodiments, the yeast cells may be of the species *Saccharomyces cerevisiae* (*S. cerevisiae*). In certain embodiments, the yeast cells may be of the species *Schizosaccharomyces pombe*. In certain embodiments, the yeast cells may be of the species *Pichia pastoris*. Yeast is of interest as a host cell because cytochrome P450 proteins, which are involved in some biosynthetic pathways of interest, are able to fold properly into the endoplasmic reticulum membrane so that their activity is maintained.

Yeast strains of interest that find use in the invention include, but are not limited to, CEN.PK (Genotype: MA Ta/a ura3-52/ura3-52 trp1-289/trp1-289 leu2-3_112/leu2-3_112 his3 Δ1/his3 Δ1 MAL2-8C/MAL2-8C SUC2/SUC2), S288C, W303, D273-10B, X2180, A364A, Σ1278B, AB972, SK1, and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATa/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATa; ade2-1; his3-11, -15; leu2-3, -112; ura3-1; canR; cyr+) which express the *Arabidopsis thaliana* NADPH-P450 reductase ATR1 and the yeast NADPH-P450 reductase CPR1, respectively. In another embodiment, the yeast cell is W303alpha (MATα; his3-11, 15 trp1-1 leu2-3 ura3-1 ade2-1). The identity and genotype of additional yeast strains of interest may be found at EUROSCARF (web.uni-frankfurt.de/fb15/mikro/euroscarf/col_index.html).

In some instances, the host cell is a fungal cell. In certain embodiments, the fungal cells may be of the *Aspergillus* species and strains include *Aspergillus niger* (ATCC 1015, ATCC 9029, CBS 513.88), *Aspergillus oryzae* (ATCC 56747, RIB40), *Aspergillus terreus* (NIH 2624, ATCC 20542) and *Aspergillus nidulans* (FGSC A4).

In certain embodiments, heterologous coding sequences may be codon optimized for expression in *Aspergillus* sp. and expressed from an appropriate promoter. In certain embodiments, the promoter may be selected from phosphoglycerate kinase promoter (PGK), MbfA promoter, cytochrome c oxidase subunit promoter (CoxA), SrpB promoter, TvdA promoter, malate dehydrogenase promoter (MdhA), beta-mannosidase promoter (ManB). In certain embodiments, a terminator may be selected from glucoamylase terminator (GlaA) or TrpC terminator. In certain embodiments, the expression cassette consisting of a promoter, heterologous coding sequence, and terminator may be expressed from a plasmid or integrated into the genome of the host. In certain embodiments, selection of cells maintaining the plasmid or integration cassette may be performed with antibiotic selection such as hygromycin or nitrogen source utilization, such as using acetamide as a sole nitrogen source. In certain embodiments, DNA constructs may be introduced into the host cells using established transformation methods such as protoplast transformation, lithium acetate, or electroporation. In certain embodiments, cells may be cultured in liquid ME or solid MEA (3% malt extract, 0.5% peptone, and ±1.5% agar) or in Vogel's minimal medium with or without selection.

In some instances, the host cell is a bacterial cell. The bacterial cell may be selected from any bacterial genus. Examples of genera from which the bacterial cell may come include *Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella*, and *Zymomonas*. Examples of bacterial species which may be used with the methods of this disclosure include *Arthrobacter nicotianae, Acetobacter aceti, Arthrobacter arilaitensis, Bacillus cereus, Bacillus coagulans, Bacillus licheniformis, Bacillus pumilus, Bacillus sphaericus, Bacillus stearothermophilus, Bacillus subtilis, Bifidobacterium adolescentis, Brachybacterium tyrofermentans, Brevibacterium linens, Carnobacterium divergens, Corynebacterium flavescens, Enterococcus faecium, Gluconacetobacter europaeus, Gluconacetobacter johannae, Gluconobacter oxydans, Hafnia alvei, Halomonas elongata, Kocuria rhizophila, Lactobacillus acidifarinae, Lactobacillus jensenii, Lactococcus lactis, Lactobacillus yamanashiensis, Leuconostoc citreum, Macrococcus caseolyticus, Microbacterium foliorum, Micrococcus lylae, Oenococcus oeni, Pediococcus acidilactici, Propionibacterium acidipropionici, Proteus vulgaris, Pseudomonas fluorescens, Psychrobacter celer, Staphylococcus condimenti, Streptococcus thermophilus, Streptomyces griseus, Tetragenococcus halophilus, Weissella cibaria, Weissella koreensis, Zymomonas mobilis, Corynebacterium glutamicum, Bifidobacterium bifidum/breve/longum, Streptomyces lividans, Streptomyces coelicolor, Lactobacillus plantarum, Lactobacillus sakei, Lactobacillus casei, Pseudoalteromonas citrea, Pseudomonas putida, Clostridium ljungdahlii/aceticum/acetobutylicum/beijerinckii/butyricum*, and *Moorella themocellum/thermoacetica*.

In certain embodiments, the bacterial cells may be of a strain of *Escherichia* coll. In certain embodiments, the strain of *E. coli* may be selected from BL21, DH5α, XL1-Blue, HB101, BL21, and K12, In certain embodiments, heterologous coding sequences may be codon optimized for expression in *E. coli* and expressed from an appropriate promoter. In certain embodiments, the promoter may be selected from T7 promoter, tac promoter, trc promoter, tetracycline-inducible promoter (tet), lac operon promoter (lac), lacO1 promoter. In certain embodiments, the expression cassette consisting of a promoter, heterologous coding sequence, and terminator may be expressed from a plasmid or integrated into the genome. In certain embodiments, the plasmid is selected from pUC19 or pBAD. In certain embodiments, selection of cells maintaining the plasmid or integration cassette may be performed with antibiotic selection such as kanamycin, chloramphenicol, streptomycin, spectinomycin, gentamycin, erythromycin or ampicillin. In certain embodiments, DNA constructs may be introduced into the host cells using established transformation methods such as conjugation, heat shock chemical transformation, or electroporation. In certain embodiments, cells may be cultured in liquid Luria-Bertani (LB) media at about 37° C. with or without antibiotics.

In certain embodiments, the bacterial cells may be a strain of *Bacillus subtilis*. In certain embodiments, the strain of *B. subtilis* may be selected from 1779, GP25, RO-NN-1, 168, BSn5, BEST195, 1A382, and 62178. In certain embodiments, heterologous coding sequences may be codon optimized for expression in *Bacillus* sp. and expressed from an appropriate promoter. In certain embodiments, the promoter may be selected from grac promoter, p43 promoter, or trnQ promoter. In certain embodiments, the expression cassette consisting of the promoter, heterologous coding sequence, and terminator may be expressed from a plasmid or integrated into the genome. In certain embodiments, the plasmid is selected from pHP13 pE194, pC194, pHT01, or pHT43. In certain embodiments, integrating vectors such as pDG364 or pDG1730 may be used to integrate the expression cassette into the genome. In certain embodiments, selection of cells maintaining the plasmid or integration cassette may be performed with antibiotic selection such as erythromycin, kanamycin, tetracycline, and spectinomycin. In certain embodiments, DNA constructs may be introduced into the host cells using established transformation methods such as natural competence, heat shock, or chemical transformation. In certain embodiments, cells may be cultured in liquid Luria-Bertani (LB) media at 37° C. or M9 medium plus glucose and tryptophan.

Genetic Modifications to Host Cells

The host cells may be engineered to include one or more modifications (such as two or more, three or more, four or more, five or more, or even more modifications) that provide for the production of TAs of interest. In some cases, by modification is meant a genetic modification, such as a mutation, addition, or deletion of a gene or fragment thereof, or transcription regulation of a gene or fragment thereof. In some cases, the one or more (such as two or more, three or more, or four or more) modifications is selected from: a feedback inhibition alleviating mutation in a biosynthetic enzyme gene native to the cell; a transcriptional modulation modification of a biosynthetic enzyme gene native to the cell; an inactivating mutation in an enzyme native to the cell; a heterologous coding sequence that encodes an enzyme; and a heterologous coding sequence that encodes a protein which modifies the sub-cellular trafficking and/or localization of an enzyme or a metabolite. A cell that includes one or more modifications may be referred to as a modified cell.

A modified cell may overproduce one or more precursor TA, TA, or modified TA molecules. By overproduce is meant that the cell has an improved or increased production of a TA molecule of interest relative to a control cell (e.g., an unmodified cell). By improved or increased production is meant both the production of some amount of the TA of interest where the control has no TA precursor production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some TA of interest production.

In some cases, the host cell is capable of producing an increased amount of putrescine relative to a control host cell that lacks the one or more modifications (e.g., as described herein). In certain instances, the increased amount of putrescine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of N-methylpyrrolinium relative to a control host cell that lacks the one or more modifications (e.g., as described herein). In certain instances, the increased amount of N-methylpyrrolinium is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of tropine relative to a control host cell that lacks the one or more modifications (e.g., as described herein). In certain instances, the increased amount of tropine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of phenylpyruvic acid relative to a control host cell that lacks the one or more modifications (e.g., as described herein). In certain instances, the increased amount of phenylpyruvic acid is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of phenyllactic acid relative to a control host cell that lacks the one or more modifications (e.g., as described herein). In certain instances, the increased amount of phenyllactic acid is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of littorine relative to a control host cell that lacks the one or more modifications (e.g., as described herein). In certain instances, the increased amount of littorine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of hyoscyamine relative to a control host cell that lacks the one or more modifications (e.g., as described herein). In certain instances, the increased amount of hyoscyamine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of scopolamine relative to a control host cell that lacks the one or more modifications (e.g., as described herein). In certain instances, the increased amount of scopolamine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some embodiments, the host cell is capable of producing a 10% or more yield of tropine from a starting compound such as arginine, such as 20% or more, 30% or more, 40% or more, 50% or more, 60% or more, 70% or more, 80% or more, or even 90% or more yield of tropine from a starting compound.

In some embodiments, the host cell is capable of producing a 10% or more yield of phenyllactic acid from a starting compound such as phenylalanine, such as 20% or more, 30% or more, 40% or more, 50% or more, 60% or more, 70% or more, 80% or more, or even 90% or more yield of phenyllactic acid from a starting compound.

In some embodiments, the host cell is capable of producing a 10% or more yield of hyoscyamine from a starting compound such as arginine or phenylalanine, such as 20% or more, 30% or more, 40% or more, 50% or more, 60% or more, 70% or more, 80% or more, or even 90% or more yield of hyoscyamine from a starting compound.

In some embodiments, the host cell is capable of producing a 10% or more yield of scopolamine from a starting compound such as arginine or phenylalanine, such as 20% or more, 30% or more, 40% or more, 50% or more, 60% or more, 70% or more, 80% or more, or even 90% or more yield of scopolamine from a starting compound.

In some embodiments, the host cell overproduces one or more TA of interest molecules selected from the group consisting of arginine, ornithine, agmatine, putrescine, N-methylputrescine, 4-methylaminobutanal, N-methylpyrrolinium, 4-(1-methyl-2-pyrrodinyl)-3-oxobutanoic acid, tropinone, tropine, phenylalanine, prephenic acid, phenylpyruvic acid, phenyllactic acid, glucose-1-O-phenyllactate, littorine, hyoscyamine aldehyde, hyoscyamine, anisodamine, and scopolamine.

Any convenient combinations of the one or more modifications may be included in the subject host cells. In some cases, two or more (such as two or more, three or more, or four or more) different types of modifications are included. In certain instances, two or more (such as three or more, four or more, five or more, or even more) distinct modifications of the same type of modification are included in the subject cells.

In some embodiments of the host cell, when the cell includes one or more heterologous coding sequences that encode one or more enzymes, it includes at least one additional modification selected from the group consisting of: a feedback inhibition alleviating mutations in a biosynthetic enzyme gene native to the cell; a transcriptional modulation modification of a biosynthetic enzyme gene native to the cell; and an inactivating mutation in an enzyme native to the cell. In certain embodiments of the host cell, when the cell includes one or more feedback inhibition alleviating mutations in one or more biosynthetic enzyme genes native to the cell, it includes a least one additional modification selected from the group consisting of: a transcriptional modulation modification of a biosynthetic enzyme gene native to the cell; an inactivating mutation in an enzyme native to the cell; and a heterologous coding sequence that encode an enzyme. In some embodiments of the host cell, when the cell includes one or more transcriptional modulation modifications of one or more biosynthetic enzyme genes native to the cell, it includes at least one additional modification selected from the group consisting of: a feedback inhibition alleviating mutation in a biosynthetic enzyme gene native to the cell; an inactivating mutation in an enzyme native to the cell; a heterologous coding sequence that encodes an enzyme; and a heterologous coding sequence that encodes a protein which modifies the sub-cellular trafficking and/or localization of an enzyme or a metabolite. In certain instances of the host cell, when the cell includes one or more inactivating mutations in one or more enzymes native to the cell, it includes at least one additional modification selected from the group consisting of: a feedback inhibition alleviating mutation in a biosynthetic enzyme gene native to the cell; a transcriptional modulation modification of a biosynthetic enzyme gene native to the cell; a heterologous coding sequence that encodes an enzyme; and a heterologous coding sequence that encodes a protein which modifies the sub-cellular trafficking and/or localization of an enzyme or a metabolite.

In certain embodiments of the host cell, the cell includes one or more feedback inhibition alleviating mutations in one or more biosynthetic enzyme genes native to the cell; and one or more transcriptional modulation modifications of one or more biosynthetic enzyme gene native to the cell. In certain embodiments of the host cell, the cell includes one or more feedback inhibition alleviating mutations in one or more biosynthetic enzyme genes native to the cell; and one or more inactivating mutations in an enzyme native to the cell. In certain embodiments of the host cell, the cell includes one or more feedback inhibition alleviating mutations in one or more biosynthetic enzyme genes native to the cell; and one or more heterologous coding sequences. In some embodiments, the host cell includes one or more modifications (e.g., as described herein) that include one or more of the genes of interest described in Table 1.

Feedback Inhibition Alleviating Mutations

In some instances, the host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). As used herein, the term "feedback inhibition alleviating mutation" refers to a mutation that alleviates a feedback inhibition control mechanism of a host cell. Feedback inhibition is a control mechanism of the cell in which an enzyme in the synthetic pathway of a regulated compound is inhibited when that compound has accumulated to a certain level, thereby balancing the amount of the compound in the cell. In some instances, the one or more feedback inhibition alleviating mutations is in an enzyme described in a biosynthetic pathway of FIGS. 1-4 or in the schematic of FIG. 8. A mutation that alleviates feedback inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes native to the host cell that are directed to regulation of levels of TA precursors may be targeted for alleviation in the host cell. The host cell may include one or more feedback inhibition alleviating mutations in one or more biosynthetic enzyme genes native to the cell. The mutation may be located in any convenient biosynthetic enzyme genes native to the host cell where the biosynthetic enzyme is subject to regulatory control. In some embodiments, the one or more biosynthetic enzyme genes encode one or more enzymes selected from an ornithine decarboxylase (ODC), an ornithine decarboxylase antizyme, and a putrescine N-methyltransferase. In some embodiments, the one or more biosynthetic enzyme genes encode an ornithine decarboxylase. In some instances, the one or more biosynthetic enzyme genes encode an ornithine decarboxylase antizyme. In some embodiments, the one or more biosynthetic enzyme genes encode a putrescine N-methyltransferase. In certain instances, the one or more feedback inhibition alleviating mutations are present in a biosynthetic enzyme gene selected from SPE1, OAZ1, and PMT. In certain instances, the one or more feedback inhibition alleviating mutations are present in a biosynthetic enzyme gene that is SPE1. In certain instances, the one or more feedback inhibition alleviating mutations are present in a biosynthetic enzyme gene that is OAZ1. In certain instances, the one or more feedback inhibition alleviating mutations are present in a biosynthetic enzyme gene that is PMT. In some embodiments, the host cell includes one or more feedback inhibition alleviating mutations in one or more biosynthetic enzyme genes such as one of those genes described in Table 1.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the feedback inhibited copy of the enzyme is under the native cell transcriptional regulation. In some instances, feedback inhibited copy of the enzyme is introduced with engineered constitutive or dynamic regulation of protein expression by placing it under the control of a synthetic promoter.

In certain embodiments, the host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes native to the host cell.

Transcriptional Modulation Modifications

The host cells may include one or more transcriptional modulation modifications (such as two or more, three or more, four or more, five or more, or even more modifications) of one or more biosynthetic enzyme genes of the cell. In some cases, the one or more biosynthetic enzyme genes are native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Any convenient biosynthetic enzyme genes may be transcriptionally modulated, and include but are not limited to, those biosynthetic enzymes described in FIGS. 1-3, such as ARG2, CAR1, SPE1, FMS1, PHA2, ARO8, ARO9, and UGP1. In some instances, the one or more biosynthetic enzyme genes is selected from ARG2, CAR1, SPE1, and FMS1. In some cases, the one or more biosynthetic enzyme genes is ARG2. In certain instances, the one or more biosynthetic enzyme genes is CAR1. In some embodiments, the one or more biosynthetic enzyme genes is SPE1. In some embodiments, the one or more biosynthetic enzyme genes is FMS1. In some embodiments, the host cell includes one or more transcriptional modulation modifications to one or more genes such as one of those genes described in Table 1. In some embodiments, the host cell includes one or more transcriptional modulation modifications to one or more genes such as one of those genes described in a biosynthetic pathway of one of FIGS. 1-4 or in the schematic of FIG. 8.

In some embodiments, the transcriptional modulation modification includes substitution of a strong promoter for a native promoter of the one or more biosynthetic enzyme genes or the expression of an additional copy(ies) of the gene or genes under the control of a strong promoter. The promoters driving expression of the genes of interest may be constitutive promoters or inducible promoters, provided that the promoters may be active in the host cells. The genes of interest may be expressed from their native promoters, or non-native promoters may be used. Although not a requirement, such promoters should be medium to high strength in the host in which they are used. Promoters may be regulated or constitutive. In some embodiments, promoters that are not glucose repressed, or repressed only mildly by the presence of glucose in the culture medium, are used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673 684 (1987)). Other strong promoters of interest include, but are not limited to, the ADHI promoter of baker's yeast (Ruohonen L., et al, *J. Biotechnol.* 39:193 203 (1995)), the phosphate-starvation induced promoters such as the PHOS promoter of yeast (Hinnen, A., et al, in *Yeast Genetic Engineering*, Barr, P. J., et al. eds, Butterworths (1989), the alkaline phosphatase promoter from *B. licheniformis* (Lee. J. W. K., et al., *J. Gen. Microbiol.* 137:1127 1133 (1991)), GPD1 and TEF1. Yeast promoters of interest include, but are not limited to, inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, phosphoglycerate kinase (PGK), triose phosphate isomerase (TPI), etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., *E. coli*. In some cases, promoter selection may be used to optimize transcription, and hence, enzyme levels to maximize production while minimizing energy resources.

Inactivating Mutations

Figure 8:
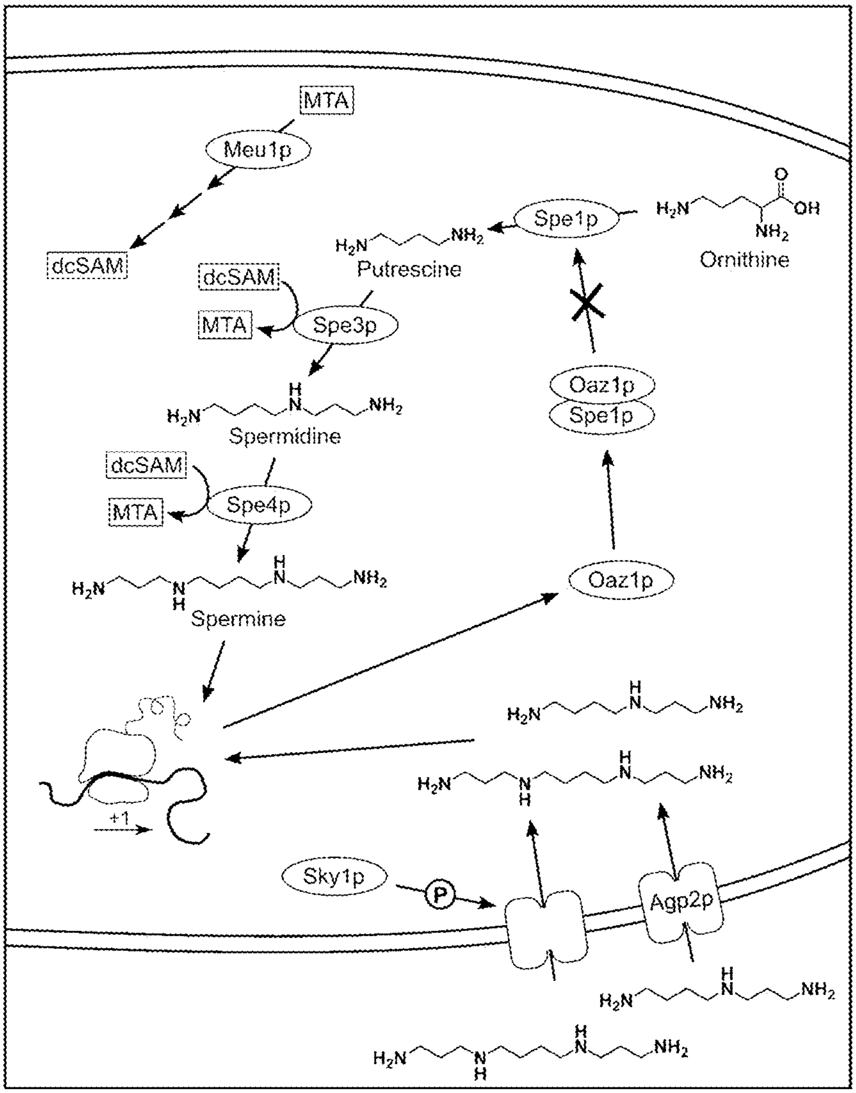
FIG. 8 illustrates the endogenous regulatory pathways that tightly control intracellular putrescine levels during normal yeast growth.
Figure 9:
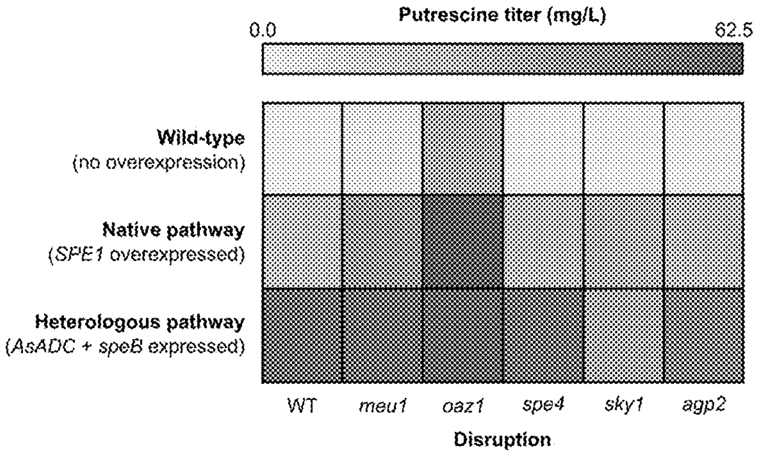
FIG. 9 shows a heat map of putrescine production in yeast strains with disruptions to endogenous polyamine biosynthesis regulatory mechanisms. For overexpression of native or heterologous putrescine pathways, indicated genes were expressed from low-copy plasmids in wild-type yeast (WT) or each single disruption strain. Strains were cultured in selective (YNB-DO) media with 2% dextrose at 30° C. for 72 h before LC-MS/MS analysis. All data represent the mean of at least three biological replicates. This figure shows that yeast strains that have single disruptions of polyamine metabolism genes and overexpressed endogenous or heterologous putrescine biosynthetic pathways can produce putrescine in liquid culture.

The host cells may include one or more inactivating mutations to an enzyme of the cell (such as two or more, three or more, four or more, five or more, or even more). The inclusion of one or more inactivating mutations may modify the flux of a synthetic pathway of a host cell to increase the levels of a TA of interest or a desirable enzyme or precursor leading to the same. In some cases, the one or more inactivating mutations are to an enzyme native to the cell. FIG. 8 illustrates the native regulatory mechanisms in yeast which act on polyamine production pathways and FIG. 9 shows the effects of disruptions to these native regulatory systems on production of putrescine. As used herein, by "inactivating mutation" is meant one or more mutations to a gene or regulatory DNA sequence of the cell, where the mutation(s) inactivates a biological activity of the protein expressed by that gene of interest. In some cases, the gene is native to the cell. In some instances, the gene encodes an enzyme that is inactivated and is part of or connected to the synthetic pathway of a TA of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60% or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some embodiments, the cell includes an inactivating mutation in an enzyme native to the cell. Any convenient enzymes may be targeted for inactivation. Enzymes of interest include, but are not limited to, those enzymes described in FIGS. 1-4, 8, 11, 22, and 41 whose action in the biosynthetic pathways of the host cell tends to reduce the levels of a TA of interest. In some cases, the enzyme has methylthioadenosine phosphorylase activity. In certain embodiments, the enzyme that includes an inactivating mutation is MEU1 (see e.g., FIGS. 8, 9, and 13). In some cases, the enzyme has ornithine decarboxylase antizyme activity. In certain embodiments, the enzyme that includes an inactivating mutation is OAZ1. In some cases, the enzyme has spermidine synthase activity. In certain embodiments, the enzyme that includes an inactivating mutation is SPE3. In some cases, the enzyme has spermine synthase activity. In some embodiments, the enzyme that includes an inactivating mutation is SPE4. In some cases, the enzyme is a membrane transporter with polyamine export activity. In certain embodiments, the enzyme or protein that includes an inactivating mutation is TPOS. In some cases, the enzyme has phenylacrylic acid decarboxylase activity. In certain embodiments, the enzyme that includes an inactivating mutation is PAD1. In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from HFD1, ALD2, ALD3, ALD4, ALD5, and ALD6. In certain embodiments, the enzyme that includes and inactivating mutation(s) is HFD1. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some cases, the enzyme has glucosidase activity. In certain embodiments, the enzyme that includes an inactivating mutation is selected from EXG1, SPR1, and EGH1. In certain embodiments, the enzyme that includes an inactivating mutation(s) is EXG1. In certain embodiments, the enzyme that includes an inactivating mutation(s) is SPR1. In certain embodiments, the enzyme that includes an inactivating mutation(s) is EGH1. In some embodiments, the host cell includes one or more inactivating mutations to one or more genes described in Table 1.

Methods for Performing TA Acyl Transfer Reactions Using Functional Expression of Acyltransferases in Non-Plant Hosts Some methods, processes, and systems provided herein describe the concerted reaction of one or more TA precursors comprising an acyl donor group with one or more TA precursors comprising an acyl acceptor group to produce one or more TAs within a non-plant cell (hereafter referred to as TA acyl transfer reactions). Some of these methods, processes, and systems may comprise an engineered host cell. In some examples, the TA acyl transfer reaction is a key step in the conversion of a substrate to a diverse range of alkaloids. In some examples, the TA acyl transfer reaction comprises a condensation reaction.

In some examples, the TA acyl transfer may involve at least one condensation reaction. In some cases, at least one of the condensation reactions is carried out in the presence of an enzyme. In some cases, at least one of the condensation reactions is catalyzed by an enzyme. In some cases, at least one enzyme is useful to catalyze the condensation reaction.

In some methods, processes and systems described herein, a condensation reaction may be performed in the presence of an enzyme. In some examples, the enzyme may be an acyltransferase. The acyltransferase may use a TA with an alcohol or carboxylate functional group as a substrate. The acyltransferase may use a TA containing a carboxylate group activated via a 1-O-β glycosidic linkage to a sugar (hereafter referred to as a glycoside) as a substrate. The acyltransferase may convert the TA alcohol and carboxylate/glycoside functional groups to a corresponding ester derivative. Non-limiting examples of enzymes suitable for condensation of TA precursors in this disclosure include serine carboxypeptidase-like acyltransferases (SCPL-ATs). For example, littorine synthase (EC 2.3.1.-) may condense tropine and other TA precursors containing alcohol functional groups with 1-O-β-phenyllactoyl-glucose and other TA glycoside precursors to littorine and other corresponding ester products. In some examples, a protein that comprises an SCPL-AT domain of any one of the preceding examples may perform the condensation. In some examples, the SCPL-AT may catalyze the condensation reaction within a host cell, such as an engineered host cell, as described herein. In yet other examples, the SCPL-AT may catalyze the condensation reaction within a sub-cellular compartment inside a host cell, such as an engineered host cell, as described herein.

In some embodiments of the invention, the amino acid sequence of an acyltransferase enzyme which is used to perform a TA acyl transfer reaction, such as an SCPL-AT enzyme, is subject to one or more modifications which alters the post-translational processing, trafficking, folding, oligomerization, and/or sub-cellular localization of the enzyme. As some acyltransferase enzymes, including SCPL-AT enzymes, have never been demonstrated to exhibit catalytic activity in living, non-plant cells, such modifications may prove useful, or may be necessary, for activity in non-plant host cells. Examples of such modifications include, but are not limited to: addition, removal, or replacement of N-terminal signal peptide sequences; addition, removal, or replacement of internal propeptide sequences; addition or removal of asparagine-linked N-glycosylation sites; addition or removal of serine-linked O-glycosylation sites; and fusion of protein domains to the N- and/or C-terminus of the acyltransferase domain.

In one embodiment of the invention, an SCPL-AT enzyme domain is modified at its N-terminus by fusion of a soluble protein domain. This soluble domain masks any internal signal sequences in the acyltransferase domain, thereby modifying the trafficking and/or sub-cellular localization of the fused SCPL-AT domain. In some examples, the N-terminally fused domain induces trafficking of the SCPL-AT domain to sub-cellular compartments including, but not limited to, the ER membrane, ER lumen, cis-Golgi, trans-Golgi, lysosome, vacuole membrane, and vacuole lumen. The N-terminally fused soluble domain can also modify the oligomerization state of the SCPL-AT domain from its native state (monomer) to any state including, but not limited to, homodimer, heterodimer, homotrimer, heterotrimer, homotetramer, heterotetramer, homohexamer, heterohexamer, homooctamer, heterooctamer, or greater degrees of oligomerization.

In one example, the N-terminally fused soluble protein domain is a fluorescent protein selected from the group including, but not limited to, fluorescent proteins derived from *Aequoria* sp. and fluorescent proteins derived from *Discosoma* sp. In one example, the N-terminally fused soluble protein domain is red fluorescent protein from *Discosoma* sp. (DsRed). In other examples, the N-terminally fused soluble protein domain is another enzyme in the TA biosynthetic pathway, including but not limited to, ornithine decarboxylase, putrescine N-methyltransferase, pyrrolidine ketide synthase, tropinone reductase, phenylpyruvate reductase, phenyllactate UDP-glucosyltransferase 84A27, and hyoscyamine dehydrogenase.

Examples of amino acid sequences of soluble protein domains which can be fused to the N-terminus of a SCPL-AT domain that can then be used to perform a TA acyl transfer reaction within a non-plant cell are provided in Table 3. An amino acid sequence for a SCPL-AT enzyme comprising a fused N-terminal domain and that is utilized in TA acyl transfer reactions in non-plant cells may be 50% or more identical to a given amino acid sequence as listed in Table 3. For example, an amino acid sequence for such an acyltransferase may comprise an amino acid sequence that is at least 50% or more, 55% or more, 60% or more, 65% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered non-plant host cell may be provided that produces an acyltransferase that catalyzes a TA acyl transfer reaction, wherein the acyltransferase comprises an amino acid sequence whose N-terminus is fused to the amino acid sequence of a soluble protein domain selected from the group consisting of those sequences in Table 3. The acyltransferase that is produced within the engineered host cell may be recovered and purified so as to form a biocatalyst. The one or more enzymes that are recovered from the engineered host cell that produces the acyltransferase may be used in a process for carrying out a TA acyl transfer reaction. The process may include contacting the TA precursors possessing an alcohol and/or a carboxylate/glycoside functional group with an acyltransferase in an amount sufficient to convert the alcohol and/or carboxylate/glycoside group to a corresponding ester group. In examples, the TA precursors possessing an alcohol and/or a carboxylate/glycoside functional group may be contacted with a sufficient amount of the one or more enzymes such that at least 5% of said TA precursors are converted to the corresponding ester. In further examples, the TA possessing an alcohol and/or a carboxylate/glycoside functional group may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said TA precursors are converted to the corresponding ester.

The one or more enzymes that may be used to carry out a TA acyl transfer reaction may contact the TA precursors in vitro. Additionally, or alternatively, the one or more enzymes that may be used to carry out a TA acyl transfer reaction may contact the TA precursors in vivo. Additionally, the one or more enzymes that may be used to carry out a TA acyl transfer reaction may be provided to a cell having the TA precursors within, or may be produced within an engineered non-plant host cell.

In some examples, the methods provide for engineered non-plant host cells that produce an alkaloid product, wherein the TA acyl transfer reaction may comprise a key step in the production of an alkaloid product. In some examples, the alkaloid produced is a medicinal TA. In still other embodiments, the alkaloid produced is derived from a medicinal TA, including, for example, non-natural TAs. In still other embodiments, the alkaloid product is selected from the group consisting of medicinal TA, non-medicinal TA, and non-natural TA.

In some examples, the substrates are TA precursors selected from the group consisting of tropine, pseudotropine, ecgonine, methylecgonine, phenyllactic acid, cinnamic acid, ferulic acid, coumaric acid, and glycosides of the listed compounds.

In some examples, the methods provide for engineered non-plant host cells that produce alkaloid products from tropine and 1-O-β-phenyllactoylglucose. The condensation of tropine and 1-O-β-phenyllactoylglucose to littorine may comprise a key step in the production of diverse alkaloid products from a precursor. In some examples, the precursor is an L-amino acid or a sugar (e.g., glucose). The diverse alkaloid products can include, without limitation, medicinal TAs, non-medicinal TAs, and non-natural TAs.

Any suitable carbon source may be used as a precursor toward a TA acyl transfer reaction. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-arginine and L-phenylalanine). In some examples, a TA or a precursor of a TA possessing an alcohol and/or a carboxylate/glycoside functional group may be added directly to an engineered host cell of the invention, including, for example, tropine, pseudotropine, ecgonine, methylecgonine, phenyllactic acid, cinnamic acid, ferulic acid, coumaric acid, and glycosides of the listed compounds.

In some embodiments, the substrate used to carry out the vacuolar TA acyl transfer reaction may comprise one or more alcohol and/or carboxylate/glycoside functional groups, wherein only one of said functional groups is condensed to the corresponding ester.

TA Alcohol-Aldehyde Interconversions

Some methods, processes, and systems provided herein describe the conversion of TAs with aldehyde functional groups to TAs with alcohol (hydroxyl) functional groups, and the conversion of TAs with alcohol functional groups to TAs with aldehyde functional groups (hereafter referred to as TA alcohol-aldehyde interconversions). Some of these methods, processes, and systems may comprise an engineered host cell. In some examples, the TA alcohol-aldehyde interconversion is a key step in the conversion of a substrate to a diverse range of alkaloids. In some examples, the conversion of a TA aldehyde group to a TA alcohol group comprises a reduction reaction. In some cases, reduction of a substrate TA aldehyde to an alcohol may be performed by reducing an aldehyde substrate to the corresponding tetrahedral oxyanion intermediate, then protonating this intermediate to a hydroxyl as provided in FIG. 2 and as represented generally in Scheme 1. As provided in Scheme 1, $R^1$ may be H, $CH_3$, or a higher order alkyl group; $R^2$ and $R^3$ may be H, OH, or $OCH_3$; $R^4$ may be H; and $R^5$ may be H, OH, $C_1$-$C_4$ alkyl, $C_1$-$C_4$ alkoxy, $C_1$-$C_4$ acyl, F, Cl, or Br.

Scheme 1

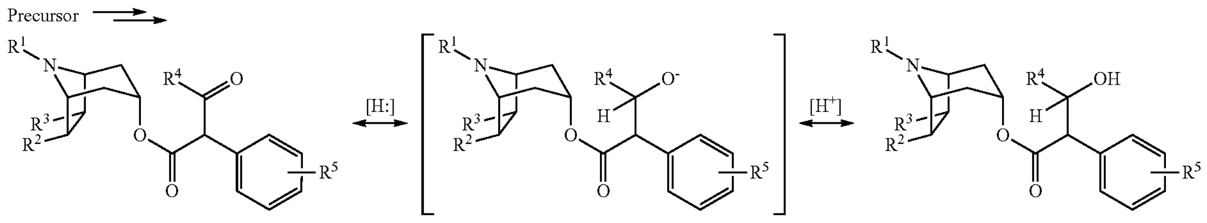

TA with aidehyde functional group (e.g., hyoscyamine aldehyde)    TA with tetrahedral intermediate    TA with alcohol functional group (e.g., hyoscyamine)

In some examples, the TA alcohol-aldehyde interconversion may involve at least one oxidation reaction or at least one reduction reaction. In some cases, at least one of the oxidation or reduction reactions is carried out in the presence of an enzyme. In some cases, at least one of the oxidation or reduction reactions is catalyzed by an enzyme. In some cases, the oxidation and reduction reactions are both carried out in the presence of at least one enzyme. In some cases, at least one enzyme is useful to catalyze the oxidation and reduction reactions. The oxidation and reduction reactions may be catalyzed by the same enzyme.

In some methods, processes and systems described herein, an oxidation or reduction reaction may be performed in the presence of an enzyme. In some examples, the enzyme may be a dehydrogenase. The dehydrogenase may use a TA with an alcohol or aldehyde functional group as a substrate. The dehydrogenase may convert the TA alcohol or aldehyde functional group to a corresponding aldehyde or alcohol derivative. The dehydrogenase may be referred to as hyoscyamine dehydrogenase (HDH). Non-limiting examples of enzymes suitable for oxidation and/or reduction of TAs in this disclosure include a cytochrome P450 oxidase, a 2-oxoglutarate-dependent oxidase, a flavoprotein oxidase, a short-chain dehydrogenase-reductase (SDR), a medium-chain dehydrogenase-reductase (MDR), a cinnamyl alcohol dehydrogenase (CAD), and an aldo-keto reductase (AKR). For example, tropinone reductase 1 (EC 1.1.1.206) may oxidize tropinone and other TA precursors with ketone functional groups to tropine (3α-tropanol) and other corresponding alcohol products. In some examples, a protein that comprises a dehydrogenase domain of any one of the preceding examples may perform the oxidation or reduction. In some examples, the dehydrogenase may catalyze the oxidation and/or reduction reactions within a host cell, such as an engineered host cell, as described herein.

Examples of amino acid sequences of a dehydrogenase enzyme that may be used to perform a TA alcohol-aldehyde interconversion are provided in Table 2. An amino acid sequence for a dehydrogenase that is utilized in TA alcohol-aldehyde interconversions may be 50% or more identical to a given amino acid sequence as listed in Table 2. For example, an amino acid sequence for such a dehydrogenase may comprise an amino acid sequence that is at least 50% or more, 55% or more, 60% or more, 65% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces a dehydrogenase that catalyzes a TA alcohol-aldehyde interconversion, wherein the dehydrogenase comprises an amino acid sequence selected from the group consisting of those sequences in Table 2. The dehydrogenase that is produced within the engineered host cell may be recovered and purified so as to form a biocatalyst. The one or more enzymes that are recovered from the engineered host cell that produces the dehydrogenase may be used in a process for carrying out a TA alcohol-aldehyde interconversion. The process may include contacting the TA possessing an alcohol and/or an aldehyde functional group with a dehydrogenase in an amount sufficient to convert the alcohol and/or aldehyde group of the TA to a corresponding aldehyde and/or alcohol group. In examples, the TA possessing an alcohol and/or an aldehyde functional group may be contacted with a sufficient amount of the one or more enzymes such that at least 5% of said TA is converted to its corresponding aldehyde and/or alcohol group. In further examples, the TA possessing an alcohol and/or an aldehyde functional group may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said TA is converted to its corresponding aldehyde and/or alcohol group.

The one or more enzymes that may be used to carry out a TA alcohol-aldehyde interconversion may contact the TA in vitro. Additionally, or alternatively, the one or more enzymes that may be used to carry out a TA alcohol-aldehyde interconversion may contact the TA in vivo. Additionally, the one or more enzymes that may be used to carry out a TA alcohol-aldehyde interconversion may be provided to a cell having the TA within, or may be produced within an engineered host cell.

In some examples, the methods provide for engineered host cells that produce an alkaloid product, wherein the TA alcohol-aldehyde interconversion may comprise a key step in the production of an alkaloid product. In some examples, the alkaloid produced is a medicinal TA. In still other embodiments, the alkaloid produced is derived from a medicinal TA, including, for example, non-natural TAs. In another embodiment, a TA possessing an alcohol and/or an aldehyde functional group is an intermediate toward the product of the engineered host cell. In still other embodiments, the alkaloid product is selected from the group consisting of medicinal TA, non-medicinal TA, and non-natural TA.

In some examples, the substrate is a TA or a precursor of a TA selected from the group consisting of littorine, hyoscyamine aldehyde, hyoscyamine, anisodamine, and scopolamine.

In some examples, the methods provide for engineered host cells that produce alkaloid products from hyoscyamine aldehyde. The reduction of hyoscyamine aldehyde to hyoscyamine may comprise a key step in the production of diverse alkaloid products from a precursor. In some examples, the precursor is an L-amino acid or a sugar (e.g., glucose). The diverse alkaloid products can include, without limitation, medicinal TAs, non-medicinal TAs, and non-natural TAs.

Any suitable carbon source may be used as a precursor toward a TA alcohol-aldehyde interconversion. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-arginine and L-phenylalanine). In some examples, a TA or a precursor of a TA possessing an alcohol and/or an aldehyde functional group may be added directly to an engineered host cell of the invention, including, for example, tropine, pseudotropine, ecgonine, methylecgonine, littorine, hyoscyamine aldehyde, hyoscyamine, anisodamine, and scopolamine.

In some embodiments, the substrate used to carry out the TA alcohol-aldehyde interconversion may comprise one or more alcohol and/or aldehyde functional groups, wherein only one of said functional groups is oxidized or reduced to the corresponding aldehyde or alcohol group.

Methods for Increasing Intracellular and Extracellular Metabolite Transport

Some methods, processes, and systems provided herein describe the use of proteins (hereafter referred to as 'transporters') to translocate metabolites across lipid membranes (hereafter referred to as 'transmembrane transport'). Some of these methods, processes, and systems may comprise an engineered host cell. In some examples, transmembrane transport is a key step in the conversion of a substrate to a diverse range of alkaloids.

In certain embodiments, the host cell includes one or more heterologous coding sequences for one or more transporters or active fragments thereof that localize to a lipid membrane and translocate a TA or a TA precursor across the same lipid membrane. In some examples, the lipid membrane is the vacuole membrane. In other examples, the lipid membrane is the ER membrane. In some examples, the lipid membrane is the peroxisome membrane. In other examples, the lipid membrane is the cellular plasma membrane.

In some examples, TAs and TA precursors transported in this manner include, but are not limited to, putrescine, N-methylputrescine, 4-methylaminobutanal, N-methylpyrrolinium, tropinone, tropine, phenyllactic acid, 1-O-β-phenyllactoylglucose, littorine, hyoscyamine, anisodamine, and scopolamine. The accumulation of such TAs or TA precursors in specific sub-cellular compartments can preclude access by operably linked biosynthetic enzymes in different compartments; therefore, the use of transporters which translocate TAs or TA precursors from one compartment to another can mitigate such transport limitations. In certain cases, the expression of heterologous coding sequences for one or more transporters within a host cell can increase production of a TA or a TA precursor.

In some embodiments, the transporter or active fragment thereof is a multidrug and toxin extrusion (MATE) transporter. Any convenient MATE transporters which transport one or more of the aforementioned TAs or TA precursors find use in the subject host cells. Transporter proteins of interest include, but are not limited to, enzymes such as *Nicotiana tabacum* jasmonate-inducible alkaloid transporter 1 (NtJAT1), *N. tabacum* MATE1, *N. tabacum* MATE2, or any others as described in Table 1 and Table 4.

In certain embodiments, the transporter or active fragment thereof is a nitrate/peptide family (NPF) transporter. Any convenient NPF transporters which transport one or more of the aforementioned TAs or TA precursors find use in the subject host cells. In other embodiments, the transporter or active fragment thereof is an ATP-binding cassette (ABC) transporter. Any convenient NPF transporters which transport one or more of the aforementioned TAs or TA precursors find use in the subject host cells. In some embodiments, the transporter or active fragment thereof is a pleiotropic drug resistance (PDR) transporter. Any convenient PDR transporters which transport one or more of the aforementioned TAs or TA precursors find use in the subject host cells.

In certain embodiments, the host cell includes a heterologous coding sequence for a transporter or an active fragment thereof. In some embodiments of the invention, the amino acid sequence of a transporter is subject to one or more modifications which alters the sub-cellular localization, the direction of substrate translocation, and/or the topological orientation of the enzyme. Examples of such modifications include, but are not limited to: addition, removal, or replacement of N-terminal, C-terminal, or internal signal sequences; addition, removal, replacement, or rearrangement of transmembrane helices; and fusion of protein domains to the N- and/or C-terminus of the transporter.

Examples of amino acid sequences of transporters which can be used to mitigate substrate transport limitations and/or to increase accumulation of TAs or TA precursors in specific cellular compartments are provided in Table 4. An amino acid sequence for a transporter that is utilized in this manner in non-plant cells may be 50% or more identical to a given amino acid sequence as listed in Table 4. For example, an amino acid sequence for such a transporter may comprise an amino acid sequence that is at least 50% or more, 55% or more, 60% or more, 65% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered non-plant host cell may be provided that produces a transporter which translocates one or more TAs or TA precursors from one cellular compartment to another, wherein the transporter comprises an amino acid sequence selected from the group consisting of those sequences in Table 4. In some examples, the methods provide for engineered non-plant host cells that produce an alkaloid product, wherein TA transmembrane transport may comprise a key step in the production of an alkaloid product. In some examples, the alkaloid produced is a medicinal TA. In still other embodiments, the alkaloid produced is derived from a medicinal TA, including, for example, non-natural TAs. In still other embodiments, the alkaloid product is selected from the group consisting of medicinal TA, non-medicinal TA, and non-natural TA.

Heterologous Coding Sequences

In some instances, the host cells are cells that harbor one or more heterologous coding sequences (such as two or more, three or more, four or more, five or more, or even more) which encode activity(ies) that enable the host cells to produce desired TAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

In examples, the engineered host cell comprises a plurality of heterologous coding sequences each encoding an enzyme. In some examples, the plurality of enzymes encoded by the plurality of heterologous coding sequences may be distinct from each other. In some examples, some of the plurality of enzymes encoded by the plurality of heterologous coding sequences may be distinct from each other and some of the plurality of enzymes encoded by the plurality of heterologous coding sequences may be duplicate copies.

In some examples, the heterologous coding sequences may be operably connected. Heterologous coding sequences that are operably connected may be within the same pathway of producing a particular tropane alkaloid product. In some examples, the operably connected heterologous coding sequences may be directly sequential along the pathway of producing a particular tropane alkaloid product. In some examples, the operably connected heterologous coding sequences may have one or more native enzymes between one or more of the enzymes encoded by the plurality of heterologous coding sequences. In some examples, the heterologous coding sequences may have one or more heterologous enzymes between one or more of the enzymes encoded by the plurality of heterologous coding sequences. In some examples, the heterologous coding sequences may have one or more non-native enzymes between one or more of the enzymes encoded by the plurality of heterologous coding sequences.

In some embodiments, the host cell includes putrescine N-methyltransferase (PMT) activity. Any convenient PMT enzymes find use in the subject host cells. PMT enzymes of interest include, but are not limited to, enzymes such as EC 2.1.1.53, as described in Table 1. In certain embodiments, the host cell includes a heterologous coding sequence for a PMT or an active fragment thereof.

In some instances, the host cell includes one or more heterologous coding sequences for one or more enzymes or active fragments thereof that convert NMP to 4MAB. In certain cases, the one or more enzymes is selected from plant methylputrescine oxidases (MPOs) and eukaryotic MPOs (e.g., EC 1.4.3.22).

In certain embodiments, the cell includes one or more heterologous coding sequences for one or more enzymes or active fragments thereof that convert NMPy to MPOB. In certain cases, the one or more enzymes is a type III polyketide synthase (e.g., EC 2.3.1.-). The one or more heterologous coding sequences may be derived from any convenient species (e.g., as described herein). In some cases, the one or more heterologous coding sequences may be derived from a species described in Table 1. In some cases, the one or more heterologous coding sequences are present in a gene or enzyme selected from those described in Table 1.

In certain embodiments, the host cell includes tropinone synthase activity. Any convenient tropinone synthase enzymes (e.g., CYP82M3) find use in the subject host cells. Tropinone synthase enzymes of interest include, but are not limited to, enzymes such as EC 1.14.14.-, as described in Table 1. In certain embodiments, the host cell includes a heterologous coding sequence for a tropinone synthase or an active fragment thereof.

In certain embodiments, the host cell includes tropinone reductase activity. Any convenient tropinone reductase enzymes find use in the subject host cells. Tropinone reductase enzymes of interest include, but are not limited to, enzymes such as EC 1.1.1.206, as described in Table 1. In certain embodiments, the host cell includes a heterologous coding sequence for a tropinone reductase or an active fragment thereof.

In some instances, the host cell includes phenylpyruvate reductase (PPR) activity. Any convenient PPR enzymes find use in the subject host cells. Some PPR enzymes of interest include, but are not limited to, enzymes such as EC 1.1.1.237, as described in Table 1. In certain embodiments, the host cell includes a heterologous coding sequence for a PPR or an active fragment thereof.

In certain embodiments, the host cell includes phenyllactate glycosyltransferase activity. Any convenient phenyllactate glycosyltransferase enzymes find use in the subject host cells. Glycosyltransferase enzymes include, but are not limited to, enzymes such as 2.4.1.-, which transfer a glucose moiety from UDP-glucose to phenyllactate by means of a glycosidic ester linkage, as described in Table 1. In certain embodiments, the host cell includes a heterologous coding sequence for a phenyllactate glycosyltransferase or an active fragment thereof.

In certain embodiments, the cell includes one or more heterologous coding sequences for one or more enzymes or active fragments thereof that convert tropine and 1-O-β-phenyllactoylglucose to littorine. In some embodiments, the host cell includes littorine synthase activity. Any convenient littorine synthase enzymes or enzymes comprising littorine synthase active fragments find use in the subject host cells. Littorine synthase enzymes of interest include, but are not limited to, enzymes such as EC 2.3.1.-, as described in Table 1, and enzymes comprising littorine synthase enzymes whose N-termini are fused to soluble protein domains described in Table 3. In certain embodiments, the host cell includes a heterologous coding sequence for a littorine synthase or an active fragment thereof.

In certain instances, the host cell includes littorine mutase activity. Any convenient littorine mutase enzymes find use in the subject host cells. Littorine mutase enzymes of interest include, but are not limited to, enzymes such as EC 1.14.19.-, as described in Table 1. In certain embodiments, the host cell includes a heterologous coding sequence for a littorine mutase or an active fragment thereof.

In some embodiments, the host cell includes hyoscyamine dehydrogenase (HDH) activity. Any convenient HDH enzymes find use in the subject host cells. Some HDH enzymes of interest include, but are not limited to, those sequences described in Table 2. In certain embodiments, the host cell includes a heterologous coding sequence for an HDH or an active fragment thereof.

In certain embodiments, the host cell includes hyoscyamine 6β-hydroxylase/dioxygenase (H6H) activity. Any convenient H6H enzymes find use in the subject host cells. Some H6H enzymes of interest include, but are not limited to, enzymes such as EC 1.14.11.11, as described in Table 1. In certain embodiments, the host cell includes a heterologous coding sequence for an H6H or an active fragment thereof.

In certain examples, the engineered host cell comprises a plurality of heterologous coding sequences each encoding a transmembrane metabolite transporter. In some examples, the plurality of transporters encoded by the plurality of heterologous coding sequences may be distinct from each other. In some examples, some of the plurality of transporters encoded by the plurality of heterologous coding sequences may be distinct from each other and some of the plurality of transporters encoded by the plurality of heterologous coding sequences may be duplicate copies.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained. Also included are fusions of one or more enzymes or catalytic protein domains with one or more non-catalytic protein domains in a manner by which the non-catalytic protein domain facilitates the solubilization, folding, maturation, and/or activity of the fused catalytic domain.

Operable fragments, mutants or truncated forms may be identified by modeling and/or screening. This is made possible by addition or deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

Aspects of the present invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a decarboxylase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc. In certain embodiments, an "equivalent" amino acid sequence contains at least 80%-99% identity at the amino acid level to the specific amino acid sequence, in some cases at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

The host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

In some instances, where ablation of expression of a protein may be of interest, the alteration is in proteins involved in the pleiotropic drug response, including, but not limited to, ATP-binding cassette (ABC) transporters, multidrug resistance (MDR) pumps, and associated transcription factors. These proteins are involved in the export of TA molecules and TA precursors into the culture medium, thus deletion controls the export of the compounds into the media, making them more available for incorporation into the desired product. In some embodiments, host cell gene deletions of interest include genes associated with the unfolded protein response and endoplasmic reticulum (ER) proliferation. Such gene deletions may lead to improved TA production. The expression of cytochrome P450s may induce the unfolded protein response and may cause the ER to proliferate. Deletion of genes associated with these stress responses may control or reduce overall burden on the host cell and improve pathway performance. Genetic alterations may also include modifying the promoters of endogenous genes to increase expression and/or introducing additional copies of endogenous genes. Examples of this include the construction/use of strains which overexpress the endogenous yeast NADPH-P450 reductase Ncp1p to increase activity of heterologous P450 enzymes. In addition, endogenous enzymes such as Spe1p, Fms1p, Car1p, Arg2p, Aro8p, Aro9p, Pha2p, Ugp1p, and Leu2p which are directly involved in the synthesis of intermediate metabolites, may also be overexpressed.

Heterologous coding sequences of interest include but are not limited to sequences that encode enzymes, either wild-type or equivalent sequences, that are normally responsible for the production of TAs and precursors in plants. In some cases, the enzymes for which the heterologous sequences code may be any of the enzymes in the TA pathway, and may be from any convenient source. The choice and number of enzymes encoded by the heterologous coding sequences for the particular synthetic pathway may be selected based upon the desired product. In certain embodiments, the host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

In some cases, polypeptide sequences encoded by the heterologous coding sequences are as reported in GENBANK. Enzymes of interest include, but are not limited to, those enzymes described herein and those shown in Table 1. The host cells may include any combination of the listed enzymes, from any source. Unless otherwise indicated, accession numbers in Table 1 refer to GenBank. Some accession numbers refer to the *Saccharomyces* genome database (SGD), which is available on the world-wide web at yeastgenome.org.

In some embodiments, the host cell (e.g., a yeast strain) is engineered for selective production of a TA of interest by localizing one or more enzymes to a compartment in the cell. In some cases, an enzyme may be located in the host cell such that the compound produced by this enzyme spontaneously rearranges, or is converted by another enzyme to a desirable metabolite before reaching a localized enzyme that may convert the compound into an undesirable metabolite. The spatial distance between two enzymes may be selected to prevent one of the enzymes from acting directly on a compound to make an undesirable metabolite, and restrict production of undesirable end products (e.g., an undesirable opioid by-product). In some other cases, an enzyme may be localized in the host cell such that the sub-cellular compartment in which it is located provides a more optimum pH, cofactor concentration, redox potential, substrate concentration, and/or other biochemical parameter for its activity than the compartment in which the enzyme is naturally found. In certain cases, an enzyme may be localized to a specific compartment within the host cell such that the intracellular trafficking pathway by which the enzyme is transported to said compartment provides the necessary post-translational modifications for the enzyme to exhibit activity. Such post-translational modifications include, but are not limited to, acetylation, acetylglycosylation, amidation, carboxylation, methylation, glutathionylation, hydroxylation, glycosylation, phosphorylation, sulfonation, disulfide bond formation, cleavage of signal sequences, and multi-enzyme complex formation. In certain embodiments, any of the enzymes described herein, either singularly or together with a second enzyme, may be localized to any convenient compartment in the host cell, including but not limited to, an organelle, endoplasmic reticulum, golgi, vacuole, nucleus, plasma membrane, mitochondrion, peroxisome, periplasm, the lumen of any of the aforementioned organelles, or the membrane enclosing or associated with any of the aforementioned organelles. In cases where one or more enzymes are localized to a membrane associated with any of the aforementioned organelles, the enzyme may be oriented such that the catalytic domain of the enzyme faces the cytosol, the lumen of the organelle, and/or any other intracellular space. In some embodiments, the host cell includes one or more of the enzymes that include a localization tag. Any convenient tags may be utilized. In some cases, the localization tag is a peptidic sequence that is attached at the N-terminus and/or C-terminus of the enzyme.

Any convenient methods may be utilized for attaching a tag to the enzyme. In some cases, the localization tag is derived from an endogenous yeast protein. Such tags may provide a route to a variety of yeast organelles including, but not limited to, the endoplasmic reticulum (ER), Golgi apparatus (GA), mitochondria (MT), plasma membrane (PM), peroxisome (POX), and vacuole (V). In certain embodiments, the tag is an ER routing tag (e.g., ER1). In certain embodiments, the tag is a vacuole tag (e.g., V1). In certain embodiments, the tag is a plasma membrane tag (e.g., P1). In certain embodiments, the tag is a peroxisome-targeting sequence (e.g., PTS1). In certain instances, the tag includes or is derived from, a transmembrane domain from within the tail-anchored class of proteins. In some embodiments, the localization tag locates the enzyme on the outside of an organelle. In certain embodiments, the localization tag locates the enzyme on the inside of an organelle. In some embodiments, the localization tag locates the enzyme such that one or more portions of the enzyme are found both inside and outside of an organelle.

In some embodiments of the invention, the host cell is modified by expression of one or more coding sequences encoding one or more enzymes comprising a localization tag described above. In certain embodiments, the host cell is modified by expression of one or more heterologous coding sequences such that one or more enzymes is expressed in the cytosol. Examples of such enzymes include, but are not limited to, arginine decarboxylases, putrescine N-methyltransferases, pyrrolidine ketide synthases, tropinone reductases, phenylpyruvate reductases, UDP-glucosyltransferases, and 2-oxoglutarate-dependent dioxygenases such as hyoscyamine 6β-hydroxylase/dioxygenase. In certain embodiments, the host cell is modified by expression of one or more heterologous coding sequences such that one or more enzymes is expressed in the ER membrane. Examples of such enzymes include, but are not limited to, cytochromes P450 such as tropinone synthase (CYP82M3) and littorine mutase (CYP80F1), and $NADP^+$-cytochrome P450 reductases. In certain embodiments, the host cell is modified by expression of one or more heterologous coding sequences such that one or more enzymes is expressed in the mitochondria. Examples of such enzymes include, but are not limited to, N-acetylglutamate synthases. In other embodiments, the host cell is modified by expression of one or more heterologous coding sequences such that one or more enzymes is expressed in the peroxisome. Examples of such enzymes include, but are not limited to, amine oxidases such as N-methylputrescine oxidase. In other embodiments, the host cell is modified by expression of one or more heterologous coding sequences such that one or more enzymes is expressed in the vacuole lumen. Examples of such enzymes include, but are not limited to, serine carboxypeptidase-like acyltransferases such as littorine synthase, and engineered variants thereof. In other embodiments, the host cell is modified by expression of one or more heterologous coding sequences such that one or more enzymes or proteins is expressed in the vacuole membrane. Examples of such proteins include, but are not limited to, multidrug and toxin extrusion transporters, nitrate/peptide family transporters, and ATP-binding cassette transporters. In other embodiments, the host cell is modified by expression of one or more heterologous coding sequences such that one or more enzymes or proteins is expressed in the plasma membrane. Examples of such proteins include, but are not limited to, ATP-binding cassette transporters, pleiotropic drug resistance transporters, and multidrug resistance transporters.

In some instances, the expression of each type of enzyme is increased through additional gene copies (i.e., multiple copies), which increases intermediate accumulation and/or TA of interest production. Embodiments of the present invention include increased TA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

In some embodiments, the host cell includes multiple copies of a heterologous coding sequence for an enzyme, such as 2 or more, 3 or more, 4 or more, 5 or more, or even 10 or more copies. In certain embodiments, the host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some embodiments of the host cell, the heterologous coding sequence is from a source organism selected from the group consisting of *Escherichia coli, Bacillus coagulans, Lactobacillus casei, Lactobacillus plantarum, Lactobacillus* spp, *Wickerhamia fluorescens, Aequoria* spp, *Discosoma* spp, *Arabidopsis thaliana, Avena sativa, Solanum lycoper-*

*sicum, Solanum tuberosum, Nicotiana tabacum, Nicotiana benthamiana, Atropa belladonna, Hyoscyamus niger, Hyoscyamus muticus, Datura stramonium, Datura metel, Datura innoxia, Duboisia myoporoides, Anisodus luridus, Anisodus tanguticus, Anisodus acutangulus, Brugmansia arborea, Brugmansia* x *candida, Brugmansia sanguinea, Erythroxylum coca, Cochlearia officinalis, Solanum* spp, *Nicotiana* spp, *Atropa* spp, *Hyoscyamus* spp, *Datura* spp, *Duboisia* spp, *Anisodus* spp, *Brugmansia* spp, *Erythroxylum* spp, or *Cochlearia* spp. In certain instances, the heterologous coding sequence is from a source organism selected from *A. belladonna, H. niger*, and *D. stramonium*. In some embodiments, the host cell includes a heterologous coding sequence from one or more of the source organisms described in Table 1.

The engineered host cell medium may be sampled and monitored for the production of TAs of interest. The TAs of interest may be observed and measured using any convenient methods. Methods of interest include, but are not limited to, LC-MS methods (e.g., as described herein) where a sample of interest is analyzed by comparison with a known amount of a standard compound. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Methods

Process Steps

As summarized above, aspects of the invention include methods of preparing a tropane alkaloid (TA) of interest. As such, aspects of the invention include culturing a host cell under conditions in which the one or more host cell modifications (e.g., as described herein) are functionally expressed such that the cell converts starting compounds of interest into product TAs of interest or precursors thereof (e.g., pre-esterification TAs). Also provided are methods that include culturing a host cell under conditions suitable for protein production such that one or more heterologous coding sequences are functionally expressed and convert starting compounds of interest into product TAs of interest. In some instances, the method is a method of preparing a tropane alkaloid (TA), include culturing a host cell (e.g., as described herein); adding a starting compound to the cell culture; and recovering the TA from the cell culture. In some embodiments of the method, the starting compound, TA product and host cell are described by one of the entries of Table 1.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing host cells may be employed for producing the TA precursors and downstream TAs of interest. The particular protocol that is employed may vary, e.g., depending on host cell, the heterologous coding sequences, the desired TA precursors and downstream TAs of interest, etc. The cells may be present in any convenient environment, such as an environment in which the cells are capable of expressing one or more functional heterologous enzymes. In vitro, as used herein, simply means outside of a living cell, regardless of the location of the cell. As used herein, the term in vivo indicates inside a living cell, regardless of the location of the cell. In some embodiments, the cells are cultured under conditions that are conducive to enzyme expression and with appropriate substrates available to allow production of TA precursors and downstream TAs of interest in vivo. In some embodiments, the functional enzymes are extracted from the host for production of TAs under in vitro conditions. In some instances, the host cells are placed back into a multicellular host organism. The host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 20-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

A batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A fed-batch fermentation is similar to a batch fermentation, except that the substrate is added in intervals to the system over the course of the fermentation process. Fed-batch systems are used to reduce the impact of catabolite repression on the metabolism of the host cells and under other circumstances where it is desired to have limited amounts of substrate in the growth media.

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, anti-foam, salts, chelating agents, surfactants, and organic liquids.

Any convenient codon optimization techniques for optimizing the expression of heterologous polynucleotides in host cells may be adapted for use in the subject host cells and methods, see e.g., Gustafsson, C. et al. (2004) *Trends Biotechnol,* 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to μM amount such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the TA of interest from the cell culture. Any convenient methods of separation and isolation (e.g., chromatography methods or precipitation methods) may be adapted for use in the subject methods to recover the TA of interest from the cell culture. Filtration methods may be used to separate soluble from insoluble fractions of the cell culture. In some cases, liquid chromatography methods (e.g., reverse phase HPLC, size exclusion, normal phase chromatography) may be used to separate the TA of interest from other soluble components of the cell culture. In some cases, extraction methods (e.g., liquid extraction, pH based purification, etc.) may be used to separate the TA of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., TAs) may be separated from the cells, cellular debris and waste, and other nutrients, sugars, and organic molecules may remain in the spent culture medium. This process may be used to yield a TA-enriched product.

In an example, a product stream having a tropane alkaloid (TA) product is formed by providing engineered yeast cells and a feedstock including nutrients and water to a batch reactor. The engineered yeast cells may have at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. When the engineered yeast cells are within the batch reactor, the engineered yeast cells may be subjected to fermentation. In particular, the engineered yeast cells may be subjected to fermentation by incubating the engineered yeast cells for a time period of at least about 5 minutes to produce a solution comprising the TA product and cellular material. Once the engineered yeast cells have been subjected to fermentation, at least one separation unit may be used to separate the TA product from the cellular material to provide the product stream comprising the TA product. In particular, the product stream may include the TA product as well as additional components, such as a clarified yeast culture medium. Additionally, a TA product may comprise one or more TAs of interest, such as one or more TA compounds.

Different methods may be used to remove cells from a bioreactor medium that include a TA of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable TAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

TAs of interest may be extracted from the clarified spent culture medium through liquid-liquid extraction by the addition of an organic liquid that is immiscible with the aqueous culture medium. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of TAs of interest from the host cells by continuously removing TA precursors or TAs to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, TAs of interest may be extracted from a fermentation medium using adsorption methods. In particular, TAs of interest may be extracted from clarified spent culture medium by the addition of a resin such as Amberlite® XAD4 or another agent that removes TAs by adsorption. The TAs of interest may then be released from the resin using an organic solvent. Examples of suitable organic solvents include, but are not limited to, methanol, ethanol, ethyl acetate, or acetone.

TAs of interest may also be extracted from a fermentation medium using filtration. At high pH, the TAs of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation TA precursor- or TA-enriched product using methods known in the art to recover individual product species of interest to high purity.

In one example, TA precursors or TAs extracted in an organic phase may be transferred to an aqueous solution. In some cases, the organic solvent may be evaporated by heat and/or vacuum, and the resulting powder may be dissolved in an aqueous solution of suitable pH. In a further example, the TA precursors or TAs may be extracted from the organic phase by addition of an aqueous solution at a suitable pH that promotes extraction of the TA precursors or TAs into the aqueous phase. The aqueous phase may then be removed by decantation, centrifugation, or another method.

The TA precursor- or TA-containing solution may be further treated to remove metals, for example, by treating with a suitable chelating agent. The TA precursor- or TA-containing solution may be further treated to remove other impurities, such as proteins and DNA, by precipitation. In one example, the TA precursor- or TA-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the TA precursor-, TA-, or modified TA-containing solution may be extracted to high purity by continuous cross-flow filtration using methods known in the art.

If the solution contains a mixture of TA precursors or TAs, it may be subjected to acid-base treatment to yield individual TA of interest species using methods known in the art. In this process, the pH of the aqueous solution is adjusted to precipitate individual TA precursors or TAs at their respective pKas.

For high purity, small-scale preparations, the TA precursors or TAs may be purified in a single step by liquid chromatography.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of nightshade leaves (CNL), which is used by active pharmaceutical ingredient (API) manufacturers for extraction of tropane alkaloids to be subjected to further chemical processing and purification. For the purposes of this invention, CNL is a representative example of any type of purified plant extract from which the desired alkaloids product(s) may ultimately be further purified. Table 5 highlights the impurities in these two products that may be specific to either CYCM or CNL or may be present in both. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Tables 2 and 3) may not be present at that API stage of the product. Indeed, many of the API products derived from yeast strains of the present invention may be largely indistinguishable from the traditional plant-derived APIs. In some cases, however, conventional alkaloid compounds may be subjected to chemical modification using chemical synthesis approaches which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically derived product, the resulting impurities may be present but in a lesser amount than would be expected in an API that only or primarily contains chemically derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized tropane alkaloid APIs but not in biosynthesized APIs include hydrogen halides such as hydrogen chloride, hydrogen iodide, and hydrogen bromide formed by chemical N-alkylation, such as N-methylation and N-butylation of hyoscyamine and scopolamine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CNL) may be analyzed as described above.

Methods of Engineering Host Cells

Also included are methods of engineering host cells for the purpose of producing TAs of interest or precursors thereof. Inserting DNA into host cells may be achieved using any convenient methods. The methods are used to insert the heterologous coding sequences into the host cells such that the host cells functionally express the enzymes and convert starting compounds of interest into product TAs of interest.

Any convenient promoters may be utilized in the subject host cells and methods. The promoters driving expression of the heterologous coding sequences may be constitutive promoters or inducible promoters, provided that the promoters are active in the host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the *B. subtilis* tsr gene (encoding the promoter region of the fructose bisphosphate aldolase gene) or the promoter from yeast *S. cerevisiae* gene coding for glyceraldehyde 3-phosphate dehydrogenase (GPD, GAPDH, or TDH3), the ADH1 promoter of baker's yeast, the phosphate-starvation induced promoters such as the PHOS promoter of yeast, the alkaline phosphatase promoter from *B. licheniformis*, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-$\alpha$ promoter (TEF), cytochrome c-oxidase promoter (CYC1), MRP7 promoter, phosphoglycerate kinase (PGK), triose phosphate isomerase (TPI), etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., *E. coli*. One may also use promoter selection to optimize transcript, and hence, enzyme levels to maximize production while minimizing energy resources.

Any convenient vectors may be utilized in the subject host cells and methods. Vectors of interest include vectors for use in yeast and other cells. The types of yeast vectors may be broken up into 4 general categories: integrative vectors (YIp), autonomously replicating high copy-number vectors (YEp or 2p plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques.

Utility

The host cells and methods of the invention, e.g., as described above, find use in a variety of applications. Applications of interest include, but are not limited to: research applications and therapeutic applications. Methods of the invention find use in a variety of different applications including any convenient application where the production of TAs is of interest.

The subject host cells and methods find use in a variety of therapeutic applications. Therapeutic applications of interest include those applications in which the preparation of pharmaceutical products that include TAs is of interest. The host cells described herein produce tropane alkaloid precursors (TA precursors) and TAs of interest. Tropinone and tropine are major branch point intermediates of interest in the synthesis of TAs including engineering efforts to produce end products such as medicinal TA products. The subject host cells may be utilized to produce TA precursors from simple and inexpensive starting materials that may find use in the production of TAs of interest, including tropinone, tropine, and TA end products. As such, the subject host cells find use in the supply of therapeutically active TAs or precursors thereof.

In some instances, the host cells and methods find use in the production of commercial scale amounts of TAs or precursors thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of TAs of interest or precursors thereof for therapeutic products. Such applications may include the industrial-scale production of TAs of interest from fermentable carbon sources such as cellulose, starch, and free sugars.

The subject host cells and methods find use in a variety of research applications. The subject host cells and methods may be used to analyze the effects of a variety of enzymes on the biosynthetic pathways of a variety of TAs of interest or precursors thereof. In addition, the host cells may be engineered to produce TAs or precursors thereof that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards TAs of interest or precursors thereof. In certain cases, research applications include the production of precursors for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of TA metabolites produced in these strains.

The subject host cells and methods may be used as a production platform for plant specialized metabolites. The subject host cells and methods may be used as a platform for drug library development as well as plant enzyme discovery. For example, the subject host cells and methods may find use in the development of natural product based drug libraries by taking yeast strains producing interesting scaffold molecules, such as hyoscyamine and scopolamine, and further functionalizing the compound structure through combinatorial biosynthesis or by chemical means. By producing drug libraries in this way, any potential drug hits are already associated with a production host that is amenable to large-scale culture and production. As another example, these subject host cells and methods may find use in plant enzyme discovery. The subject host cells provide a clean background of defined metabolites to express plant expressed sequence tag (EST) libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., host cells, starting compounds, heterologous coding sequences, vectors, culture medium, etc., as described herein. In some embodiments, the subject kit includes a host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bi-directional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be precombined into a reagent mixture in a single container, as desired.

Also provided are systems for producing a TA of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of TA compounds produced by the fermented host cells. In certain embodiments, one or more starting compounds (e.g., as described herein) are added to the system, under conditions by which the engineered host cells in the fermenter produce one or more desired TA products or precursors thereof. In some instances, the host cells produce a TA of interest (e.g., as described herein). In certain cases, the TA products of interest are medicinal TA products, such as hyoscyamine, N-methylhyoscyamine, anisodamine, scopolamine, N-methylscopolamine, and N-butylscopolamine.

In some cases, the system includes means for monitoring and or analyzing one or more TA compounds or precursors thereof produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to TA products or precursors of interest is complete, the fermentation may be halted and purification of the TA products may be done. As such, in some cases, the subject system includes a purification component suitable for purifying the TA products or precursors of interest from the host cell medium into which it is produced. The purification component may include any convenient means that may be used to purify the TA products or precursors of fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of TA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example Methods

The following section provides examples of methods and procedures which can be used to construct, culture, and test microbial strains, such as yeast strains, for the production of TA precursors and TAs, as well as to conduct fermentations of such strains to produce TA precursors and TAs. Also included are examples of methods, procedures, and materials which can be used to generate the DNA sequences required for modification of microbial hosts, and to introduce desired DNA sequences into microbial hosts.

Chemical compounds and standards. Chemical standards of TA precursors and TAs for verifying the identity of and quantifying metabolites produced by engineered host cells may be purchased from commercial vendors. For example, putrescine dihydrochloride, N-methylputrescine, hygrine, tropinone, and tropine may be purchased from Santa Cruz Biotechnology (Dallas, TX). 4-(Methylamino)butyric acid hydrochloride may be purchased from Sigma (St. Louis, MO). γ-Methylaminobutyraldehyde (4MAB) diethyl acetal and littorine may be purchased from Toronto Research Chemicals (Toronto, ON). A chemical standard for NMPy can be synthesized by deprotecting one volume of the diethyl acetal with five volumes of 2 M HCl at 60° C. for 30 min as described previously (see Feth, F., Wray, V. & Wagner, K. G. Determination of methylputrescine oxidase by high performance liquid chromatography. Phytochemistry 24, 1653-1655 (1985)), incubating overnight at room temperature, and then washing the resulting concentrate twice with three volumes of diethyl ether to remove residual organic impurities.

Plasmid construction. Oligonucleotides used for generation of novel DNA sequences by polymerase chain reaction (PCR) and for DNA sequencing can be obtained from a DNA synthesis company, such as IDT DNA, Twist Bioscience, or the Stanford Protein and Nucleic Acid Facility (Stanford, CA). Native yeast genes can be amplified from *S. cerevisiae* genomic DNA via colony PCR (see Kwiatkowski, T. J., Zoghbi, H. Y., Ledbetter, S. A., Ellison, K. A. & Chinault, A. C. Rapid identification of yeast artificial chromosome clones by matrix pooling and crude iysate PCR. Nucleic Acids Res. 18, 7191 (1990)). Gene sequences for heterologous enzymes may be codon-optimized to improve expression in *S. cerevisiae* using suitable codon optimization software, such as the GeneArt GeneOptimizer software (Thermo Fisher Scientific). Heterologous gene sequences can then be synthesized as linear, double-stranded DNA fragments by a commercial DNA synthesis company. Two types of plasmids can be used for gene expression in yeast: direct expression (DE) plasmids for testing biosynthetic genes of interest and yeast integration (YI) holding plasmids to provide a template for genomic integration of selected promoter-gene-terminator cassettes.

DE plasmids comprise a gene of interest flanked by a constitutive promoter and terminator, a low-copy CEN6/ARS4 yeast origin of replication, and an auxotrophic selection marker. DE plasmids may be constructed by PCR-amplifying genes of interest to append 5' and 3' restriction sites using primer overhangs, digesting PCR products or synthesized gene fragments with appropriate pairs of restriction enzymes (for example, SpeI, BamHI, EcoRI, PstI, or XhoI), and then ligating gene fragments into similarly digested vectors with suitable yeast promoters, terminators, and replication sequences, such as plasmids pAG414GPD-ccdB, pAG415GPD-ccdB, or pAG416GPD-ccdB (see Alberti, S., Gitler, A. D. & Lindquist, S. A suite of Gateway cloning vectors for high-throughput genetic analysis in *Saccharomyces cerevisiae*. Yeast 24, 913-9 (2007)) using T4 DNA ligase.

YI plasmids comprise a gene of interest flanked by a constitutive promoter and terminator but lack a yeast origin of replication or auxotrophic selection marker. YI plasmids may be constructed by linearizing empty holding vectors with suitable promoters and terminators using 'around-the-horn' PCR with primers designed to bind at the 3' and 5' ends of the promoter and terminator, respectively. Genes of interest can also be PCR-amplified to append 5' and 3' overhangs with 35-40 bp of homology to the termini of the linearized vector backbones. Assembly of genes into YI vectors may then be performed using Gibson assembly. DE plasmids expressing GFP fusions of biosynthetic enzymes may be prepared by first assembling PCR-amplified DNA fragments separately encoding GFP, the target enzyme, and a YI vector backbone using Gibson assembly, and subsequently subcloning the fusion constructs from YI plasmids into DE vectors using restriction enzymes and ligation cloning as described.

PCR amplification may be performed using any high-fidelity recombinant DNA polymerase available from commercial suppliers and linear DNA may be purified using a suitable DNA column purification kit. Assembled plasmids can be propagated in any chemically competent *E. coli* strain using heat-shock transformation and selection in Luria-Bertani (LB) broth or on LB-agar plates with carbenicillin (100 μg/mL), kanamycin (50 μg/mL), or another antibiotic selection. Plasmid DNA can be isolated by alkaline lysis from overnight *E. coli* cultures grown at 37° C. and 250 rpm in selective LB media using plasmid purification columns according to the manufacturer's protocol. Plasmid sequences should be verified by Sanger sequencing.

Yeast strain construction. Any suitable laboratory strain of yeast may be used as a host organism. Yeast strains described in the examples of the Experimental section are derived from the parental strain CEN.PK2-1 D (see Entian, K. D. & Kötter, P. 25 Yeast Genetic Strain and Plasmid Collections. Methods Microbiol. 36, 629-666 (2007)), referred to as CEN.PK2. Strains can be grown non-selectively in yeast-peptone media supplemented with 2% w/v dextrose (YPD media), yeast nitrogen base (YNB) defined media supplemented with synthetic complete amino acid mixture (YNB-SC) and 2% w/v dextrose, or on agar plates of the aforementioned media. Strains transformed with plasmids bearing auxotrophic selection markers (URA3, TRP1, HIS3, and/or LEU2) may be grown selectively in YNB media supplemented with 2% w/v dextrose and the appropriate dropout solution (YNB-DO) or on YNB-DO agar plates. Yeast strains which are deficient in acetate metabolism can be grown on the aforementioned media supplemented with 0.1% w/v potassium acetate (i.e., YPAD or YNBA).

Yeast genomic modifications may be performed using the CRISPRm method (see Ryan, O. W. et al. Selection of chromosomal DNA libraries using a multiplex CRISPR system. Elife 3, 1-15 (2014)). CRISPRm plasmids express *Streptococcus pyogenes* Cas9 and a single guide RNA (sgRNA) targeting a locus of interest in the yeast genome, and may be constructed by assembly PCR and Gibson assembly of DNA fragments encoding SpCas9, tRNA promoter and HDV ribozyme, a 20-nt guide RNA sequence, and tracrRNA and terminator. For gene insertions, integration fragments comprising one or more genes of interest flanked by unique promoters and terminators may be constructed using PCR amplification and cloned into holding vectors by Gibson assembly. Integration fragments are PCR amplified using a suitable high-fidelity DNA polymerase with flanking 40 bp microhomology regions to adjacent fragments and/or to the yeast genome at the integration site. For gene disruptions, integration fragments comprise 6-8 stop codons in all three reading frames flanked by 40 bp of microhomology to the disruption site, which is located within the first half of the open reading frame. For complete gene deletions, integration fragments comprise an auxotrophic marker gene flanked by 40 bp of microhomology to the deletion site. Each integration fragment is co-transformed with the CRISPRm plasmid targeting the desired genomic site. Positive integrants may be identified by yeast colony PCR, Sanger sequencing, and/or functional screening by liquid chromatography and tandem mass spectrometry (LC-MS/MS).

Yeast transformations. Yeast strains may be transformed using any suitable method, including heat-shock, electroporation, and chemical transformation. For example, yeast strains described in the examples of the Experimental section were chemically transformed using the Frozen-EZ Yeast Transformation II Kit (Zymo Research). Individual yeast colonies are inoculated into YP(A)D media and grown overnight at 30° C. and 250 rpm. Saturated cultures are back-diluted between 1:10 and 1:50 in YP(A)D media and grown for an additional 5-7 hours to reach exponential phase. Cultures are pelleted by centrifugation at 500×g for 4 min and then washed twice by resuspending the pellet in 50 mM Tris-HCl buffer, pH 8.5. Washed pellets are resuspended in 20 μL of EZ2 solution per transformation and then mixed with 100-600 ng of total DNA and 200 μL of EZ3 solution. The yeast suspensions are incubated at 30° C. with gentle rotation for one hour. For plasmid transformations, the transformed yeast are directly plated onto YNB(A)-DO agar plates. For Cas9-mediated chromosomal modifications, yeast suspensions are instead mixed with 1 mL YP(A)D media, pelleted by centrifugation at 500×g for 4 min, and then resuspended in 250 μL of fresh YP(A)D media. The suspensions are then incubated at 30° C. with gentle rotation for an additional two hours to enable production of G418 resistance proteins and then spread onto YP(A)D plates containing 400 mg/L G418 (geneticin) sulfate. Plates are then incubated at 30° C. for 48-60 hours to allow colony formation.

Spot dilution assays. Strains are inoculated into YNB(A)-DO media and grown overnight at 30° C. and 250 rpm. Saturated overnight cultures are pelleted by centrifugation at 500×g for 4 min and resuspended in sterile Tris-HCl buffer, pH 8.0 to a concentration of $10^7$ cells/mL based on $OD_{600}$. Ten-fold serial dilutions of each strain are then prepared in Tris-HCl buffer and 10 μL of each dilution is spotted on pre-warmed YNB(A)-DO plates. Plates are incubated at 30° C. and imaged after 48 hours.

Growth conditions for metabolite assays. Small-scale metabolite production tests may be conducted in YNB(A)-SC or YNB(A)-DO media. Yeast colonies may be inoculated into 300-500 μL of media and grown in 2 mL deep-well 96-well plates covered with a gas-permeable film for 48-72 hours at 30° C., 460 rpm, and 80% relative humidity in a shaker.

Analysis of metabolite production. Metabolite profiles and titers may be analyzed using liquid chromatography and tandem mass spectrometry (LC-MS/MS). To separate cells from media for analysis, fermentation cultures may be pelleted by centrifugation at 3,500×g for 5 min at 12° C. and 100-200 μL aliquots of the supernatant can then be removed for direct analysis. Metabolite production may be analyzed by LC-MS/MS using any suitable HPLC device paired with a triple quadrupole mass spectrometer, such as the Agilent 1260 Infinity Binary HPLC and Agilent 6420 Triple Quadrupole mass spectrometer. Chromatography may be performed using a C18 reverse phase column, such as a Zorbax EclipsePlus C18 column (2.1×50 mm, 1.8 μm; Agilent Technologies), with 0.1% v/v formic acid in water as mobile phase solvent A and 0.1% v/v formic acid in acetonitrile as solvent B. The column is operated with a constant flow rate of 0.4 mL/min at 40° C. and a sample injection volume of 5 μL. Compound separation may be performed using the following gradient: 0.00-0.75 min, 1% B; 0.75-1.33 min, 1-25% B; 1.33-2.70 min, 25-40% B; 2.70-3.70 min, 40-60% B; 3.70-3.71 min, 60-95% B; 3.71-4.33 min, 95% B; 4.33-4.34 min, 95-1% B; 4.34-5.00 min, equilibration with 1% B. The LC eluent is directed to the MS from 0.01-5 min operating with electrospray ionization (ESI) in positive mode, source gas temperature 350° C., gas flow rate 11 L/min, and nebulizer pressure 40 psi. Metabolites can be quantified by integrated peak area based on multiple reaction monitoring (MRM) parameters and standard curves.

Fluorescence microscopy. Individual colonies of yeast strains transformed with plasmids encoding biosynthetic enzymes fused to fluorescent protein reporters are inoculated into 1 mL YNB-DO media and grown overnight at 30° C. and 250 rpm. Overnight cultures are pelleted by centrifugation at 500×g for 4 min and resuspended in 2 mL YNB-DO media with 2% w/v dextrose and then grown at 30° C. and 250 rpm for an additional 4-6 hours to reach exponential phase and allow expressed fluorescent proteins to fold completely. Approximately 5-10 μL of culture is then spotted onto a glass microscope slide and covered with a glass coverslip and then imaged using a suitable inverted fluorescence microscope with a 60× oil immersion objective. Fluorescence excitation may be performed using a xenon arc lamp and the following filter settings: GFP, ET470/40X excitation filter and ET525/50 emission filter; mCherry, ET572/35X excitation filter and ET632/60 emission filter. Emitted light is captured with a CCD camera, and subsequent image analysis may performed in any suitable scientific image analysis software, such as ImageJ (NIH).

Identification of novel gene variants from transcriptome databases. Novel genes and variants thereof may be identified using sequence alignment-based searches of transcriptome and genome databases. For example, orthologs of *N. tabacum* N-methylputrescine oxidase (NtMPO1) were identified using a tBLASTn search of the transcriptomes of *D. metel* and *A. belladonna* in the 1000 Plants Project database (see Matasci, N. et al. Data access for the 1,000 Plants (1KP) project. Gigascience 3, 17 (2014)). Coding sequences for putative genes identified using these search strategies can then be optimized for yeast expression and then cloned into expression vectors as described previously.

Enzyme structural analysis. Heterologous enzymes may be analyzed for structural features that may prove problematic during expression in yeast, such as large unstructured regions, by examining homology models constructed using any suitable homology modeling or de novo structure prediction software, such as RaptorX or Rosetta. Resultant protein models can be visualized using any three-dimensional molecular viewing software, such as PyMOL (Schrodinger) or UCSF Chimera. Enzyme affinity for specific substrates may be analyzed using any suitable ligand docking simulation software, such as AutoDock, SwissDock, GOLD, or Glide.

Analysis of protein expression in yeast by Western blot. For immunoblot analysis of yeast-expressed proteins, a suitable strain is transformed with an expression vector harboring an epitope-tagged protein of interest. Three days post-transformation, transformed colonies are inoculated into 2 mL YNB-DO media and grown overnight (~16-20 h) to stationary phase at 30° C. and 460 rpm. Cells are pelleted by centrifugation at 3,000×g for 5 min, resuspended in 200 μL $H_2O$, mixed with 200 μL of 0.2 M NaOH, and incubated at room temperature for 5 min to allow hydrolysis of cell wall glycoproteins. Cells are re-pelleted at 3,000×g for 5 min, resuspended in 75 μL $H_2O$, mixed with 25 μL of 4× NuPAGE LDS sample buffer (Thermo Fisher), and then boiled at 95° C. for 3 min to lyse cells. Suspensions are pelleted by centrifugation at 16,000×g for 5 min to remove insoluble debris and supernatants are transferred to pre-chilled tubes. For analysis under reducing conditions, protein lysates are mixed with β-mercaptoethanol (final concentration 10%) and incubated at 70° C. for 10 min. Approximately 20-40 μg of total protein is loaded onto NuPAGE Bis-Tris 4-12% acrylamide gels (Thermo Fisher) with Precision Plus Dual Color protein molecular weight marker (BioRad). Electrophoresis is conducted in 1× NuPAGE MOPS SDS running buffer at 150 V for 90 min. Transfer of protein to a nitrocellulose membranes is performed at 15 V for 15 min using a Trans-Blot Semi-Dry apparatus (BioRad) and NuPAGE transfer buffer (Thermo Fisher) per manufacturer instructions. For reducing conditions, NuPAGE antioxidant (Thermo Fisher) is added to a final concentration of 1× to both the running buffer and transfer buffer. Membranes with transferred protein are washed for 5 min in Tris-buffered saline with Tween (TBS-T; 137 mM NaCl, 2.7 mM KCl, 19 mM Tris base, 0.1% Tween20, pH 7.4) and then blocked with 5% skim milk in TBS-T for 1 h at room temperature. Membranes are incubated overnight at 4° C. with a suitable dilution of an HRP-conjugated antibody in TBS-T with 5% milk, washed three times for 5 min each with TBS-T, and then visualized using Western Pico PLUS HRP substrate (Thermo Fisher) and a suitable imager.

EXPERIMENTAL

A series of specific genetic modifications provide a biosynthetic process in *Saccharomyces cerevisiae* for the production of TAs from simple, inexpensive feedstocks or precursor molecules. Methods for constructing novel strains capable of producing the early TA molecules putrescine, N-methylputrescine, 4-methylaminobutanal, N-methylpyrrolinium (NMPy), tropinone, tropine, phenyllactic acid (PLA), and 1-O-β-phenyllactoylglucose (PLA glucoside) from non-TA precursors or simple feedstocks are described. NMPy is the natural precursor to all known TA molecules. Methods for manipulating the regulation of yeast biosynthetic pathways and for optimizing the production of amino acid-derived TA precursors are also described. Methods for constructing novel strains capable of producing non-medicinal TAs such as pseudotropine alkaloids and calystegines from simple feedstocks are described. Additionally, methods for constructing novel strains capable of producing medicinal TAs such as hyoscyamine, anisodamine, and scopolamine from non-TA precursors or simple feedstocks are described. Furthermore, methods for constructing novel strains capable of producing non-natural TAs such as cinnamoyltropine from non-TA precursors or simple feedstocks are described.

Example 1. Engineering a Platform Yeast Strain for High Levels of Putrescine Production The tropine moiety of TAs is derived from the amino acid arginine via the polyamine molecule putrescine. Strains of *S. cerevisiae* are developed with improved flux through the arginine and polyamine biosynthesis pathways for the purposes of increasing intracellular concentrations of TA precursor molecules including putrescine, NMP, 4MAB, and NMPy. These strains combine genetic modifications for the purpose of increasing carbon and nitrogen flux from central metabolism towards arginine and polyamine biosynthesis in general, and include the introduction of key heterologous enzymes for additional production of the TA precursor putrescine. Genetic modifications are employed including the introduction of feedback inhibition alleviating mutations to genes encoding native biosynthetic enzymes and regulatory proteins, tuning of transcriptional regulation of native biosynthetic enzymes, deletion or disruption of genes encoding enzymes that divert precursor molecules away from the intended pathway, and introduction of heterologous enzymes for the conversion of endogenous molecules into TA precursor molecules.

Figure 4:
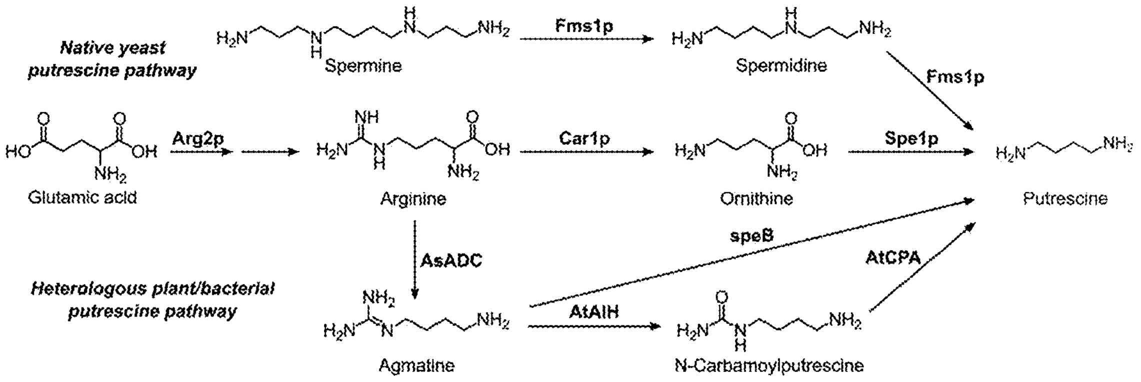
FIG. 4 illustrates exemplary biosynthetic pathways for the production of putrescine from amino acids and other polyamine molecules. This figure shows how endogenous yeast and heterologous biosynthetic pathways can be used to make putrescine from central metabolites.

1.1) The biosynthetic pathway in the engineered strain incorporates overexpression of native yeast genes involved in arginine metabolism and polyamine biosynthesis (FIG. 4).

1.1.1) Examples of overexpressed native genes in yeast include, but are not limited to: glutamate N-acetyltransferase (Arg2p), which catalyzes the first step in arginine biosynthesis from glutamate; arginase (Car1p), which removes the guanidinium group of arginine to produce ornithine in the mitochondrial matrix; a mitochondrial membrane transporter (Ort1p), which exports ornithine from the mitochondrial matrix to the cytosol; ornithine decarboxylase (Spe1p), which decarboxylates cytosolic ornithine to putrescine; and a polyamine oxidase (Fms1p), which dealkylates spermine and spermidine to putrescine.

Figure 5:
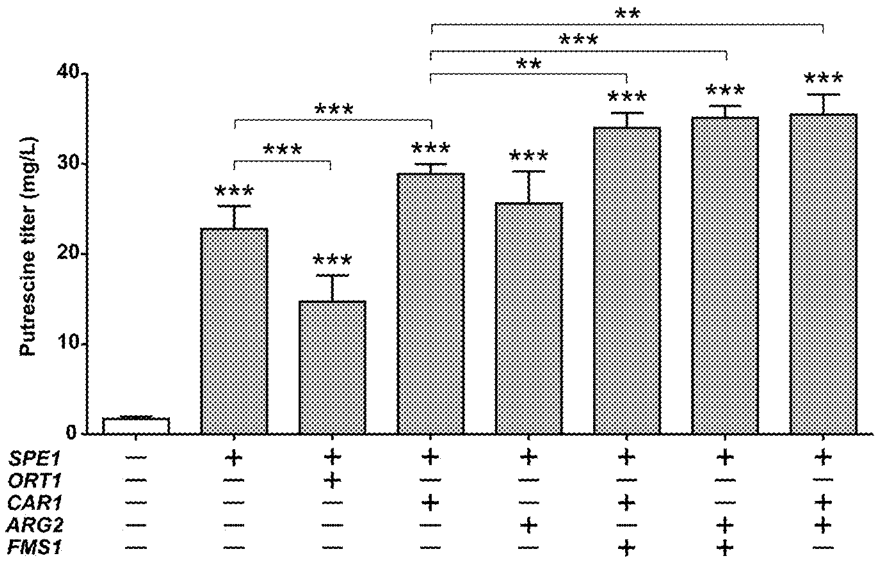
FIG. 5 shows that yeast strains engineered for overexpression of endogenous biosynthetic enzymes involved in arginine and polyamine metabolism can produce putrescine in liquid culture. Additional copies of native genes were expressed from low-copy plasmids in wild-type yeast (CEN.PK2). Transformed strains were cultured in selective media with 2% dextrose at 30° C. for 48 h before LC-MS/MS analysis. All data represent the mean of at least three biological replicates and error bars show standard deviation. Student's two-tailed t-test: * $P<0.05$,  $P<0.01$, * $P<0.001$. Unless otherwise indicated, statistical significance is shown relative to the corresponding control (i.e., CEN.PK2).

1.1.2) The impact of overexpression of these native enzymes on putrescine production was examined by co-transforming a yeast strain with different combinations of three low-copy plasmids, each expressing one of SPE1, ORT1, CAR1, ARG2, FMS1, or blue fluorescent protein (BFP) as a negative control. The titer of putrescine accumulated in the extracellular medium of co-transformed cells following 48 hours of growth in selective media was quantified by LC-MS/MS (FIG. 5). Overexpression of SPE1 alone resulted in a 13.4-fold increase in putrescine titer to 23 mg/L. While co-overexpression of CAR1 or ARG2 with SPE1 resulted in 27% and 12% increases in putrescine production relative to SPE1 alone, overexpression of ORT1 with SPE1 caused a 35% decrease in putrescine titer compared to SPE1. Overexpression of any three of SPE1, CAR1, ARG2, and FMS1 collectively increased extracellular putrescine titers to 34-35 mg/L.

1.2) The biosynthetic pathway in the engineered strain incorporates expression of heterologous enzymes from polyamine production pathways found in organisms other than yeast to further increase putrescine production (FIG. 4).

1.2.1) In addition to the ornithine-dependent pathway found in most plants, animals, and fungi, whereby putrescine is synthesized via deguanidination of arginine followed by decarboxylation of ornithine, many bacteria and plants also express an alternate route through which arginine is first decarboxylated by arginine decarboxylase (ADC) to yield agmatine. In plants, the guanidine group of agmatine is then converted to a urea by an iminohydrolase (AIH) to produce N-carbamoylputrescine (NCP), from which the amide group is then removed by an amidase (CPA) to yield putrescine (see Patel, J. et al. Dual functioning of plant arginases provides a third route for putrescine synthesis. Plant Sci. 262, 62-73 (2017)). Some bacteria have evolved an agmatine ureohydrolase (AUH) enzyme that enables direct removal of the guanidine group from agmatine to produce putrescine without an N-carbamoylated intermediate (see Klein, R. D. et al. Reconstitution of a bacterial/plant polyamine biosynthesis pathway in *Saccharomyces cerevisiae*. Microbiology 145 (Pt 2, 301-7 (1999)).

1.2.2) To reconstruct the heterologous putrescine biosynthetic pathways in yeast, the following enzymes may be used: ADC, AIH, CPA, and AUH. As an example of an engineered strain which possesses these enzymatic activities, an ADC from oat (*Avena sativa*; AsADC) with previously demonstrated activity in *S. cerevisiae* (see Klein, R. D. et al. Reconstitution of a bacterial/plant polyamine biosynthesis pathway in *Saccharomyces cerevisiae*. Microbiology 145 (Pt 2, 301-7 (1999)), an AIH from *Arabidopsis thaliana* (AtAIH), two CPA orthologs from tomato (*Solanum lycopersicum*; SlCPA) and *A. thaliana* (AtCPA), and two AUHs from *E. coli* (speB) and *A. thaliana* (AtARGAH2) were selected for expression in yeast.

Figure 6:
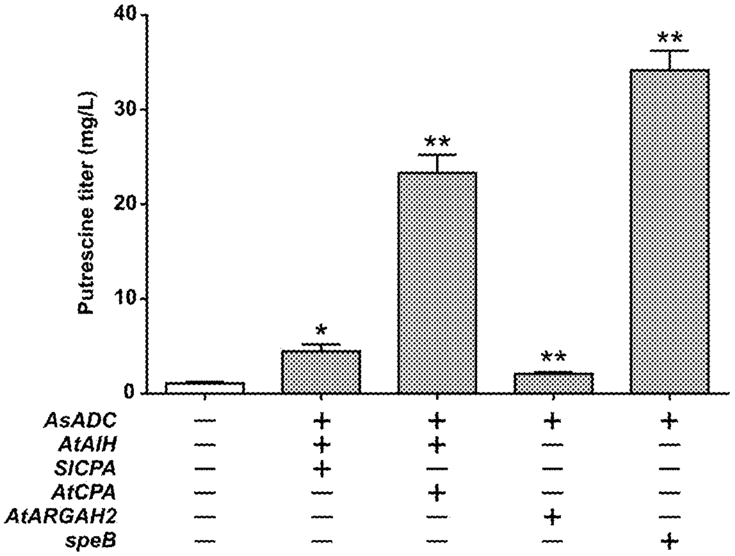
FIG. 6 shows that yeast strains engineered for heterologous expression of biosynthetic enzymes from organisms other than yeast that are involved in arginine and polyamine metabolism can produce putrescine production in liquid culture. In this example, the yeast strains are engineered to express a heterologous biosynthetic pathway from plants and bacteria. Heterologous enzymes were expressed from low-copy plasmids in wild-type yeast. Transformed strains were cultured in selective media with 2% dextrose at 30° C. for 48 h before LC-MS/MS analysis. All data represent the mean of at least three biological replicates and error bars show standard deviation. Student's two-tailed t-test: * $P<0.05$,  $P<0.01$, * $P<0.001$. Unless otherwise indicated, statistical significance is shown relative to the corresponding control (i.e., CEN.PK2).
Figure 7:
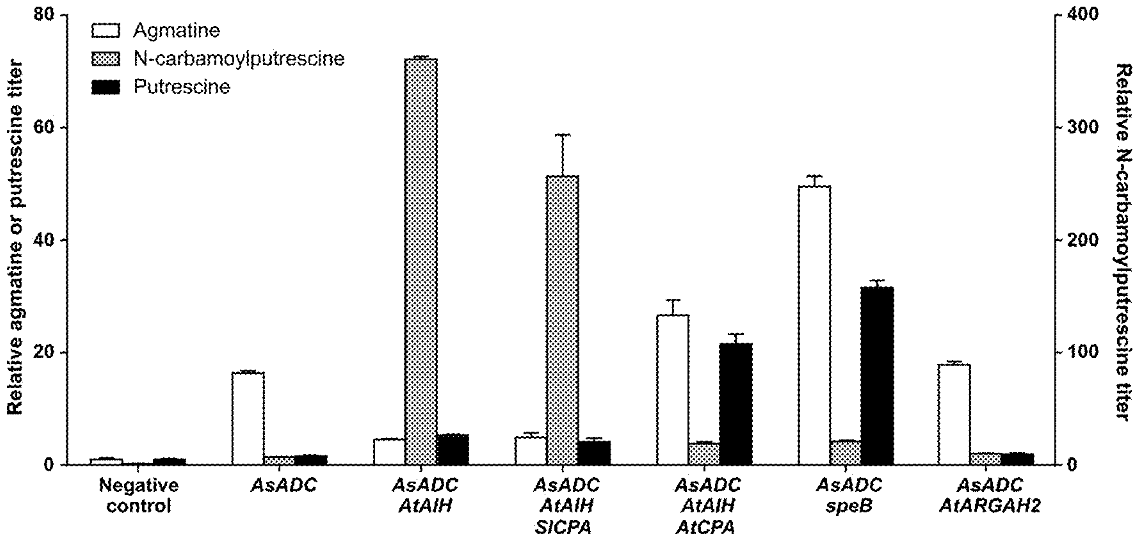
FIG. 7 shows that yeast strains engineered for heterologous expression of biosynthetic enzymes involved in arginine and polyamine metabolism from organisms other than yeast can produce TA precursors and intermediates agmatine, N-carbamoylputrescine, and putrescine in liquid culture. This figure shows the functional validation of agmatine/putrescine biosynthetic pathway genes in yeast. Wild-type yeast strain CEN.PK2 was transformed with three low-copy plasmids to co-express between zero (negative control) and three of the indicated biosynthetic genes. Plasmids expressing blue fluorescent protein (BFP) were used as negative controls for each of the three auxotrophic selection markers URA3, TRP1, and LEU2. Transformed strains were cultured in selective media with 2% dextrose at 30° C. for 48 h prior to LC-MS/MS analysis of metabolite production. All data show titers as measured by LC-MS/MS peak area relative to the negative control (CEN.PK2). Data represent the mean of at three biological replicates and error bars show standard deviation.

1.2.3) In order to establish the functionality of each heterologous enzyme in yeast, the three-step (arginine→agmatine→NCP→putrescine) or two-step (arginine→agmatine→putrescine) putrescine pathways were reconstituted in a stepwise fashion by co-transforming the wild-type yeast strain with low-copy plasmids expressing AsADC, AtAIH, and either S/CPA or AtCPA; or AsADC and either speB or AtARGAH2. To eliminate effects on cell growth and metabolite production arising from different levels of auxotrophy, all transformations were performed with three low-copy plasmids harboring different auxotrophic markers, using BFP as a negative control in place of a blank or absent plasmid. The relative accumulation of agmatine, NCP, and putrescine in the extracellular medium of transformed cells following 48 hours of growth in selective media were analyzed by LC-MS/MS, which indicated that all enzymes except for SlCPA and AtARGAH2 retained activity in yeast (FIG. 6, 7). Reconstitution of the plant-specific pathway comprising AsADC, AtAIH, and AtCPA enabled putrescine production at titers of 23 mg/L, a 22-fold improvement relative to wild-type titers. The orthologous CPA from tomato (SlCPA) enabled putrescine production at titers of 4.5 mg/L when combined with AsADC and AtAIH, similar to putrescine levels in cells expressing AsADC and AtAIH. Reconstitution of the bacterial shortcut pathway via AsADC and the *E. coli* ureohydrolase (speB) enabled putrescine production at titers of 34 mg/L, 32-fold higher than wild-type.

1.3) The biosynthetic pathway in the engineered strain incorporates overexpression of native yeast genes involved in arginine and polyamine biosynthesis and expression of heterologous biosynthetic enzymes from polyamine production pathways found in organisms other than yeast to further increase putrescine production.

Figure 10:
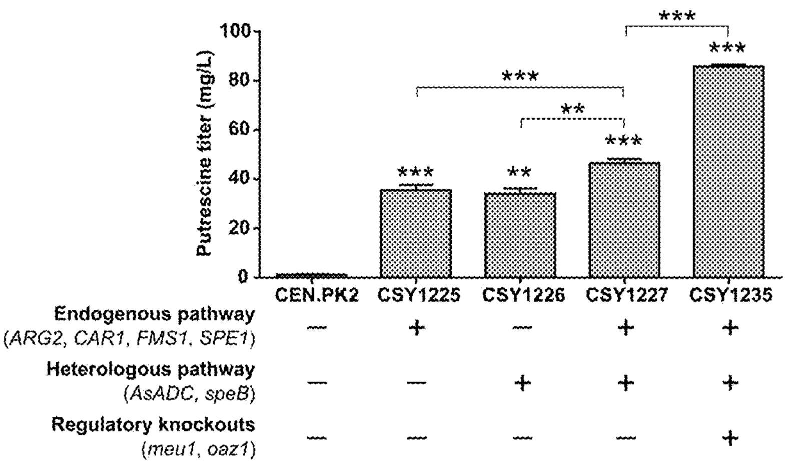
FIG. 10 provides a summary of engineering efforts for increasing putrescine production in yeast. '+' symbol indicates expression of at least one gene from the pathway, whereas '−' indicates expression of no genes from the pathway. Strains were cultured in selective media with 2% dextrose at 30° C. for 48 h before LC-MS/MS analysis. All data represent the mean of at least three biological replicates and error bars show standard deviation. Student's two-tailed t-test: * $P<0.05$,  $P<0.01$, * $P<0.001$. Unless otherwise indicated, statistical significance is shown relative to the corresponding control (i.e., CEN.PK2).

1.3.1) The top-performing triad of overexpressed native genes for putrescine biosynthesis (SPE1, ARG2, CAR1; 1.1.2) was combined with the top-performing heterologous putrescine pathway (AsADC, speB; 1.2.3) by co-transforming the wild-type yeast strain with a low-copy plasmid encoding SPE1, AsADC, and speB and low-copy plasmids encoding ARG2 and CAR1. Putrescine titers in the culture medium of transformed cells were measured by LC-MS/MS analysis after 48 hours. The resulting strain produced putrescine at titers of 47 mg/L, (FIG. 10).

1.4) Polyamine biosynthesis in yeast is regulated by several mechanisms (FIG. 8). The biosynthetic pathway in the engineered strain incorporates disruptions of one or more of these regulatory mechanisms to reduce feedback inhibition of putrescine production.

1.4.1) Native yeast genes involved in regulation of polyamine biosynthesis, and which may therefore be disrupted to improve intracellular putrescine accumulation, include but are not limited to the following examples (FIG. 8). Methylthioadenosine phosphorylase (Meu1p) catalyzes the driving step in the recycling pathway for decarboxylated S-adenosylmethionine (dcSAM), which constitutes the alkyl group donor for conversion of putrescine to spermidine and spermine catalyzed by spermidine synthase (Spe3p) and spermine synthase (Spe4p) (see Chattopadhyay, M. K., Tabor, C. W. & Tabor, H. Methylthioadenosine and polyamine biosynthesis in a *Saccharomyces cerevisiae* meu1Δ mutant. Biochem. Biophys. Res. Commun. 343, 203-207 (2006)). Methylthioadenosine is known to inhibit the activity of spermidine synthase (see Chattopadhyay, M. K., Tabor, C. W. & Tabor, H. Studies on the regulation of ornithine decarboxylase in yeast: Effect of deletion in the MEU1 gene. Proc. Natl. Acad. Sci. 102, 16158-16163 (2005)). Polyamine biosynthesis is regulated by means of an antizyme-mediated negative feedback loop conserved across fungi and metazoans (see Pegg, A. E. Regulation of ornithine decarboxylase. Journal of Biological Chemistry 281, 14529-14532 (2006)). In yeast, the OAZ1 gene comprises two exons separated by a single nucleotide which collectively encode antizyme-1, a competitive inhibitor of ornithine decarboxylase (Spe1p). A polyamine-induced ribosomal frameshifting mechanism enables translation of the full-length antizyme only at high polyamine levels, thereby imposing feedback inhibition of their biosynthesis. Finally, polyamine uptake from the extracellular environment is mediated by a signaling pathway involving Agp2p, a permease of the plasma membrane with affinity towards carnitine, spermidine, and spermine, and Sky1p, a protein kinase thought to interact with Agp2p.

1.4.2) Yeast single-gene disruption strains for each of MEU1, OAZ1, SPE4, SKY1, and AGP2 were constructed by inserting a series of tandem nonsense mutations within the first third of each open reading frame in wild-type yeast. To characterize the effects of each regulatory disruption in the context of the native and heterologous putrescine production pathways, either yeast ODC (SPE1) was overexpressed, or AsADC and speB were co-expressed from low-copy plasmids in each of the single-gene disruption strains. Putrescine titers in the extracellular medium were measured via LC-MS/MS after 72 hours of growth (FIG. 9). MEU1 disruption improved putrescine titers by 68% when the native putrescine production pathway via SPE1 was overexpressed. Similarly, OAZ1 disruption markedly improved putrescine production by 174% when combined with overexpression of SPE1. Disruption of OAZ1 resulted in a 21-fold increase in putrescine titer in untransformed cells with neither the native nor heterologous putrescine pathways overexpressed. Disruption of SKY1 and AGP2 resulted in 29% and 14% respective increases in putrescine titer when overexpressed with SPE1. SKY1 disruption resulted in a 41% decrease in putrescine titer when combined with heterologous expression of AsADC and speB.

1.5) The biosynthetic pathway in the engineered strain combines the MEU1 and OAZ1 regulatory gene knockouts with overexpression of the native and heterologous putrescine biosynthetic genes in order to further increase putrescine production in the engineered strain. Additional copies of the native arginine and polyamine biosynthetic genes ARG2, CAR1, and FMS1 were integrated into the genome of a meu1/oaz1 double-disruption strain. This strain was transformed with a low-copy plasmid expressing SPE1, AsADC, and speB. LC-MS/MS analysis of the extracellular medium of this transformed strain indicated that putrescine titers reached 86 mg/L after 48 hours of growth in selective media (FIG. 10).

Example 2. Engineering Yeast Strains for Production of NMPy

Strains of *S. cerevisiae* are developed by modifying the putrescine-overproducing strain developed in Example 1 for the production of the TA precursor NMPy. These strains combine genetic modifications for the purpose of increasing carbon and nitrogen flux from putrescine towards NMPy biosynthesis, and include the introduction of key heterologous enzymes for production of the TA precursors NMP, 4MAB, and NMPy. Genetic modifications are employed including modification of the N- and/or C-terminal domains of enzymes of interest to improve activity in a heterologous host, and deletion or disruption of genes encoding enzymes that diver precursor molecules away from the intended pathway.

Figure 11:
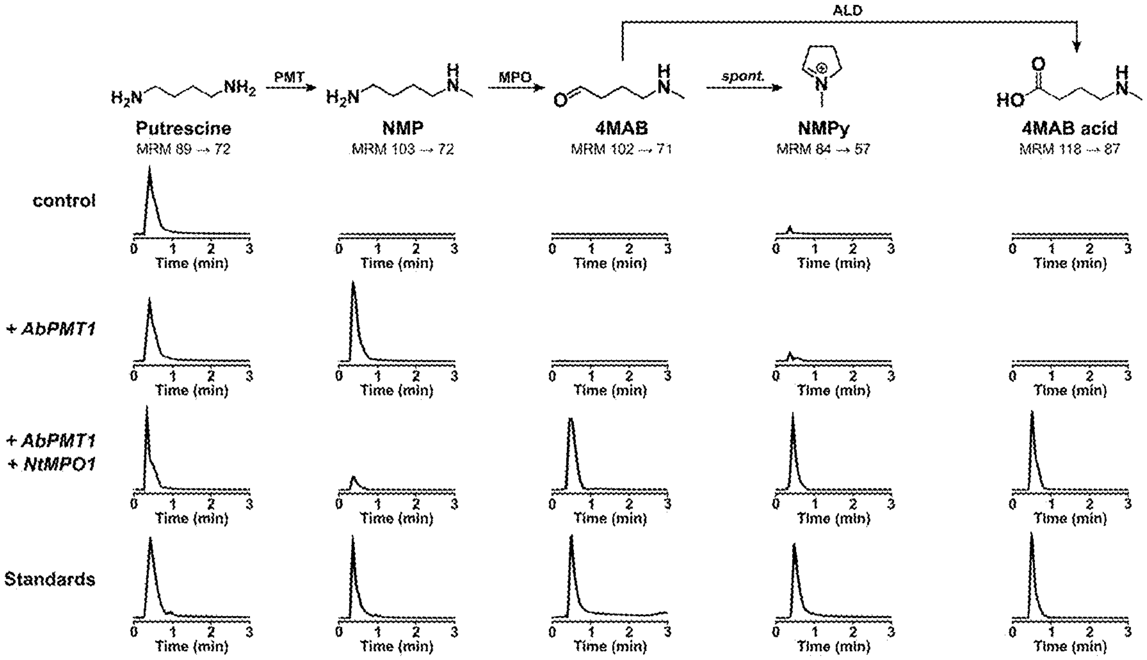
FIG. 11 shows LC-MS/MS chromatograms which illustrate the stepwise conversion of putrescine to the TA intermediate NMPy and the side product 4MAB acid via the intermediates NMP and 4MAB in engineered yeast, in accordance with embodiments of the invention. The proposed mechanism for formation of the 4MAB acid side product via activity of an endogenous yeast enzyme (ALD) is shown. Extracted ion chromatogram MRM traces are shown for each metabolite along the pathway and for authentic standards using the highest precursor ion/product ion transition for each metabolite. Control represents strain CSY1235 (see Example 1.5) expressing SPE1, AsADC, and speB on a low-copy plasmid. Chromatogram traces are representative of three biological replicates. Enzyme symbols: PMT, putrescine N-methyltransferase; MPO, N-methylputrescine oxidase; ALD, aldehyde dehydrogenase.

2.1) The biosynthetic pathway in the engineered strain enables production of NMPy from endogenous putrescine. Putrescine is first converted to N-methylputrescine (NMP) by a SAM-dependent N-methyltransferase (PMT), which is subsequently oxidized to 4-methylaminobutanal (4MAB) by a copper-dependent diamine oxidase (MPO). 4MAB, like many aldehyde compounds, is unstable in aqueous solution and spontaneously cyclizes via base-catalyzed nucleophilic attack to form NMPy (FIG. 11).

Figure 12:
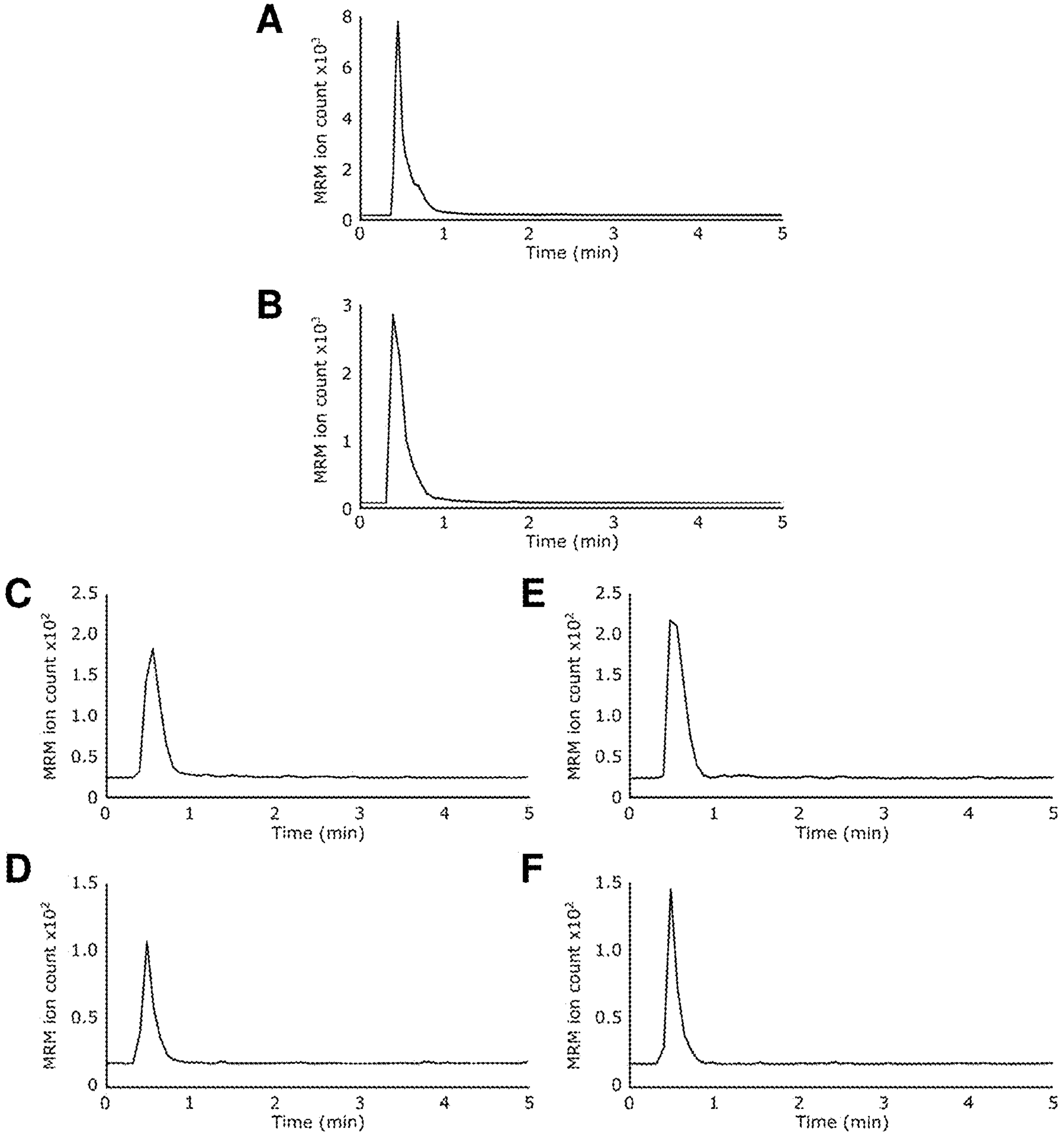
FIG. 12 shows LC-MS/MS chromatograms illustrating relative production of the TA precursors (A) putrescine, (B) NMP, (C,E) 4MAB, and (D,F) NMPy in liquid cultures of engineered yeast expressing AbPMT1 and an MPO enzyme, in accordance with embodiments of the invention. (A) MRM chromatogram of putrescine (m/z+ 89→72) for CSY1235 harboring pCS4239 for putrescine overproduction. (B) MRM chromatogram of NMP (m/z+ 103→72) for CSY1235 harboring pCS4239 and expressing AbPMT1 from a low-copy plasmid. (C,D) MRM chromatograms of 4MAB (m/z+ 102→71) and NMPy (m/z+ 84→57), respectively, for CSY1235 harboring pCS4239 and expressing AbPMT1 and NtMPO1 from low-copy plasmids. (E,F) MRM chromatograms of 4MAB (m/z+ 102→71) and NMPy (m/z+ 84→57), respectively, for CSY1235 harboring pCS4239 and expressing AbPMT1 and DmMPO1ΔC-PTS1 from low-copy plasmids. Y-axes of traces are raw MRM ion counts. All chromatograms were generated by LC-MS/MS analysis of the extracellular medium after 48 hours of growth at 30° C. in selective media with 2% dextrose. Traces are representative of at least three biological replicates.

2.1.1) The putrescine overproducing strain of Example 1.5, which harbors a low-copy plasmid expressing SPE1, AsADC, and speB for putrescine overproduction, was co-transformed with additional low-copy plasmids expressing a PMT from *A. belladonna* (AbPMT1) and a subsequent MPO enzyme from *Nicotiana tabacum* (NtMPO1). The accumulation of intermediates in the extracellular medium of transformed cells expressing each successive enzyme between putrescine and NMPy was compared via LC-MS/MS analysis after 48 hours of growth. The immediate product of NtMPO1 (4MAB) as well as its spontaneous cyclization product (NMPy) were produced with expression of AbPMT1 and NtMPO1 (FIG. 11), as well as their precursors, NMP and putrescine (FIG. 12).

Figure 13:
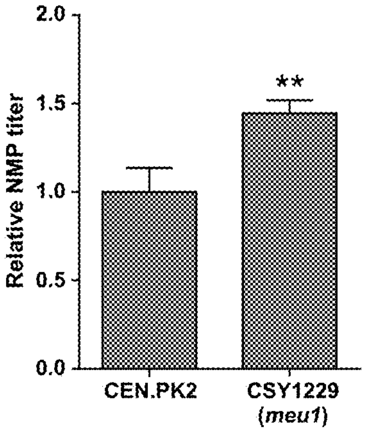
FIG. 13 shows the effect of MEU1 disruption on SAM-dependent putrescine N-methylation by AbPMT1. Wild-type strain CEN.PK2 or meu1 disruption strain CSY1229 were co-transformed with low-copy plasmids expressing SPE1, AsADC, and speB and AbPMT1. Data indicate mean NMP titer relative to CEN.PK2 control as quantified by LC-MS/MS peak area for three biological replicates after 48 hours of growth at 30° C. in selective media with 2% dextrose. Error bars show standard deviation. Student's two-tailed t-test: * $P<0.05$,  $P<0.01$, * $P<0.001$.

2.1.2) The accumulation of NMP was measured in the growth medium of putrescine-overproducing yeast strains with and without disruption of the MEU1 gene (described in Example 1.4.2) by LC-MS/MS analysis. This analysis indicated that the prior disruption of MEU1 in the putrescine-overproducing strain and its concomitant impact on SAM recycling did not inhibit putrescine N-methylation by AbPMT1 (FIG. 13).

2.2) Enzymes may localize to different sub-cellular compartments when heterologously expressed than in their original host organism, resulting in reduced function. The biosynthetic pathway in the engineered strain may incorporate modifications to the polypeptide sequences of native and heterologous enzymes to induce localization of these modified enzymes to sub-cellular compartments other than those to which they localize naturally. For example, prior studies have shown that while NtPMT is expressed in the cytosol of tobacco cells, NtMPO1 localizes to the peroxisome lumen (see Naconsie, M., Kato, K., Shoji, T. & Hashimoto, T. Molecular evolution of n-methylputrescine oxidase in Tobacco. Plant Cell Physiol. 55, 436-444 (2014)).

2.2.1) The sub-cellular localization of NtMPO1 was examined by performing in silico prediction of enzyme subcellular localization using the SherLoc2 utility for signal peptide detection (see Briesemeister, S. et al. SherLoc2: A high-accuracy hybrid method for predicting subcellular localization of proteins. J. Proteome Res. 8, 5363-5366 (2009)). This analysis indicated that NtMPO1 harbors a strong yeast consensus peroxisome-targeting sequence (PTS) at its C-terminus (Ala-Lys-Leu, denoted PTS1), which suggests that NtMPO1 may localize to peroxisomes when expressed heterologously in yeast (FIG. 14).

Figure 15:
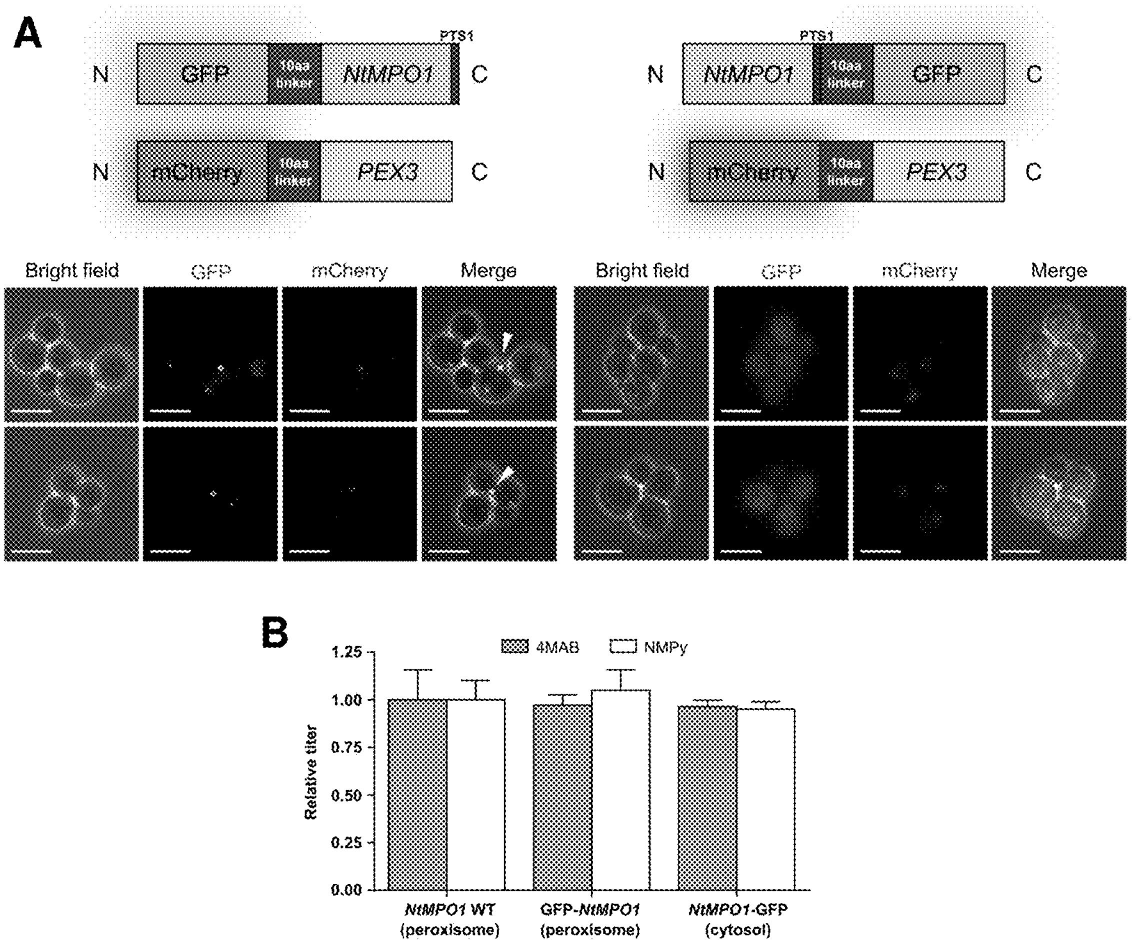
FIG. 15 illustrates (A) colocalization of N- and C-terminal GFP-tagged NtMPO1 with a PEX3 peroxisomal marker and (B) the effect of N- and C-terminal GFP tagging of NtMPO1 on the production of the TA precursors 4MAB and NMPy in liquid cultures of engineered yeast, in accordance with embodiments of the invention. This figures shows an experimental validation of NtMPO1 subcellular localization. (A) Fluorescence microscopy of NtMPO1 N- and C-terminal GFP fusions co-expressed with peroxisome marker mCherry-PEX3 in wild-type yeast (CEN.PK2). White arrows indicate colocalization of GFP-tagged NtMPO1 with peroxisomes. Scale bar, 10 μm. (B) Effect of forcing cytosolic localization of NtMPO1 on 4MAB or NMPy production. Wild-type yeast (CEN.PK2) was co-transformed with low-copy plasmids expressing wild-type NtMPO1 or N- or C-terminal GFP fusions together with low-copy plasmids expressing SPE1, AsADC, and speB and AbPMT1. LC-MS/MS analysis was performed after 48 hours of growth at 30° C. in selective media with 2% dextrose. Data represent mean of three biological replicates; error bars show standard deviation. Most probable sub-cellular compartment is indicated based on microscopy data in (a).
Figure 16:
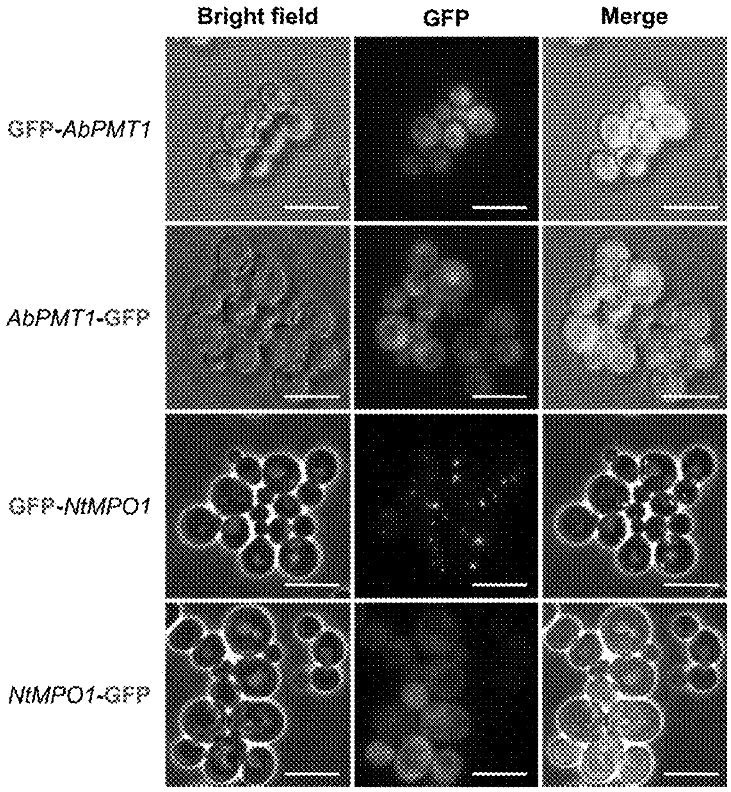
FIG. 16 provides fluorescence microscopy data depicting the sub-cellular localization of AbPMT1 and NtMPO1 when expressed heterologously in yeast. Microscopy was performed on wild-type yeast expressing N- or C-terminal GFP-tagged AbPMT1 or NtMPO1 from low-copy plasmids. Scale bar, 10 μm.

2.2.2) Fluorescence microscopy of wild-type yeast cells expressing either N- or C-terminal GFP-tagged AbPMT1 and NtMPO1 from low-copy plasmids indicated that while AbPMT1 is found primarily in the cytosol, localization of NtMPO1 to peroxisomes is contingent on an exposed C-terminal PTS (FIG. 15*a*, 16).

2.2.3) Cytosolic expression of NtMPO1 achieved by masking the C-terminal PTS with a GFP fusion did not significantly impact extracellular 4MAB or NMPy levels (FIG. 15*b*).

2.3) The biosynthetic pathway in the engineered strain may incorporate orthologs of biosynthetic enzymes other than those listed in Table 1. Different orthologs of an enzyme may exhibit significant differences in activity when expressed in heterologous hosts. Therefore, orthologs of biosynthetic enzymes provided as examples herein and listed in Table 1 may also be used in engineered non-plant cells to perform the same biochemical conversions.

Figure 17:
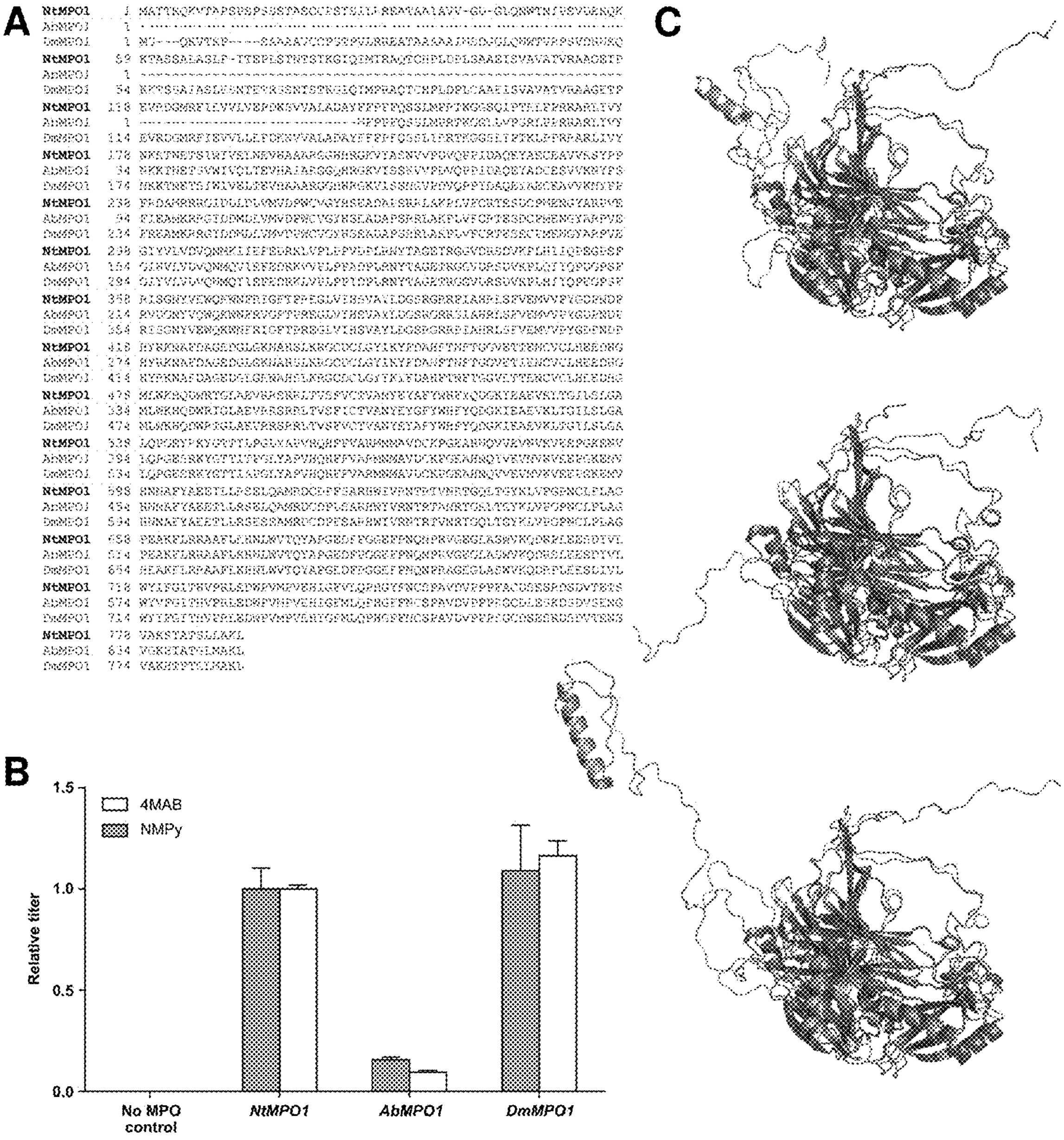
FIG. 17 illustrates (A) a sequence alignment of NtMPO1 and the putative MPO enzymes AbMPO1 and DmMPO1 identified from plant transcriptome data (from top to bottom: SEQ ID NO: 27-29), (B) a comparison of the production of the TA precursors 4MAB and NMPy in liquid cultures of engineered yeast strains expressing NtMPO1, AbMPO1, or DmMPO1, and (C) a comparison of the predicted three-dimensional structures of NtMPO1, AbMPO1, and DmMPO1 determined from homology modeling, in accordance with embodiments of the invention. (A) Alignment of query NtMPO1 sequence against AbMPO1 and DmMPO1 candidates from 1000 Plants Project database. Blue indicates conservation of amino acid structure; red indicates mismatches. (B) Comparison of relative activities of MPO orthologs. Putrescine overproducing strain CSY1235 (see Example 1.5) was co-transformed with low-copy plasmids expressing SPE1, AsADC, and speB, AbPMT1, and one of the three MPO variants. LC-MS/MS analysis was performed after 48 hours of growth in selective media at 30° C. Data represent mean of three biological replicates; error bars show standard deviation. (C) Homology models of MPO enzymes (pink) constructed based on the crystal structure of *Pisum sativum* copper-containing amino oxidase (PDB: 1KSI, blue) using the RaptorX web server. Top: NtMPO1; center: AbMPO1; bottom: DmMPO1.

2.3.1) A tBLASTn search of the transcriptomes of *A. belladonna* and *Datura metel* in the 1000 Plants Project database (see Matasci, N. et al. Data access for the 1,000 Plants (1KP) project. Gigascience 3, 17 (2014)) was performed using the amino acid sequence of NtMPO1 as a query and an E-value threshold of $10^{-150}$. Two full-length ortholog sequences denoted AbMPO1 and DmMPO1 were identified, which each shared 91% sequence identity with NtMPO1 (FIG. 17*a*).

2.3.2) Yeast codon-optimized sequences for AbMPO1 and DmMPO1 were obtained and cloned into low-copy expression plasmids. To evaluate their activity, each of the three MPO variants was co-expressed with AbPMT1 from low-copy plasmids in the putrescine-overproducing strain of Example 1.5, and 4MAB and NMPy accumulation were measured in the extracellular medium by LC-MS/MS following 48 hours of growth in selective media. DmMPO1 showed comparable levels of 4MAB and NMPy production to the original NtMPO1 variant (FIG. 17*b*).

2.3.3) Differences in activity between orthologous enzymes can often be at least partially attributed to structural differences in their active sites. Template-based homology models of NtMPO1, AbMPO1, and DmMPO1 were constructed based on the crystal structure of a *Pisum sativum* copper-containing amino oxidase (PDB: 1KSI) using the RaptorX web server (see Källberg, M. et al. Template-based protein structure modeling using the RaptorX web server. Nat. Protoc. 7, 1511-22 (2012)). The homology models indicated that the orthologs possess long, unstructured N- and C-terminal tail regions (FIG. 17*c*).

Figure 18:
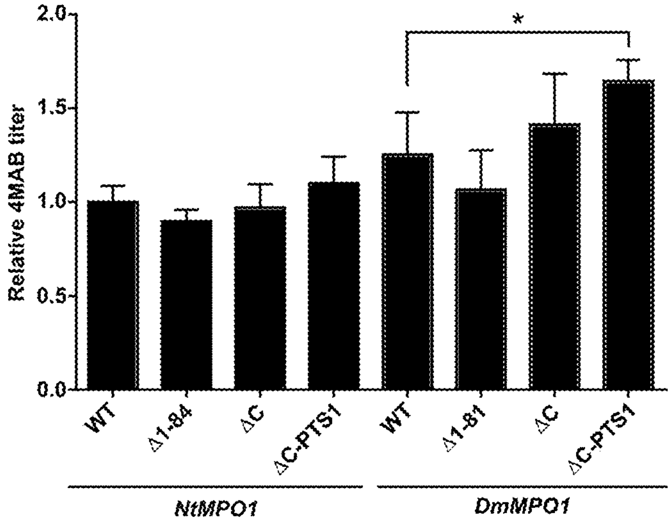
FIG. 18 illustrates 4MAB production in liquid culture of engineered yeast strains overproducing putrescine and expressing AbPMT1 and N- and C-terminal truncations of NtMPO1 and DmMPO1. This figure shows the effect of N- and C-terminal truncations to methylputrescine oxidase on 4MAB production in engineered yeast. Wild-type (WT) enzymes and indicated truncations were expressed from low-copy plasmids in putrescine-overproducing strain CSY1235 (see Example 1.5). Strains were cultured in selective media with 2% dextrose at 30° C. for 48 h before LC-MS/MS analysis. All data represent the mean of at least three biological replicates and error bars show standard deviation. Student's two-tailed t-test: * P<0.05,  P<0.01, * P<0.001.

2.3.4) Truncations of the two active orthologs, NtMPO1 and DmMPO1, were tested for activity in engineered yeast. N-terminal truncations removed the first 84 and 81 residues of the two orthologs, respectively. C-terminal truncations removed the last 21 residues. C-terminal truncations were also constructed wherein the unstructured tail was removed but the PTS was retained (denoted$^{\Delta C\text{-}PTS1}$). Each of the MPO truncations was coexpressed with AbPMT1 from low-copy plasmids in the putrescine-overproducing strain of Example 1.5, and 4MAB and NMPy accumulation in the media after 48 hours of growth were quantified by LC-MS/MS. No significant differences in activity were observed between the NtMPO1 truncations (FIG. 18). Removal of the C-terminal unstructured region from DmMPO1 while retaining the C-terminal PTS tripeptide resulted in a 31% increase in extracellular 4MAB levels relative to the wild-type DmMPO1 enzyme.

2.4) The biosynthetic pathway in the engineered strain incorporates one or more genetic modifications to reduce or eliminate the metabolic flux of undesirable side reactions. Biosynthetic enzymes expressed in heterologous hosts may participate in undesirable side reactions that draw metabolite flux away from the biosynthesis of desired compounds. For example, yeast aldehyde dehydrogenases may oxidize heterologous aldehyde molecules, such as 4MAB, to their cognate carboxylic acids. Based on LC-MS/MS analysis, accumulation of 4MAB acid was observed in the growth media of the putrescine-overproducing strain of Example 1.5 when AbPMT1 and DmMPO1$^{\Delta C\text{-}PTS1}$ were co-expressed from low-copy plasmids, but not in the absence of the MPO enzyme (FIG. 11).

Figure 19:
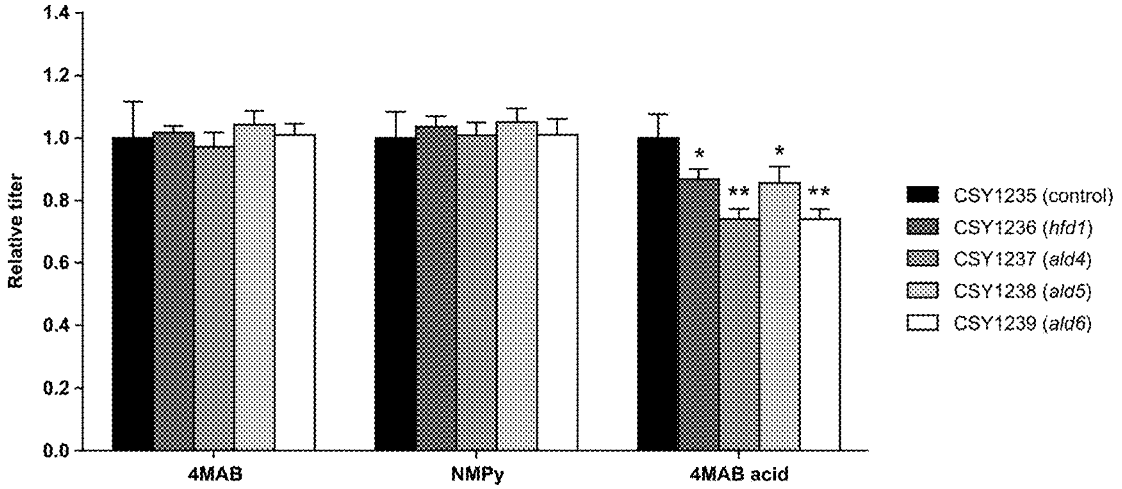
FIG. 19 illustrates the production of the TA precursors 4MAB and NMPy and the side product 4MAB acid in liquid cultures of engineered yeast strains harboring single disruptions of one of four native aldehyde dehydrogenase genes. This figures shows the effect of disrupting individual aldehyde dehydrogenases on 4MAB acid accumulation. Putrescine overproducing strain CSY1235 (control) or daughter strains with nonsense mutation disruptions of hfd1, ald4, ald5, or ald6 were transformed with low-copy plasmids expressing SPE1, AsADC, and speB, AbPMT1, and DmMPO1$^{\Delta C\text{-}PTS1}$. Bars indicate relative 4MAB acid titer as measured by LC-MS/MS peak area normalized to CSY1235 (no ALD disruptions) after 48 hours of growth in selective media at 30° C. Data represent mean of three biological replicates and error bars show standard deviation. Student's two-tailed t-test: * P<0.05,  P<0.01, * P<0.001.

2.4.1) Six yeast genes (ALD2-ALD6 and HFD1) have been demonstrated in the literature to encode enzymes with aldehyde dehydrogenase activity (see Datta, S., Annapure, U. S. & Timson, D. J. Different specificities of two aldehyde dehydrogenases from *Saccharomyces cerevisiae* var. *boulardii*. Biosci. Rep. 37, BSR20160529 (2017); and also Nakahara, K. et al. The Sjögren-Larsson Syndrome Gene Encodes a Hexadecenal Dehydrogenase of the Sphingosine 1-Phosphate Degradation Pathway. Mol. Cell 46, 461-471 (2012)). The ALD2 and ALD3 genes encode a pair of nearly identical cytosolic dehydrogenases which catalyze the oxidation of 3-aminopropanal to β-alanine in the biosynthesis of pantothenic acid (see White, W. H., Skatrud, P. L., Xue, Z. & Toyn, J. H. Specialization of Function Among Aldehyde Dehydrogenases: Genetics 163, 69-77 (2003)). The ALD4, ALD5, and ALD6 genes respectively encode two mitochondrial and one cytosolic acetaldehyde dehydrogenase which, in addition to oxidizing acetaldehyde to acetate during fermentative growth on glucose and ethanol (see Saint-Prix, F., Bönquist, L. & Dequin, S. Functional analysis of the ALD gene family of *Saccharomyces cerevisiae* during anaerobic growth on glucose: The NADP+-dependent Ald6p and Ald5p isoforms play a major role in acetate formation. Microbiology 150, 2209-2220 (2004)), have been shown to oxidize an array of diverse aliphatic and aromatic aldehydes to carboxylic acids (see Datta, S., Annapure, U. S. & Timson, D. J. Different specificities of two aldehyde dehydrogenases from *Saccharomyces cerevisiae* var. *boulardii*. Biosci. Rep. 37, BSR20160529 (2017)). Individual knockouts strains for these four target genes were constructed by inserting a series of tandem nonsense mutations within the first third of their open reading frames in the putrescine-overproducing strain of Example 1.5. The contribution of each of the four dehydrogenases toward 4MAB oxidation was evaluated by co-expressing AbPMT1 and DmMPO1$^{\Delta C\text{-}PTS1}$ from low-copy plasmids in each single disruption strain and measuring 4MAB acid accumulation in the media by LC-MS/MS after 48 hours of growth. Marginal decreases in 4MAB acid levels were observed with the individual HFD1 and ALD4-6 disruptions (FIG. 19).

Figure 20:
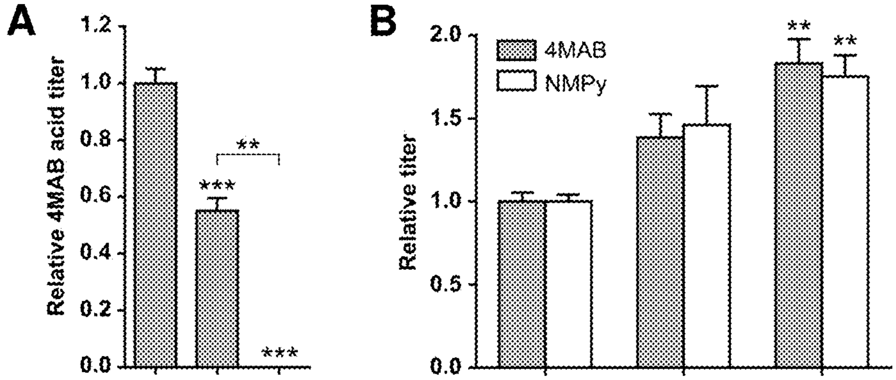
FIG. 20 illustrates production of (A) the 4MAB acid side product as well as (B) the TA precursors 4MAB and NMPy in liquid cultures of engineered yeast strains harboring one or more disruptions to native aldehyde dehydrogenases. This figure shows the effect of aldehyde dehydrogenase gene disruptions on production of (A) the 4MAB acid side product and (B) 4MAB and NMPy in engineered yeast. '+' and '−' symbols indicate presence or absence of functional enzyme, respectively. Strains were cultured in selective (YNB-DO) media with 2% dextrose at 30° C. for 48 h before LC-MS/MS analysis. All data represent the mean of at least three biological replicates and error bars show standard deviation. Student's two-tailed t-test: * P<0.05,  P<0.01, * P<0.001. Unless otherwise indicated, statistical significance is shown relative to the corresponding control (CSY1235).

2.4.2) Although ALD4-6 are considered essential genes due to their role in acetate and acetyl-CoA production, prior studies have demonstrated that the three genes are at least partially redundant and that the lethal phenotype of double and triple knockouts can be rescued by supplementing media with acetate (see Saint-Prix, F., Bönquist, L. & Dequin, S. Functional analysis of the ALD gene family of *Saccharomyces cerevisiae* during anaerobic growth on glucose: The NADP+-dependent Ald6p and Ald5p isoforms play a major role in acetate formation. Microbiology 150, 2209-2220 (2004); and also Luo, Z., Walkey, C. J., Madilao, L. L., Measday, V. & Van Vuuren, H. J. J. Functional improvement of *Saccharomyces cerevisiae* to reduce volatile acidity in wine. FEMS Yeast Res. 13, 485-494 (2013)). A quadruple knockout yeast strain was constructed with disruptions to the open reading frames of HFD1 and ALD4-6, and which expressed both AbPMT1 and DmMPO1$^{\Delta C\text{-}PTS1}$ from low-copy plasmids. This strain showed a 45% reduction in 4MAB acid levels (FIG. 20*a*) and a concomitant 46% increase in NMPy production compared to the strain with no disruptions (FIG. 20*b*).

2.4.3) An ALD-null strain was constructed by deleting the tandem ALD2-ALD3 genes from the genome of the quadruple knockout strain of example 2.4.2 and co-expressing AbPMT1 and DmMPO1$^{\Delta C\text{-}PTS1}$ from low-copy plasmids. Following 48 hours of growth, LC-MS/MS analysis indicated that deletion of ALD2 and ALD3 completely eliminated the 4MAB acid side product and increased 4MAB and NMPy production by 83% and 75%, respectively, compared to the strain with all six ALD genes intact (FIG. 20*a, b*).

Figure 21:
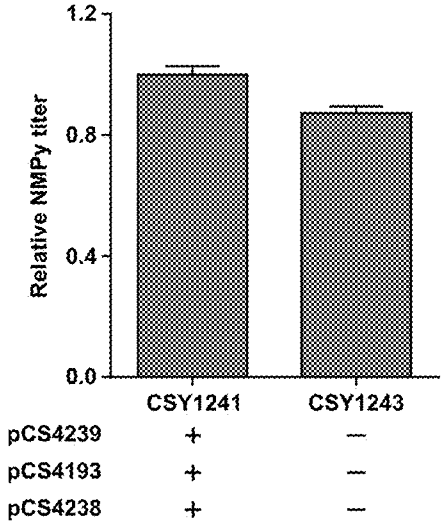
FIG. 21 illustrates a comparison of the production of the TA precursor NMPy in liquid cultures of engineered yeast strains with either low-copy plasmid-based or genomic expression of putrescine overproduction genes, AbPMT1, and a DmMPO1 truncation, in accordance with embodiments of the invention. This figure provides a comparison of 4MAB and NMPy production with plasmid-based (CSY1241) and genomic (CSY1243) expression of NMPy biosynthetic genes. Strain CSY1241 was transformed with low-copy plasmids expressing putrescine overproduction genes (SPE1, AsADC, speB), AbPMT1, and DmMPO1$^{\Delta C\text{-}PTS1}$. Strain CSY1243 expressed all of the aforementioned genes from genomic integrated copies. NMPy levels were quantified by LC-MS/MS following growth in selective (CSY1241) or non-selective (CSY1243) media at 30° C. for 48 h. Data represent the mean of at least two biological replicates and error bars indicate standard deviation.

2.4.4) An NMPy-producing yeast strain was constructed by integrating a previously plasmid-borne putrescine-overproduction gene cassette (SPE1, AsADC, speB) into the genome of the ALD-null strain of Example 2.4.3, and additionally integrating AbPMT1 and DmMPO1$^{\Delta C\text{-}PTS1}$ LC-MS/MS analysis confirmed that NMPy production in this strain after 48 hours of growth in non-selective media was comparable to that of the ALD-null strain of example 2.4.3 expressing the requisite putrescine production genes, AbPMT1 and DmMPO1$^{\Delta C\text{-}PTS1}$, from low-copy plasmids and cultured in selective media (FIG. 21).

Figure 22:
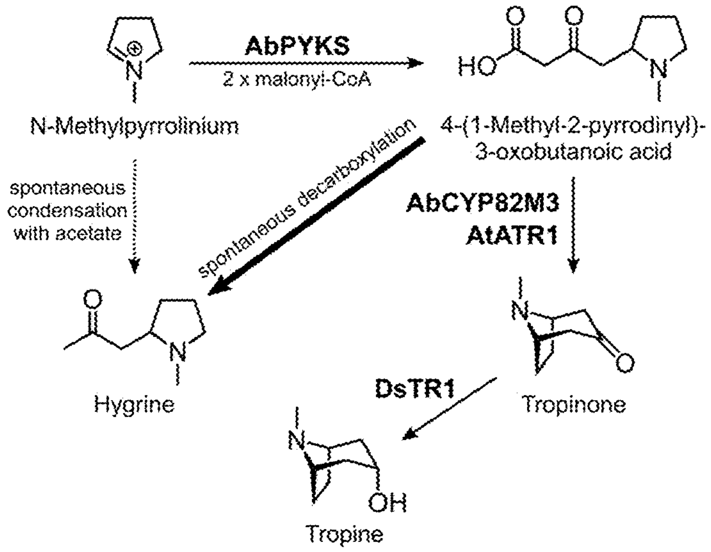
FIG. 22 illustrates biosynthetic pathways for the production of the side product hygrine from NMPy and MPOB, in accordance with embodiments of the invention. Putative major and minor side reactions in yeast are indicated by bold and dotted arrows, respectively.

Example 3. Engineered Yeast Strains for Production of Tropine from Simple Sugars and Nutrients A type III polyketide synthase (PKS) and a cytochrome P450 enable conversion of NMPy to tropinone by way of the TA precursor MPOB. Tropinone can be reduced by a stereospecific reductase, denoted tropinone reductase 1 (TR1), to produce tropine (see Kim, N., Estrada, O., Chavez, B., Stewart, C. & D'Auria, J. C. Tropane and Granatane Alkaloid Biosynthesis: A Systematic Analysis. Molecules 21, (2016)) (FIG. 22).

3.1) The biosynthetic pathway in the engineered strain incorporates a pyrrolidine ketide synthase, a tropinone synthase CYP82M3, one or more cytochrome P450 reductases, and a tropinone reductase 1 to convert NMPy to tropine.

Figure 23:
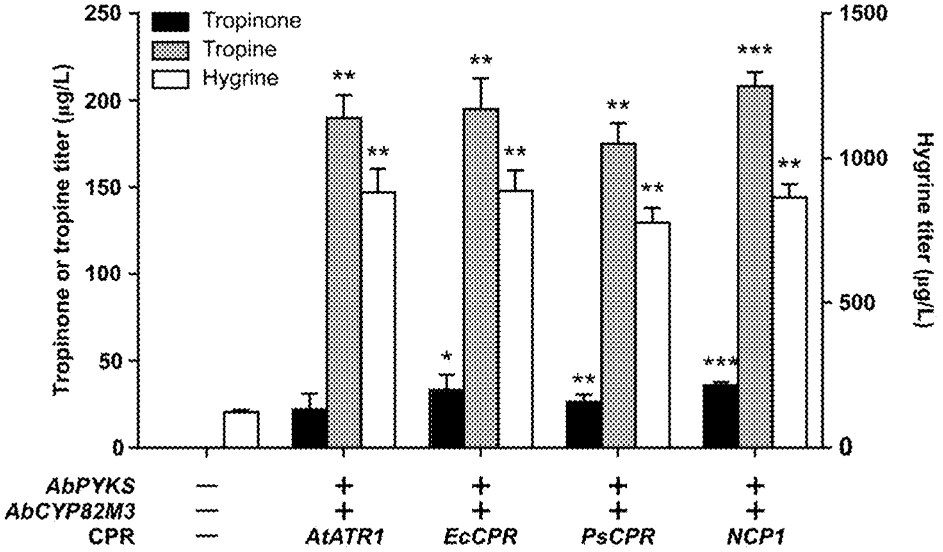
FIG. 23 illustrates a comparison of production of the TA precursors tropinone and tropine and the side product hygrine in liquid cultures of engineered yeast strains expressing low-copy plasmid-based AbPYKS, AbCYP82M3, DsTR1, and one of four different CPRs. This figure shows production of tropine and related intermediates with expression of AbPYKS, AbCYP82M3, and DsTR1 in engineered yeast. Indicated genes were expressed from low-copy plasmids in CSY1246; '+' and '−' symbols indicate presence or absence of enzyme. Strains were cultured in selective media with 2% dextrose at 30° C. for 48 h before LC-MS/MS analysis. Data represent the mean of three biological replicates and error bars show standard deviation. Student's two-tailed t-test: * P<0.05,  P<0.01, * P<0.001.

3.1.1) Yeast codon-optimized DNA sequences encoding *A. belladonna* pyrrolidine ketide synthase (AbPYKS), tropinone synthase (AbCYP82M3), and *Datura stramonium* tropinone reductase 1 (DsTR1) were obtained. Yeast codon-optimized sequences for a panel of four different CPRs, including three plant CPRs from *A. thaliana, Eschscholzia californica* (California poppy), and *Papaver somniferum* (opium poppy), and the native yeast CPR (NCP1), were also obtained for expression in yeast, since P450 enzymes require NADP-cytochrome P450 reductase (CPR) partners for continued electron exchange. A yeast strain was constructed by integrating DsTR1 into the genome of the NMPy-producing strain of Example 2.4.4, and expressing AbPYKS, AbCYP82M3, and each of the four CPRs from low-copy plasmids. To validate enzyme activity and identify potential bottlenecks, the accumulation of NMPy, MPOB, tropinone, and tropine were monitored by LC-MS/MS in the media of the transformed strains after 48 hours of growth (FIG. 23). Comparable levels of de novo tropine production (175-210 μg/L) were observed with all four CPR partners under the assay conditions.

3.2) The presence of metabolic bottlenecks, which are defined as biosynthetic enzymes or spontaneous steps whose low activity limits flux through a portion of a biosynthetic pathway, can result in sub-optimal production of desired TAs and precursors.

Figure 24:
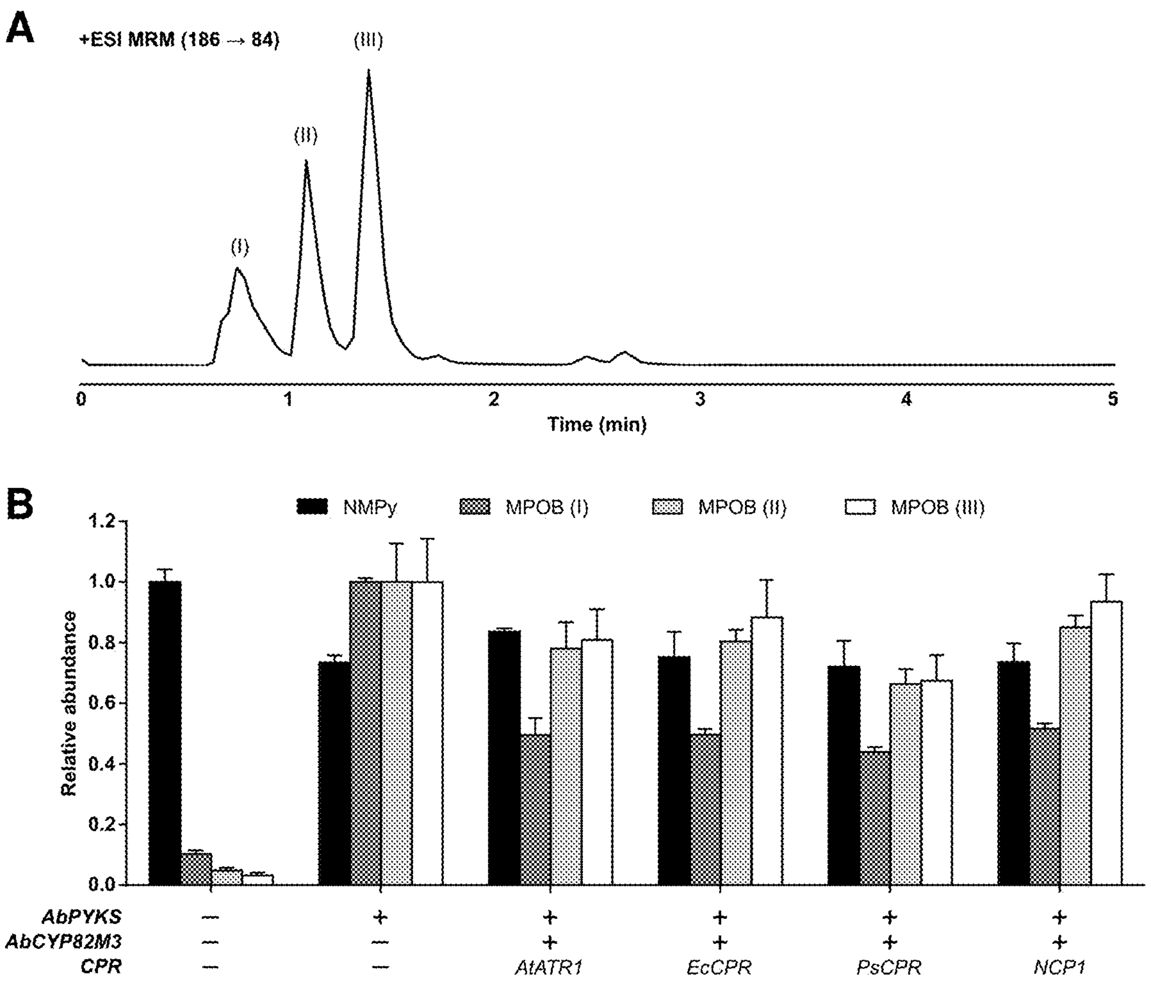
FIG. 24 illustrates (A) a LC-MS/MS chromatogram illustrating the characteristic triple peak of the TA precursor MPOB produced in liquid cultures of engineered yeast strains, and (B) production of the TA precursors NMPy and MPOB in liquid cultures of yeast strains engineered to express AbPYKS, AbCYP82M3, and one of four CPRs from plasmids. This figure shows accumulation of NMPy and MPOB in the media of engineered strains expressing AbPYKS. (A) Representative LC-MS/MS multiple reaction monitoring (MRM) chromatogram for detection of MPOB in the extracellular medium of CSY1246 expressing AbPYKS only from a low-copy plasmid. The three characteristic MPOB isoform peaks are labelled with (I), (II), and (III). LC-MS/MS analysis was performed after growth in selective media at 30° C. for 48 h. (B) Relative abundance of NMPy and MPOB (all 3 peaks) in the extracellular media of CSY1246 expressing AbPYKS, AbCYP82M3, and one of four CPRs from low-copy plasmids after 48 h of growth at 30° C. in selective media. '+' and '−' symbols indicate presence or absence of gene. Data represent mean of three biological replicates; error bars indicate standard deviation.

3.2.1) For example, analysis of the accumulation of TA intermediates in the media of the engineered strains of Example 3.1.1 indicated that although accumulation of tropinone, the product of AbCYP82M3, was minimal, a substantial portion of MPOB produced by AbPYKS remained unconsumed by AbCYP82M3 (FIG. 24).

Figure 28:
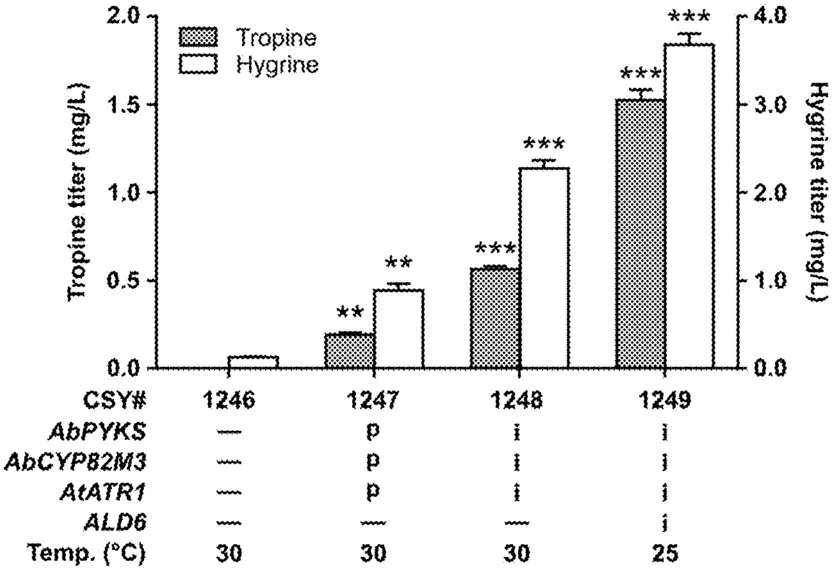
FIG. 28 illustrates the progression of improvements to production of the TA precursor tropine and the side product hygrine in liquid cultures of engineered yeast strains. This figure provides a summary of strains engineered to increase tropine production in yeast. '−' symbol indicates absence of gene; 'p' and 'i' indicate gene expression from low-copy plasmid or genomic integration, respectively. Strains were cultured in selective or non-selective media with 2% dextrose at 30° C. or 25° C. for 48 h before LC-MS/MS analysis. Data represent the mean of three biological replicates and error bars show standard deviation. Student's two-tailed t-test: * $P<0.05$,  $P<0.01$, * $P<0.001$.

3.2.2) Integration of the tropine biosynthesis genes into the yeast genome can improve tropine production by enabling more stable AbCYP82M3 expression. A tropine-producing platform strain was constructed by integrating AtATR1 with AbPYKS and AbCYP82M3 into the genome of the NMPy-producing strain of Example 3.1.1. Tropine and hygrine accumulation for the integrated strain was compared to plasmid-based expression of the same genes via LC-MS/MS analysis after 48 hours (FIG. 28). Genomic expression of AbPYKS, AbCYP82M3, and AtATR1 increased tropine titers by nearly three-fold (565 μg/L) relative to plasmid-based expression (189 μg/L). The engineered strain also showed a 2.6-fold increase in hygrine accumulation.

3.3) The accumulation of side products in the biosynthetic pathway of the engineered strain can result in sub-optimal production of desired TAs and precursors.

3.3.1) For example, analysis of the accumulation of TA intermediates in the media of the engineered strains of Example 3.1.1 indicated substantial accumulation of hygrine, a derivative of NMPy, to titers almost four-fold greater than tropine (775-900 μg/L). In the relevant literature, hygrine has been observed to accumulate via spontaneous decarboxylation of MPOB (see Bedewitz, M. A., Jones, A. D., D'Auria, J. C. & Barry, C. S. Tropinone synthesis via an atypical polyketide synthase and P450-mediated cyclization. Nat. Commun. 9, 5281 (2018)) (FIG. 22). As another example, LC-MS/MS analysis of the growth media of the engineered strains of Example 3.1.1 indicated that hygrine also accumulated in the negative control strain lacking AbPYKS and AbCYP82M3 due to decarboxylative condensation with NMPy (FIG. 22).

Figure 25:
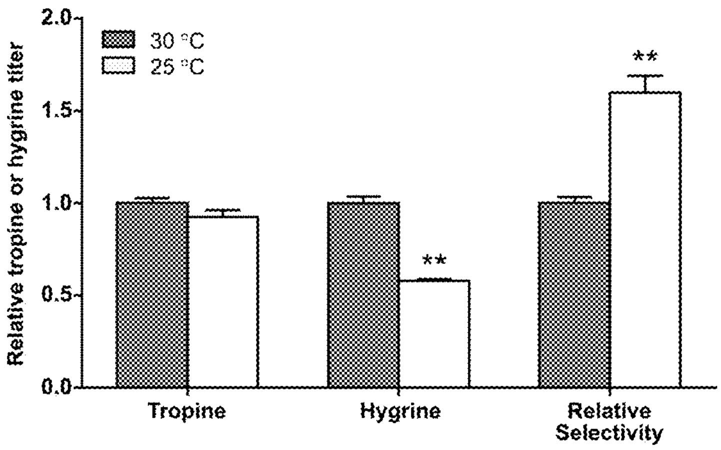
FIG. 25 illustrates the effect of growth temperature on the production of the TA precursor tropine and the side product hygrine in liquid cultures of engineered yeast. This figure shows the effect of growth temperature on spontaneous hygrine production in the tropine-producing yeast strain (CSY1248). Relative selectivity represents the ratio of relative tropine titer to relative hygrine titer. Strains were cultured in non-selective media with 2% dextrose at 30° C. or 25° C. for 48 h before LC-MS/MS analysis. Data represent the mean of three biological replicates and error bars show standard deviation. Student's two-tailed t-test: * $P<0.05$,  $P<0.01$, * $P<0.001$.

3.3.2) Modulation of growth temperature may be used to reduce the accumulation of side products in the biosynthetic pathway of the engineered strain to increase flux towards desired TAs and precursors. In one example, the impact of temperature on spontaneous hygrine production was evaluated by leveraging a kinetic principle that the rates of enzymatic and spontaneous reactions are decreased at lower temperatures. Since *A. belladonna* and other TA-producing Solanaceae are adapted for optimal growth at cooler climates, growth of yeast strains expressing Solanaceae genes at 25° C. may improve enzyme folding and/or activity, enabling comparable production of enzymatically-generated tropine to growth at 30° C. while reducing the rate of spontaneous hygrine production. Cultures of the tropine-producing strain of Example 3.2.2 were grown in non-selective defined media at 30° C. and 25° C. and the accumulation of tropine and hygrine was compared via LC-MS/MS analysis of the growth medium after 48 hours. Tropine titers were minimally impacted by the decrease in temperature. Hygrine accumulation was decreased by 42% at 25° C. compared to at 30° C., resulting in a 60% increase in the ratio of tropine to hygrine produced (FIG. 25).

Figure 26:
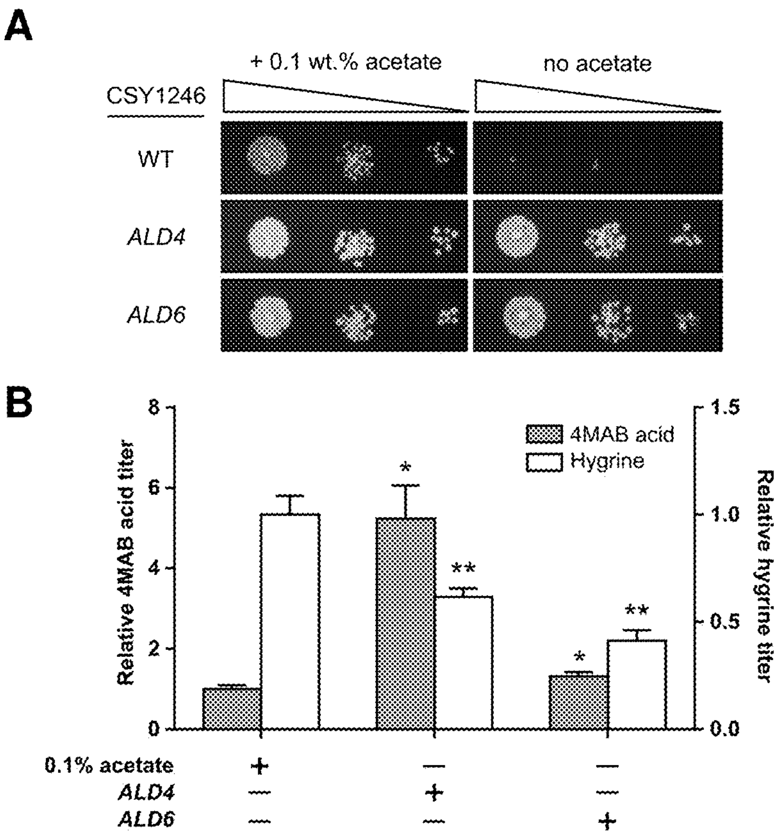
FIG. 26 illustrates (A) the effect of ALD4 and ALD6 reconstitution on the growth of tropine-producing engineered yeast strains on media with or without acetate supplementation, and (B) the effect of eliminating acetate auxotrophy on the production of the side products 4MAB acid and hygrine in liquid cultures of tropine-producing engineered yeast strains, in accordance with embodiments of the invention. This figure shows the effect of elimination of acetate auxotrophy in engineered tropine-producing yeast strain. (A) Effect of reconstituting functional ALD4 or ALD6 genes on the growth of the NMPy-producing yeast strain (CSY1246) with and without acetate supplementation. ALD4 and ALD6 were expressed from low-copy plasmids. 'WT' indicates CSY1246 with control (BFP) plasmid. Adjacent columns show ten-fold dilutions. (B) Production of 4MAB acid and hygrine side products with reconstituted acetate metabolism in engineered yeast. '+' and '−' symbols indicate presence or absence of fed metabolite (acetate) or ALD4 and ALD6 genes expressed from low-copy plasmids. Strains were cultured in selective (YNB-DO) media with 2% dextrose at 30° C. for 48 h before LC-MS/MS analysis. Data represent the mean of three biological replicates and error bars show standard deviation. Student's two-tailed t-test: * $P<0.05$,  $P<0.01$, * $P<0.001$.

3.3.3) Reduction or elimination of undesirable side reactions can be used to improve metabolite flux towards desirable TAs and TA precursors in the biosynthetic pathway of the engineered strain. In one example, flux towards the TA precursor tropine may be improved by reducing hygrine production resulting from spontaneous decarboxylative condensation with acetate. The impact of removing fed acetate from the media of the NMPy-producing strain of Example 2.4.4 on hygrine and tropine production was evaluated. The effect of abolishing acetate auxotrophy in the engineered strain of Example 2.4.4 was evaluated by expressing functional copies of ALD4 and ALD6 on low-copy plasmids and then monitoring the accumulation of hygrine and 4MAB acid via LC-MS/MS analysis after 48 hours of growth. While reconstitution of ALD4 or ALD6 enabled growth on selective media in the absence of fed acetate (FIG. 26*a*), addition of ALD4 caused a five-fold increase in the accumulation of 4MAB acid while ALD6 did not produce a significant increase (FIG. 26*b*). Moreover, the elimination of acetate feeding with either ALD4 or ALD6 resulted in 38% and 59% decreases in hygrine accumulation, respectively (FIG. 26*b*).

Figure 27:
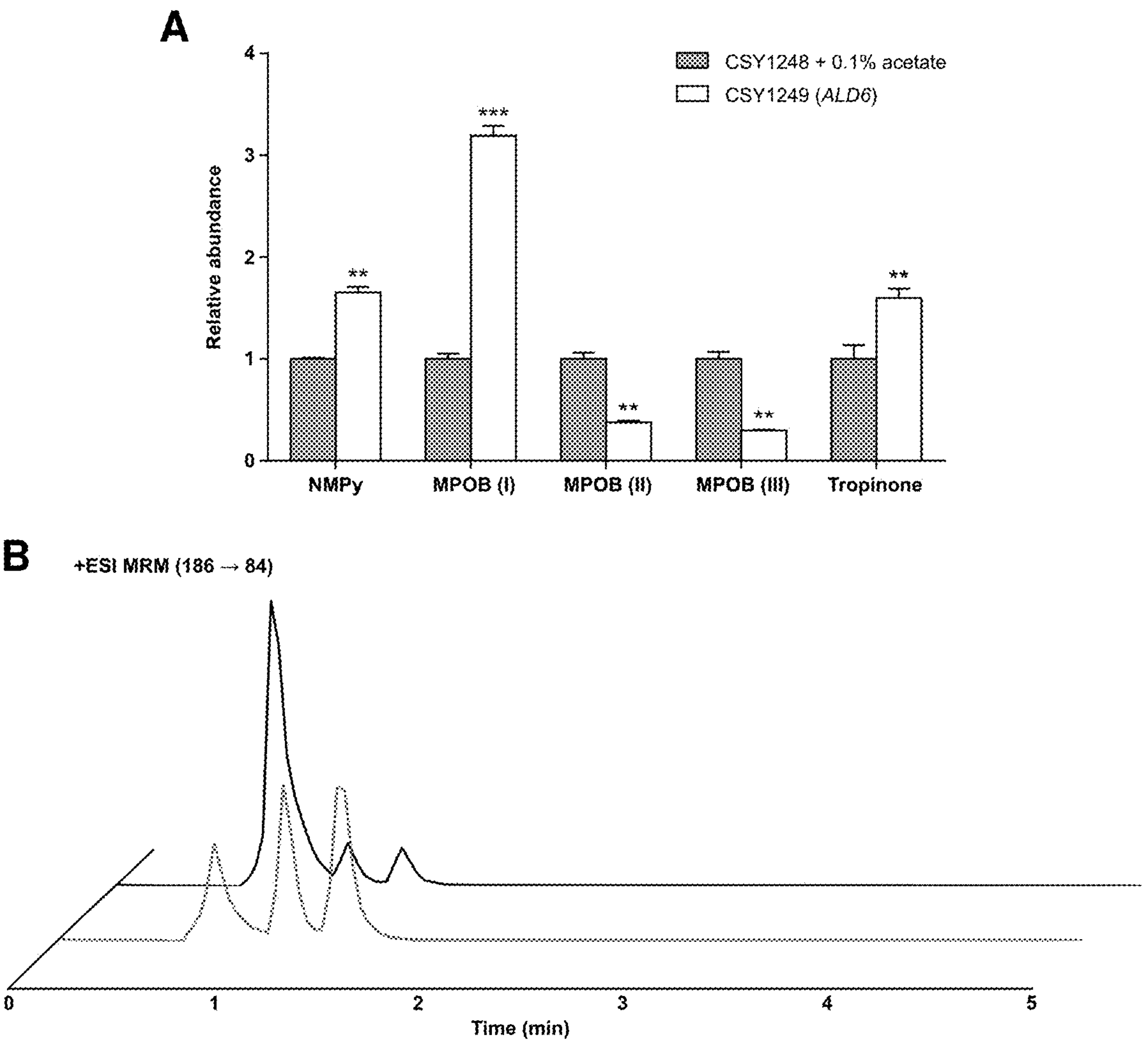
FIG. 27 illustrates (A) the effect of acetate auxotrophy on the accumulation of the TA precursors between NMPy and tropinone in liquid cultures of yeast strains engineered to produce tropine, and (B) representative LC-MS/MS chromatograms of the TA precursor MPOB produced in liquid cultures of yeast strains engineered to produce tropine with and without acetate auxotrophy, in accordance with embodiments of the invention. This figure shows the effect of reconstituting ALD6 activity on metabolite flux through NMPy towards tropine in engineered yeast. (A) Production of intermediates between NMPy and tropinone in engineered strains with and without functional Ald6p. Intermediate abundances were measured by LC-MS/MS MRM in the extracellular media of the integrated tropine-producing strain (CSY1248) grown in non-selective media supplemented with 0.1% w/v potassium acetate (grey) or the tropine-producing strain with reconstituted ALD6 (CSY1249) grown in non-selective media without acetate supplementation (pink) at 25° C. for 48 h. Data represent mean of three biological replicates; error bars indicate standard deviation. Student's two-tailed t-test: * $P<0.05$,  $P<0.01$, * $P<0.001$. (B) Representative MRM chromatograms for MPOB production from CSY1248 (grey) and CSY1249 (red) cultured as described in (a).

3.3.4) A functional copy of the ALD6 gene was reintegrated into the tropine-producing strain of Example 3.2.2 at the previously disrupted ald6 locus. The impact of this integration on the accumulation of all metabolites between NMPy and tropine was measured via LC-MS/MS analysis after 48 hours of growth in non-selective media. Restoration of acetate metabolism via Ald6p resulted in a 2.7-fold increase in tropine titers, as well as a 1.6-fold increase in hygrine accumulation (FIG. 28). Moreover, ALD6 integration resulted in substantial increases in the production of NMPy and tropinone as well as increased consumption of MPOB (FIG. 27).

Figure 29:
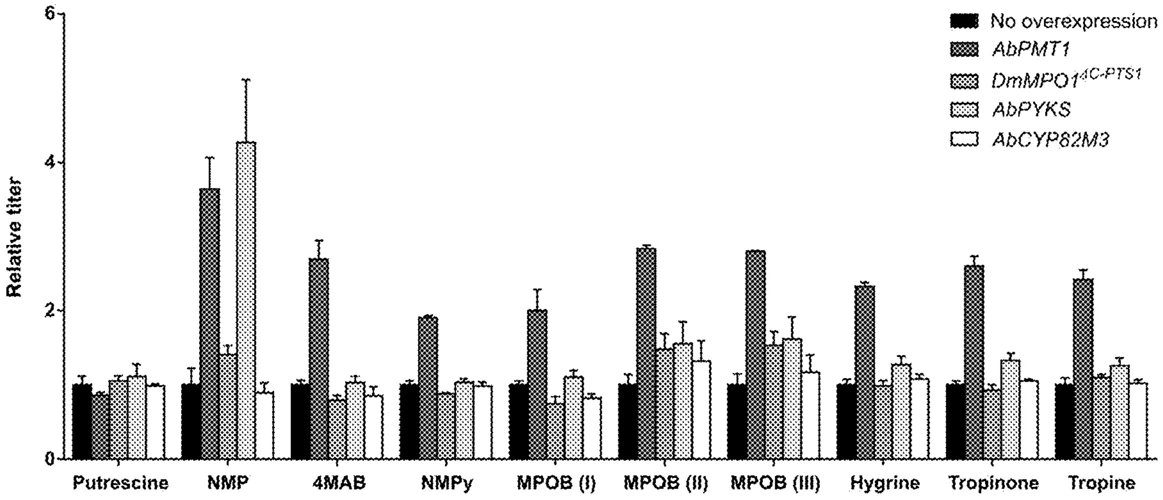
FIG. 29 illustrates the effect of expressing additional copies of the heterologous biosynthetic enzymes PMT, MPO, PYKS, and CYP82M3 on the production of each TA precursor between putrescine and tropine in liquid cultures of engineered yeast, in accordance with embodiments of the invention. This figure identifies of metabolic bottlenecks in optimized tropine-producing strain (CSY1249). Strain CSY1249 was transformed with a control plasmid expressing BFP ("no overexpression") or a low-copy plasmid expressing an additional copy of AbPMT1, DmMPO1$^{\Delta C\text{-}PTS1}$, AbPYKS, or AbCYP82M3. Intermediate levels in the extracellular medium were quantified by LC-MS/MS following growth at 25° C. in selective media for 48 h. Data indicate mean of three biological replicates and error bars show standard deviation.
Figure 30:
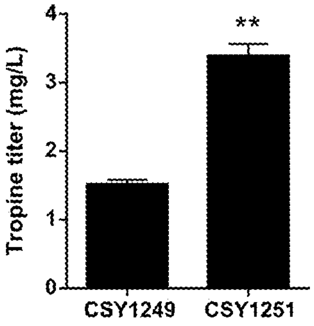
FIG. 30 illustrates the impact of additional copies of bottleneck enzymes PMT and PYKS on tropine production in engineered yeast. This figure shows alleviation of metabolic bottlenecks through genomic integration of additional copies of PMT and PYKS enzymes. Tropine-producing strains CSY1249 and CSY1251 were cultured in non-selective media at 25° C. for 48 h before LC-MS/MS analysis of growth medium. Data represent mean of three biological replicates and error bars show standard deviation. Student's two-tailed t-test: * $P<0.05$,  $P<0.01$, * $P<0.001$.

3.3.5) An additional copy of each biosynthetic enzyme gene between putrescine and tropine (i.e., AbPMT1, DmMPO1$^{\Delta C\text{-}PTS1}$, AbPYKS, and AbCYP82M3) was expressed from a low-copy plasmid in the engineered strain of Example 3.3.4 and production of TA intermediates was compared to that of the same strain expressing BFP by LC-MS/MS after 48 hours of growth in selective media. Expression of an additional copy of AbPYKS resulted in a 4.3-fold increase in NMP accumulation and a 1.3-fold increase in tropine production (FIG. 29). Expression of an additional copy of AbPMT1 resulted in significant improvements in the production of all TA precursors between NMP and tropinone, as well as a 2.4-fold increase in tropine production (FIG. 29). Accordingly, additional copies of PMT (AbPMT1 and DsPMT1) and PYKS (AbPYKS) were integrated into the genome of the tropine-producing strain of Example 3.3.4 (CSY1249) at the PAD1 locus. The resulting engineered strain (CSY1251) was grown at 25° C. in non-selective media for 48 hours, resulting in tropine production at titers of 3.4 mg/L, 2.2-fold greater than the tropine-producing strain (CSY1249) in Example 3.3.4 (FIG. 30).

Example 4: Yeast Engineered for the Production of Pseudotropine Alkaloids from L-Arginine Yeast strains can be engineered for the production of non-medicinal TAs from early amino acid precursors such as L-arginine. As an example, the platform yeast strains described in Example 3 can be further engineered to produce pseudotropine alkaloids from L-arginine (FIG. 1).

The platform yeast strain producing tropinone from L-arginine (see descriptions in Example 3) can be further engineered to incorporate a stereospecific reductase, for example tropinone reductase 2 (TR2; EC 1.1.1.236), to convert the biosynthesized tropinone to pseudotropine. An expression cassette harboring a strong constitutive promoter such as TDH3 and a coding sequence for a TR2 variant, for example TR2 from *Datura stramonium* (DsTR2), can be integrated into the genome of the tropinone-producing platform yeast strain. The resulting strain can be further engineered to produce hydroxylated derivatives of pseudotropine, for example calystegines, by integrating one or more expression cassettes harboring a strong constitutive promoter such as PGK1 and a hydroxylating enzyme such as a cytochrome P450 that acts on the pseudotropine scaffold. By incorporating multiple P450 enzymes, each acting on a different position of the pseudotropine skeleton, a variety of calystegines and derivatives thereof can be biosynthesized. The engineered strains can then be cultured in nonselective synthetic complete media at 30° C. or 25° C. for 48 to 96 hours, after which the accumulation of pseudotropine alkaloids in the culture media can be analyzed by LC-MS/MS.

Example 5: Yeast Engineered for Overproduction of Phenylpyruvate and Associated TA Precursors Yeast strains can be engineered for the overproduction of phenylpyruvate, which represents the precursor of acyl donor molecules required for production of medicinal TAs (FIG. 2), for the purpose of increasing carbon and nitrogen flux from central metabolism towards desired TAs and TA precursors. Yeast strains can be engineered for overproduction of phenylpyruvate by incorporating genetic modifications, including but not limited to the tuning of transcriptional regulation of native biosynthetic enzymes, deletion or disruption of genes encoding enzymes that divert precursor molecules away from the intended pathway, and introduction of heterologous enzymes for the conversion of endogenous molecules into TA precursor molecules.

In one example, a yeast strain can be engineered for increased phenylpyruvate production by incorporating additional copies of native genes which encode biosynthetic enzymes that produce phenylpyruvate from amino acids or other central metabolites. These additional copies can be controlled by strong constitutive promoters, such as GPD, TEF1, or PGK1. Examples of native gene targets include, but are not limited to, the aromatic acid aminotransferases ARO8 and ARO9, and the dehydratase PHA2. In one instance, one or more additional copies of ARO8 can be incorporated into the engineered strain under the control of a strong constitutive promoter. In one instance, one or more additional copies of ARO9 can be incorporated into the engineered strain under the control of a strong constitutive promoter. In another instance, one or more additional copies of PHA2 can be incorporated into the engineered strain under the control of a strong constitutive promoter. In one embodiment of the invention, one or more additional copies of one or more genes selected from the group including ARO8, ARO9, and PHA2 can be incorporated into the engineered strain under the control of unique, strong constitutive promoters.

Example 6: Yeast Engineered for the Production of Acyl Donors from L-Phenylalanine or L-Tyrosine for Biosynthesis of TA Scaffolds Yeast strains can be engineered for the production of diverse phenylpropanoid acyl donor compounds from L-phenylalanine and L-tyrosine, including PLA, cinnamic acid, coumaric acid, ferulic acid, benzoic acid, and coenzyme A thioester and glycoside derivatives of these compounds, which can undergo esterification with tropine, pseudotropine, or derivatives thereof to biosynthesize medicinal TAs, non-medicinal TAs, and non-natural TAs (FIG. 1-3).

Figure 31:
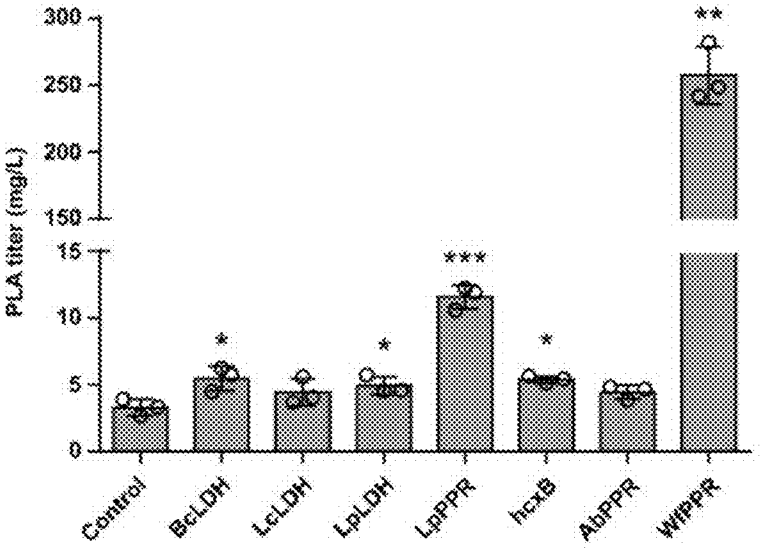
FIG. 31 illustrates the production of the TA precursor acyl donor compound PLA in liquid cultures of engineered yeast strains expressing heterologous lactate dehydrogenase and phenylpyruvate reductase enzymes. This figure shows LC-MS/MS analysis of yeast strains engineered to convert L-phenylalanine to 3-phenyllactic acid. Yeast strains are engineered to have a low-copy CEN/ARS plasmid harboring a LEU2 selection marker, a TDH3 promoter, and a coding sequence for BFP as a negative control; an LDH variant from *B. coagulans* (BcLLDH), *L. casei* (LcLLDH), *L. plantarum* (LpLLDH); or a PPR variant from *A. belladonna* (AbPPR), *L. plantarum* (LpPPR), *Escherichia coli* (hcxB) or *W. fluorescens* (WfPPR). Yeast were grown from freshly transformed colonies in 300 μL selective media (-Leu) in 96-well deep-well microtiter plates. After 72 hours of growth in a shaking incubator at 25° C. and 460 rpm, the yeast were pelleted and the media supernatant was analyzed by LC-MS/MS. Data show relative 3-phenyllactic acid titers normalized to trace levels present in negative control based on extracted ion chromatograms (ammonium adduct, EIC $m/z^{+}=184$). Data represent the mean of three biological replicates and error bars show standard deviation. Student's two-tailed t-test: * $P<0.05$,  $P<0.01$, * $P<0.001$.

6.1) As wild-type yeast produce only trace levels of PLA, production of this TA precursor must be increased to permit sufficient accumulation of downstream TAs. To improve PLA production, heterologous phenylpyruvate reductases (PPRs) may be expressed in the engineered host cells. PPR orthologs from *E. coli, Lactobacillus, A. belladonna*, and *Wickerhamia fluorescens*, as well as lactate dehydrogenases (LDHs) from *Bacillus* and *Lactobacillus* with reported activity on 3-phenylpyruvate (Table 1) were screened for activity in yeast by expressing each enzyme from a low-copy plasmid in CSY1251 and measuring PLA production by LC-MS/MS after 72 h of growth in selective media. All LDH candidates as well as the PPRs from *L. plantarum, E. coli*, and *A. belladonna* yielded modest (1.3- to 3.5-fold) improvements in PLA production relative to control, whereas expression of the PPR from *W. fluorescens* resulted in a nearly 80-fold increase in PLA production to ~250 mg/L (FIG. 31). As such, WfPPR was selected for integration into CSY1251 to make strain CSY1287.

Figure 32:
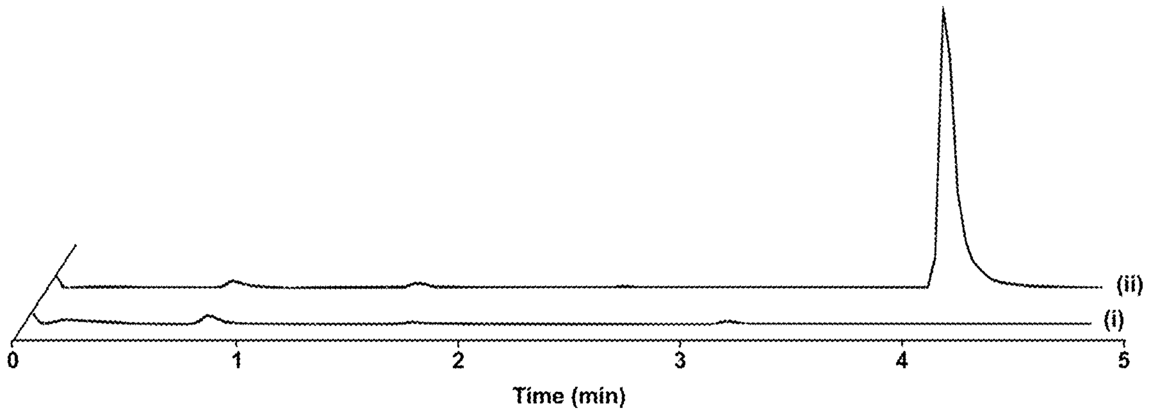
FIG. 32 shows LC-MS/MS chromatograms illustrating the production of the TA precursor acyl donor compound cinnamic acid in liquid cultures of engineered yeast strains expressing phenylalanine ammonia-lyase. This figure shows LC-MS/MS analysis of yeast strains engineered to convert L-phenylalanine to cinnamic acid. Yeast strains are engineered to have low-copy CEN/ARS plasmid harboring a TRP1 selective marker, a TEF1 promoter, and a coding sequence for (i) BFP or (ii) *A. thaliana* phenylalanine ammonia-lyase (AtPAL1). Yeast were grown from freshly transformed colonies in 300 μL selective media (-Trp) in 96-well deep-well microtiter plates. After 48 hours of growth in a shaking incubator at 30° C. and 460 rpm, the yeast were pelleted and the media supernatant was analyzed by LC-MS/MS. Chromatogram traces show cinnamic acid produced by these strains based on the most abundant multiple reaction monitoring (MRM) transition for cinnamic acid ($m/z+$ 149→131). Each trace is representative of three samples.

6.2) As another example, yeast strains can be engineered for the production of cinnamic acid and coumaric acid, which are phenylpropanoids that can be used as acyl donor compounds for esterification with tropine or pseudotropine to form non-natural TAs, from L-phenylalanine and L-tyrosine, respectively. Yeast can be engineered for production of cinnamic acid from L-phenylalanine by incorporating an ammonia-lyase such as a phenylalanine ammonia-lyase (PAL; EC 4.3.1.24). Similarly, yeast can be engineered for production of coumaric acid from L-tyrosine by incorporating an ammonia-lyase such as a tyrosine ammonia-lyase (TAL; EC 4.3.1.23). A yeast strain was engineered to produce cinnamic acid from L-phenylalanine by transforming it with a low-copy CEN/ARS plasmid with a TRP1 selective marker, TEF1 promoter, and a coding sequence for a PAL variant from *Arabidopsis thaliana* (AtPAL1). The resulting strain harboring the low-copy plasmid was grown in synthetic complete media with the appropriate amino acid drop-out solution (-Ura) at 30° C. After 48 hours of growth, the media was analyzed for cinnamic acid content by LC-MS/MS analysis (FIG. 32).

6.3) In *A. belladonna*, PLA is activated for acyl transfer to tropine via glucosylation by UDP-glucosyltransferase 84A27 (AbUGT) (see Qiu, F. et al., Functional genomics analysis reveals two novel genes required for littorine biosynthesis. New Phytol., nph. 16317 (2019)). As plant UGTs participate in the biosynthesis of diverse phenylpropanoids and often exhibit broad substrate scope (see Ross, J., Li, Y., Lim, E.-K., D. J. Bowles, Higher plant glycosyltransferases. Genome Biol. 2, 3004.1-3004.6 (2001)), it is necessary to select a UGT with sufficiently high activity on a desired acyl donor.

6.3.1) As an example, the activity of AbUGT on different phenylpropanoid acyl donors, including the canonical substrate, PLA, was evaluated by expressing AbUGT from a low-copy plasmid in CSY1251 and measuring conversion of three phenylpropanoid acyl donors (PLA, cinnamic acid, ferulic acid) to their respective glucosides. While AbUGT glucosylated ~60% and 90% of cinnamic acid and ferulic acid, respectively, glucosylation of PLA was the lowest of the tested substrates at <3% conversion (FIG. 33).

6.3.2) Orthologs of AbUGT from other TA-producing Solanaceae may be evaluated for activity on PLA and other phenylpropanoids. In this example, transcripts encoding UGT84A27 from the transcriptomes of *Brugmansia sanguinea* (BsUGT) and *D. metel* (DmUGT) in the 1000 Plants Database using a tBLASTn search. Yeast codon-optimized sequences encoding these orthologous UGTs were screened for activity by expressing AbUGT, BsUGT, DmUGT, or a BFP negative control from low-copy plasmids in CSY1251. Glucoside production was measured in cultures of the transformed strains via LC-MS/MS after 72 h of growth in selective media supplemented with 500 μM PLA, cinnamic acid (CA), or ferulic acid (FA) as glucose acceptors. All three UGT orthologs exhibited substantial glucosylation of CA (34-65% conversion) and FA (85-90% conversion) and only trace activity on PLA (<3% conversion), with AbUGT showing the greatest conversion of PLA (2.7%) (FIG. 33, 34).

6.3.3) Given the disproportionate variation in activity of AbUGT on the structurally similar substrates cinnamate, ferulate, and PLA, a structure-guided rational mutagenesis approach may be implemented to engineer the active site of AbUGT for improved activity on PLA. In this example, a homology model of AbUGT bound to UDP-glucose was first constructed based on the crystal structure of *Arabidopsis thaliana* salicylate UDP-glucosyltransferase UGT74F2 (PDB: 5V2K) using the RaptorX web server (FIG. 35). Next, the docking of D-PLA in the active site was simulated using the Maestro/GlideXP software suite. Based on the energy-minimizing binding mode, the aryl ring of D-PLA is likely stabilized by pi-stacking interactions with F130, while its α-hydroxyl and carboxylate groups are respectively stabilized by hydrogen bonds with Q151 and H24, such that the nucleophilic carboxylate oxygen is within 4 Å of the electrophilic C1 carbon of UDP-glucose (FIG. 35). D-PLA is additionally adjacent to the residues L205 and 1292, neither of which appear to interact with either substrate. This suggests that mutation of (i) F130 to tyrosine might preserve pi-stacking with the aryl ring of D-PLA while providing an additional hydrogen bond to stabilize the α-hydroxyl oxygen of D-PLA, which is absent from cinnamate and ferulate; (ii) L205 to phenylalanine might increase pi-stacking stabilization of D-PLA with F130Y; and (iii) 1292 to glutamine would generate two additional stabilizing hydrogen bonds with D-PLA and UDP-glucose (FIG. 35). The F130Y, L205F, and 12920 point mutants of AbUGT were screened for activity by expressing each mutant, wild-type AbUGT, or a BFP control from a low-copy plasmid in CSY1251 and measured glucoside production by LC-MS/MS after 72 h of growth in selective media supplemented with 500 μm PLA, CA, or FA. All three mutants exhibited comparably low (and statistically indistinguishable) activity on PLA relative to wild-type AbUGT (<3% conversion), although the F130Y and 12920 mutations significantly decreased UGT activity on CA (FIG. 36).

6.3.4) Based on the results described in sections 6.1 and 6.3, strain CSY1288 was constructed by integrating yeast codon-optimized WfPPR and AbUGT into the genome of CSY1251, validated by verification of PLA production (66 mg/L) and minimal PLA glucoside accumulation (FIG. 37).

6.4) As poor activity of AbUGT on PLA is likely to limit flux of TA precursors towards downstream TAs, flux of phenylalanine to PLA glucoside may be increased by incorporating genetic modifications which promote UDP-glucose accumulation and decrease glycoside degradation.

6.4.1) UDP-glucose is critical for the formation of storage polysaccharides, cell wall glucans, and glycoproteins, and thus its biosynthesis is tightly regulated (see Nishizawa, M., Tanabe, M., Yabuki, N., Kitada, K., Toh-e, A. Pho85 kinase, a yeast cyclin-dependent kinase, regulates the expression of UGP1 encoding UDP-glucose pyrophosphorylase. Yeast. 18, 239-249 (2001)). During growth on glucose, yeast direct glucose-6-phosphate along two major metabolic routes, glycolysis and starch biosynthesis. As citrate is an allosteric inhibitor of the glycolytic rate-limiting enzyme phosphofructokinase (see Li, Y. et al., Production of Rebaudioside A from Stevioside Catalyzed by the Engineered *Saccharomyces cerevisiae*. Appl. Biochem. Biotechnol. 178, 1586-1598 (2016)), partial suppression of glycolysis via citrate supplementation might increase UDP-glucose availability and glucoside production (FIG. 38). Strain CSY1288, which encodes genomic WfPPR and AbUGT for endogenous PLA glucoside production, was cultured in media supplemented with 2% citrate and 500 μM CA or FA, and glucoside production was compared by LC-MS/MS after 72 h of growth. Citrate supplementation decreased glucosylation of PLA, CA, and FA by 83%, 56%, and 78%, respectively (FIG. 39).

6.4.2) Overexpression of PGM2 and UGP1, whose gene products respectively catalyze the isomerization of glucose-6-phosphate to glucose-1-phosphate and conversion of glucose-1-phosphate to UDP-glucose, can be used to increase UDP-glucose supply.

6.4.2.1) Extra copies of PGM2 and UGP1 were expressed from low-copy plasmids in CSY1288 and PLA glucoside production was measured following 72 h of growth in selective media. While PGM2 overexpression yielded no improvement relative to control, overexpression of UGP1 resulted in a ~1.8-fold increase in PLA glucoside production (FIG. 40), supporting that increasing the UDP-glucose pool improves PLA utilization by AbUGT.

6.4.2.2) Native glucosidases may act on PLA and other TA precursor glucosides to reduce accumulation, as other heterologous glucosides have been shown to be hydrolyzed in this manner in yeast (see Schmidt, S., Rainieri, S., Witte, S., Matern, U., Martens, S., Identification of a *Saccharomyces cerevisiae* glucosidase that hydrolyzes flavonoid glucosides. Appl. Environ. Microbiol. 77, 1751-1757 (2011); see also Wang, H. et al., Engineering *Saccharomyces cerevisiae* with the deletion of endogenous glucosidases for the production of flavonoid glucosides. Microb. Cell Fact. 15, 1-12 (2016)). In this example, three native glucosidase genes—EXG1, SPR1, and EGH1—were disrupted in CSY1288 and PLA glucoside production was measured following 72 h of growth of disruption mutants in non-selective media. The disruption of EGH1 more than doubled PLA glucoside production (FIG. 41), indicating that hydrolysis by Egh1p constitutes a substantial loss of TA precursor flux.

Example 7: Yeast Engineered for Conversion of Littorine to Hyoscyamine Aldehyde Yeast strains can be engineered for the conversion of littorine to hyoscyamine aldehyde (FIG. 2). For example, the tropine- and PLA glucoside-producing yeast strain described in Example 6 can be further engineered to express a cytochrome P450 CYP80F1 (EC 1.14.19.-) to catalyze the rearrangement of littorine to hyoscyamine aldehyde, and a cytochrome P450 reductase (CPR; EC 1.6.2.4) to support the activity of the P450 enzyme. A yeast strain was engineered to convert fed littorine to hyoscyamine aldehyde by transforming it with a low-copy CEN/ARS plasmid with a LEU2 selection marker, TDH3 promoter, and coding sequence for a CYP80F1 variant from *A. belladonna* (AbCYP80F1); and with a low-copy CEN/ARS plasmid with a TRP1 selection marker, TEF1 promoter, and a coding sequence for a cytochrome P450 reductase (CPR) from *S. cerevisiae* (NCP1) or from *A. thaliana* (AtATR1). The resulting strain harboring the low-copy plasmids was grown in synthetic complete media with the appropriate amino acid dropout solution (-Leu-Trp) supplemented with 1 mM littorine at 30° C. After 48 hours of growth, the media was analyzed for hyoscyamine aldehyde content by LC-MS/MS analysis (FIG. 42).

Example 8: Yeast Engineered for Conversion of Hyoscyamine to Scopolamine

Yeast strains can be engineered for conversion of hyoscyamine to scopolamine (FIG. 2). For example, the yeast strain described in Example 7 can be further engineered to incorporate enzymes which possess hydroxylase activity at the 6β position of hyoscyamine to form anisodamine and enzymes which possess dioxygenase activity at the 6β-hydroxyl position of anisodamine to form scopolamine, or enzymes which possess both of these activities (EC 1.14.11.11). Yeast strains were engineered to convert fed hyoscyamine to scopolamine by transforming them with a low-copy CEN/ARS plasmid with a LEU2 selection marker, TDH3 promoter, and coding sequence for a hyoscyamine 6β-hydroxylase/dioxygenase (H6H) from *D. stramonium* (DsH6H), *Anisodus acutangulus* (AaH6H), *Brugmansia arborea* (BaH6H), or *Datura metel* (DmH6H). The resulting strains harboring the low-copy plasmids were grown in synthetic complete media with the appropriate amino acid dropout solution (-Leu) and supplemented with 1 mM hyoscyamine at 30° C. After 72 hours of growth, the media was analyzed for scopolamine content by LC-MS/MS analysis (FIG. 43). The strain expressing the H6H variant from *D. stramonium* exhibited the greatest conversion of fed hyoscyamine to scopolamine, although all tested variants showed H6H activity in vivo. Further optimization of cofactor requirements was performed by supplementing different cofactors in the culture media of this engineered yeast strain and analyzing the media by LC-MS/MS after 72 hours of growth. This analysis identified that ferrous iron supplementation increases conversion of hyoscyamine to scopolamine (FIG. 44).

Example 9. Identification of Hyoscyamine Dehydrogenase Enzyme Candidates and Reduction of Hyoscyamine Aldehyde to Hyoscyamine in Engineered Non-Plant Cells To identify a dehydrogenase enzyme suitable for performing the TA alcohol-aldehyde interconversions of the methods disclosed herein, and in particular to reduce hyoscyamine aldehyde to hyoscyamine, a hyoscyamine dehydrogenase (HDH) open reading frame was identified from publically available plant RNA sequencing data.

9.1) Tissue-specific abundances (fragments per kilobase of contig per million mapped reads, FPKM) and putative protein structural and functional annotations for each of 43,861 unique transcripts identified from the *A. belladonna* transcriptome were obtained from the Michigan State University Medicinal Plant Genomics Resource. Transcripts encoding hyoscyamine dehydrogenase candidates were identified based on clustering of tissue-specific expression profiles with those of the bait genes CYP80F1 (littorine mutase) and H6H (hyoscyamine 6β-hydroxylase/dioxygenase), which respectively precede and follow the dehydrogenase step in the TA biosynthetic pathway, using the following computational filtering algorithm.

First, the complete list of 43,861 transcripts was filtered for those annotated with any of the following protein family (PFAM) IDs: PF00106, PF13561, PF08659, PF08240, PF00107, PF00248, PF00465, PF13685, PF13823, PF13602, PF16884, PF00248; or any of the following functional annotation keywords: alcohol dehydrogenase, aldehyde reductase, short chain, aldo/keto. Additionally, any transcripts with functional annotations containing the keywords putrescine, tropinone, and tropine were included in the filter as positive control TA-associated genes to validate clustering with bait genes. Next, mean tissue-specific expression profiles were generated for the CYP80F1 and H6H bait genes. For each of the two bait genes, linear regression models were constructed to express the bait gene expression profile (in FPKM) as a linear function of each candidate gene profile and correlation p-values were computed for each candidate. The candidates identified using each of the two bait genes were pooled and duplicates were removed. Combined p-values for each candidate were computed as the sum of the log 10 p-values of the correlations with each of the two bait genes. Transcripts matching known dehydrogenases in the TA biosynthetic pathway (i.e., tropinone reductases I and II) were removed, and the remaining candidates were ranked by combined p-value and by distance from bait genes via hierarchical clustering of tissue-specific expression profiles (FIG. 45).

9.2) Nearly all candidates identified in Example 9.1 exhibited the same secondary root-specific expression pattern observed for known TA biosynthetic genes. A BLASTp search of the resulting ~30 candidates against the UniPROT/SwissPROT database revealed that many transcripts were missing terminal or internal sequence regions. To address this, de novo transcriptome assembly was repeated from deposited raw RNAseq reads using the Trinity software package (see Haas, B. J. et al., De novo transcript sequence reconstruction from RNA-seq using the Trinity platform for reference generation and analysis. Nat. Protoc. 8, 1494-512 (2013)), and all missing sequence fragments for twelve of the HDH candidates were reconstituted by performing BLAST alignments of incomplete sequence regions against the newly assembled transcriptome (Table 2).

9.3) The missing HDH activity was identified by screening the candidates generated in Examples 9.1 and 9.2 in yeast.

9.3.1) Lack of an authentic commercial standard for hyoscyamine aldehyde and insufficient yield from chemical syntheses necessitated co-expression of HDH candidates with the upstream biosynthetic enzyme—the cytochrome P450 littorine mutase (CYP80F1)—for activity screening in vivo via fed littorine (see Example 7). As littorine exhibits similar chromatographic and mass spectrometric properties as the HDH product hyoscyamine, an HDH screening strain (CSY1292) was constructed by integrating yeast codon-optimized AbCYP80F1 and DsH6H (see Example 8) into the genome of CSY1251, enabling screening of HDH candidates via detection of scopolamine ($m/z^+$ 304) produced from fed littorine ($m/z^+$ 290) via a three-step biosynthetic pathway (FIG. 2).

9.3.2) Yeast codon-optimized sequences encoding each of the twelve HDH candidates were expressed from a low-copy plasmid in strain CSY1292, and scopolamine production was measured following 72 h of growth in media supplemented with 1 mM littorine. One of the twelve candidates, HDH2 (referred to as AbHDH), exhibited a 35% decrease in hyoscyamine aldehyde levels and measurable accumulation of scopolamine (7.2 μg/L), indicating that it encoded the missing HDH activity (FIG. 46).

9.4) Structural and phylogenetic analyses provided further insight into the catalytic mechanism and evolutionary history of HDH.

9.4.1) A homology model of AbHDH was constructed based on the crystal structure of *Populus tremuloides* sinapyl alcohol dehydrogenase (PtSAD; PDB: 1YQD) (FIG. 47). AbHDH is a member of the zinc-dependent alcohol dehydrogenase (ZADH) family within the medium-chain dehydrogenase/reductase (MDR) superfamily. Typical of this family, AbHDH exhibits a bilobular structure with a well-conserved nucleotide-binding domain and a more variable substrate-binding domain. Alignment of residues S216, T217, S218, and K221 within the AbHDH nucleotide-binding domain with the phosphate-stabilizing residues S214, T215, S216, and K219 in PtSAD suggests that AbHDH is an NADPH-dependent oxidoreductase. Also typical of ZADHs, AbHDH appears to bind a structural $Zn^{2+}$ using a tetrad of cysteine residues near the protein surface (C105, C108, C111, and C119) and a catalytic $Zn^{2+}$ within the active site.

9.4.2) The catalytic mechanism of AbHDH was elucidated via molecular docking of the substrate, hyoscyamine aldehyde, into the active site using the Maestro/Glide software package (FIG. 47). The most favorable binding mode positions the aldehyde group of the substrate within ~5 Å of both the catalytic $Zn^{2+}$ and NADPH hydride donor. The docking result and the general mechanism of ZADHs (see Bomati, E. K., Noel, J. P., Structural and kinetic basis for substrate selectivity in *Populus tremuloides* sinapyl alcohol dehydrogenase. Plant Cell. 17, 1598-1611 (2005)) suggests the following catalytic mechanism for AbHDH. In the absence of substrate, the catalytic $Zn^{2+}$ within the active site is stabilized by C52, H74, C168, and a water molecule, which is positioned via polar interaction with S54 and displaced upon binding of hyoscyamine aldehyde. Nucleophilic attack of the aldehyde carbonyl by a dihydronicotinamide hydride forms an oxyanion intermediate stabilized by interaction with the catalytic $Zn^{2+}$, and which is likely protonated via a proton shuttle between the ribose group of $NADP^+$ and S54.

9.5) To confirm whether orthologous oxidoreductases catalyze hyoscyamine biosynthesis in other TA-producing Solanaceae, variants of the AbHDH coding sequence were identified from transcriptomes of *Datura innoxia* and *Datura stramonium* using a tBLASTx search (FIG. 48). HDH activity of the two identified orthologs (DiHDH, DsHDH) was validated by co-expressing yeast codon-optimized sequences with an additional copy of the flux-limiting DsH6H from low-copy plasmids in CSY1292 and measuring scopolamine production in media supplemented with 1 mM littorine. DsHDH showed the highest substrate depletion and product accumulation of the variants tested (FIG. 49).

9.6) The medicinal TA biosynthetic branch comprising optimal enzyme variants and overexpression of a flux-limiting enzyme was integrated into a platform yeast strain. Strain CSY1294 was constructed by integrating yeast codon-optimized WfPPR and AbUGT, DsHDH, and a second copy of DsH6H into CSY1292. Scopolamine production from fed littorine was verified in CSY1294 (FIG. 50).

Example 10: Yeast Engineered for the Esterification of Acyl Donors and Acceptors for Production of TA Scaffolds Yeast strains can be engineered to express enzymes which catalyze the esterification of activated acyl donor compounds and acyl acceptor compounds to produce diverse TA scaffolds (FIG. 2, 3). Activation of the acyl donor group can be achieved by engineering an acyl donor-producing yeast strain to incorporate an enzyme which appends a chemical moiety with high group-transfer potential, such as coenzyme A (CoA) or glucose (glucoside), to the carboxyl group of the acyl donor, as described in Example 6. Examples of acyl donor-activating enzymes which can be utilized in this capacity include CoA ligases and UDP-glycosyltransferases. Examples of esterifying enzymes which can be used to catalyze the esterification of activated acyl donor compounds and acyl acceptors such as tropine and pseudotropine are acyltransferases, including serine carboxypeptidase-like acyltransferases (SCPL-ATs) and BAHD-type acyltransferases. The coding sequence of such acyltransferases may be modified to improve their activity when expressed in a heterologous host such as yeast.

10.1) In plants, where SCPL-ATs are typically found to occur naturally, the coding sequence of SCPL-ATs include N-terminal signal peptides which direct the nascent polypeptide to the endoplasmic reticulum (ER). Once localized to the ER, the SCPL-AT polypeptide is transported by way of the secretory trafficking pathway through the Golgi to the vacuole lumen, where they are found to exhibit activity. During this ER-to-vacuole trafficking process, they undergo several post-translational modifications (FIG. 51), including but not limited to signal peptide cleavage, N-glycosylation, removal of internal propeptide sequences, and disulfide bond formation (see Stehle, F., Stubbs, M. T., Strack, D., & Milkowski, C. Heterologous expression of a serine carboxypeptidase-like acyltransferase and characterization of the kinetic mechanism, FEBS Journal, 275, (2008)). However, as intracellular trafficking pathways and patterns of post-translational modifications differ between organisms, expression of SCPL-ATs in heterologous hosts may result in incorrect sub-cellular localization and/or incorrect post-translational modification for activity. As an example, the coding sequence of a SCPL-AT such as littorine synthase (LS) (Table 1) may be modified to improve activity when expressed in yeast.

10.1.1) Signal peptide sequences can impact the processing and localization of SCPL-ATs in yeast.

10.1.1.1) The presence of a putative N-terminal signal peptide in AbLS suggests that it follows the expected SCPL ER-to-vacuole trafficking pathway in planta. AbLS localization in yeast was examined by expressing N- and C-terminal GFP fusions of AbLS from low-copy plasmids in CSY1294. Fluorescence microscopy revealed that the N-terminal fusion (GFP-AbLS) co-localized with the vacuolar membrane stain FM4-64 (FIG. 52). No fluorescence was detected for the C-terminal fusion (AbLS-GFP), consistent with reports that a native C-terminus is crucial for stability of SCPL acyltransferases (see Stehle, F., Stubbs, M. T., Strack, D., & Milkowski, C. Heterologous expression of a serine carboxypeptidase-like acyltransferase and characterization of the kinetic mechanism, FEBS Journal, 275, (2008)).

10.1.1.2) Vacuolar sequestration of SCPL-ATs in yeast might preclude access to cytosolic substrate pools, as yeast likely lack the requisite tonoplastic transporters present in plants for exchange of secondary metabolites with the cytosol. To determine whether forced localization of AbLS to other yeast compartments—presumably, with improved access to cytosolic metabolites—would enable activity, the wild-type N-terminal SP sequence was replaced with a panel of N-terminal signal sequences taken from yeast proteins targeted to the vacuole lumen (Prc1p and Pep4p), vacuole membrane facing the lumen (Dap2p), trans-Golgi network (Ochi p), ER membrane facing the lumen (Mns1p), and mitochondrial matrix (Citi p) (FIG. 53). The wild-type SP was also removed entirely, and for another variant a canonical peroxisome-targeting sequence (PTS1) was appended to the C-terminus. These chimeric AbLS variants were expressed from high-copy plasmids in CSY1294 and transformants were screened for activity by LC-MS/MS after 96 h of growth in selective media. No production of littorine or downstream intermediates was observed with any of the variants (FIG. 53).

10.1.2) Incorrect post-translational processing of SCPL-ATs in yeast might prevent expression of active enzyme.

10.1.2.1) Protein N-glycosylation patterns differ between yeast and plants, and previous reports have suggested that correct N-glycosylation of diverse plant enzymes is important for their folding, stability, and/or activity (see Kar, B., Verma, P., den Haan, R., Sharma, A. K., Effect of N-linked glycosylation on the activity and stability of a β-glucosidase from *Putranjiva roxburghii*. Int. J. Biol. Macromol. 112, 490-498 (2018); see also Podzimek, T. et al., N-glycosylation of tomato nuclease TBN1 produced in *N. benthamiana* and its effect on the enzyme activity. Plant Sci. 276, 152-161 (2018); see also Strasser, R., Plant protein glycosylation. Glycobiology. 26, 926-939 (2016)). In silico analysis of the AbLS polypeptide predicted four N-glycosylation sites (N152, N320, N376, N416) and no O-glycosylation of this protein was detected in *N. benthamiana* (FIG. 54). C-terminally HA-tagged wild-type AbLS, each of the four N→Q mutants (where mutation of N to Q abolishes N-glycosylation (23)), or a quadruple N→Q mutant were expressed in CSY1294 and in *N. benthamiana*, and glycosylation profiles were compared by Western blot. Whereas wild-type AbLS, N→Q single mutants, and the quadruple mutant all appeared as single bands in *N. benthamiana*, indicating a single glycosylation state, only the quadruple N→Q mutant produced a single band in yeast; all other variants appeared as either double or triple bands, indicating a combination of multiple glycosylation states (FIG. 55). However, as the denser of the two wild-type AbLS bands in yeast showed partial overlap with that of wild-type AbLS in tobacco, at least some fraction of yeast-expressed AbLS must be in a correct glycosylation state, and mis-glycosylation is unlikely to account for the complete lack of AbLS activity in yeast. (FIG. 54-55).

10.1.2.2) A subset of SCPL acyltransferases, including sinapoylglucose:choline sinapoyltransferase from *Arabidopsis thaliana* (AtSCT) and an avenacin synthase from *Avena strigosa* (AsSCPL1), have been shown to contain an internal propeptide linker which is proteolytically removed to produce an active heterodimer joined by disulfide bonds (see Shirley, A. M., Chapple, C., Biochemical characterization of sinapoylglucose: choline sinapoyltransferase, a serine carboxypeptidase-like protein that functions as an acyltransferase in plant secondary metabolism. J. Biol. Chem. 278, 19870-19877 (2003); see also Mugford, S. T. et al., A serine carboxypeptidase-like acyltransferase is required for synthesis of antimicrobial compounds and disease resistance in oats. Plant Cell. 21, 2473-2484 (2009)). Comparison of the AbLS amino acid sequence with those of previously characterized plant serine carboxypeptidases and SCPL acyltransferases revealed the presence of an internal 25- to 30-residue sequence which aligns with the highly variable propeptide of AtSCT, AsSCPL1, and wheat carboxypeptidase 2 (TaCBP2), suggesting that AbLS too undergoes endoproteolytic cleavage to form a heterodimer (FIG. 56). Additionally, a homology model of AbLS suggested that the predicted internal propeptide blocks the active site, thereby necessitating removal for activity (FIG. 57). However, wild-type AbLS expressed in *N. benthamiana* does not appear to undergo proteolytic cleavage, as no expected ~20-25 kDa C-terminal fragment was detected by Western blot under disulfide-reducing conditions (FIG. 54, 55). As the putative propeptide does not appear to be cleaved or removed in planta, AbLS might adopt a native conformation in plants which shifts the propeptide away from the active site, but differences in the biochemical environment of the yeast secretory pathway and/or vacuole prevents this shift, blocking activity.

To address this failure mode, split AbLS controls were constructed in which the N- and C-terminal domains flanking the putative propeptide linker were expressed independently, with or without separate signal peptides. Additionally, AbLS variants in which the putative propeptide was replaced with either a flexible $(GGGGS)_n$ (SEQ ID NO: 26) linker, the internal propeptide from AtSCT previously demonstrated to be cleaved in yeast (see Shirley, A. M., Chapple, C., Biochemical characterization of sinapoylglucose:choline sinapoyltransferase, a serine carboxypeptidase-like protein that functions as an acyltransferase in plant secondary metabolism. J. Biol. Chem. 278, 19870-19877 (2003)), or a synthetic linker containing a poly-arginine site cleaved by the trans-Golgi protease Kex2p (see Chen, X., Zaro, J. L., Shen, W. C., Fusion protein linkers: Property, design and functionality. Adv. Drug Deliv. Rev. 65, 1357-1369 (2013); see also Redding, K., Seeger, M., Payne, G. S., Fuller, R. S., The effects of clathrin inactivation on localization of Kex2 protease are independent of the TGN localization signal in the cytosolic tail of Kex2p. Mol. Biol. Cell. 7, 1667-1677 (1996)) were constructed (FIG. 58). Each of the split AbLS controls and propeptide/linker variants were expressed from low-copy plasmids in CSY1294 and transformants were screened for LS activity by LC-MS/MS after 96 h of growth in selective media. No production of littorine or downstream TAs was observed with any of these variants.

To troubleshoot protein expression, each of the above C-terminal HA-tagged AbLS variants was expressed from low-copy plasmids in CSY1294 and apparent protein sizes were compared to split-AbLS controls by Western blot (FIG. 58). Neither the AtSCT nor the poly-arginine linkers produced the 20-25 kDa C-terminal fragment expected from proteolytic cleavage. In the latter case, failure of the poly-arginine AbLS variant to be cleaved suggests that the protein becomes stalled in the secretion pathway upstream of the trans-Golgi network (TGN; also referred to as the late Golgi in yeast), which may account for the severe growth defect observed in CSY1294 expressing wild-type or Golgi-targeted (Ochi p SP-fused) AbLS.

10.1.3) Functional expression of SCPL-ATs in yeast can be achieved by engineering N-terminal fusions that alter sorting from the TGN. Transport of soluble yeast proteins from the TGN to the vacuole requires recognition of a typically N-terminal signal sequence by vacuole protein sorting (Vps) cargo transport proteins, whereas integral membrane proteins which reach the yeast TGN appear to be sorted to the vacuole by default (see Stack, J. H., Receptor-Mediated Protein Sorting to the Vacuole in Yeast: Roles for Protein Kinase, Lipid Kinase and GTP-Binding Proteins. Annu. Rev. Cell Dev. Biol. 11, 1-33 (1995); see also Roberts, C. J., Nothwehr, S. F., Stevens, T. H., Membrane protein sorting in the yeast secretory pathway: Evidence that the vacuole may be the default compartment. J. Cell Biol. 119, 69-83 (1992)). Conversion of SCPL-ATs into transmembrane proteins by masking the SP with an N-terminally fused soluble domain can therefore resolve the obstruction in TGN sorting.

10.1.3.1) In one example, AbLS variants were constructed with a panel of N-terminally fused soluble domains, including fluorescent proteins from the *Aequoria* (GFP, BFP, mVenus) and *Discosoma* (mCherry, DsRed) families; small ubiquitin-related modifier (Smt3p) with a mutated protease cleavage site (SUMO*); and the upstream enzyme in the TA pathway, AbUGT. These variants and wild-type AbLS were expressed from low-copy plasmids in CSY1294 and screened for littorine synthase activity following 96 h of growth in selective media. All N-terminally fused AbLS variants exhibited measurable accumulation of hyoscyamine and scopolamine. Fusion of *Aequoria* GFP-derived fluorescent proteins to AbLS resulted in hyoscyamine and scopolamine production of ~1 μg/L and ~0.1 μg/L, respectively; whereas fusion of *Discosoma*-derived fluorescent proteins led to considerably higher TA production, with the greatest titers achieved via DsRed fusion (10.3 μg/L hyoscyamine, 0.87 μg/L scopolamine) (FIG. 59). Enhancement of AbLS activity appeared to be correlated with the oligomerization state of the N-terminal domain, with scopolamine production increasing in order from monomeric (GFP, BFP, mVenus, mCherry, SUMO*) to homodimeric (AbUGT) to homotetrameric (DsRed) domains.

10.2) To generate a strain capable of complete TA biosynthesis, a yeast codon-optimized DsRed-AbLS and a second copy of UGP1 were integrated into the genome of CSY1294 at the disrupted EGH1 site to generate CSY1296. CSY1296 exhibited de novo hyoscyamine and scopolamine production at titers of 10.2 μg/L and 1.0 μg/L, respectively.

Example 11. Alleviation of Intracellular Substrate Transport Limitations Using Heterologous Transporters As the enzymes which carry out TA biosynthesis are distributed across multiple sub-cellular compartments (cytosol, ER membrane, peroxisome, vacuole, mitochondria), and yeast are unlikely to possess the transporters found in plants which enable mobilization of TA biosynthetic intermediates between different compartments, intracellular metabolite transport is likely to restrict TA production.

11.1) Inter-compartment transport limitations may be addressed by functional expression of plant transporters in non-plant host cells. Vacuolar compartmentalization of DsRed-AbLS (FIG. 60) necessitates the import of cytosolic tropine and PLA glucoside to the vacuole lumen and export of vacuolar littorine to the cytosol. Several multidrug and toxin extrusion (MATE) transporters responsible for vacuolar alkaloid and glycoside sequestration have been identified in Solanaceae, including three with observed or predicted activity on TAs (see Morita, M. et al., Vacuolar transport of nicotine is mediated by a multidrug and toxic compound extrusion (MATE) transporter in *Nicotiana tabacum*. Proc. Natl. Acad. Sci. U.S.A. 106, 2447-2452 (2009); see also Shoji, T. et al., Multidrug and toxic compound extrusion-type transporters implicated in vacuolar sequestration of nicotine in tobacco roots. Plant Physiol. 149, 708-718 (2009)). In one example, *N. tabacum* jasmonate-inducible alkaloid transporter 1 (NtJAT1) and two MATEs (NtMATE1, NtMATE2) were expressed from low-copy plasmids in CSY1296 and accumulation of TAs was measured following 96 h of growth in selective media. Expression of NtJAT1 and NtMATE2 improved TA production, with the former resulting in 74% and 18% increases in hyoscyamine and scopolamine titers, respectively (FIG. 61).

11.2) To evaluate the subcellular localization of these transporters, and determine likely mechanisms of action, fluorescence microscopy of CSY1296 expressing C-terminal GFP fusions of NtJAT1 or NtMATE2 from low-copy plasmids was performed. The analysis supports that NtJAT1 localizes almost exclusively to the vacuolar membrane (co-localizing with DsRed-AbLS), whereas NtMATE2 is partitioned between the vacuolar and plasma membranes (FIG. 60), suggesting that both transporters might function to dissipate vacuolar substrate transport limitations while the latter might also improve cellular TA export.

Example 12: Yeast Engineered for the Production of Non-Natural TAs from L-Phenylalanine or L-Tyrosine and L-Arginine In addition to being engineered for the production of medicinal and non-medicinal TAs which occur naturally in organisms, yeast can also be engineered for the production of non-natural TAs (FIG. 3). For example, yeast can be engineered to express biosynthetic pathways for the production of acyl donor compounds not naturally incorporated into TAs by plants.

12.1) In one example, the platform tropine-producing yeast strain described in Example 3 can be further engineered to produce the acyl donor compound cinnamic acid (as described in Example 6) and to express cinnamate-activating enzymes and esterifying enzymes to produce non-natural TAs such as cinnamoyltropine.

12.1.1) Cinnamate can be produced from phenylalanine via a phenylalanine ammonia-lyase, for example PAL1 from *A. thaliana* (AtPAL1). Since EcCS requires a coenzyme A (CoA)-activated acyl donor, a 4-coumarate-CoA ligase with established activity on cinnamate, such as 4CL5 from *A. thaliana* (At4CL5) (see Eudes, A. et al. Exploiting members of the BAND acyltransferase family to synthesize multiple hydroxycinnamate and benzoate conjugates in yeast. Microbial Cell Factories, 15, (2016)), can be expressed to enable cinnamoyl-CoA biosynthesis in yeast. The platform tropine-producing yeast strain described in Example 3 was transformed with a low-copy plasmid enabling production of cinnamic acid as described in Example 6.

12.1.2) The engineered strain of Example 12.1.1 was further modified to produce cinnamoyltropine by transforming it with a high-copy 2p plasmid with a URA3 selective marker, HXT7 and PMA1 promoters, and coding sequences for a 4-coumarate-CoA ligase variant from *A. thaliana* (At4CL5) and a cocaine synthase from *Erythroxylum* coca (EcCS). The resulting strain harboring the low- and high-copy plasmids was grown in synthetic complete media with the appropriate amino acid dropout solution (-Ura-Trp) at 25° C. After 72 hours of growth, the culture medium was analyzed for cinnamoyltropine by LC-MS/MS analysis (FIG. 62). Tandem MS/MS and fragmentation analysis were used to detect and verify the identity of cinnamoyltropine. Comparison of MS/MS spectra corresponding to the parent mass of cinnamoyltropine ($m/z^+=272$) revealed a novel peak at a retention time of 3.684 min, and which produced fragments whose masses appeared to match transitions for a genuine cinnamoyltropine standard (FIG. 62*a*). The most abundant mass transition, $m/z^+$ 272→124, is consistent with the primary $m/z^+$ =124 tropine fragment produced during fragmentation of hyoscyamine (see Bedewitz, M. A., et al. A Root-Expressed L-Phenylalanine:4-Hydroxyphenylpyruvate Aminotransferase Is Required for Tropane Alkaloid Biosynthesis in *Atropa belladonna*. The Plant Cell, 26, (2014)).

12.1.3) Based on the 272→124 LC-MS/MS transition for cinnamoyltropine described in Example 12.1.2, a multiple reaction monitoring (MRM) LC-MS/MS method was developed to measure de novo cinnamoyltropine production. Cinnamoyltropine accumulated to substantial levels in the extracellular medium of the engineered strain of example 12.1.2, but not in the absence of AtPAL1, At4CL5, and EcCS (FIG. 62*b*). The titer of cinnamoyltropine produced de novo was estimated to be 6.0 μg/L based on a standard curve.

Example 13: Modification of Growth Media to Improve Production of TAs and TA Precursors Production titers of TA precursors and TAs can be improved by modifying the culture media composition. For example, the media types can vary in the media base (e.g., yeast peptone, yeast nitrogen base), carbon source (e.g., glucose, maltodextrin), and nitrogen source (e.g., amino acids, ammonium sulfate, urea). Media types can also vary in the relative proportions of each component, such as the concentration of carbon source and the concentration of nitrogen source, or the concentration of each individual amino acid.

13.1) Tropine-producing yeast strains (as described in Example 3) were initially grown in defined media (i.e., YNB with ammonium sulfate and all amino acids) with varying carbon sources and tropine production assayed after 48 hours of growth at 25° C. The highest production of tropine was observed with 2% galactose (FIG. 63*a*). However, some engineered strains either failed to grow or suffered severely reduced growth with certain carbon sources, such as glycerol, arabinose, and sorbitol, likely due to an inability to assimilate these carbon sources into central metabolism.

13.2) Tropine-producing yeast strains (as described in Example 3) were cultured in defined media with 2% dextrose for growth and supplemented with 2% of an additional carbon source, and tropine production was assayed after 48 hours of growth at 25° C. The highest production of tropine was observed with 2% dextrose and 2% glycerol (FIG. 63*b*). Glycerol is a non-sugar carbon source which may contribute to higher production of TA precursors and TAs through several mechanisms, including stabilization of cellular lipid membranes, improved folding and stability of heterologous proteins, and regeneration of the NADPH cofactor required for the activity of cytochrome P450s and some short-chain dehydrogenase/reductase enzymes (see Li, Y. et al. Complete biosynthesis of noscapine and halogenated alkaloids in yeast. Proc. Natl. Acad. Sci. U.S.A. 2018, 115(17) E3922-E3931).

13.3) Improvements in de novo medicinal TA biosynthesis in engineered yeast can be achieved via alleviation of flux bottlenecks and transport limitations.

13.3.1) Improvements in TA production were achieved via overexpression of bottleneck enzymes and media optimization. As production of tropine in CSY1296 (~mg/L) is unlikely to limit flux to scopolamine (~μg/L), metabolic bottlenecks limiting scopolamine production were identified by expressing an additional copy of each heterologous enzyme between phenylpyruvate and scopolamine (FIG. 2) from low-copy plasmids in CSY1296 and measuring production of TAs and intermediates. Additional copies of WfPPR and DsH6H resulted in 64% and 89% increases in hyoscyamine and scopolamine titers, respectively, indicating that these enzymes were primary limiters of pathway flux (FIG. 64).

13.3.2) An improved scopolamine-producing strain was constructed by integrating NtJAT1 and a second copy of WfPPR and DsH6H into CSY1296. The resulting strain CSY1297 showed 2.4- and 7.1-fold respective increases in hyoscyamine and scopolamine accumulation relative to CSY1296 (FIG. 65).

TABLE 1

Genes of interest as components of the engineered metabolic pathways

| Enzyme | Abbrev. | Catalyzed Reactions | Source organisms | GenBank # |
|---|---|---|---|---|
| N-acetylglutamate synthase | GAT, ARG2 | Acetyl-CoA + L-glutamate → CoA + N-acetyl-L-glutamate (EC 2.3.1.1) | *Saccharomyces cerevisiae* | NP_012464.1 |
| Arginine decarboxylase | ADC | L-arginine → agmatine + $CO_2$ (EC 4.1.1.19) | *Arabidopsis thaliana*<br>*Avena sativa*<br>*Escherichia coli*<br>*Erythroxylum coca*<br>*Nicotiana tabacum* | NP_179243.1,<br>NP_195197.1,<br>CAA40137.1<br>NP_417413.1<br>AEQ02349.1<br>BAA21617.1 |
| Arginase | CAR1 | $H_2O$ + L-arginine → L-ornithine + urea (EC 3.5.3.1) | *Saccharomyces cerevisiae* | NP_015214.1 |
| Agmatine ureohydrolase | AUH, speB | Agmatine + $H_2O$ → putrescine + urea (EC 3.5.3.11) | *Escherichia coli*<br>*Bacillus subtilis*<br>*Homo sapiens* | NP_417412.1<br>NP_391629.1<br>NP_079034.3 |
| Ornithine decarboxylase | ODC, SPE1 | L-ornithine → $CO_2$ + putrescine (EC 4.1.1.17) | *Saccharomyces cerevisiae*<br>*Homo sapiens*<br>*Erythroxylum coca*<br>*Datura stramonium*<br>*Atropa belladonna* | NP_012737.1<br>NP_001274118.1<br>AEQ02350.1<br>CAA61121.1<br>AIC34713.1<br>NP_013733.1 |
| Polyamine oxidase | PAO, FMS1 | $H_2O$ + $O_2$ + spermine → 3-aminopropanal + $H_2O_2$ + spermidine<br>$H_2O$ + $O_2$ + spermidine → 3-aminopropanal + $H_2O_2$ + putrescine (EC 1.5.3.17) | *Saccharomyces cerevisiae* | |
| Aldehyde dehydrogenase | HFD1, ALD2-6 | 4-methylaminobutanal → 4-methylaminobutyric acid (EC 1.2.1.3) | *Saccharomyces cerevisiae* | NP_013828.1<br>NP_013893.1<br>NP_013892.1<br>NP_015019.1<br>NP_010996.2<br>NP_015264.1 |

TABLE 1-continued

Genes of interest as components of the engineered metabolic pathways

| Enzyme | Abbrev. | Catalyzed Reactions | Source organisms | GenBank # |
|---|---|---|---|---|
| Putrescine N-methyltransferase | PMT | Putrescine + S-adenosyl-L-methionine → N-methylputrescine + S-adenosyl-L-homocysteine (EC 2.1.1.53) | *Nicotiana tabacum*<br>*Atropa belladonna*<br>*Hyoscyamus niger*<br>*Calystegia sepium*<br>*Anisodus acutangulus*<br>*Datura stramonium*<br>*Datura innoxia* | NP001312037.1<br>BAA82261.1,<br>BAA82262.1<br>BAA82263.1<br>CAJ46252.1<br>ACF21005.1<br>CAE47481.1<br>CAJ46254.1 |
| N-methylputrescine oxidase | MPO | N-methylputrescine → 4-methylaminobutanal (EC 1.4.3.22) | *Nicotiana tabacum*<br>*Datura metel* | NP_001312728,<br>NP_001311739<br>JNVS_scaffold_2009311 (from 1000 Plants database) |
| Pyrrolidine ketide synthase | PYKS | N-methylpyrrolinium + 2 malonyl-CoA → 4-(1-methyl-2-pyrrolidinyl)-3-oxobutanoic acid (EC 2.3.1.-) | *Atropa belladonna*<br>*Datura stramonium* | AYU65302.1<br>n/a |
| Tropinone synthase | CYP82M3 | 4-(1-methyl-2-pyrrolidinyl)-3-oxobutanoic acid → tropinone (EC 1.14.14.-) | *Atropa belladonna* | AYU65303.1 |
| Cytochrome P450-NADP$^+$ reductase | CPR | NADPH + H+ + n oxidized hemoprotein = NADP+ + a reduced hemoprotein (EC 1.6.2.4) | *Eschscholzia californica*<br>*Papaver somniferum*<br>*Homo sapiens*<br>*Saccharomyces cerevisiae*<br>*Arabidopsis thaliana* | NM118585, many others (Ref PMID 19931102) |
| Tropinone reductase 1 | TR1 | Tropinone + NADPH + $H^+$ → tropine + NADP$^+$ (EC 1.1.1.206) | *Datura stramonium*<br>*Atropa belladonna*<br>*Hyoscyamus niger*<br>*Datura innoxia*<br>*Brugmansia arborea*<br>*Datura metel*<br>*Anisodus luridus* | AAA33281.1<br>AFP55030.1<br>BAA13547.1<br>AIN39992.1<br>AIN39993.1<br>AKY01854.1<br>AGL76989.1 |
| Tropinone reductase 2 | TR2 | Tropinone + NADPH + $H^+$ → pseudotropine + NADP$^+$ (EC 1.1.1.236) | *Datura stramonium*<br>*Hyoscyamus niger*<br>*Atropa belladonna*<br>*Anisodus luridus* | AAA33282.1<br>AAB09776.1<br>AGH24753.1<br>AGL76990.1 |
| Prephenate dehydratase | PHA2 | Prephenate + $H^+$ → 3-phenylpyruvate + $CO_2$ + $H_2O$ (EC 4.2.1.51) | *Saccharomyces cerevisiae* | NP_014083.2 |
| Aromatic aminotransferase | ARO8<br>ARO9 | 2-oxoglutarate + aromatic L-amino acid (phenylalanine, tyrosine) → aromatic oxoacid (phenylpyruvate, hydroxyphenylpyruvate) + L-glutamate (EC 2.6.1.57) | *Saccharomyces cerevisiae* | NP_011313.1<br>NP_012005.1 |
| Phenylpyruvate reductase | PPR, hcxB | 3-phenylpyruvate + NADH + $H^+$ → 3-phenyllactate + NAD$^+$ (EC 1.1.1.237) | *Escherichia coli*<br>*Lactobacillus* sp.<br>Wickerhamia fluorescens<br>*Lactobacillus plantarum*<br>*Atropa belladonna* | NP_415322.1<br>ALB78224.1<br>BAK09193.1<br>AWO81908.1<br>AZL88830.1 |
| Lactate dehydrogenase | LDH,<br>L-LDH,<br>D-LDH | 3-phenylpyruvate + NADH + $H^+$ → 3-phenyllactate + NAD$^+$ (EC 1.1.1.27) | *Bacillus coagulans*<br>*Lactobacillus casei*<br>*Lactobacillus plantarum* | ADN38376.1<br>WP_003567646.1<br>WP_003642078.1 |
| 3-phenyllactic acid UDP-glucosyltransferase 84A27 | UGT84A27 | 3-phenyllactate + UDP-glucose → 1-O-β-phenyllactoyl-glucose + UDP (EC 2.4.1.-) | *Atropa belladonna* | ATG80135.1 |
| UDP-glucose pyrophosphorylase | UGP | Glucose-1-phosphate + UTP → pyrophosphate + UDP-glucose (EC 2.7.7.9) | *Saccharomyces cerevisiae* | P32861 |
| Littorine synthase | LS | 1-O-β-phenyllactoyl-glucose + tropine → (R)-littorine (EC 2.3.1.-) | *Atropa belladonna* | ATG80136.1 |
| Littorine mutase | CYP80F1 | (R)-Littorine → 2 hyoscyamine aldehyde (EC 1.14.19.-) | *Atropa belladonna*<br>*Duboisia myoporoides*<br>*Hyoscyamus niger*<br>*Anisodus luridus* | AHZ34577.1<br>AQU12715.1<br>ABD39696.1<br>AGL76933.1 |
| Hyoscyamine 6β-hydroxylase/dioxygenase | H6H | 2-oxoglutarate + (S)-hyoscyamine + $O_2$ → (S)-anisodamine + $CO_2$ + succinate (S)-anisodamine → (S)-scopolamine (EC 1.14.11.11) | *Datura stramonium*<br>*Atropa belladonna*<br>*Hyoscyamus niger*<br>*Brugmansia arborea*<br>*Anisodus luridus*<br>*Anisodus acutangulus*<br>*Datura metel* | ALD59774.1<br>AEN79443.1<br>AAA33387.1<br>ALD59773.1<br>AGL76991.1<br>ABM74185.1<br>AAQ04302.1 |

TABLE 1-continued

Genes of interest as components of the engineered metabolic pathways

| Enzyme | Abbrev. | Catalyzed Reactions | Source organisms | GenBank # |
|---|---|---|---|---|
| Multidrug and toxin extrusion transporter/ jasmonate-inducible transporter | MATE/ JAT | TA precursor (compartment A) → TA precursor (compartment B) TA (compartment A) → TA (compartment B) | *Nicotiana tabacum* | AM991692 A3KDM4 A3KDM5 |
| Phenylalanine ammonia-lyase | PAL | L-phenylalanine → $NH_4^+$ + trans-cinnamate (EC 4.3.1.24) | *Arabidopsis thaliana* *Zea mays* | NP_181241.1 AAL40137.1 |
| Tyrosine ammonia-lyase | TAL | L-tyrosine → $NH_4^+$ + trans-4-coumarate (EC 4.3.1.25) | *Rhodosporidium toruloides* | CAA31209.1 |
| 4-coumarate-CoA ligase | 4CL | 4-coumarate + ATP + CoA → 4-coumaroyl-CoA + AMP + diphosphate Cinnamate + ATP + CoA → cinnamoyl-CoA + AMP + diphosphate (promiscuous activity on a variety of aromatic acids: 4CL1-5) | *Arabidopsis thaliana* *Oryza sativa* *Salvia miltiorrhiza* *Solanum tuberosum* | NP_175579.1, NP_188761.1, NP_176686.1, NP_188760.3 XP_015650830.1 AGW27193.1 P31685 Many others |
| Cocaine synthase | CS | Promiscuous acyltransferase: Aromatic acyl-CoA + tropine or pseudotropine → tropane ester E.g., cinnamoyl-CoA + tropine → cinnamoyltropine | *Erythroxylum coca* | AGT56097.1 |

TABLE 2

Example full-length amino acid sequences of hyoscyamine dehydrogenase (HDH) candidates and experimentally validated enzymes.

| Sequence | Description | SEQ. ID NO. |
|---|---|---|
| Experimentally validated, no observable HDH activity | | |
| MLETVKYLLGSAGPSGYGSKSTAEKVTEQSIHLRSITAIITGATSGIGAETARVLAKRGAKLILPARSLKAAEETKSRILSESPDADIIVMSLDLSSLSSVRKFVAQFEYLNFRLNILINNAGKFAHQHAISEDGIEMTFATNHLGHFLLTKLLLKNMIETANKTGVQGRIVNVSSSIHGWFSGDAIQYLRLITKDKSQYDATRAYALSKLANVIHTKELAQILKKMVANVTVNCVHPGIVRTRLTREREGLVTDLVFFLTSKLLKTIPQAAATTCYVATHPRLADVSGKYFADCNEISSSKLGSNLTEAARIWSASEIMVAKNSNAN* | *A. belladonna* plant source; full-length amino acid sequence >aba_locus_3722_iso_1_len_ 1302_ver_2 >HDH1 | SEQ ID NO. 1 |
| MSKTTPNHTQAVSGWAALDSSGKITPYIFNRRENGVNDVTIKILYCGICHTDLHYAKNDWGVTIYPVVPGHEITGIVVEVGSNVTNFKTGDKVGVGCMSASCLQCESCKNSEENYCDKVQFTYNGVFWDGSITYGGYSKMLVADYRFVVAVPENLPMDRAAPLLCAGVTVFVPMKDNNLIGSPRKNIGVIGLGGLGHLAIKFAKAFGHRVTVISTSLSKEKDAKTKLGADDFIVSSNAQQMQSRQKTLDFILDTVSADHSLGPYLELLKIKGTFVIVGAPDKPMGLPAFPLIFGKRTVKGSMIGSIKETQEMLDICGKYNIMCDIEIVTPDRINEAYERIEKNDIKYRFVIDIDGQSSKL* | *A. belladonna* plant source; full-length amino acid sequence >aba_locus_5175_iso_1_len_ 1282_ver_2 >HDH3 | SEQ ID NO. 2 |

TABLE 2-continued

Example full-length amino acid sequences of hyoscyamine dehydrogenase (HDH) candidates and experimentally validated enzymes.

| Sequence | Description | SEQ. ID NO. |
|---|---|---|
| MAMEGTKVARIKLGSDGLEVSAQGLGCMGMSAFYGPPKPEPDMIQLIHHAINSGVTFLDTSDIYGPHTNEILLGKALKGGIRERVELATKFGISFADGKREVRGDPAYVRATCVASLKRLDVDCIDLYYQHRIDTRVPIEVTVGELKKLVEEGKVKYIGLSEASASTIRRAHAVHPITAVELEWSLWSRDVEEELVPTCRELGIGIVAYSPLGRGFLSSGSKLLEDMSNEDYRKHLPRFQSENLEHNKKLYERICQTAARMGCTPSQLALAWVHHQGNDVCPIPGTTKIENLNQNIEALSIKLTSEDMTELESIASANAVQGDRYGSGASTYKDSETPPLSAWKVT* | *A. belladonna* plant source; full-length amino acid sequence >aba_locus_5694_iso_2_len_ 1279_ver_2 >HDH4 | SEQ ID NO. 3 |
| MEVKNKYVAIKSNINGAPQESHFEIKVENLSLIVEPDSKEVIIKNLFVSIDPYQLNRMKSESSSQAAISYASAITPGKAIDTYGVGRVLVSDRPEFKKDDLVAGLLTWGEYTVVKEGSLLNKLDPLGFPLSNHVGVLGFSGLAAYGGFFEVCKPKPGEKVFVSAASGSVGNLVGQYAKLLGCHVVGSAGSQEKVKLLKETLGFDDAFNYKEETDLKSALKRCFPQGIDVCFDNVGGKMLEAAVANMNLFGRVAICGVISEYTNASTRAAPEMLDIVYKRITIQGFLAADFMKVYADFLSETVEYLQDGKLKAVEDVSEGVESIPSAFIGLFNGDNIGKKIVKVADE* | *A. belladonna* plant source; full-length amino acid sequence >aba_locus_6801_iso_1_len_1156_ver_2 >HDH5 | SEQ ID NO. 4 |

TABLE 2-continued

Example full-length amino acid sequences of hyoscyamine dehydrogenase (HDH) candidates and experimentally validated enzymes.

| Sequence | Description | SEQ. ID NO. |
|---|---|---|
| MLRIRSRIISISRSLILRQTSSNKFSTHSERKLEGKVAVITGAASGIGKETAAKFISHGAKVIIADIQKQLGQETASELGPNATFVSCDVTKESDISDVVDFAVSKHGQLDIMYNNAGIACRTTFSIVDLDLAQFDRIMAINVRGVVAGIKHAARVMIPQGSGCILCTGSITGVMGGLAQPTYSTTKSCVIGIVKSTTGELCKHGIRINCISPFATPTAFSLDEMKEYFPGVEPEGLVKILQNASELKGAYCEPIDVANAAIFLASEDAKFISGENLMVDGGFTSFKKLNLSHLVQ* | *A. belladonna* plant source; full-length amino acid sequence >aba_locus_8950_iso_1_len_1109_ver_2 >HDH6 | SEQ ID NO. 5 |
| MASNGISHVNGTLAKVITCRAAVAYGPGQPLVVEQVQVDPPQKMEVRIKILFTSICHTDLSAWKGENEAQRVYPRILGHEASGVVESVGEGVTDMKTGDHVVPIFNGECGECVYCNSSKKTNLCGKFRVNPFKSVMANDGKCRFRNKDGNPIYHFLNTSTFSEYTVVDSACLVNIDPHAPLDKMTLLSCGVSTGLGAAWNTADVQTGETVAVFGLGAVGLAVVEGARTRGASRIIGVDINSEKRIKGQAIGITDFINPKEIDVPVHEKIREMTGGGVHYSFECAGNLEVLREAFSSTHDGWGMTIVLGIHPTPRLLPLHPMELFDGRRIVASVFGDFKGKSQLPFFAKQCMAGWKLDEFITHELPFEKINEGFQLLVDGKSLRCLLHL* | *A. belladonna* plant source; full-length amino acid sequence >aba_locus_11748_iso_1_len_557_ver_2 >HDH7 | SEQ ID NO. 6 |
| MAEKITSLESTRYAVVTGGNKGIGYETCRQLVSKGVVVVLTARDEKRGIEATERLKEESSFTDDQIMFHQLDVVDPDSISSLVDFINTKFGRLDILVNNAGVGGLMVEGDVVILKDLIEGDFVSVSTENEEEGDTEKSIEGIVTNYELTKQCVETNFYGAKRMSEAFIPLLQLSNSPTIVNVASFLGKLKLLCNEWAIKVLSNANNLTEDRVDEVVNEFLKDFTEKSIEAKGWPTYFAAYKVSKAAMIAYTRVLATKYPNFRINSVCPGYCKTDLTANTGSLTAEEGAESLVKLALLPNDGPSGLFFYRKDVAAL* | *A. belladonna* plant source; full-length amino acid sequence >aba_locus_12989_iso_1_len_1050_ver_2 >HDH8 | SEQ ID NO. 7 |
| MASVSFLSTIGKRLEGKVAMVTGGASGIGEAIAKLFYEHGAKVAIADVQDELGNSVSNALGGSSNSIYIHCDVTNEDDVQEAVDKTISTFGKLDIMICNAGISDETKPRIIDNTKADFERVLSINVTGVFLTMKHAARVMVPARIGCIISTSSVSSRVGAAASHAYCSSKHAVLGLTKNLAVELGQFGIRVNCLSPYAMVTPLAEKVIGLENEELEKALDMVGNLKGVTLRVDDVAKAALFLASDDSKYISGHNLFIDGGFTVYNPGLGMFKYPES* | *A. belladonna* plant source; full-length amino acid sequence >aba_locus_13944_iso_1_len_94_ver_2 >HDH9 | SEQ ID NO. 8 |
| MLRIASRGGITSRSLQLLQTFNKEFSTHIERKLEGKVALITGAASGIGKETAAKFINNGAKVIIADVQKQLGQETASQLGPNATFVLCDVTKESDVSNAVDFAVSNHGQLDIMYNNAGIICRTPRNIADLDLDAFDRVMAINVRGMMAGIKHAARVMIPRKAGSILCTASITGTMGGLAQPTYSTTKSCVIGMMRSVTAELCQNGIRINCISPFAIPTPFYIDEMKSYYPGVEPEVLVKMLYRASELNGAYCEPVDVANAAVFLASDDAKYVSGQNLVIDGGFTSYKSLNFPMSDQE* | *A. belladonna* plant source; full-length amino acid sequence >aba_locus_16663_iso_1_len_466_ver_2 >HDH10 | SEQ ID NO. 9 |
| MGIPSSVTPIVRRLEGKVAVITGGASGIGEAATRLFVKHGAKVVVADVRDDLGRALCKELGSNDTISFAHCSVTDENDVQNAIDGAVSRYGMLDIMFNNAGITGNMKDPSILATDYKNFKNVFDVNVYGAFLGARIAAKAMIPTKQGSILFTASIASVIGGIASPTTYASSKHAWGLTNHLAVELGQYGIRVNCISPYTVATPLVREILGKMDKEKAEEVTMETANLKGKTLEPEDIAEAAVYLGSDESKYVSGINLVIDGGYSKTNPLASMVMQNYI* | *A. belladonna* plant source; full-length amino acid sequence >aba_locus_114040_iso_ 1_len_645_ver_2 >HDH11 | SEQ ID NO. 10 |
| MESKSGEGKIVCVTGASGFIASWLVKLLLHRGYTVNATVRNLKDTSKVAHLLGLDGANERLHLFKAELLEEQSFDAAVDGCEGVFHTASPVSLTAKSKEELVDPAVKGTLNVLRSCAKSPSVLRVVITSSTASVICNKNMSTPGAVADETWYSDPEFCEEREEWYQLSKTLAEQAAWKFAKENEMDLVTLHPGLVIGPLLQPTLNFSCEATVNFIKEGKEAWSGGVYRFVDVRDVANAHTLAFEVPSANGRYCLVGVNGYSSLVLKIVQKLYPSITLPENFEDGLPLTPHFQVSSERAKGLGVKFTPLELSVKDTVESLMEKNFLHI* | *A. belladonna* plant source; full-length amino acid sequence >aba_locus_1_125882_iso_len_348_ver_2A >HDH13 | SEQ ID NO. 11 |
| MESKSGEGKIVCVTGASGFIASWLVKLLLHRGYTVNATVRNLKDTSKVAHLLGLDGANERLHLFKAELLEEQSFDAAVDGCEGVFHTASPVSLTAKSKEELVDPAVKGTLNVLRSCAKSPSVLRVVITSSTASVICNKNMSTPGAVADETWYSDPEFCEERKEWYQLSKTLAEKAARRFAKENGIDLVTLHPGLVIGPLLQPTLNFSCEAIVNFIKEGKEAWSGGVYRFVDVRDVANAHILAFEVPSANGRYCLVGVNGYSSLVLKIVQKLYPSITLPENFEDGLPLTPHFQVSSERAKGLGVKFTPLELSVKDTVESLMEKNFLHI* | *A. belladonna* plant source; full-length amino acid sequence >aba_locus_ 125 882_ iso_1 _len_348_ver_2B >HDH14 | SEQ ID NO. 12 |

TABLE 2-continued

Example full-length amino acid sequences of hyoscyamine dehydrogenase (HDH) candidates and experimentally validated enzymes.

| Sequence | Description | SEQ. ID NO. |
|---|---|---|
| Experimentally validated, observable HDH activity | | |
| MASEKSLEEKQAENTFGWAAMDSSGVLSPFTFSRRATGEEDVRLKVLYCGICHSDLGCIKNEWGWCSYPLVPGHEIVGIATEVGSKVTKFKVGDRVGVGCMVGSCGTCQNCTQNQESYCPEVIMTCASAYPDGTPTYGGFSNQMVANEKFVIRIPNSLPLDAAAPLLCAGSTVYSAMKFYGLCSQGLHLGVVGLGGLGHVAVKFAKAFGMKVTVISTSLGKKEEAINQLGADSFLINTDTEQMQGAMEVMDGIIDTVSALHPIEPLLGLLKSHQGKLIIVGLPNKQPELPVFSLINGRKMIGGSAVGGVKETQEMIDFAAEHNITADIEIVPMDYVNTAMERLEKGDVKFRFVIDVENTLVAAQT* | *A. belladonna* plant source: full-length amino acid sequence >aba_locus_4635_iso_1_len_1351_ver_2 >AbHDH (HDH2) | SEQ ID NO. 13 |
| MAAEKLSEEEAVKTFGWAAMDSSGVLSPFEFSRRATGAEDVRLKVLYCGICHSDLGCVKNEWGWCSYPLVPGHEIVGIATEVGSRVTKFKVGDRVGVGCMVGSCGSCQNCSQNLESYCPEVIMTCASAYPDGTPTYGGFSNQMVANEKFVIQIPEKLPLDAAAPLLCAGSTVYSPMKFYGLCSPGLHLGVVGLGGLGHVAVKFAKAFGMKVTVISTSIGKKEEAINQLGADSFLTSTDTEQMQGAMETMDGIIDTVSALHPIEPLVGLLKSHQGKLIIVGLPNKQPELPVFSLINGRKMIGGSAVGGVKETQEMIDFAAKHNITADIEIVRMDYVNTAMERLEKGDVKFRFVIDVENTLVPAQT* | *D. innoxia* plant source; full-length amino acid sequence >DiHDH | SEQ ID NO. 14 |
| MAAEKLEERKRWETFGWAAMDSSGVLSPFEFSRRATGEEDVRLKVLYCGICHSDLGCIKNEWGWCSYPLVPGHEIVGIATEVGSRVTKFKVGDRVGVGCMVGSCGSCQNCSQNLESYCPEVIMTCASAYPDGTPTYGGFSNQMVANEKFVIQIPEKLPLDAAAPLLCAGSTVYSPMKFYGLCSPGLHLGVVGLGGLGHVAVKFAKAFGMKVTVISTSIGKKEEAINQLGADSFLISTDTEQMQGAMETMDGIIDTVSALHPIEPLVGLLKSHRGKLIIVGLPNKQPELPVFSLINGRKMIGGSAVGGVKETQEMIDFAAKHNITADIEIVGMDYVNTAMERLEKGDVKFRFVIDVENTLVPAQT* | *D. stramonium* plant source; full-length amino acid sequence >DsHDH | SEQ ID NO. 15 |

TABLE 3

Example full-length amino acid sequences of soluble protein domains that can be fused to the N-terminus of serine carboxypeptidase-like acyltransferases to enable functional acyltransferase expression in non-plant cells.

| Sequence | Description | SEQ ID NO. |
|---|---|---|
| MSKGEELFTGVVPILVELDGDVNGHKFSVSGEGEGDATYGKLTLKFICTTGKLPVPWPTLVTTFGYGVQCFARYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGIIHGMDELYK | Green fluorescent protein: full-length amino acid sequence >GFP | SEQ ID NO. 16 |
| MSELIKENMHMKLYMEGTVDNHHFKCTSEGEGKPYEGTQTMRIKVVEGGPLPFAFDILATSFLYGSKTFXNHTQGIPDFFKQSFPEGFTWERVTTYEDGGVLTATQDTSLQDGCLIYNVKIRGVNFTSNGPVMQKKTLGWEAFTETLYPAPGGLEGRNDMALKLVGGSHLIANIKTTYRSKKPAKNLKMPGVYYVDYRLERIKEANNETYVEQHEVAVARYCDLPSKLGHKLN | Blue fluorescent protein: full-length amino acid sequence >BFP | SEQ ID NO. 17 |
| MSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSKLSKDPNEKRDHMVLLEFVTAAGITHGMDELYK | Yellow fluorescent protein, variant mVenus; full-length amino acid sequence >mVenus | SEQ ID NO. 18 |
| MSDSEVNQEAKPEVKPEVKPETHINLKVSDGSSEIFFKIKKTTPLRRLMEAFAKRQGKEMDSLTFLYDGIEIQADQTPEDLDMEDNDIIEAHREQIGG | Small ubiquitin-related modified with mutated protease cleavage site: full-length amino acid sequence >SUMO* | SEQ ID NO. 19 |
| MVSKGEEDNMAIIKEFMRFKVHMEGSVNGHEFEIEGEGEGRPYEGTQTAKLKVTKGGPLPFAWDILSPQFMYGSKAYVKHPADIPDYLKLSFPEGFKWERVMNFEDGGVVTVTQDSSLQDGEFIYKVKLRGTNFPSDGPVMQKKTMGWEASSERMYPEDGALKGEIKQRLKLKDGGHYDAEVKTTYKAKKPVQLPGAYNVNIKLDITSHNEDYTIVEQYERAEGRHSTGGMDELYK | Red-fluorescent protein, variant mCherry; full-length amino acid sequence >mCherry | SEQ ID NO. 20 |
| MGSQGTNIDSIIHVFLISFPGQGHVNPLLRLGKRLASKGVLVSFCAPECVGKDMRAANNNIISDEPTPYGDGFIRFEFFDGWEYTQPKENRQLEIELANLEVVGRAVLPAMLKENEAKGRPVSCLINNPFIPWVCDVADS | *Atropa belladonna* UDP-glucosyltransferase 84A27: full-length amino acid sequence >AbUGTT84A27 | SEQ ID NO. 21 |

TABLE 3-continued

Example full-length amino acid sequences of soluble protein domains that can be fused to the N-terminus of serine carboxypeptidase-like acyltransferases to enable functional acyltransferase expression in non-plant cells.

| Sequence | Description | SEQ ID NO. |
|---|---|---|
| LGIPCAVLWVQSCASFSAYY<br>HYHFNLAPFPNESNPNIDVH<br>LPNMPILKWDELPSFLLPSN<br>PYPALANAILRQFNYLSKPI<br>RIFIESFDELEKDIVDYMSD<br>FLPIKTVGPLLVEDPKIEQV<br>VRADLVKADSSITQWLNSKP<br>PSSVVYISFGSIVVPSQEQV<br>DEIAYGILNSGLNFLWIMKP<br>PRKNSSFPTVVLPQGYLDKI<br>GDKGKVVEWCLQEQVLAHPS<br>LACFVTHCGWNSSMEVIANG<br>VPIVAFPQWGDQVTDAKYLV<br>DEFKIGVRLSRGVTENRVIP<br>RDEVERSLHDVTSGPKVAEM<br>KENALKWKMKATEAVAEGGS<br>SDLNLKSFVDELRTLQNSNK<br>NLAKLAPLSN | | |
| MASSEDVIKEFMRFKVRMEG<br>SVNGHEFEIEGEGEGRPYEG<br>TQTAKLKVTKGGPLPFAWDI<br>LSPQFQYGSKVYVKHPADIP<br>DYKKLSFPEGFKWERVMNFE<br>DGGVVTVTQDSSLQDGRFIY<br>KVKFIGVNFPSDGPVMQKKT<br>MGWEPSTERLYPRDGVLKGE<br>IHKALKLKDGGHYLVEFKSI<br>YMAKKPVQLPGYYYVDSKLD<br>ITSHNEDYTIVEQYERTEGR<br>HHLFL | Red-fluorescent protein, variant DsRed; full-length amino acid sequence >DsRed | SEQ ID NO. 22 |

TABLE 4

Example full-length amino acid sequences of heterologous transporter which can be expressed in engineered non-plant cells to translocate TAs, TA derivatives, and/or TA precursors across cellular lipid membranes.

| Sequence | Description | SEQ ID NO. |
|---|---|---|
| MVEELPQSLKEKKWQINWDA<br>VSQELKKTSRFMAPMVAVTV<br>FQYLLQVVSVMMVGHLGELA<br>LSSVAIATSLTNVTGFSLLT<br>GLVGGMETLCGQAYGAQQYH<br>KLSTYTYTAIISLFLVCIPI<br>CVLWCFMDKLLILTGQDHSI<br>SVEARKYSLWVIPAIFGGAI<br>SKPLSRYSQAQSLILPMLLS<br>SFAVLCFHLPISWALIFKLE<br>LGNIGAAIAFSISSWLYVLF<br>LASYVKLSSSCEKTRAPFSM<br>EAFLCIRQFFRLAVPSAVMV<br>CLKWWSFEVLALVSGLLPNP<br>KLETSVMSICITISQLHFSI<br>PYGFGAAASTRVSNELGAGN<br>PQKARMAVQVVMFLTVVETL<br>VFNTSLFGSRHVLGKAFSNE<br>KQVVDYIAAMTPFLCLSIVT<br>DSLQIVITGIARGSGWQHIG<br>AYINLWFYVIAIPLAWLGFV | *Nicotiana tabacum* jasmonate-inducible alkaloid transporter 1; full-length amino acid sequence >NtJATI | SEQ ID NO. 23 |

TABLE 4-continued

Example full-length amino acid sequences of heterologous transporter which can be expressed in engineered non-plant cells to translocate TAs, TA derivatives, and/or TA precursors across cellular lipid membranes.

| Sequence | Description | SEQ ID NO. |
|---|---|---|
| LHLKAKGLWIGIWGCAIQSI<br>VLSIVTGFTDWEKQAKKARE<br>RVHEGRS | | |
| MGKSMKSEVEQPLLIAAHGG<br>SSELEEVLSDTQLPYFRRLR<br>YASWIEFQLLYRLAAPSVAV<br>YMINNAMSMSTRIFSGQLGN<br>LQLAAASLGNQGIQLFAYGL<br>MLGMGSAVETLCGQAYGAHR<br>YEMLGVYLQRATVVLSVTGI<br>PLTVVYLFSKNILLALGESK<br>LVASAAAVFVYGLIPQIFAY<br>AVNFPIQKFLQAQSIVAPSA<br>FISLGTLFVHILLSWVVVYK<br>IGLGLLGASLVLSFSWWIIV<br>VAQFIYIIKSERCKATWAGF<br>RWEAFSGLCQFVKLSAGSAV<br>MLCLETWYMQILVLLSGLLK<br>NPEIALASISVCLAVNGLMF<br>MVAVGFNAAASVRVSNELGA<br>AHSKSAAFSVFMVTFISFLI<br>AVVEAIIVLSLRNVISYAFT<br>EGEIVAKEVSELCPFLAVTL<br>ILNGIQPVLSGVAVGCGWQA<br>FVAYVNVGCYYGVGIPLGCL<br>LGFKFDLGAKGIWTGMIGGT<br>VMQTVILLWVTFRTDWNKKV<br>ECAKKRLDKWENLKGPLNKE | *Nicotiana tabacum* multidrug and toxin extrusion transporter 1; full-length amino acid sequence >NtMATE1 | SEQ ID NO. 24 |
| MGKSMKSEVEQPLLAAAHGG<br>SSELEEVLSDSQLPYFRRLR<br>YASWIEFQLLYRLAAPSVAV<br>YMINNAMSMSTRIFSGQLGN<br>LQLAAASLGNQGIQLFAYGL<br>MLGMGSAVETLCGQAYGAHR<br>YEMLGVYLQRATVVLSLTGI<br>PLAVVYLFSKNILLALGESK<br>LVASAAAVFVYGLIPQIFAY<br>AVNFPIQKFLQSQSIVAPSA<br>FISLGTLFVHILLSWVVVYK<br>IGLGLLGASLVLSFSWWIIV<br>VAQFIYILKSERCKATWAGF<br>RWEAFSGLWQFVKLSAGSAV<br>MLCLETWYFQILVLLSGLLK<br>NPEIALASISVCLAVNGLMF<br>MVAVGFNAAASVRVSNELGA<br>AHPKSAAFSVFMVTFISFLI<br>AVVEAIIVLSLRNVISYAFT<br>EGEVVAKEVSSLCPYLAVTL<br>ILNGIQPVLSGVAVGCGWQA<br>FVAYVNVGCYYGVGIPLGCL<br>LGFKFDFGAKGIWTGMIGGT<br>VMQTIILLWVTFSTDWNKEV<br>ESARKRLDKWENLKGPLNKE | *Nicotiana tabacum* multidrug and toxin extrusion transporter 2; full-length amino acid sequence >NtMATE2 | SEQ ID NO. 25 |

TABLE 5

Comparison of impurities that may be present in concentrate of nightshade leaves and clarified yeast culture medium.

| Impurities: | | Concentrate of Nightshade Leaves | Clarified Yeast Culture Medium |
|---|---|---|---|
| Inorganic | Sodium | ✓ | ✓ |
| | Magnesium | ✓ | ✓ |
| | Silicon | ✓ | × (not in culture medium) |
| | Phosphorus | ✓ | ✓ |
| | Sulfur | ✓ | ✓ |
| | Chloride | ✓ | ✓ |
| | Potassium | ✓ | ✓ |
| | Calcium | ✓ | ✓ |
| | Copper | ✓ | ✓ |
| | Zinc | ✓ | ✓ |
| | Molybdenum | ✓ | ✓ (sodium molybdate in medium) |
| | Iron | ✓ | ✓ |
| | Manganese | ✓ | ✓ |
| | Ammonium | ✓ | ✓ |
| | Boron | ✓ | ✓ |
| Organic | Polysaccharides (starch, cellulose, xylan) | ✓ | × (yeast fed simple sugars) |
| | Lignin (p-coumaryl, coniferyl, sinapyl alcohols) | ✓ | × |
| | Pigments (chlorophyll, anthocyanins, carotenoids) | ✓ | × |
| | Flavonoids | ✓ | × |
| | Phenanthreoids | ✓ | × |
| | Latex, gum, and wax | ✓ | × |
| | Rubisco | ✓ | × |
| | Cuscohygrine | ✓ | × |
| Other | Pesticides, Fungicides, Herbicides | ✓ | × |
| | Pollen | ✓ | × |

Notwithstanding the appended clauses, the disclosure may be defined by the following clauses:

Clause 1. An engineered non-plant cell that produces a tropane alkaloid product, a precursor of a tropane alkaloid product, or a derivative of a tropane alkaloid product.

Clause 2. The cell of clause 1, wherein the cell is a microbial cell.

Clause 3. The cell of clauses 1 or 2, wherein the engineered cell comprises a plurality of heterologous coding sequences for encoding a plurality of enzymes, wherein at least one of the enzymes is selected from the group consisting of arginine decarboxylase, agmatine ureohydrolase, agmatinase, putrescine N-methyltransferase, N-methylputrescine oxidase, pyrrolidine ketide synthase, tropinone synthase, cytochrome P450 reductase, tropinone reductase, phenylpyruvate reductase, 3-phenyllactic acid UDP-glucosyltransferase 84A27, littorine synthase, littorine mutase, hyoscyamine dehydrogenase, hyoscyamine 6β-hydroxylase/dioxygenase, and cocaine synthase.

Clause 4. The cell of any of clauses 1-3, wherein endogenous arginine metabolism is modified in the cell.

Clause 5. The cell of any of clauses 1-4, wherein endogenous phenylalanine and phenylpropanoid metabolism is modified clauses the cell.

Clause 6. The cell of any of claims 1-5, wherein endogenous polyamine regulatory mechanisms are disrupted in the cell.

Clause 7. The cell of any of the clauses 1-6, wherein endogenous acetate metabolism is modified in the cell.

Clause 8. The cell of any of the clauses 1-7, wherein endogenous glycoside metabolism is modified in the cell.

Clause 9. The cell of any of clauses 1-8, wherein the cell produces a tropane alkaloid product, a precursor of a tropane alkaloid product, or a derivative of a tropane alkaloid product selected from the group consisting of a hyoscyamine, atropine, anisodamine, scopolamine, calystegine, cocaine, or a non-natural tropane alkaloid.

Clause 10. The cell of any of the clauses 1-9, wherein the engineered cell comprises a plurality of heterologous coding sequences encoding for a plurality of enzymes which comprise one or more soluble protein domains fused to the N-terminus of a serine carboxypeptidase-like acyltransferase domain.

Clause 11. The cell of any of the clauses 1-10, wherein the transport of TAs, TA precursors, and/or TA derivatives across intracellular membranes or across the plasma membrane is modified in the cell.

Clause 12. The cell of any of the clauses 1-11, wherein the engineered cell comprises a plurality of heterologous coding sequences for encoding a plurality of transporters, wherein at least one of the transporters is selected from the group consisting of a multidrug and toxin extrusion transporter, a nitrate/peptide family transporter, an ATP-binding cassette transporter, and a pleiotropic drug resistance transporter.

Clause 13. A method for producing a tropane alkaloid, a precursor of a tropane alkaloid product, or a derivative of a tropane alkaloid product comprising (a) culturing a cell of any of clauses 1-12 under conditions suitable for protein production;

(b) adding a starting compound to the cell culture; and (c) recovering the tropane alkaloid or the precursor of a tropane alkaloid product from the culture.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An engineered non-plant cell that produces a precursor of a tropane alkaloid product, a tropane alkaloid product, or a derivative of a tropane alkaloid product, wherein the engineered non-plant cell comprises a heterologous coding sequences encoding hyoscyamine dehydrogenase (HDH) within a pathway for producing the precursor of a tropane alkaloid product, the tropane alkaloid product, or the derivative of a tropane alkaloid product.

2. The engineered cell of claim 1, wherein the cell further comprises one or more alterations to one or more endogenous metabolic pathways or regulatory mechanisms selected from the group of endogenous arginine metabolism, endogenous phenylalanine and phenylpropanoid metabolism, endogenous polyamine regulatory mechanisms and metabolism, and endogenous acetate metabolism.

3. The engineered cell of claim 2, wherein endogenous arginine metabolism is altered in the cell by modifications to one or more coding sequences of one or more endogenous enzymes, wherein at least one of the enzymes is selected from the group consisting of glutamate N-acetyltransferase, acetylglutamate kinase, N-acetyl-y-glutamyl-phosphate reductase, acetylornithine aminotransferase, ornithine acetyltransferase, ornithine carbamoyltransferase, argininosuccinate synthase, argininosuccinate lyase, and arginase.

4. The engineered cell of claim 2, wherein endogenous phenylalanine and phenylpropanoid metabolism is altered in the engineered cell by modifications to one or more coding sequences of one or more endogenous enzymes, wherein at least one of the enzymes is selected from the group consisting of pentafunctional AROM polypeptide, chorismate synthase, chorismate mutase, prephenate dehydratase, aromatic aminotransferase, and phenylacrylic acid decarboxylase.

5. The engineered cell of claim 2, wherein endogenous polyamine regulatory mechanisms are altered in the engineered cell by modifications to one or more coding sequences of one or more endogenous proteins, wherein at least one of the proteins is selected from the group consisting of methylthioadenosine phosphorylase, ornithine decarboxylase, ornithine decarboxylase antizyme, polyamine oxidase, spermidine synthase, spermine synthase, polyamine transporter, and polyamine permease.

6. The engineered cell of claim 2, wherein endogenous acetate metabolism is altered in the engineered cell by modifications to one or more coding sequences of one or more endogenous enzymes, wherein at least one of the enzymes is selected from the group consisting of alcohol dehydrogenase and aldehyde dehydrogenase.

7. The engineered cell of claim 1, wherein the engineered cell further comprises one or more alterations to endogenous glycoside metabolism.

8. The engineered cell of claim 7, wherein endogenous glycoside metabolism is altered in the engineered cell by modifications to one or more coding sequences of one or more endogenous enzymes, wherein at least one of the enzymes is selected from the group consisting of glucan 1,3-f3-glucosidase and steryl-P-glucosidase.

9. The engineered cell of claim 8, wherein the modifications to one or more coding sequences is selected from the group consisting of a feedback inhibition alleviating mutation in a biosynthetic enzyme or regulatory protein gene native to the cell, a transcriptional modulation modification of a biosynthetic enzyme gene native to the cell, and an inactivating mutation in an enzyme or protein native to the cell.

10. The engineered cell of claim 1, wherein the engineered cell is selected from the group consisting of a microbial cell, a fungal cell, a yeast cell, and a bacterial cell.

11. The engineered cell of claim 10, wherein the engineered cell is a fungal cell.

12. The engineered cell of claim 1, wherein the engineered cell further comprises one or more heterologous coding sequences for one or more enzymes, wherein at least one of the enzymes is selected from the group consisting of arginine decarboxylase, agmatine ureohydrolase, agmatinase, putrescine N-methyltransferase, N-methylputrescine oxidase, pyrrolidine ketide synthase, tropinone synthase, cytochrome P450 reductase, tropinone reductase, phenylalanine ammonia-lyase, tyrosine ammonia-lyase, phenylpyruvate reductase, 4-coumarate-CoA ligase, 3-phenyllactic acid UDP-glucosyltransferase 84A27, littorine synthase, littorine mutase, hyoscyamine 6β-hydroxylase/dioxygenase, and cocaine synthase.

13. The engineered cell of claim 1, wherein the engineered cell further comprises one or more heterologous coding sequences encoding one or more enzymes which comprise one or more soluble protein domains fused to the N-terminus of a serine carboxypeptidase-like acyltransferase domain for the purpose of enabling functional expression of the acyltransferase domain in a sub-cellular compartment of the engineered cell.

14. The engineered cell of claim 1, wherein the engineered cell produces a precursor of a tropane alkaloid product selected from the group consisting of an agmatine, N-carbamoylputrescine, N-methylputrescine, 4-methylaminobutanal, N-methylpyrrolinium, 4-(1-methyl-2-pyrrodiny 1)-3-oxobutanoic acid, tropinone, tropine, pseudotropine, ecgonine, methylecgonine, coenzyme A covalently bonded to phenyllactic acid by means of a thioester linkage, a sugar covalently bonded to cinnamic acid, ferulic acid, coumaric acid, and phenyllactic acid by means of a glycosidic linkage.

15. The engineered cell of claim 1, wherein the engineered cell produces a tropane alkaloid product selected from the group consisting of a hyoscyamine, atropine, anisodamine, scopolamine, calystegine, cocaine, and a non-natural tropane alkaloid.

16. The engineered cell of claim 15, wherein the engineered cell produces a tropane alkaloid product selected from the group consisting of a hyoscyamine, atropine, and a scopolamine.

17. The engineered cell of claim 1, wherein the engineered cell produces a derivative of a tropane alkaloid product selected from the group consisting of p-hydroxyatropine, p-hydroxyhyoscyamine, p-fluorohyoscyamine, p-chlorohyoscyamine, p-bromohyoscyamine, p-fluoroscopolamine, p-chloropscopolamine, p-bromoscopolamine, N-methylhyoscyamine, N-butylhyoscyamine, N-methylscopolamine, N-butylscopolamine, N-acetylhyoscyamine, and N-acetylscopolamine.

18. The engineered cell of claim 1, wherein transport of one or more tropane alkaloids, one or more tropane alkaloid precursors, and/or one or more tropane alkaloid derivatives across intracellular membranes or across the plasma membrane is modified in the cell.

19. The engineered cell of claim 18, wherein modified transport is enabled by one or more heterologous coding sequences encoding one or more transporters, wherein at least one of the transporters is selected from the group consisting of a multidrug and toxin extrusion transporter, a nitrate/peptide family transporter, an ATP-binding cassette transporter, and a pleiotropic drug resistance transporter.

* * * * *